(12) United States Patent
Yousef et al.

(10) Patent No.: US 9,017,692 B2
(45) Date of Patent: Apr. 28, 2015

(54) ANTIMICROBIAL AGENT, BACTERIAL STRAIN, BIOSYNTHESIS, AND METHODS OF USE

(71) Applicant: Ohio State Innovation Foundation, Columbus, OH (US)

(72) Inventors: Ahmed E. Yousef, Columbus, OH (US); Yaoqi Guo, Columbus, OH (US); En Huang, Columbus, OH (US); Chunhua Yuan, Columbus, OH (US); Liwen Zhang, Delaware, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 13/705,936

(22) Filed: Dec. 5, 2012

(65) Prior Publication Data
US 2013/0164317 A1    Jun. 27, 2013

Related U.S. Application Data

(60) Provisional application No. 61/643,617, filed on May 7, 2012, provisional application No. 61/566,831, filed on Dec. 5, 2011.

(51) Int. Cl.
| | |
|---|---|
| A61K 39/02 | (2006.01) |
| C12N 1/12 | (2006.01) |
| C12N 1/20 | (2006.01) |
| A01N 37/18 | (2006.01) |
| A61K 38/00 | (2006.01) |
| A61P 31/04 | (2006.01) |
| C07K 7/08 | (2006.01) |
| C07K 7/50 | (2006.01) |
| C11D 3/37 | (2006.01) |
| C11D 3/38 | (2006.01) |
| C11D 3/48 | (2006.01) |
| C12R 1/01 | (2006.01) |

(52) U.S. Cl.
CPC ... *C12N 1/20* (2013.01); *C07K 7/08* (2013.01); *C07K 7/50* (2013.01); *C11D 3/3719* (2013.01); *C11D 3/38* (2013.01); *C11D 3/48* (2013.01); *C12R 1/01* (2013.01)

(58) Field of Classification Search
USPC ...................................................... 424/190.1
See application file for complete search history.

(56) References Cited

U.S. PATENT DOCUMENTS

| | | | |
|---|---|---|---|
| 6,602,500 B1 | 8/2003 | Kharbanda et al. | |
| 6,989,370 B2 | 1/2006 | Stern et al. | |
| 7,071,293 B1 | 7/2006 | Tack et al. | |
| 7,407,940 B2 * | 8/2008 | Falla et al. | 514/2.4 |
| 2002/0176910 A1 | 11/2002 | Raczek | |
| 2011/0245152 A1 | 10/2011 | Yousef et al. | |
| 2012/0141423 A1 | 6/2012 | Yousef et al. | |

FOREIGN PATENT DOCUMENTS

| | | |
|---|---|---|
| CA | 2575769 | 2/2006 |
| WO | WO 2005/019250 | 3/2005 |
| WO | WO 2006/016558 | 2/2006 |
| WO | WO 2010029159 A1 * | 3/2010 |
| WO | WO 2011/069227 | 6/2011 |
| WO | WO 2013/086003 | 6/2013 |
| WO | WO 2013/180699 | 12/2013 |

OTHER PUBLICATIONS

Dietrich et al "The *Ashbya gossypii* Genome as a Tool for Mapping the Ancient *Saccharomyces cerevisiae* genome" Science 304:304-307. Published Apr. 9, 2004.*
Nascimento et al "Comparative Genomics of Two *Leptospira interrogans* Serovars Reveals Novel Insights into Physiology and Pathogenesis" J Bacteriology 186:2164-2172. Published Apr. 2004.*
Bulach et al "Genome reduction in *Leptospira borgpetersenii* reflects limited transmission potential" Proc. Natl. Acad. Sci. 103:14560-14565. Published Sep. 26, 2006.*
Ren et al "Unique physiological and pathogenic features of *Leptospira interrogans* revealed by whole-genome sequencing" Nature 422:888-893. Published Apr. 24, 2003.*
CAS RN 485111-54-4. Entry date Feb. 3, 2003.*
Guo Y et al "Isolation of a *Paenibacillus* sp. Strain and Structural Elucidation of Its Broad-Spectrum Lipopeptide Antibiotic" Appl. Environ. Microbiol. 78:3156-3165. Published online Feb. 24, 2012.*
Alfonso, R. G. 1990. Remington's Pharmaceutical Sciences, 18th edition, Mack Publishing Company, Easton, Pa.
Ball, L. J., C. M. Goult, J. A. Donarski, J. Micklefield, and V. Ramesh. 2004. NMR structure determination and calcium binding effects of lipopeptide antibiotic daptomycin. Org. Biomol. Chem. 2:1872-1878.

(Continued)

*Primary Examiner* — James H Alstrum Acevedo
*Assistant Examiner* — Zachary J Miknis
(74) *Attorney, Agent, or Firm* — Michael Best & Friedrich LLP

(57) ABSTRACT

Provided herein is a biologically pure culture of *Paenibacillus thiaminolyticus*, identified as OSY-SE, as well as an antimicrobial agent isolated and/or purified from the culture having any one of SEQ ID NOs:1-3 and 64-66. The disclosure also provides compositions and articles of manufacture comprising an antimicrobial agent and/or the bacterial cell of *Paenibacillus thiaminolyticus*, identified as OSY-SE. Further provided are methods of use, including methods of affecting microbial activity, methods of inhibiting growth and/or proliferation of a microbe, methods of treating a condition or disease associated with the presence of a microbe, and methods of treating a microbial infection in a subject comprising contacting a microbial cell with at least one active agent of SEQ ID NOs:1-3 and 64-66 and/or the bacterial cell *Paenibacillus thiaminolyticus*, identified as OSY-SE. The disclosure also provides the biosynthetic machinery (e.g., utilizing a NRPS mechanism) including isolated proteins, isolated polynucleotides, vectors, and host cells for production of the antimicrobials described herein.

4 Claims, 19 Drawing Sheets

(56) References Cited

OTHER PUBLICATIONS

Bax, A., and Summers, M.F., J. Am. Chem. Soc., vol. 108(8), pp. 2093-2094, 1986.

Bothner-By, A.A., et al., J. Am. Chem. Soc., vol. 106(3), ppp. 811-813, 1984.

Brunger, A. T., P. D. Adams, G. M. Clore, W. L. DeLano, P. Gros, R. W. Grosse-Kunstleve, J. S. Jiang, J. Kuszewski, M. Nilges, N. S. Pannu, R. J. Read, L. M. Rice, T. Simonson, and G. L. Warren. 1998. Crystallography & NMR system: A new software suite for macromolecular structure determination. Acta. Crystallogr. D 54:905-921.

Cavanagh, J. and M. Rance, J. Magn Reson., vol. 88, pp. 72-85, 1990.

Chan, W.C. et al., FEBS Lett., vol. 252(1), 29-36, 1989.

Chen, S., S. Zhao, D. G. White, C. M. Schroeder, R. Lu, H. Yang, P. F. McDermott, S. Ayers, and J. Meng. 2004. Characterization of multiple-antimicrobial-resistant *Salmonella* serovars isolated from retail meats. Appl. Environ. Microbiol. 70:1-7.

Clardy, J., M. A. Fischbach, and C. T. Walsh. 2006. New antibiotics from bacterial natural products. Nat. Biotechnol. 24:1541-1550.

Cornwell, G.G. et al., Biochem. Biophys. Res. Commun., vol. 154, pp. 648-653, 1988.

Delaglio, F., S. Grzesiek, G. W. Vuister, G. Zhu, J. Pfeifer, and A. Bax. 1995. NMRPipe: a multidimensional spectral processing system based on UNIX pipes. J. Biomol. NMR 6:277-293.

Drancourt, M., C. Bollet, A. Carlioz, R. Martelin, J. P. Gayral, and D. Raoult. 2000. 16S ribosomal DNA sequence analysis of a large collection of environmental and clinical unidentifiable bacterial isolates. J. Clin. Microbiol. 38:3623-3630.

Drider, D., et al., Prokaryotic Antimicrobial Peptides: From Genes to Applications, Springer, N.Y. (2011).

E.K. Kelenkamp, M.B., et al., FEBS Left., vol. 579(9), pp. 1917-1922, 2005.

Furihata, K., and H. Seto. 1998. Constant time HMBC (CT-HMBC), a new HMBC technique useful for improving separation of cross peaks. Tetrahedron Lett. 39:7337-7340.

Gerard, J., R. Lloyd, T. Barsby, P. Haden, M. T. Kelly, and R. J. Andersen. 1997. Massetolides A-H, antimycobacterial cyclic depsipeptides produced by two pseudomonads isolated from marine habitats. J. Nat. Prod. 60:223-229.

Gordon, R. E., W. C. Haynes, and C. H.-N. Pang. 1973. The Genus *Bacillus*. Agriculture Handbook No. 427. U.S. Department of Agriculture, Washington, D.C.

Hamaki, T., M. Suzuki, R. Fudou, Y. Jojima, T. Kajiura, A. Tabuchi, K. Sen, and H. Shibai. 2005. Isolation of novel bacteria and actinomycetes using soil-extract agar medium. J. Biosci. Bioeng. 99:485-492.

He, Z., D. Kisla, L. Zhang, C. Yuan, K. B. Green-Church, and A. E. Yousef. 2007. Isolation and identification of a *Paenibacillus polymyxa* strain that coproduces a novel lantibiotic and polymyxin. Appl. Environ. Microbiol. 73:168-178.

Hsu, D. I., M. P. Okamoto, R. Murthy, and A. Wong-Beringer. 2005. Fluoroquinolone-resistant *Pseudomonas aeruginosa*: risk factors for acquisition and impact on outcomes. J. Antimicrob. Chemother. 55:535-541.

Janssen, P. H., P. S. Yates, B. E. Grinton, P. M. Taylor, and M. Sait. 2002. Improved culturability of soil bacteria and isolation in pure culture of novel members of the divisions Acidobacteria, Actinobacteria, Proteobacteria, and Verrucomicrobia. Appl. Environ. Microbiol. 68:2391-2396.

Jeener, J. et al., J. Chem. Phys., vol. 71(11), pp. 4546-4553, 1979.

Johnson, B. A., and R. A. Blevins. 1994. NMR VIEW: a computer-program for the visualization and analysis of NMR data. J. Biomol. NMR 4:603-614.

Jung G., Angew. Chem. Int. ed. Eng, vol. 30, pp. 1051-1192, 1991.

Kajimura, Y., and M. Kaneda. 1996. Fusaricidin A, a new depsipeptide antibiotic produced by *Bacillus polymyxa* KT-8. Taxonomy, fermentation, isolation, structure elucidation and biological activity. J. Antibiot. 49:129-135.

Kaletunc, G., J. Lee, H. Alpas, and F. Bozoglu. 2004. Evaluation of structural changes induced by high hydrostatic pressure in *Leuconostoc mesenteroides*. Appl. Environ. Microbiol. 70:1116-1122.

Kay, L.E., et al., J. Am. Chem. Soc., vol. 114(26), pp. 10663-10665, 1992.

Khianngam, S., A. Akaracharanya, S. Tanasupawat, K. C. Lee, and J. S. Lee. 2009. *Paenibacillus thailandensis* sp. nov. and *Paenibacillus nanensis* sp. nov., xylanase-producing bacteria isolated from soil. Int. J. Syst. Evol. Microbiol. 59:564-568.

Kline, T., D. Holub, J. Therrien, T. Leung, and D. Ryckman. 2001. Synthesis and characterization of the colistin peptide polymyxin E1 and related antimicrobial peptides. J. Pept. Res. 57:175-187.

Lin, S. C., M. A. Minton, M. M. Sharma, and G. Georgiou. 1994. Structural and immunological characterization of a biosurfactant produced by *Bacillus licheniformis* JF-2. Appl. Environ. Microbiol. 60:31-38.

Linden, P.K. et al., Clin Infect. Dis., vol. 37, pp. 154-160, 2003.

Loo, V. G., L. Poirier, M. A. Miller, M. Oughton, M. D. Libman, S. Michaud, A. M. Bourgault, T. Nguyen, C. Frenette, M. Kelly, A. Vibien, P. Brassard, S. Fenn, K. Dewar, T. J. Hudson, R. Horn, P. Rene, Y. Monczak, and A. Dascal. 2005. A predominantly clonal multi-institutional outbreak of *Clostridium difficile*-associated diarrhea with high morbidity and mortality. N. Engl. J. Med. 353:2442-2449.

Martin et al., Biochemistry, vol. 43, pp. 3049-3056, 2004.

Martin, N. I., H. Hu, M. M. Moake, J. J. Churey, R. Whittal, R. W. Worobo, and J. C. Vederas. 2003. Isolation, structural characterization, and properties of mattacin (polymyxin M), a cyclic peptide antibiotic produced by *Paenibacillus kobensis* M. J. Biol. Chem. 278:13124-13132.

McSpadden Gardener, B. B. 2004. Ecology of *Bacillus* and *Paenibacillus* spp. In Agricultural Systems. Phytopathology 94:1252-1258.

Misumi, S., M. Tsuruta, K. Furuishi, and S. Shoji. 1995. Determination of N-myristoyl peptide sequence both by Maldi Tof Mass and with an N-myristoyl cleaving enzyme (polymyxin acylase). Biochem. Biophys. Res. Commun. 217:632-639.

Moran, G. J., A. Krishnadasan, R. J. Gorwitz, G. E. Fosheim, L. K. McDougal, R. B. Carey, and D. A. Talan. 2006. Methicillin-resistant *S. aureus* infections among patients in the emergency department. N. Engl. J. Med. 355:666-674.

Mori, S.A.C., et al., J. Magn Reson., vol. B108, pp. 94-98, 1995.

Ongena, M., and P. Jacques. 2008. *Bacillus* lipopeptides: versatile weapons for plant disease biocontrol. Trends Microbiol. 16:115-125.

Piuru et al., "A Novel Antimicrobial Activity of a *Paenibacillus polymyxa* strain Isolated from Regional Fermented Sausages", Letters in Applied Microbiology, vol., 27, p. 9-13—entire article, esp. introduction, Results, Table 1, 1998.

Rance, M. et al., Biochem. Biophys. Res. Commun., vol. 117(2), pp. 479-485, 1983.

Rodrigues, L., I. M. Banat, J. Teixeira, and R. Oliveira. 2006. Biosurfactants: potential applications in medicine. J. Antimicrob. Chemother. 57:609-618.

Rodriguez-Palacios, A., and J. T. Lejeune. 2011. Moist-heat resistance, spore aging, and superdormancy in *Clostridium difficile*. Appl. Environ. Microbiol. 77:3085-3091.

Sambrook, J., E. F. Fritsch, and T. Maniatis. 1989. Molecular cloning: a laboratory manual, 2nd ed., Cold Spring Harbor Laboratory Press, Cold Spring Harbor, N.Y.

Shaka, A.J. et al., J. Magn Reson., vol. 77(2), pp. 274-293, 1988.

Sklenar, V., M. Piotto, R. Leppik, and V. Saudek. 1993. Gradient-tailored water suppression for 1H-15N HSQC experiments optimized to retain full sensitivity. J. Magn. Reson. 102:241-245.

Stackebrandt, E., and B.M. Goebel, Int J. Syst. Bacteriol., vol. 44, pp. 846-849, 1994.

Tankovic, J. et al., J. Clin. Microbiol., vol. 32, pp. 2677-2681, 1994.

Troy, D. B. 2006. Remington: The Science and Practice of Pharmacy, 21st ed., Lippincott Williams & Wilkins, A Wolters Kluwer Company, Philadelphia, Pa.

Van de Kamp, M. et al., Eur J. Biochem., vol. 227, pp. 757-771, 1995.

Van de Kamp, M. et al., Eur J. Biochem., vol. 230, pp. 587-600, 1995.

(56) References Cited

OTHER PUBLICATIONS

Van de Ven, F.J., and Jung, G., Antoine Van Leeuwenhoeek, vol. 69(2), pp. 99-107, 1996.
Von Der Weid et al., "Diversity of *Paencibacillus polymyxa* strains isolated from the rhizosphere of maize planted in Cerrado soil," Res. Microbiol., 2003, vol. 151, pp. 369-381.
Wang et al., "Medium optimazation for antifungal active substances production from a newly isolated *Paenibacillus* sp. using response surface methodology" Bioresourse Technology, Apr. 29, 2008, vol. 99, No. 17, pp. 8245-8251, ISSN 0960-8524.
Weisburg, W. G., S. M. Barns, D. A. Pelletier, and D. J. Lane. 1991. 16S ribosomal DNA amplification for phylogenetic study. J. Bacteriol. 173:697-703.
Wescombe, P.A. and J.R. Tagg, Appl. Environ. Microbiol., vol. 69, pp. 2737-2747, 2003.
Whitford, M.F. et al., Appl. Environ. Microbiol., vol. 67, pp. 569-574, 2001.
Wishart, D.S. et al., J. Biomol. NMR, vol. 5(1), pp. 67-81, 1995.
Wishart, D.S. et al., J. Biomol. NMR, vol. 6(2), pp. 135-140, 1995.
Wu, X. C., C. D. Qian, H. H. Fang, Y. P. Wen, J. Y. Zhou, Z. J. Zhan, R. Ding, O. Li, and H. Gao. 2011. Paenimacrolidin, a novel macrolide antibiotic from *Paenibacillus* sp. F6-B70 active against methicillin-resistant *Staphylococcus aureus*. Microb. Biotechnol. 4:491-502.
Wüthrich, K. 1986. NMR of Proteins and Nucleic Acids. Wiley Interscience, New York.
Yakimov, M. M., K. N. Timmis, V. Wray, and H. L. Fredrickson. 1995. Characterization of a new lipopeptide surfactant produced by thermotolerant and halotolerant subsurface *Bacillus licheniformis* BAS50. Appl. Environ. Microbiol. 61:1706-1713.
International Search Report and Written Opinion for Application No. PCT/US2012/039964 dated Nov. 26, 2012 (11 pages).
International Search Report and Written Opinion for Application No. PCT/US2012/067958 dated Mar. 28, 2013 (16 pages).
United States Patent Office Action for U.S. Appl. No. 12/443,609 dated Jun. 15, 2012 (6 pages).
United States Patent Office Action for U.S. Appl. No. 12/489,820 dated Aug. 13, 2012 (9 pages).
United States Patent Office Action for U.S. Appl. No. 12/489,820 dated Mar. 26, 2012 (9 pages).
United States Patent Office Action for U.S. Appl. No. 12/489,820 dated Aug. 25, 2014 (11 pages).

\* cited by examiner

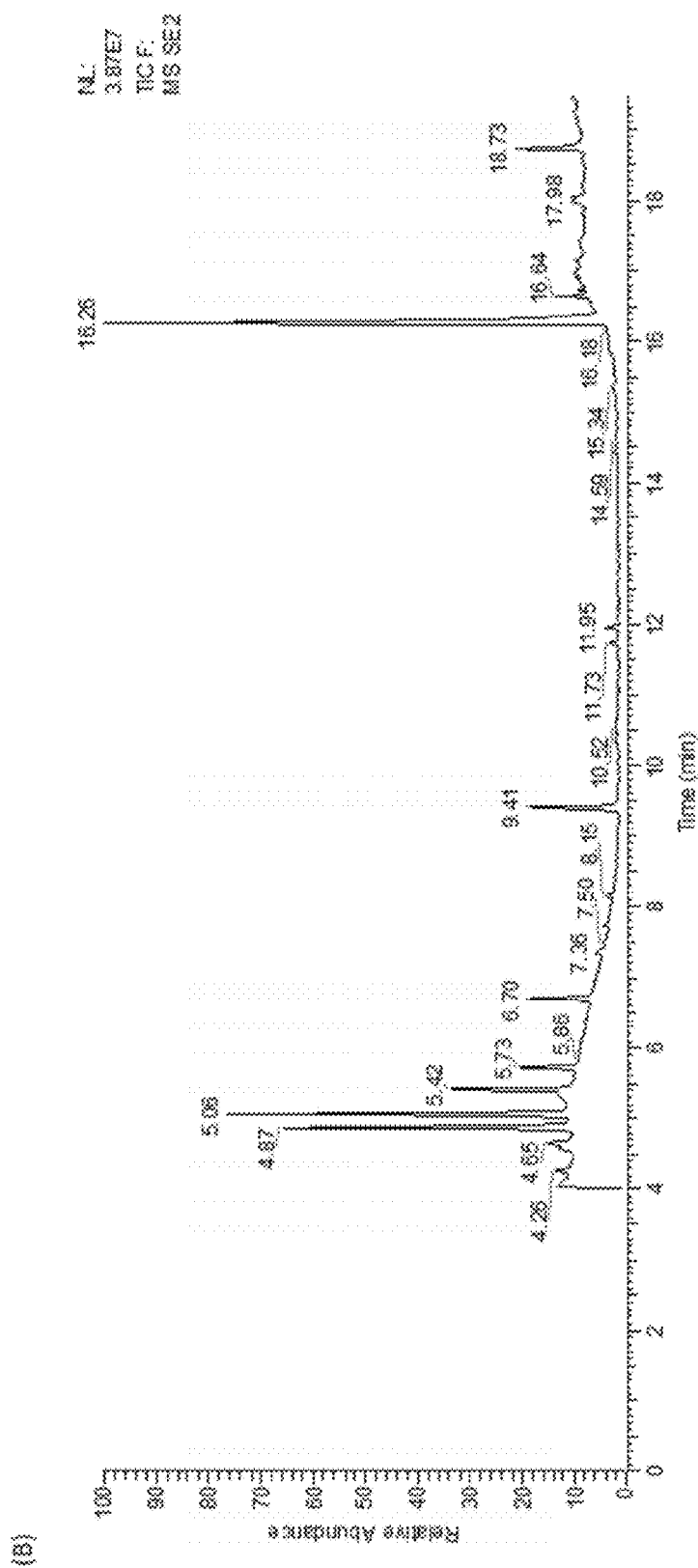
FIG. 9 (con't)

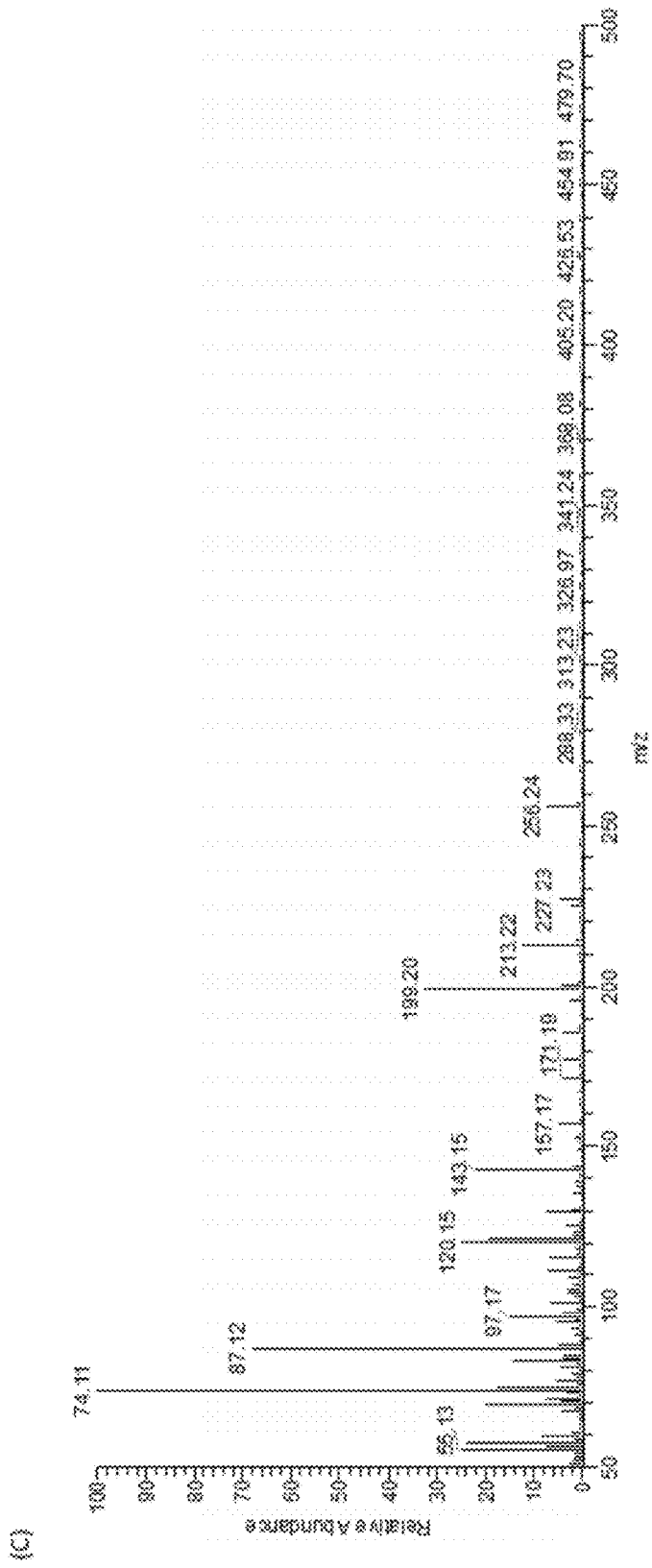
FIG. 9 (con't)

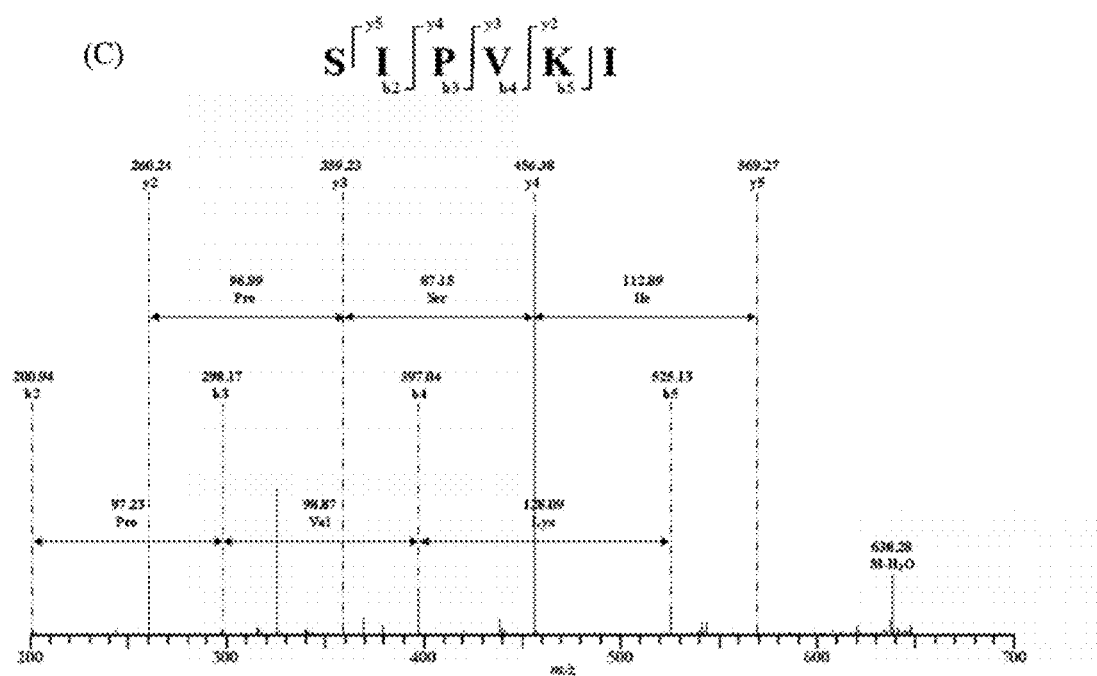
FIG. 10 (con't)

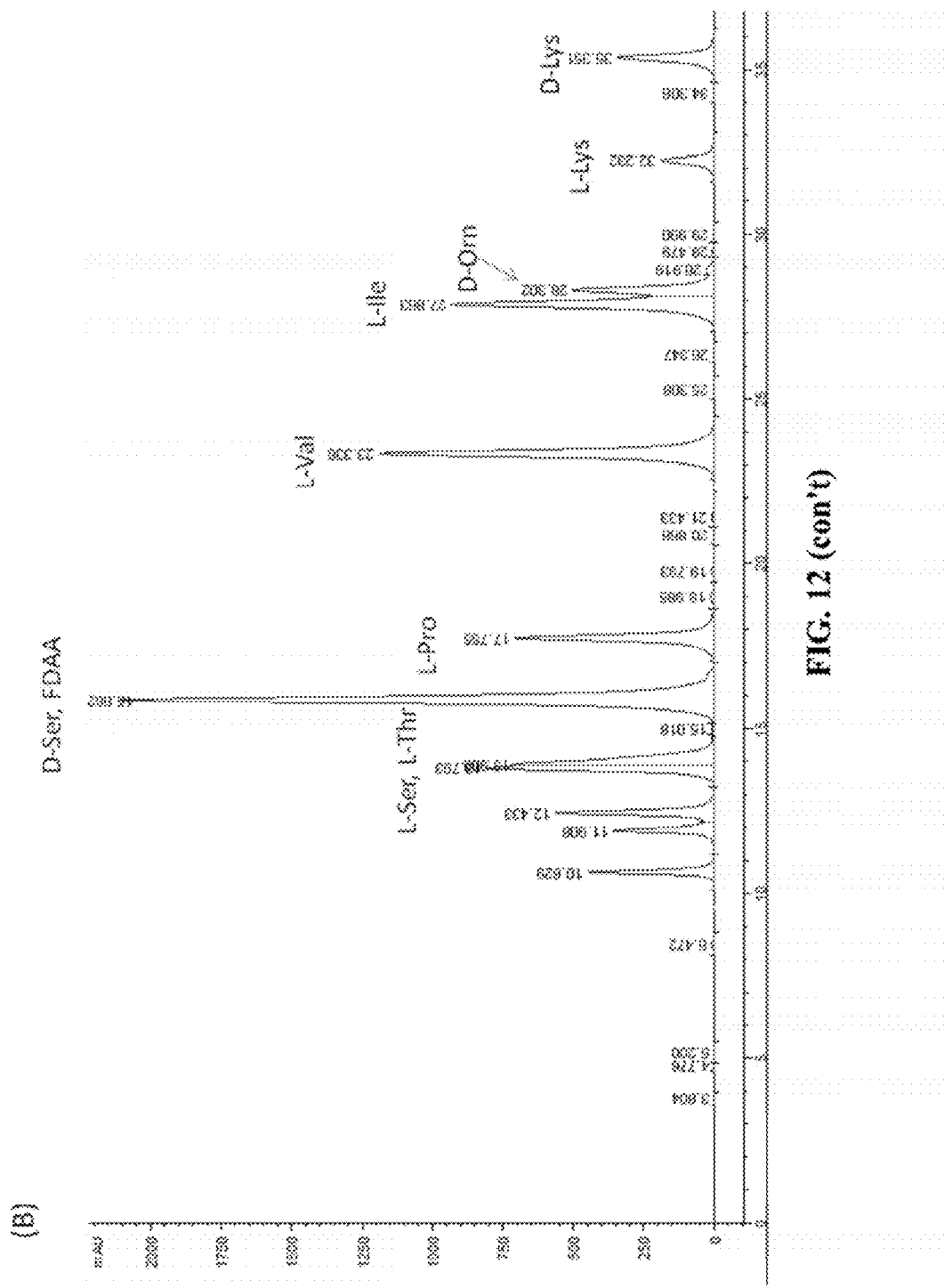
FIG. 12 (con't)

SEQUENCE LISTING

```
<160> NUMBER OF SEQ ID NOS: 70

<210> SEQ ID NO 1
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is the modified amino acid ornithine.  A
      fatty acid group is incorporated before position (1).
<220> FEATURE:
<221> NAME/KEY: Xaa
<222> LOCATION: (4)..(4)
<223> OTHER INFORMATION: Xaa is the modified amino acid ornithine.

<400> SEQUENCE: 1

Xaa Val Thr Xaa Ser Val Lys Ser Ile Pro Val Lys Ile
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is a charged amino acid.  A fatty acid
      group is incorporated before position (1).
<220> FEATURE:
<221> NAME/KEY: Xaa
<222> LOCATION: (2)..(2)
<223> OTHER INFORMATION: Xaa is a hydrophobic amino acid.
<220> FEATURE:
<221> NAME/KEY: Xaa
<222> LOCATION: (3)..(3)
<223> OTHER INFORMATION: Xaa is an amino acid that can form a hydrogen
      bond, a disulfide bond, a thioether bond, or an ester bond.
<220> FEATURE:
<221> NAME/KEY: Xaa
```

```
<222> LOCATION: (4)..(4)
<223> OTHER INFORMATION: Xaa is a charged amino acid.
<220> FEATURE:
<221> NAME/KEY: Xaa
<222> LOCATION: (5)..(5)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (6)..(6)
<223> OTHER INFORMATION: Xaa is a hydrophobic amino acid.
<220> FEATURE:
<221> NAME/KEY: Xaa
<222> LOCATION: (7)..(7)
<223> OTHER INFORMATION: Xaa is a charged amino acid.
<220> FEATURE:
<221> NAME/KEY: Xaa
<222> LOCATION: (8)..(8)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (9)..(11)
<223> OTHER INFORMATION: Xaa is a hydrophobic amino acid.
<220> FEATURE:
<221> NAME/KEY: Xaa
<222> LOCATION: (12)..(12)
<223> OTHER INFORMATION: Xaa is a charged amino acid.
<220> FEATURE:
<221> NAME/KEY: Xaa
<222> LOCATION: (13)..(13)
<223> OTHER INFORMATION: Xaa is a hydrophobic amino acid.

<400> SEQUENCE: 2

Xaa Xaa Xaa Xaa Xaa Xaa Xaa Xaa Xaa Xaa Xaa Xaa Xaa
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is a charged amino acid.  A fatty acid
      group is incorporated before position (1).
<220> FEATURE:
<221> NAME/KEY: Xaa
<222> LOCATION: (2)..(2)
<223> OTHER INFORMATION: Xaa is a hydrophobic amino acid.
<220> FEATURE:
<221> NAME/KEY: Xaa
<222> LOCATION: (4)..(4)
<223> OTHER INFORMATION: Xaa is a charged amino acid.
<220> FEATURE:
<221> NAME/KEY: Xaa
<222> LOCATION: (5)..(5)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (7)..(7)
<223> OTHER INFORMATION: Xaa is a charged amino acid.
<220> FEATURE:
<221> NAME/KEY: Xaa
<222> LOCATION: (8)..(8)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (10)..(10)
<223> OTHER INFORMATION: Xaa is a hydrophobic amino acid.
<220> FEATURE:
<221> NAME/KEY: Xaa
<222> LOCATION: (12)..(12)
```

<223> OTHER INFORMATION: Xaa is a charged amino acid.

<400> SEQUENCE: 3

Xaa Xaa Thr Xaa Xaa Val Xaa Xaa Ile Xaa Val Xaa Ile
1               5                   10

<210> SEQ ID NO 4
<211> LENGTH: 19818
<212> TYPE: DNA
<213> ORGANISM: Paenibacillus thiaminolyticus OSY-SE

<400> SEQUENCE: 4

| | | | | | |
|---|---|---|---|---|---|
| atggaaatga | tgcatccgaa | taccaccgtc | tctaccgttg | caggaacttt | agtcattcga | 60 |
| ggcgaggtag | acgcggctgt | gctgaaggag | tctatctgcc | aagtaattac | gcagcacgat | 120 |
| gctttccgca | tcagaatcat | gactcaagac | aatcaaccca | ttcagcggct | cgagcccgaa | 180 |
| tcggctatca | ctccagaagt | agactatatg | gaatgggatg | accatttgga | agctaaagac | 240 |
| tggttgaatc | gtttcaatcg | aattccaatc | agtattttg | atgataaatt | atataatttc | 300 |
| acagtattta | acgttaacaa | tcaagagtat | tggattcact | aaaaattaa | ccatattata | 360 |
| gctgatggcg | taacttcgca | tcttataggc | aataaaatca | tgcaaaccta | tatggagctt | 420 |
| acaagcggaa | cgttctcggc | taatgacaag | aagaactctt | atctcgatta | cacttatgcg | 480 |
| gagcaggaat | atgaaaagtc | cgatcgctat | cagaaagata | aggcatactg | gctgaaaaag | 540 |
| ttccaaacca | tgcccgagac | gacaggaatt | aaaccgtatc | ctccatactc | cataagcacc | 600 |
| gaggcgaaaa | gagcgtacgt | tgccctcacc | ggcgagcgtt | acgaacagct | gaaggtcttc | 660 |
| agcgagcaaa | acaacattag | cctgttcaca | ctattttgg | caacggtata | catgttttta | 720 |
| tataaaacaa | ctggaaattt | ggatattgct | gtggggacag | catacgcgaa | ccggacgtca | 780 |
| aggaaagaaa | aagaaatgtt | gggcatgttt | gtaagcacag | tcgcgactcg | attgtcgctt | 840 |
| gatcccaacc | aagatctgat | ttccatccta | cataatgtct | ccaaagagca | aaagacgaat | 900 |
| ttgcgtcatc | agaaatatcc | gtacaaccag | cttattctgg | atttgagaaa | ggagcataag | 960 |
| cacagcgata | tccaagatct | ctatggcgtg | tctgtggact | atatgcctat | taattggtcc | 1020 |
| agctatggac | agctcagcat | tcagcagcgg | agcagttttt | gcggtcacga | agtggatgac | 1080 |
| ttggcggttc | atgtcgaaga | tatgctggac | gatcaacagc | ttgtcatcaa | tgtggattat | 1140 |
| cggattcaat | tgttcgaaga | gcgtgaaatc | actcgaatta | tcgagcagat | gcttaccata | 1200 |
| gtcgatggaa | ttctgcataa | tccgcagcag | acgctgcacg | agctgaccat | gttgaacaac | 1260 |
| gaagaagcgc | gtaaaatatt | gacccaattc | aacgacacgg | ccgcagagtt | ccctagggac | 1320 |
| aagaccgtgc | accaattatt | cgaggagcaa | gcggcgcgca | cgcccaatca | tgttgcggcc | 1380 |
| gtgtatgagg | atgagcagtt | gacataccgg | gaattgaacg | aacgggccaa | tcggctagcg | 1440 |
| cggacattgc | gagccgaggg | cgtgcagccg | gagcaattag | tgggcattat | ggcagaccgc | 1500 |
| tcgctggaga | tgattgtggg | cattctggct | atcttgaaag | ctggcggggc | ttatgtgcca | 1560 |
| atcgatccgg | aatacccgga | ggagcgcatc | cgctatatgc | tggatgattc | gaacgcgcgg | 1620 |
| gtgctgttgg | cccagcgtca | tctgcaggca | cgaattgcgt | tcaccggcac | atgggtgatt | 1680 |
| cttgatgaga | atgcgttcta | cgacgaagac | ggcaccaacc | ttgaatcgaa | caatgacccg | 1740 |
| tctaatttga | gctatgtcat | ctacacatca | gggacgacag | gcaagccgaa | ggggtcatg | 1800 |
| atcgagcata | gacagctggt | ggccatggca | cacgcctgga | atcccggta | tcacttgcat | 1860 |
| gaggcgggca | ttcgctggtt | gcagtgggcg | agcttctcgt | tcgacgtatt | ctcgggagac | 1920 |

```
atggtccgca cgctcttgaa tggcggagag cttattctgt gtcccggtca cgcgcgggcg     1980
aacccggaag ctatctgcga attgattcgc aagcatcgca tccagatgtt cgagtcgacg     2040
ccggccctcg ttgtcccgct gatggaatat atatacgaca caaaatggca cattcacagt     2100
ctgcaattgt taatcatcgg ctcggattac tgtccggctg aagaattcca gaagctgatg     2160
gaacgattcg gctcacaaat gcgaattctg aatagctatg gcgtaaccga agcgtgcgtc     2220
gatgccagtt atttcgaaca gacgattcc gatgcgcttc gaacgctgcc gataggcaaa      2280
ccattaccag ccgtatccat gatggttctg gacgataacc gctcgttgca gccgatcggg     2340
ataacgggcg aactatatat cggcggggct tgtgtgggaa gaggatattt gaatcggcca     2400
gatctgacgg ccgagaagtt cgtcgacaat ccatatgcgc aagcgagat gatgtaccgg      2460
acgggcgact ggcgcgttg gttgccggac ggcaatatcg aatatttggg gcggatcgat      2520
catcaggtga agattcgggg ataccgcatc gagataggcg aaattgaatc tcaattgctc     2580
aaagcggagt ccgttcgaga gtcagtcgtc gtcgcacggg aggacggaag cggacagaag     2640
gtgctgtgtg catactacgt ggcagaccgc gagctcacag tgaatgagct gaggggaaag     2700
atggcggaag aactgccggg atacatgatt ccatcgtatt tcatgcagct ggaacagatg     2760
ccattgacgc cgaacggcaa ggtcgaccgc aaggggctgc cggctccgga aggaagcgcg     2820
cataccggaa cggaatatgt ggagccgagt tctgcagcgg agaagatgct ggctgccgtg     2880
tggcaagctg tattgggtat agaacgggtc ggcgcgagcg agcatttctt cgagcttggc     2940
ggcgattcca tcaagtcgat tcaagtgtct tcccgattgc gtcaggccgg ctacaaaatg     3000
gagatccggg atttattcaa ataccccgacc attgcggagc tgagtctgca catccagcca    3060
gccggaagaa tggccgatca gagcgaagtg gttgggaaag cggagctgac accgatccag    3120
cgttggtttt tcgcacaacg gttcgccgat ccgcatcact ataaccaatc gatcatgctg    3180
taccgcaagg aaggcttcga cgaagcagcg attcgcaaga cgctggagaa gatcgccgag    3240
catcacgatg cgttgcggat ggtattccgc aagaccgaat ccggatacgc cgcttggaac    3300
cgaggaatcg gagaaggcga gctatacagg ctgaatgtgg cggacttccg taatgaatcg    3360
gcttgcgggc cgttgattgc agcgcaagcg aacgagattc aaggcgggat cgacatcgag    3420
acagggccat tggtgcgggc aggattgttc caatgcgcgg atggggatca tttactgctc    3480
gtcattcacc atactgtcat tgatggcgtc tcttggcgca ttttactgga agatatcgcg    3540
gttggttacg agcaagcgtt gaagggagaa gaggttcgtc ttccgagcaa aaccgatgct    3600
tatcgcactt ggtccgagcg actggcctct tatgctgaca gtcagactgt aattaatgaa    3660
cgtgcctatt ggcagcgtat cacacagacg gaaatgaatc ctttgcctaa ggattatgaa    3720
gcggattgct ccttgcagaa ggatagcgaa tccgtcatcg tccagtggag cccagaggac    3780
acagagcagc tattgaaaca cgtgcacaag gcatataaca cggaaatgaa cgacattttg    3840
ttgacagctc tagggacggc tgtgcagaga tggagcggcc gcgaccgggt gctggtgaat    3900
ctggaaggac acgccgcga ggccatcatc gcagacatcg acatctcacg cactgtaggt     3960
tggtttacaa gcgagtatcc ggtgctgctc gaaatggagc aggccaaggg cttgtcctac    4020
cggattaaaa aggtgaagga ggacttgcgc caaatcccga caagggtat tgggtatggc     4080
atatgccgtt atatgtccga cctcccgtat gaagcctctt ggggcgcgaa tccagaaatc    4140
agctttaact acctgggca gttcgatcag gatttgcaaa gcaacgggat gctcatgtct     4200
cccttgtcga gcggctcgaa cacaagcggc aaccaagcgc gccaatacgc gctggacatc    4260
aacggaatga ttatggatgg ctcgttagtc ttcgatctaa gctatggcag caaggaatat    4320
```

```
cgaagggaga cgattgagga tcttgccggg atgctgcaag agatcctgcg ggaaatcatt     4380
gcgcactgca ctgcgaagga gcggccgaaa ttgaccccga gcgatgtctt gctgcaggga     4440
ctgagtgtgg aggaactgga gcagatcgtg aacagacac agcacatcgg ggacattgaa      4500
aatatgtaca agttgacacc gatgcagaaa ggtatgtggt tccacagcgc catggatcgg     4560
caggcgggcg cgtattttga acaaacgcgg tttaccttgc aaggggatct cgacgtggat     4620
gccttcgcca agagctggac cgcattggca gcgcggcata ctgtgttgcg gacgaatttc     4680
cacaacggtt ggaagggcga accgctgcaa atcgtatacc gtgacaagcg gattgggttc     4740
gcttatgaag atgtgagcgc tctgaagccg gctaagcaaa gagcgcatat cgagaacgct     4800
gtgaatgaag acaagctgcg cgggtttgac ttagagcaag atgaacttat gcgggtgtta     4860
gtgatgcgta cggcacaaga gagctatcac gtgctctgga gctcgcatca tatcctgatg     4920
gacggctggt gcttgccgct ggttgccaaa gaagtgttcg atacgtactc tgcctatgtg     4980
cggcatcggc atctcgaaaa gacaacggta cctgcgtaca gtcaatatat tgaatggttg     5040
gaacagcaag atgaagaggc ggcatccgca tattggtccg agtatttggc tggatacgac     5100
cagcatacgg cgctgccgca agggaaagat caaggacgaa gcgaagcata cgctgcggag     5160
cacatcgatt gcgaactggg caaagacttg agcgtgcggc tcaacgaggc ggcgaaacgg     5220
aatttggtga ccctgagtac gttactgcaa caacatggg gcatcatgtt gcagaagtat      5280
aacggaaccg gcgacgtggt attcggcggc gtcgtatcgg ggagaccggc ggacatgccg     5340
gggattgaag agatgatcgg cctgttcatc aacacgattc ctgttcgcgt taccgccgat     5400
gcggggagaa gcttcgccga catcatgtgc aggctgcagg aacaggcgct ggcatccgcc     5460
aagcacgatc actatccgct gtatgagatt caggcacaga gcgcgcagaa gcaagaactg     5520
atcaatcata tcatggtatt cgagaactac ccgatggaag agcaaatcga gcaattggaa     5580
agcctcgacg gcaaagggct gaaattgaag gatgtcatgg taacggaaca aacgaactat     5640
gacttcaacc tggtcatcat gcccggggac gaaattgtga ttcgtctgga ttataacgga     5700
atcgtgtttg acagaacgag tatggagcag ttgaagggtc atttagtgaa catgctggag     5760
caaatcgcgg ccaacccgca aataccggtg ggagaactgg aactggcgac agcagcggag     5820
aaagcgcaga ttgtggatgt gttcaacaac acagttgtcg agtacccgcg ggagaagacg     5880
attcatcaat tgtttgaaga acgggaagaa cgaattccgg acgcggtggc ggtgatattt     5940
gaggacaaac ggttgaccta tgcggagctg aatgccgctg ccaatcgaat tgctcatctc     6000
ttgcgggatc gaggcgtagc acgaggcaca ctggtcggca tttgcgcgga gagatccttg     6060
gagatggtgg tcggactgct gggaatcctc aaagccggcg gggcatacgt tccgatcgat     6120
ccttcctatc ctcaagaacg gattaatgcc atgctggaag atacagcaat cagcgtgatg     6180
ctcacgcagg cgcatctgca gacaagcgtg ccgaacagca ttgattccgt cttgcttgat     6240
gcagcagcag agacgattct ggaaggaagc tggccgaact tgacagatac ggcggcgacc     6300
gcggacgatg tggcctacat catctatacg tccggatcga cgggaattcc gaaaggagtc     6360
tgcgtcacgc atcgagggg ggtccggctc gttgccgatg ccaattatgt ggacatcagc      6420
agcaaagacg tattttgca aggctcgacg atatcgttcg atgcggcaac gttcgagatc      6480
tggggcagct tgctgaatgg agctgcgttg gctgtgttgc ctccgggcaa tgtatcgttg     6540
accgaatgga cacgggccat tcaacagcat caagtgacga tcctatggtt aacggcagga     6600
ctgttccacg tcatggtcga caatcagctc caagccttgc agggagtcca acaattgttg     6660
```

```
gtgggcggcg atgtcgtctc caagacgcat gccacaaagg ttctggagcg gtataacgga    6720
attcggctaa tcaatggata tggtccgacg gaaaatacga ccttcacttg ctgccacgag    6780
atttccgcag ccgatatgga gcggccgtcc attccaatcg ggcgtccaat cggcaatact    6840
caagcatatg tgctggatgg agcgggcaag ctgcttccgg caggcgtgat cggcgagttg    6900
tatacaggcg gagacggact ggcccaaggt tacttgaacc gtccggagct gacggcagag    6960
aagttcgtag acagccctat cgtgccggca cacggctat accgcacagg cgacttggcg     7020
agatggctgc cggatggaac aatcgaatac gtgggacgaa tcgatgatca agtgaaaatt    7080
cgcggttacc ggattgagct tggcgaggtg gaagcgcatc tgctgaaagt ggagccggtt    7140
cagagtgctg ccgtgatcgc acggaaggac gaaagcggcc agaatatgtt gtgcgcgtat    7200
tatgcagcgg ataaagagct tacgcaagc gagctgagat cggctttgtc gcaagaactg     7260
ccgggataca tgatcccgac acactttgtg caggtggagc ggatgccgct gacgccgaac    7320
ggaaaggtcg atcgcaaagc gctgccggag ccggaaggcc gcatcatgac aggaatagag    7380
catgtcgcgc gcggacacc gctggaatcc aagctgcgc atatctggca agaagtgctc       7440
ggacttgaga aggtcagcgt gaaggacagt ttcttcgagc ttggcggaca ctctttacgt    7500
gcaacgacgc tggtaagcaa gcttcaacag gagctgcatg tgagcatgcc gctgcgtgag    7560
gtgttccgct cccgactat tgaagagcag gcgcaagtga ttggcgggat ggagcaagag      7620
gaatacagag cgatccctca ggtcggcgaa agagaatgct atccagtgtc ttcggcccag    7680
aagcggctat atattttgca tcaattggag ggcgccgagc agacctataa catgccgggc    7740
gtgatgacac tcgcaggacc gcttgatcgg gagcggctcg aaacagcgtt ccgtaagctg    7800
atttcgcgtc atgagacgct gcgcaccggc ttcgagatgg tggatggcgt acctgtgcag    7860
cgggtatacg aagaagtgga ttttgcggtg gagtatgcgc aggcaagtga agaagcagcc    7920
ggtgaagccg ttcatgcttt catccgcgcg tttgatttgc agaagcctcc gctcttgcga    7980
atcggtctga tcgagcttgc gaaggagcgc catctcctga tgttcgacat gcaccacatc    8040
atatccgacg gggcctcgat cgggattctg atcgaagagt tcgtccggtt gtaccgtgga    8100
gaagagatct cgcctttacg tattcaatat aaggattatg ccgcctggct gcagtctgaa    8160
gcgcagcagg attggtcgaa acagcaggaa gcctattggc tggatgcgct gcgcggggaa    8220
ctgccggtct tggaattgcc gacggactat gcgcggcctc tgttccgaag ctatgaaggc    8280
agtacgttcg agttcacgat tcagcggcgc gaggcggagc gcctgcggca gctagctgct    8340
gagtccggag ctacattata tatggtgctg ttggcacttt atacgaccat gctgcataaa    8400
tacacggggc aagaagacat catcgtgggg atgccgatcg caggcagaac gcatggagat    8460
ctgcagccgc tcatcggaat gtttgtcaac acactggcca ttcgcagcta tcctgccggg    8520
gagaagacat tcttgtcctt tttggaggaa gtcaaagaca caacgatgcg ggcctatgag    8580
catcaggatt atccatttga agaactggtg gaaaatgtgc gggtgccgcg ggacgcaagc    8640
cgcaatccgt tgttcgatac ggtcttcgtc ctgcagaata cggagcaggg aacgttcgat    8700
atcgatgggc tgcagctgtt gccgcatccg gcagaacatc ctgtcgcgaa gttcgacctg    8760
accttccaca tcgaagaaga agaggaaggg ctggcatgca gcatcgaata cgccaccgcc    8820
ttgttccagc gggaaacggt cgcacggatg gcacagcact tccgccagtt ggttgaagcc    8880
gtcactggcg agccggtgga ccggttagat cggttggaga tgttgacggc agaagagaag    8940
gttcagcttg tggatcggtt caatgatacg ggagcggact atccacggga gaagacgatt    9000
cacctgctgt tcgaagaaca agcggaacgt accccggctg cagtggccgt aattttcgag    9060
```

```
aatgctcagt taacttatcg ggagctgaac gaacgtgcca atcgcttggc gcatacgctc   9120
cgggcaaaag acgtgcagac ggatagcttg gtgggcatta tggccgagcg ttcaccagaa   9180
atgatagtcg gtattctggc gattttaaaa gccggcggag cttatgtgcc aattgatccg   9240
gaatatccgg aagagcggat tcgctacatg ctggacgatt ctggagcgca ggtgctgctg   9300
cttccgcatg atctgcggga caaagttggc tttgatggga cagtcgtgat gcttgatgac   9360
gagcaatcct atgttgaaga cagctctaat ccagcaacgg ccagcaagcc gtccgatttg   9420
gcttatgtca tctataccct ctggtacaacg ggcaagccga agggacatt gattgaacat    9480 aaaaatgtcg tgcgcttatt gttcaacagc aaaaatctgt tcgacttcaa ttcggcggat   9540
acgtggacat tgttccactc cttctgcttt gatttctcgg tctgggagat gtatggggcg   9600
ctgttatacg gaggcagatt ggtggtcgtg ccgcaattga ccgccaaaaa tccggcacag   9660
ttcctggaac tgcttcacga gcagcaagtg accatattga accagacacc gacttatttt   9720
tatcagctgc tgcgggaagc gctggcagag cccggacaag aactgaaagt aagaaaagtc   9780
attttcggag gagaagcatt aaatccgcag ctgctgaaag attggaaaac gaaatatccg   9840
catacccagt taatcaatat gtatggaata acggaaacga cggtccatgt cacttataaa   9900
gaaattactc aagtggaaat cgagcaagcg aaaagcaata tcgggcgccc gatcccgacc   9960
ttgaaggtat atgtgctgga tgcgaatcgc caatgcgtgc ctgtgggtgt agctggagag  10020
atgtatgtag cgggcgatgg cttggcgcgc ggttatctgc accgtccaga actgacggct  10080
gacaagttcg tggatagtcc tttcgagtca ggcggacgta tgtacagaac gggcgatttg  10140
gcccgctggc tgccagatgg caatatcgaa tatttgggac ggatcgatca tcaggtaaag  10200
attcgcggct accggatcga actcggcgaa gtggaagcgc aattgacgaa ggtggatcct  10260
gttcgggagg ccatcgtcat cgcacgggaa gacggacacg gggagaagca gttatgcgcg  10320
tacttcgtgg ccgcccgtga gcttacggtg ggcgaattga ggcaagaact gtcgcatgcg  10380
ttgccagcct atatgattcc cgcatatttc gtgcaattgg agcggatgcc gctgacgcct  10440
aatgggaaaa tcgaccgcaa agcgctgccg gctccggaag acagcgtaaa taccggcacg  10500
gaatatatag cgccgcggac cctattggag tccgacttga cgcgtatctg gcaagatgtg  10560
cttggactgg aaagcatcgg cgtcaaagac aatttctttg agcttggcgg ccattccttg  10620
cgtgcgacca cgttggtgaa caaggtgcac caagagatga atgtcaatct tccgttgcgg  10680
gacgtcttcc gcttctcgac gatagaggag atggcttgcg cgattgcaga gatggaacaa  10740
cgcacatata tgtccatacc agcgattgaa acaagagact attacccggt atcctctgcg  10800
cagaagaggc tgtatattct ccaccagatt gagggggccg agcaaggcta caatatgccg  10860
ggcgtactgc tccttgaagg tatgctcgat caggagaaat cgaagaagc gttccacgga  10920 atcgtagcgc gtcatgaaac attgcgcacc ggctttgaaa tggttaatgg cgaaccggtg  10980
cagcgagtat atgagaaagt ggattttgca gtggaatatc ggcaggcgga cgaggaagaa  11040
gtcgaggcgg tcgtacgaga tttcgtccgc acgttcgatt tagagaagcc gccgttgctg  11100
cgaataggtt tactcgaatt ggcgaaggag cgtcatgtgc tcttgtatga tatgcaccac  11160
atcatttccg acggcgtttc gatggggatc gtggtggaag agttcgtccg tttgtacgcc  11220
ggagcagcgt tggagccgct gcgtatccag tacaaggatt atgccgcatg gcagctgtcc  11280
gaagcgcagc aggattggat gaagcggcag gaaggatatt ggcgggacgt gttccgcgga  11340
gaacttccgg tattggaaat gccgacggat tatgtgcgtc ctgccgtgca acagtatgct  11400
```

```
ggcagcacgc tttcattcga catcgatcca caaatgagcg aaggattgcg ccggattgcg    11460
gccgaaaccg ggacaacgct gtacatggtg ctgctcgcag cctataccat cctgcttcat    11520
aagtatacgg gccaagagga tgtcatcgtg ggcacgccaa ttgcgggaag aacccatggg    11580
gatctgcagc cgctcatcgg gatgttcgtc aacacgcttg ctattcgcaa ttatccggca    11640
ggggagaaaa cattccgctc ctatctggcg gaagtcaagg aaacgacctt gggggcctat    11700
gaacaccaga actatccgtt tgaagaattg gtggacaagt gcaggtcgc gagagattta    11760 agccgtaatc cgctgttcga cactatgttc gctttgaata atacggagcc cgagactttc    11820
cctctcgaag gactgcggct gacgccgtat cctagcgaat acacgatatc caaatttgat    11880
ttgagtttgg atgtgtcgga aaaaaatgac aggctggaat gcagtctgga atatgcgact    11940
gccttgtata aaccagacac ggcagaacgt atggcgcagc acttccaaca attaatcgat    12000
tccattgtcg accagccgga ggcgaagctg gtttcgctcg gcatgcttac ggaggaagag    12060
aaggctcaga ttcaacatgt gtttaacaga gcggaggcag ggcactcgca ggagaaaacg    12120
gtgcctgaat tgttcgagga gcaggtggag cgcacgccgg atcggattgc ggtcgtacac    12180
gaggacaagc agctgacgta ccgggagctg aacgaacggg cgaatcgcct ggcgcgcacg    12240
ttgagggccg agggtgtgga gcctgagcaa ctggtcggca tcatggctga tcgctcgctg    12300
gacatgatcg tgggcattat ggccatcttg aaatccggcg gagcctatgt gccgattgac    12360
ccgaaatatc cggaggatcg cattcgctac atgctgacg attcgcacgc gcaggtgctg    12420
ctggcccagc gtcatatgca agcaagcgta gcgtttgccg ggacatgggt gattctggac    12480
gaagaagcgt tctaccatga agacggcacc aacttggagc cgctcaatga gccgatgcat    12540
ttatcgtacg tcatctacac atcaggaacg acgggcaatc cgaaaggcgt catgatcgag    12600
cacagacaac tagtggccat agctgacgcc tggaaacgcg aatatcgcct ggaggaggaa    12660
ggtatccgct ggctgcagtg ggccagcttc tcgtttgacg tgttctcggg ggatatggtc    12720
cgcacgctgc tgtatggagg agagctcatt ctgtgtccgg agcaggcgcg ggcgaacccg    12780
gcggctatct ctgagttgat tcgcaagcat cagatacaga tgttcgaatc gacaccggcc    12840
ctcgtcatcc cgttcatgga ttatgtgtac gacaacaact tggacattag cagcctgaag    12900
atgttgatcg tgggttcgga ccactgcccg acggcagaat tcgataagct gaccgagcgc    12960
tgcggttcac acatgcgaat actgaatagc tatggcgtga ccgaagcttg cgtcgatgct    13020
tgctactatg aacggacaac gccggatgcg ttgcggacgt tgccgattgg caagccgttg    13080
ccggctgtaa cgatgtatat tctggatgat aaccgctcgc tgcagcctat cggtcacacg    13140
ggtgaattat atatcggcgg agccggcgtc ggccgcggct atctgaatcg accggacttg    13200
accgtcgaga aattcgtgga caatccgttc atgccgggcg cgcggatgta ccggacgggc    13260
gacttggccc gctggctgcc ggacggcaat atcgaatatg cgggccggat cgaccatcaa    13320
gtgaagattc gagggtatcg tatcgagatt ggcgaagtgg agtcccagct gctggcagcg    13380
gcaggcgtcc gcgaagcggc cgtcgtcgcg cgggaggatg gaagcggaca gaaggtgctg    13440
tgcgcgtact tcgttgcaga cagcgctcta acggtaggcg aactgagagc atcaatggcc    13500
caacaattgc caggctatat gattcctgcg cattttgtgc aattggagcg catgccgttg    13560
acaccgaacg gcaaagttga tcgcaaggga ctgccggctc cagaaggaaa cgcgtatacc    13620
ggagcagagc atgttgcgcc gcgaaccgag gcgagaagga cgctggcagc cgtgtggcag    13680
gttgtattgg gcgcagagca ggttggcttg atggatcact tcttcgaact gggcggcgat    13740
tccatcaaat cgattcaagt gtcttcccgg ctgcatcagg ccggttacaa gctggagata    13800
```

```
cgcgacttgt ttaaatatcc gactatcgcg gagctaagtc cgcatattca gccgattggc   13860
aggaaagccg accagggcgc agtgaccggc gaggcggcgc tgacgccgat tcaacactgg   13920
ttcttcgggc agcggttcgc cgacccgcat cactataacc aatcgatcat gctataccgg   13980
aaggaaggct tcgacgaagc ggcgattcgc aagacgctgg agaagatcgc cgagcatcac   14040
gatgcgctgc ggatggtatt ccgcaagacg gagcacgggt atgcggcctg aacagaggg    14100 atcggagaag gcgagctcta cagtctcaac gtggcggact tcacggatga tccggcgtgc   14160
taccgggcga tcgaagccaa ggcgaacgag atacagagcg gtattaattt gcaagccggg   14220
ccactgctca gagcggggtt attcacttgc gcacacgggc atcatttgtt aatcgtcatt   14280
caccatgctg ttaccgacgg agtctcatgg cggatcttgc tggaggatat cgcggcaggt   14340
tacgagcagg cgctgaaggg agaagcgatt cgtctgcctg cgaagacgga ctcctatcta   14400
acctggtcca agcagctgag cggatacgcg cagagtccgg ccatagagca ggaacgatcg   14460
tattggcagc gtatcgcgca gtcgaacacg aagcctctgc caaaagatcg gacagtgaat   14520
gtttctttgc aacgggatag cgaatctgtc agcgtccaat ggagccggga ggatacggag   14580
cagctgttga agcacgtcca ccgggcatac aacaccgaca tgaacgacat tctgttgacg   14640
gcgctgggaa tggccataca gcaatggagc ggccgcgatc gcatgctggt gaatctggaa   14700
ggacacggcc gcgagtccat catggcggac gtcgatatct cgcgcactgt gggctggttt   14760
acgagcgagt atccagtgct gcttgagatg gagccggaca agagcttgtc ccattgcatc   14820
aaaaaggtga aggaggactt cgccaaaatt ccgcacaagg ggatcgggta tggcatctgc   14880
cgatatctgt ccggaacgat ggaagacgcg gcgtgggca cagcacccga aatcagcttc    14940
aactacttgg ggcagtttga tcaagatctg aacagcaacg ggatggagat gtctccgtat   15000
tcgagcggca cggatgcaag tggcaagcaa gtgcgccaat acgcgttgga catcaacgga   15060
ggcattacgg acggatcgtt gtcctttgac ctgagctaca gccggaagga ataccgcagg   15120
gagacgatgg aggatctggc cgggcggctg cgtgagagct tgcaggagat tatcgcgcac   15180
tgtgcagcga aagagcgcac ggaactgacg ccgagcgacg tgctgttgca ggggttgagt   15240
gtggaggaac tggagctgat agtggagcaa acgcggcacg ttggcgagat cgaaaatata   15300
tatgcgttga cgccgatgca aaagggtatg tggttccaca acgctatcga tcaacaggcg   15360
ggcgcttatt tcgagcaaac ccgattcacc atacaggag tactcgatgt ggatgtcttc    15420
gcgatgagtt tgaacgtatt ggctaagcgc catgcggtac tgcggacgaa cttctatagc   15480
ggctggaacg gcgaaccact ccaaattgtg taccgggaca gcggattgc attcgtttat    15540 gaagatctac gccatctgcc agcagccgag cagactgcac atatcgagca cgccgcaagg   15600
gaagacaagc tgaagggatt tgatttggag caggatgcgt tggtgcgggt agcgctgatg   15660
cgcacgggag cagcaagctg ccgcgtgctc tggagctccc accacattct gatggatggc   15720
tggtgcttgc cgcagcttac gcaagagctg ttcgacacat atagctccta catgaagcag   15780
catcatgatg aacaggcact gccagcgtac agtcagtcat catacagcca gtatatcgag   15840
tggttggagc agcaggacga ggaagcagca gctgggtatt ggagcgaata cttggcaggg   15900
tacgaccaac agacgttgct gccgcaaggg aagacgcaag ggagagacga agcttacgtg   15960
ctggagcatg tcgtgtgcga actgggcaag accttgacag gacggatgag ccagctggcc   16020
aagcagcatt cagtgacgct gaatacattg ctgcaggcgg cctggggcat catcctgcag   16080
aaatacaacg gcacagacga tgtggtgttc ggcggggtcg tttcgggcag accggcagca   16140
```

```
attccgggca ttgaaacgat gatcgggctg ttcatcaaca cgattccggt gcgcgtcgct   16200
tgcgcagcgg agacgagctt tactcaggtg atgagacggc tgcaggagca ggcattggac   16260
tctggccgat acgattatta tccgttgtat gagatacaag cacagtgtgc gcaaaagcag   16320
gagttaatat cccatattat ggtgttcgag aactatccgg tggatgagca gatggagcaa   16380
accggaagca aggacagcgg aacgctgagc atcacggacg tcgaagtggc agaacaaacg   16440
aactatgatt tcaacctaat ggtcgtgccg ggcgaagaac tcgtcgttcg tttcgacttc   16500
aacggaagcg tgttcgacag aacgagcatc gagcggttga cggggcatct ggtgcatgtg   16560
cttgagcaaa ttacggccaa cccgcaaata tcggtgggag acctggaact ggcgacagca   16620
gcggagaaag tggaaattgt agatgtgttc aacgatacgg cggcggatta tccgcgggag   16680
aagacgatcc atcaaatgtt cgaagaacaa gtcgaacgaa ctccagatgc ggtggcggtc   16740
atgttcgagc aggaacggct gacgtaccgg gaactgaacg agtgtgtgaa ccgcttggcc   16800
cggacgctgc gaacgcaagg cgtccaaccg gatcagcgtg tcggcatcat ggtcgagcgc   16860
tcgttggaga tgatggtcgg catcatggcg attttgaagg ctggcggggc atatgtgccg   16920
attgctccgg attatccaga ggagcgcatt cactacatgc tggaagattc gggagcgcag   16980
gtgctcttgc tgcaaggccg ttcggggagag agcgtgtcct ttgcaggccg catcgtcaat   17040
ctggacgatg agagctccta cgccgaagat ggatcgaatc tggaatgggt caaccaggca   17100
agcgatgctg cttatgtcat ctatacgtcg ggacgacgg gcaaaccgaa gggggttctg   17160
gtggagcacg gttctgtcat caaccgcttg ctgtggatgc agaagcaata tccaatcaac   17220
gccaacgata cgattatgca gaagacgcg atcacatttg acgtctccgt ctgggagttg   17280
ttctggtggg ccttcgtcgg ttctaaagtg tgcctgctcc cggtcggcgg ggagaagaac   17340
ccggccgtca ttctggatac gatcgcgcag cagcatatca gcacgatgca ttttgtgccg   17400
tccatgctgc atgccttcct cgaatatgtc gaggagcagc cgattgcaga acgggagcgc   17460
agcttagcgg cactctcgcg ggtgttcgca agcggcgagg cgctgaccct ctcgcaagtc   17520
gagagattcg agcgttgcat tgcgccggcg agtggagcgc gcctgatcaa tctgtacggg   17580
ccgacggaag cgaccgtaga cgtgacgtac tatgattgtg aggccgggca gccatatacg   17640
agcgtgccga ttgggaagcc gattgacaat acgcaaattt atatcgttaa tcgtcaagat   17700
caactgcagc cgattggcgt agccggagaa ttatgcatcg cgggtgtggg cttgcgcgca   17760
ggttacttga agcgtccgga gctgacggcc gagaaattcg tgacgattcc gttcatgccg   17820
ggcgcgcgga tgtaccggac aggcgactta gcccgctggc tgccggatgg cagcattgaa   17880
tatttgggcc ggatcgacca tcaggtgaag atccgggggt atcgtatcga gctcggcgag   17940
atcgaggccc agctgctgca agtggaattc attcggaag cggtcgttgt cgcgagggaa   18000
gatgagagcg ggcagaaggc attatgcgcc tacttcgccg cagatagcga attgccggta   18060
agcgagctga atcagcgtt ggctgtagaa ttgccgggct acatgattcc gtcgtacttc   18120
gtgcagctgg agcgactgcc gttgtcagcg aacgggaagc tcgaccgcaa ggcgcttccg   18180
gctccgggag gaagcatgcg cagcggcaag gaacatgttg caccgcgctc gctgctcgaa   18240
gtgaagctgt tgcgaatctg gcaagaagtg ctccggactgg cgcacgtcag cgtgaaggac   18300
gacttcttcg aactcggggg acattccttg cgcgccacca ccttggttag caagctgcat   18360
aaggagctga acatcaatct gccgttgaga gacgtgttcc gctattcgat tcttgaagac   18420
atggcgctcc ctatcggcag aacggaacaa cgagagttcc agaccattcc gcaggtcgaa   18480
gcaagcgatt attatccgtt gtcttctgcg cagaagcggc tgtacatcgt gcagcaggtg   18540
```

```
gaaggggcag aacaaagcta caatatgccg ggagcgatgt cgatcagagg gcaactggac   18600
cggaatcaat tcgaggcagc gttccgcgga ttaatcgcac gtcatgaagt gttccgcact   18660
agcttcgaga tggtgggcgg cgagccgatg cagcgtgtac atcaggatac ggcatttgcg   18720
gtggagtata tgcaggcaaa tgaagaagag gctgaagcaa tcgcgcacca attcgtccgc   18780
acctttgatt tggagcagcc ttccttgctg cgtgtcggtc tgatcgaatt agaccgggaa   18840
catcatatta tgttgtttga catgcatcac atcatctctg atggagtctc catgggcata   18900
ttggtggagg aatttgcccg cttgtacagc ggggaggagc tgccgccact gcgcatccaa   18960
tacaaggact atgccgcatg gcagcaatca gaggcgcaga gtgaacggat aaaacaacag   19020
gaagcgtatt ggcttgacgc attggatggc gagctcccgc agctggaatt gccaaccgat   19080
tttgcaagac cggctcatca gagccatgaa ggagacaccc ttgattttgt aatcgattcg   19140
cacatgagcg gggggctgca gcggctcgcc gagcataccg gcacgacgct gtacatggtg   19200
ttgttagcgg cctatacgat tttactgcat aaatactcgg atcaagaaga tatcatcgtg   19260
ggcactccga tcgcgggaag aacgcatgcg gatgtggagc cgctcatcgg gatgttcgtc   19320
aactcgcttg cattgcgcag ctatccgtgc ggggagaagt cattcctctc ctacctggag   19380
gaggttaagg aaatgacctt ggctgcttat gaaaatcagg attatccgtt tgcagagctt   19440
gtggagcacg tacaggccgt ttggagccca agcagaaatc cgctgtttga caccatgttc   19500
gtcttgcaaa atacagaaga ccggaacgtt cgcttcggag agctgaccat agaaccgtat   19560
acgcaacatc acaacgtcgc caaattcgat ctgacactgg agattgcgct ggaagacggt   19620
gtaatgagcg ggcactttga atattgcacc cgattgttta caacaaacat ggttgacaac   19680
tttgccgagg atctgttgtc tatcttggct cagatctgtg agcagcctgc tatccgctta   19740
ggtgacattc acttacacgg caatgcagag gaagatgaag aggcgtcctt agcagaagaa   19800
atcgattttg tgttctaa                                                 19818
```

<210> SEQ ID NO 5
<211> LENGTH: 6605
<212> TYPE: PRT
<213> ORGANISM: Paenibacillus thiaminolyticus OSY-SE

<400> SEQUENCE: 5

```
Met Glu Met Met His Pro Asn Thr Thr Val Ser Thr Val Ala Gly Thr
1               5                   10                  15

Leu Val Ile Arg Gly Glu Val Asp Ala Ala Val Leu Lys Glu Ser Ile
            20                  25                  30

Cys Gln Val Ile Thr Gln His Asp Ala Phe Arg Ile Arg Ile Met Thr
        35                  40                  45

Gln Asp Asn Gln Pro Ile Gln Arg Leu Glu Pro Glu Ser Ala Ile Thr
    50                  55                  60

Pro Glu Val Asp Tyr Met Glu Trp Asp His Leu Glu Ala Lys Asp
65                  70                  75                  80

Trp Leu Asn Arg Phe Asn Arg Ile Pro Ile Ser Ile Phe Asp Asp Lys
                85                  90                  95

Leu Tyr Asn Phe Thr Val Phe Asn Val Asn Asn Gln Glu Tyr Trp Ile
            100                 105                 110

His Leu Lys Ile Asn His Ile Ile Ala Asp Gly Val Thr Ser His Leu
        115                 120                 125

Ile Gly Asn Lys Ile Met Gln Thr Tyr Met Glu Leu Thr Ser Gly Thr
    130                 135                 140
```

```
Phe Ser Ala Asn Asp Lys Lys Asn Ser Tyr Leu Asp Tyr Thr Tyr Ala
145                 150                 155                 160

Glu Gln Glu Tyr Glu Lys Ser Asp Arg Tyr Gln Lys Asp Lys Ala Tyr
            165                 170                 175

Trp Leu Glu Lys Phe Gln Thr Met Pro Glu Thr Thr Gly Ile Lys Pro
            180                 185                 190

Tyr Pro Pro Tyr Ser Ile Ser Thr Glu Ala Lys Arg Ala Tyr Val Ala
            195                 200                 205

Leu Thr Gly Glu Arg Tyr Glu Gln Leu Lys Val Phe Ser Glu Gln Asn
            210                 215                 220

Asn Ile Ser Leu Phe Thr Leu Phe Leu Ala Thr Val Tyr Met Phe Leu
225                 230                 235                 240

Tyr Lys Thr Thr Gly Asn Leu Asp Ile Ala Val Gly Thr Ala Tyr Ala
            245                 250                 255

Asn Arg Thr Ser Arg Lys Glu Lys Glu Met Leu Gly Met Phe Val Ser
            260                 265                 270

Thr Val Ala Thr Arg Leu Ser Leu Asp Pro Asn Gln Asp Leu Ile Ser
            275                 280                 285

Ile Leu His Asn Val Ser Lys Glu Gln Lys Thr Asn Leu Arg His Gln
290                 295                 300

Lys Tyr Pro Tyr Asn Gln Leu Ile Leu Asp Leu Arg Lys Glu His Lys
305                 310                 315                 320

His Ser Asp Ile Gln Asp Leu Tyr Gly Val Ser Val Asp Tyr Met Pro
            325                 330                 335

Ile Asn Trp Ser Ser Tyr Gly Gln Leu Ser Ile Gln Arg Ser Ser
            340                 345                 350

Phe Cys Gly His Glu Val Asp Asp Leu Ala Val His Val Glu Asp Met
            355                 360                 365

Leu Asp Asp Gln Gln Leu Val Ile Asn Val Asp Tyr Arg Ile Gln Leu
370                 375                 380

Phe Glu Glu Arg Glu Ile Thr Arg Ile Ile Glu Gln Met Leu Thr Ile
385                 390                 395                 400

Val Asp Gly Ile Leu His Asn Pro Gln Gln Thr Leu His Glu Leu Thr
            405                 410                 415

Met Leu Asn Asn Glu Glu Ala Arg Lys Ile Leu Thr Gln Phe Asn Asp
            420                 425                 430

Thr Ala Ala Glu Phe Pro Arg Asp Lys Thr Val His Gln Leu Phe Glu
            435                 440                 445

Glu Gln Ala Ala Arg Thr Pro Asn His Val Ala Ala Val Tyr Glu Asp
            450                 455                 460

Glu Gln Leu Thr Tyr Arg Glu Leu Asn Glu Arg Ala Asn Arg Leu Ala
465                 470                 475                 480

Arg Thr Leu Arg Ala Glu Gly Val Gln Pro Glu Gln Leu Val Gly Ile
            485                 490                 495

Met Ala Asp Arg Ser Leu Glu Met Ile Val Gly Ile Leu Ala Ile Leu
            500                 505                 510

Lys Ala Gly Gly Ala Tyr Val Pro Ile Asp Pro Glu Tyr Pro Glu Glu
            515                 520                 525

Arg Ile Arg Tyr Met Leu Asp Asp Ser Asn Ala Arg Val Leu Leu Ala
            530                 535                 540

Gln Arg His Leu Gln Ala Arg Ile Ala Phe Thr Gly Thr Trp Val Ile
545                 550                 555                 560
```

```
Leu Asp Glu Asn Ala Phe Tyr Asp Glu Asp Gly Thr Asn Leu Glu Ser
                565                 570                 575

Asn Asn Asp Pro Ser Asn Leu Ser Tyr Val Ile Tyr Thr Ser Gly Thr
            580                 585                 590

Thr Gly Lys Pro Lys Gly Val Met Ile Glu His Arg Gln Leu Val Ala
        595                 600                 605

Met Ala His Ala Trp Lys Ser Arg Tyr His Leu His Glu Ala Gly Ile
    610                 615                 620

Arg Trp Leu Gln Trp Ala Ser Phe Ser Phe Asp Val Phe Ser Gly Asp
625                 630                 635                 640

Met Val Arg Thr Leu Leu Asn Gly Gly Glu Leu Ile Leu Cys Pro Gly
                645                 650                 655

His Ala Arg Ala Asn Pro Glu Ala Ile Cys Glu Leu Ile Arg Lys His
            660                 665                 670

Arg Ile Gln Met Phe Glu Ser Thr Pro Ala Leu Val Val Pro Leu Met
        675                 680                 685

Glu Tyr Ile Tyr Asp Asn Lys Met Asp Ile His Ser Leu Gln Leu Leu
    690                 695                 700

Ile Ile Gly Ser Asp Tyr Cys Pro Ala Glu Glu Phe Gln Lys Leu Met
705                 710                 715                 720

Glu Arg Phe Gly Ser Gln Met Arg Ile Leu Asn Ser Tyr Gly Val Thr
                725                 730                 735

Glu Ala Cys Val Asp Ala Ser Tyr Phe Glu Gln Thr Asp Ser Asp Ala
            740                 745                 750

Leu Arg Thr Leu Pro Ile Gly Lys Pro Leu Pro Ala Val Ser Met Met
        755                 760                 765

Val Leu Asp Asp Asn Arg Ser Leu Gln Pro Ile Gly Ile Thr Gly Glu
    770                 775                 780

Leu Tyr Ile Gly Gly Ala Cys Val Gly Arg Gly Tyr Leu Asn Arg Pro
785                 790                 795                 800

Asp Leu Thr Ala Glu Lys Phe Val Asp Asn Pro Tyr Ala Pro Ser Glu
                805                 810                 815

Met Met Tyr Arg Thr Gly Asp Leu Ala Arg Trp Leu Pro Asp Gly Asn
            820                 825                 830

Ile Glu Tyr Leu Gly Arg Ile Asp His Gln Val Lys Ile Arg Gly Tyr
        835                 840                 845

Arg Ile Glu Ile Gly Glu Ile Glu Ser Gln Leu Leu Lys Ala Glu Ser
    850                 855                 860

Val Arg Glu Ser Val Val Ala Arg Glu Asp Gly Ser Gly Gln Lys
865                 870                 875                 880

Val Leu Cys Ala Tyr Tyr Val Ala Asp Arg Glu Leu Thr Val Asn Glu
                885                 890                 895

Leu Arg Gly Lys Met Ala Glu Glu Leu Pro Gly Tyr Met Ile Pro Ser
            900                 905                 910

Tyr Phe Met Gln Leu Glu Gln Met Pro Leu Thr Pro Asn Gly Lys Val
        915                 920                 925

Asp Arg Lys Gly Leu Pro Ala Pro Glu Gly Ser Ala His Thr Gly Thr
    930                 935                 940

Glu Tyr Val Glu Pro Ser Ser Ala Ala Glu Lys Met Leu Ala Ala Val
945                 950                 955                 960

Trp Gln Ala Val Leu Gly Ile Glu Arg Val Gly Ala Ser Glu His Phe
                965                 970                 975

Phe Glu Leu Gly Gly Asp Ser Ile Lys Ser Ile Gln Val Ser Ser Arg
```

```
              980             985              990
Leu Arg Gln Ala Gly Tyr Lys Met  Glu Ile Arg Asp Leu  Phe Lys Tyr
                 995              1000             1005
Pro Thr  Ile Ala Glu Leu Ser  Leu His Ile Gln Pro  Ala Gly Arg
    1010              1015              1020
Met Ala  Asp Gln Ser Glu Val  Val Gly Lys Ala Glu  Leu Thr Pro
    1025              1030              1035
Ile Gln  Arg Trp Phe Phe Ala  Gln Arg Phe Ala Asp  Pro His His
    1040              1045              1050
Tyr Asn  Gln Ser Ile Met Leu  Tyr Arg Lys Glu Gly  Phe Asp Glu
    1055              1060              1065
Ala Ala  Ile Arg Lys Thr Leu  Glu Lys Ile Ala Glu  His His Asp
    1070              1075              1080
Ala Leu  Arg Met Val Phe Arg  Lys Thr Glu Ser Gly  Tyr Ala Ala
    1085              1090              1095
Trp Asn  Arg Gly Ile Gly Glu  Gly Glu Leu Tyr Arg  Leu Asn Val
    1100              1105              1110
Ala Asp  Phe Arg Asn Glu Ser  Ala Cys Gly Pro Leu  Ile Ala Ala
    1115              1120              1125
Gln Ala  Asn Glu Ile Gln Gly  Gly Ile Asp Ile Glu  Thr Gly Pro
    1130              1135              1140
Leu Val  Arg Ala Gly Leu Phe  Gln Cys Ala Asp Gly  Asp His Leu
    1145              1150              1155
Leu Leu  Val Ile His His Thr  Val Ile Asp Gly Val  Ser Trp Arg
    1160              1165              1170
Ile Leu  Leu Glu Asp Ile Ala  Val Gly Tyr Glu Gln  Ala Leu Lys
    1175              1180              1185
Gly Glu  Glu Val Arg Leu Pro  Ser Lys Thr Asp Ala  Tyr Arg Thr
    1190              1195              1200
Trp Ser  Glu Arg Leu Ala Ser  Tyr Ala Asp Ser Gln  Thr Val Ile
    1205              1210              1215
Asn Glu  Arg Ala Tyr Trp Gln  Arg Ile Thr Gln Thr  Glu Met Asn
    1220              1225              1230
Pro Leu  Pro Lys Asp Tyr Glu  Ala Asp Cys Ser Leu  Gln Lys Asp
    1235              1240              1245
Ser Glu  Ser Val Ile Val Gln  Trp Ser Pro Glu Asp  Thr Glu Gln
    1250              1255              1260
Leu Leu  Lys His Val His Lys  Ala Tyr Asn Thr Glu  Met Asn Asp
    1265              1270              1275
Ile Leu  Leu Thr Ala Leu Gly  Thr Ala Val Gln Arg  Trp Ser Gly
    1280              1285              1290
Arg Asp  Arg Val Leu Val Asn  Leu Glu Gly His Gly  Arg Glu Ala
    1295              1300              1305
Ile Ile  Ala Asp Ile Asp Ile  Ser Arg Thr Val Gly  Trp Phe Thr
    1310              1315              1320
Ser Glu  Tyr Pro Val Leu Leu  Glu Met Glu Gln Ala  Lys Gly Leu
    1325              1330              1335
Ser Tyr  Arg Ile Lys Lys Val  Lys Glu Asp Leu Arg  Gln Ile Pro
    1340              1345              1350
Asn Lys  Gly Ile Gly Tyr Gly  Ile Cys Arg Tyr Met  Ser Asp Leu
    1355              1360              1365
Pro Tyr  Glu Ala Ser Trp Gly  Ala Asn Pro Glu Ile  Ser Phe Asn
    1370              1375              1380
```

-continued

```
Tyr Leu Gly Gln Phe Asp Gln Asp Leu Gln Ser Asn Gly Met Leu
    1385                1390                1395

Met Ser Pro Leu Ser Ser Gly Ser Asn Thr Ser Gly Asn Gln Ala
    1400                1405                1410

Arg Gln Tyr Ala Leu Asp Ile Asn Gly Met Ile Met Asp Gly Ser
    1415                1420                1425

Leu Val Phe Asp Leu Ser Tyr Gly Ser Lys Glu Tyr Arg Arg Glu
    1430                1435                1440

Thr Ile Glu Asp Leu Ala Gly Met Leu Gln Glu Ile Leu Arg Glu
    1445                1450                1455

Ile Ile Ala His Cys Thr Ala Lys Glu Arg Pro Glu Leu Thr Pro
    1460                1465                1470

Ser Asp Val Leu Leu Gln Gly Leu Ser Val Glu Glu Leu Glu Gln
    1475                1480                1485

Ile Val Glu Gln Thr Gln His Ile Gly Asp Ile Glu Asn Met Tyr
    1490                1495                1500

Lys Leu Thr Pro Met Gln Lys Gly Met Trp Phe His Ser Ala Met
    1505                1510                1515

Asp Arg Gln Ala Gly Ala Tyr Phe Glu Gln Thr Arg Phe Thr Leu
    1520                1525                1530

Gln Gly Asp Leu Asp Val Asp Ala Phe Ala Lys Ser Trp Thr Ala
    1535                1540                1545

Leu Ala Ala Arg His Thr Val Leu Arg Thr Asn Phe His Asn Gly
    1550                1555                1560

Trp Lys Gly Glu Pro Leu Gln Ile Val Tyr Arg Asp Lys Arg Ile
    1565                1570                1575

Gly Phe Ala Tyr Glu Asp Val Ser Ala Leu Lys Pro Ala Lys Gln
    1580                1585                1590

Arg Ala His Ile Glu Asn Ala Val Asn Glu Asp Lys Leu Arg Gly
    1595                1600                1605

Phe Asp Leu Glu Gln Asp Glu Leu Met Arg Val Leu Val Met Arg
    1610                1615                1620

Thr Ala Gln Glu Ser Tyr His Val Leu Trp Ser Ser His His Ile
    1625                1630                1635

Leu Met Asp Gly Trp Cys Leu Pro Leu Val Ala Lys Glu Val Phe
    1640                1645                1650

Asp Thr Tyr Ser Ala Tyr Val Arg His Arg His Leu Glu Lys Thr
    1655                1660                1665

Thr Val Pro Ala Tyr Ser Gln Tyr Ile Glu Trp Leu Glu Gln Gln
    1670                1675                1680

Asp Glu Glu Ala Ala Ser Ala Tyr Trp Ser Glu Tyr Leu Ala Gly
    1685                1690                1695

Tyr Asp Gln His Thr Ala Leu Pro Gln Gly Lys Asp Gln Gly Arg
    1700                1705                1710

Ser Glu Ala Tyr Ala Ala Glu His Ile Asp Cys Glu Leu Gly Lys
    1715                1720                1725

Asp Leu Ser Val Arg Leu Asn Glu Ala Ala Lys Arg Asn Leu Val
    1730                1735                1740

Thr Leu Ser Thr Leu Leu Gln Thr Thr Trp Gly Ile Met Leu Gln
    1745                1750                1755

Lys Tyr Asn Gly Thr Gly Asp Val Val Phe Gly Gly Val Val Ser
    1760                1765                1770
```

-continued

Gly Arg Pro Ala Asp Met Pro Gly Ile Glu Glu Met Ile Gly Leu
1775                1780                1785

Phe Ile Asn Thr Ile Pro Val Arg Val Thr Ala Asp Ala Gly Glu
1790                1795                1800

Ser Phe Ala Asp Ile Met Cys Arg Leu Gln Glu Gln Ala Leu Ala
1805                1810                1815

Ser Ala Lys His Asp His Tyr Pro Leu Tyr Glu Ile Gln Ala Gln
1820                1825                1830

Ser Ala Gln Lys Gln Glu Leu Ile Asn His Ile Met Val Phe Glu
1835                1840                1845

Asn Tyr Pro Met Glu Glu Gln Ile Glu Gln Leu Glu Ser Leu Asp
1850                1855                1860

Gly Lys Gly Leu Lys Leu Lys Asp Val Met Val Thr Glu Gln Thr
1865                1870                1875

Asn Tyr Asp Phe Asn Leu Val Ile Met Pro Gly Asp Glu Ile Val
1880                1885                1890

Ile Arg Leu Asp Tyr Asn Gly Ile Val Phe Asp Arg Thr Ser Met
1895                1900                1905

Glu Gln Leu Lys Gly His Leu Val Asn Met Leu Glu Gln Ile Ala
1910                1915                1920

Ala Asn Pro Gln Ile Pro Val Gly Glu Leu Glu Leu Ala Thr Ala
1925                1930                1935

Ala Glu Lys Ala Gln Ile Val Asp Val Phe Asn Asn Thr Val Val
1940                1945                1950

Glu Tyr Pro Arg Glu Lys Thr Ile His Gln Leu Phe Glu Glu Arg
1955                1960                1965

Glu Glu Arg Ile Pro Asp Ala Val Ala Val Ile Phe Glu Asp Lys
1970                1975                1980

Arg Leu Thr Tyr Ala Glu Leu Asn Ala Ala Ala Asn Arg Ile Ala
1985                1990                1995

His Leu Leu Arg Asp Arg Gly Val Ala Arg Gly Thr Leu Val Gly
2000                2005                2010

Ile Cys Ala Glu Arg Ser Leu Glu Met Val Val Gly Leu Leu Gly
2015                2020                2025

Ile Leu Lys Ala Gly Gly Ala Tyr Val Pro Ile Asp Pro Ser Tyr
2030                2035                2040

Pro Gln Glu Arg Ile Asn Ala Met Leu Glu Asp Thr Ala Ile Ser
2045                2050                2055

Val Met Leu Thr Gln Ala His Leu Gln Thr Ser Val Pro Asn Ser
2060                2065                2070

Ile Asp Ser Val Leu Leu Asp Ala Ala Ala Glu Thr Ile Leu Glu
2075                2080                2085

Gly Ser Trp Pro Asn Leu Thr Asp Thr Ala Ala Thr Ala Asp Asp
2090                2095                2100

Val Ala Tyr Ile Ile Tyr Thr Ser Gly Ser Thr Gly Ile Pro Lys
2105                2110                2115

Gly Val Cys Val Thr His Arg Gly Val Val Arg Leu Val Ala Asp
2120                2125                2130

Ala Asn Tyr Val Asp Ile Ser Ser Lys Asp Val Phe Leu Gln Gly
2135                2140                2145

Ser Thr Ile Ser Phe Asp Ala Ala Thr Phe Glu Ile Trp Gly Ser
2150                2155                2160

Leu Leu Asn Gly Ala Ala Leu Ala Val Leu Pro Pro Gly Asn Val

```
                2165                2170                2175
Ser Leu Thr Glu Trp Thr Arg Ala Ile Gln Gln His Gln Val Thr
    2180                2185                2190
Ile Leu Trp Leu Thr Ala Gly Leu Phe His Val Met Val Asp Asn
    2195                2200                2205
Gln Leu Gln Ala Leu Gln Gly Val Gln Gln Leu Leu Val Gly Gly
    2210                2215                2220
Asp Val Val Ser Lys Thr His Ala Thr Lys Val Leu Glu Arg Tyr
    2225                2230                2235
Asn Gly Ile Arg Leu Ile Asn Gly Tyr Gly Pro Thr Glu Asn Thr
    2240                2245                2250
Thr Phe Thr Cys Cys His Glu Ile Ser Ala Ala Asp Met Glu Arg
    2255                2260                2265
Pro Ser Ile Pro Ile Gly Arg Pro Ile Gly Asn Thr Gln Ala Tyr
    2270                2275                2280
Val Leu Asp Gly Ala Gly Lys Leu Leu Pro Ala Gly Val Ile Gly
    2285                2290                2295
Glu Leu Tyr Thr Gly Gly Asp Gly Leu Ala Gln Gly Tyr Leu Asn
    2300                2305                2310
Arg Pro Glu Leu Thr Ala Glu Lys Phe Val Asp Ser Pro Ile Val
    2315                2320                2325
Pro Ala Thr Arg Leu Tyr Arg Thr Gly Asp Leu Ala Arg Trp Leu
    2330                2335                2340
Pro Asp Gly Thr Ile Glu Tyr Val Gly Arg Ile Asp Asp Gln Val
    2345                2350                2355
Lys Ile Arg Gly Tyr Arg Ile Glu Leu Gly Glu Val Glu Ala His
    2360                2365                2370
Leu Leu Lys Val Glu Pro Val Gln Ser Ala Ala Val Ile Ala Arg
    2375                2380                2385
Lys Asp Glu Ser Gly Gln Asn Met Leu Cys Ala Tyr Tyr Ala Ala
    2390                2395                2400
Asp Lys Glu Leu Thr Ala Ser Glu Leu Arg Ser Ala Leu Ser Gln
    2405                2410                2415
Glu Leu Pro Gly Tyr Met Ile Pro Thr His Phe Val Gln Val Glu
    2420                2425                2430
Arg Met Pro Leu Thr Pro Asn Gly Lys Val Asp Arg Lys Ala Leu
    2435                2440                2445
Pro Glu Pro Glu Gly Arg Ile Met Thr Gly Ile Glu His Val Ala
    2450                2455                2460
Pro Arg Thr Pro Leu Glu Ser Lys Leu Ala His Ile Trp Gln Glu
    2465                2470                2475
Val Leu Gly Leu Glu Lys Val Ser Val Lys Asp Ser Phe Phe Glu
    2480                2485                2490
Leu Gly Gly His Ser Leu Arg Ala Thr Thr Leu Val Ser Lys Leu
    2495                2500                2505
Gln Gln Glu Leu His Val Ser Met Pro Leu Arg Glu Val Phe Arg
    2510                2515                2520
Phe Pro Thr Ile Glu Glu Gln Ala Gln Val Ile Gly Gly Met Glu
    2525                2530                2535
Gln Glu Glu Tyr Arg Ala Ile Pro Gln Val Gly Glu Arg Glu Cys
    2540                2545                2550
Tyr Pro Val Ser Ser Ala Gln Lys Arg Leu Tyr Ile Leu His Gln
    2555                2560                2565
```

```
Leu Glu Gly Ala Glu Gln Thr Tyr Asn Met Pro Gly Val Met Thr
    2570                2575                2580

Leu Ala Gly Pro Leu Asp Arg Glu Arg Leu Glu Thr Ala Phe Arg
    2585                2590                2595

Lys Leu Ile Ser Arg His Glu Thr Leu Arg Thr Gly Phe Glu Met
    2600                2605                2610

Val Asp Gly Val Pro Val Gln Arg Val Tyr Glu Val Asp Phe
    2615                2620                2625

Ala Val Glu Tyr Ala Gln Ala Ser Glu Ala Ala Gly Glu Ala
    2630                2635                2640

Val His Ala Phe Ile Arg Ala Phe Asp Leu Gln Lys Pro Pro Leu
    2645                2650                2655

Leu Arg Ile Gly Leu Ile Glu Leu Ala Lys Glu Arg His Leu Leu
    2660                2665                2670

Met Phe Asp Met His His Ile Ile Ser Asp Gly Ala Ser Ile Gly
    2675                2680                2685

Ile Leu Ile Glu Glu Phe Val Arg Leu Tyr Arg Gly Glu Glu Ile
    2690                2695                2700

Ser Pro Leu Arg Ile Gln Tyr Lys Asp Tyr Ala Ala Trp Leu Gln
    2705                2710                2715

Ser Glu Ala Gln Gln Asp Trp Ser Lys Gln Gln Glu Ala Tyr Trp
    2720                2725                2730

Leu Asp Ala Leu Arg Gly Glu Leu Pro Val Leu Glu Leu Pro Thr
    2735                2740                2745

Asp Tyr Ala Arg Pro Leu Phe Arg Ser Tyr Glu Gly Ser Thr Phe
    2750                2755                2760

Glu Phe Thr Ile Gln Arg Arg Glu Ala Glu Arg Leu Arg Gln Leu
    2765                2770                2775

Ala Ala Glu Ser Gly Ala Thr Leu Tyr Met Val Leu Leu Ala Leu
    2780                2785                2790

Tyr Thr Thr Met Leu His Lys Tyr Thr Gly Gln Glu Asp Ile Ile
    2795                2800                2805

Val Gly Met Pro Ile Ala Gly Arg Thr His Gly Asp Leu Gln Pro
    2810                2815                2820

Leu Ile Gly Met Phe Val Asn Thr Leu Ala Ile Arg Ser Tyr Pro
    2825                2830                2835

Ala Gly Glu Lys Thr Phe Leu Ser Phe Leu Glu Glu Val Lys Asp
    2840                2845                2850

Thr Thr Met Arg Ala Tyr Glu His Gln Asp Tyr Pro Phe Glu Glu
    2855                2860                2865

Leu Val Glu Asn Val Arg Val Pro Arg Asp Ala Ser Arg Asn Pro
    2870                2875                2880

Leu Phe Asp Thr Val Phe Val Leu Gln Asn Thr Glu Gln Gly Thr
    2885                2890                2895

Phe Asp Ile Asp Gly Leu Gln Leu Leu Pro His Pro Ala Glu His
    2900                2905                2910

Pro Val Ala Lys Phe Asp Leu Thr Phe His Ile Glu Glu Glu Glu
    2915                2920                2925

Glu Gly Leu Ala Cys Ser Ile Glu Tyr Ala Thr Ala Leu Phe Gln
    2930                2935                2940

Arg Glu Thr Val Ala Arg Met Ala Gln His Phe Arg Gln Leu Val
    2945                2950                2955
```

```
Glu Ala Val Thr Gly Glu Pro Val Asp Arg Leu Asp Arg Leu Glu
    2960                2965                2970

Met Leu Thr Ala Glu Glu Lys Val Gln Leu Val Asp Arg Phe Asn
    2975                2980                2985

Asp Thr Gly Ala Asp Tyr Pro Arg Glu Lys Thr Ile His Leu Leu
    2990                2995                3000

Phe Glu Glu Gln Ala Glu Arg Thr Pro Ala Ala Val Ala Val Ile
    3005                3010                3015

Phe Glu Asn Ala Gln Leu Thr Tyr Arg Glu Leu Asn Glu Arg Ala
    3020                3025                3030

Asn Arg Leu Ala His Thr Leu Arg Ala Lys Asp Val Gln Thr Asp
    3035                3040                3045

Ser Leu Val Gly Ile Met Ala Glu Arg Ser Pro Glu Met Ile Val
    3050                3055                3060

Gly Ile Leu Ala Ile Leu Lys Ala Gly Gly Ala Tyr Val Pro Ile
    3065                3070                3075

Asp Pro Glu Tyr Pro Glu Glu Arg Ile Arg Tyr Met Leu Asp Asp
    3080                3085                3090

Ser Gly Ala Gln Val Leu Leu Pro His Asp Leu Arg Asp Lys
    3095                3100                3105

Val Gly Phe Asp Gly Thr Val Val Met Leu Asp Asp Glu Gln Ser
    3110                3115                3120

Tyr Val Glu Asp Ser Ser Asn Pro Ala Thr Ala Ser Lys Pro Ser
    3125                3130                3135

Asp Leu Ala Tyr Val Ile Tyr Thr Ser Gly Thr Thr Gly Lys Pro
    3140                3145                3150

Lys Gly Thr Leu Ile Glu His Lys Asn Val Val Arg Leu Leu Phe
    3155                3160                3165

Asn Ser Lys Asn Leu Phe Asp Phe Asn Ser Ala Asp Thr Trp Thr
    3170                3175                3180

Leu Phe His Ser Phe Cys Phe Asp Phe Ser Val Trp Glu Met Tyr
    3185                3190                3195

Gly Ala Leu Leu Tyr Gly Gly Arg Leu Val Val Val Pro Gln Leu
    3200                3205                3210

Thr Ala Lys Asn Pro Ala Gln Phe Leu Glu Leu Leu His Glu Gln
    3215                3220                3225

Gln Val Thr Ile Leu Asn Gln Thr Pro Thr Tyr Phe Tyr Gln Leu
    3230                3235                3240

Leu Arg Glu Ala Leu Ala Glu Pro Gly Gln Glu Leu Lys Val Arg
    3245                3250                3255

Lys Val Ile Phe Gly Gly Glu Ala Leu Asn Pro Gln Leu Leu Lys
    3260                3265                3270

Asp Trp Lys Thr Lys Tyr Pro His Thr Gln Leu Ile Asn Met Tyr
    3275                3280                3285

Gly Ile Thr Glu Thr Thr Val His Val Thr Tyr Lys Glu Ile Thr
    3290                3295                3300

Gln Val Glu Ile Glu Gln Ala Lys Ser Asn Ile Gly Arg Pro Ile
    3305                3310                3315

Pro Thr Leu Lys Val Tyr Val Leu Asp Ala Asn Arg Gln Cys Val
    3320                3325                3330

Pro Val Gly Val Ala Gly Glu Met Tyr Val Ala Gly Asp Gly Leu
    3335                3340                3345

Ala Arg Gly Tyr Leu His Arg Pro Glu Leu Thr Ala Asp Lys Phe
```

```
            3350                3355                3360

Val  Asp  Ser  Pro  Phe  Glu  Ser  Gly  Gly  Arg  Met  Tyr  Arg  Thr  Gly
            3365                3370                3375

Asp  Leu  Ala  Arg  Trp  Leu  Pro  Asp  Gly  Asn  Ile  Glu  Tyr  Leu  Gly
            3380                3385                3390

Arg  Ile  Asp  His  Gln  Val  Lys  Ile  Arg  Gly  Tyr  Arg  Ile  Glu  Leu
            3395                3400                3405

Gly  Glu  Val  Glu  Ala  Gln  Leu  Thr  Lys  Val  Asp  Pro  Val  Arg  Glu
            3410                3415                3420

Ala  Ile  Val  Ile  Ala  Arg  Glu  Asp  Gly  His  Gly  Glu  Lys  Gln  Leu
            3425                3430                3435

Cys  Ala  Tyr  Phe  Val  Ala  Ala  Arg  Glu  Leu  Thr  Val  Gly  Glu  Leu
            3440                3445                3450

Arg  Gln  Glu  Leu  Ser  His  Ala  Leu  Pro  Ala  Tyr  Met  Ile  Pro  Ala
            3455                3460                3465

Tyr  Phe  Val  Gln  Leu  Glu  Arg  Met  Pro  Leu  Thr  Pro  Asn  Gly  Lys
            3470                3475                3480

Ile  Asp  Arg  Lys  Ala  Leu  Pro  Ala  Pro  Glu  Asp  Ser  Val  Asn  Thr
            3485                3490                3495

Gly  Thr  Glu  Tyr  Ile  Ala  Pro  Arg  Thr  Leu  Leu  Glu  Ser  Asp  Leu
            3500                3505                3510

Thr  Arg  Ile  Trp  Gln  Asp  Val  Leu  Gly  Leu  Glu  Ser  Ile  Gly  Val
            3515                3520                3525

Lys  Asp  Asn  Phe  Phe  Glu  Leu  Gly  Gly  His  Ser  Leu  Arg  Ala  Thr
            3530                3535                3540

Thr  Leu  Val  Asn  Lys  Val  His  Gln  Glu  Met  Asn  Val  Asn  Leu  Pro
            3545                3550                3555

Leu  Arg  Asp  Val  Phe  Arg  Phe  Ser  Thr  Ile  Glu  Glu  Met  Ala  Cys
            3560                3565                3570

Ala  Ile  Ala  Glu  Met  Glu  Gln  Arg  Thr  Tyr  Met  Ser  Ile  Pro  Ala
            3575                3580                3585

Ile  Glu  Thr  Arg  Asp  Tyr  Tyr  Pro  Val  Ser  Ser  Ala  Gln  Lys  Arg
            3590                3595                3600

Leu  Tyr  Ile  Leu  His  Gln  Ile  Glu  Gly  Ala  Glu  Gln  Gly  Tyr  Asn
            3605                3610                3615

Met  Pro  Gly  Val  Leu  Leu  Glu  Gly  Met  Leu  Asp  Gln  Glu  Lys
            3620                3625                3630

Phe  Glu  Glu  Ala  Phe  His  Gly  Ile  Val  Ala  Arg  His  Glu  Thr  Leu
            3635                3640                3645

Arg  Thr  Gly  Phe  Glu  Met  Val  Asn  Gly  Glu  Pro  Val  Gln  Arg  Val
            3650                3655                3660

Tyr  Glu  Lys  Val  Asp  Phe  Ala  Val  Glu  Tyr  Arg  Gln  Ala  Asp  Glu
            3665                3670                3675

Glu  Glu  Val  Glu  Ala  Val  Val  Arg  Asp  Phe  Val  Arg  Thr  Phe  Asp
            3680                3685                3690

Leu  Glu  Lys  Pro  Pro  Leu  Leu  Arg  Ile  Gly  Leu  Leu  Glu  Leu  Ala
            3695                3700                3705

Lys  Glu  Arg  His  Val  Leu  Leu  Tyr  Asp  Met  His  His  Ile  Ile  Ser
            3710                3715                3720

Asp  Gly  Val  Ser  Met  Gly  Ile  Val  Val  Glu  Glu  Phe  Val  Arg  Leu
            3725                3730                3735

Tyr  Ala  Gly  Ala  Ala  Leu  Glu  Pro  Leu  Arg  Ile  Gln  Tyr  Lys  Asp
            3740                3745                3750
```

```
Tyr Ala Ala Trp Gln Leu Ser Glu Ala Gln Gln Asp Trp Met Lys
3755                3760                3765

Arg Gln Glu Gly Tyr Trp Arg Asp Val Phe Arg Gly Glu Leu Pro
3770                3775                3780

Val Leu Glu Met Pro Thr Asp Tyr Val Arg Pro Ala Val Gln Gln
3785                3790                3795

Tyr Ala Gly Ser Thr Leu Ser Phe Asp Ile Asp Pro Gln Met Ser
3800                3805                3810

Glu Gly Leu Arg Arg Ile Ala Ala Glu Thr Gly Thr Thr Leu Tyr
3815                3820                3825

Met Val Leu Leu Ala Ala Tyr Thr Ile Leu Leu His Lys Tyr Thr
3830                3835                3840

Gly Gln Glu Asp Val Ile Val Gly Thr Pro Ile Ala Gly Arg Thr
3845                3850                3855

His Gly Asp Leu Gln Pro Leu Ile Gly Met Phe Val Asn Thr Leu
3860                3865                3870

Ala Ile Arg Asn Tyr Pro Ala Gly Glu Lys Thr Phe Arg Ser Tyr
3875                3880                3885

Leu Ala Glu Val Lys Glu Thr Thr Leu Gly Ala Tyr Glu His Gln
3890                3895                3900

Asn Tyr Pro Phe Glu Glu Leu Val Asp Lys Leu Gln Val Ala Arg
3905                3910                3915

Asp Leu Ser Arg Asn Pro Leu Phe Asp Thr Met Phe Ala Leu Asn
3920                3925                3930

Asn Thr Glu Pro Glu Thr Phe Pro Leu Glu Gly Leu Arg Leu Thr
3935                3940                3945

Pro Tyr Pro Ser Glu Tyr Thr Ile Ser Lys Phe Asp Leu Ser Leu
3950                3955                3960

Asp Val Ser Glu Lys Asn Asp Arg Leu Glu Cys Ser Leu Glu Tyr
3965                3970                3975

Ala Thr Ala Leu Tyr Lys Pro Asp Thr Ala Glu Arg Met Ala Gln
3980                3985                3990

His Phe Gln Gln Leu Ile Asp Ser Ile Val Asp Gln Pro Glu Ala
3995                4000                4005

Lys Leu Val Ser Leu Gly Met Leu Thr Glu Glu Lys Ala Gln
4010                4015                4020

Ile Gln His Val Phe Asn Arg Ala Glu Ala Gly His Ser Gln Glu
4025                4030                4035

Lys Thr Val Pro Glu Leu Phe Glu Glu Gln Val Glu Arg Thr Pro
4040                4045                4050

Asp Arg Ile Ala Val Val His Glu Asp Lys Gln Leu Thr Tyr Arg
4055                4060                4065

Glu Leu Asn Glu Arg Ala Asn Arg Leu Ala Arg Thr Leu Arg Ala
4070                4075                4080

Glu Gly Val Glu Pro Glu Gln Leu Val Gly Ile Met Ala Asp Arg
4085                4090                4095

Ser Leu Asp Met Ile Val Gly Ile Met Ala Ile Leu Lys Ser Gly
4100                4105                4110

Gly Ala Tyr Val Pro Ile Asp Pro Lys Tyr Pro Glu Asp Arg Ile
4115                4120                4125

Arg Tyr Met Leu Asp Asp Ser His Ala Gln Val Leu Leu Ala Gln
4130                4135                4140
```

```
Arg His Met Gln Ala Ser Val Ala Phe Ala Gly Thr Trp Val Ile
4145                4150                4155

Leu Asp Glu Glu Ala Phe Tyr His Glu Asp Gly Thr Asn Leu Glu
4160                4165                4170

Pro Leu Asn Glu Pro Met His Leu Ser Tyr Val Ile Tyr Thr Ser
4175                4180                4185

Gly Thr Thr Gly Asn Pro Lys Gly Val Met Ile Glu His Arg Gln
4190                4195                4200

Leu Val Ala Ile Ala Asp Ala Trp Lys Arg Glu Tyr Arg Leu Glu
4205                4210                4215

Glu Glu Gly Ile Arg Trp Leu Gln Trp Ala Ser Phe Ser Phe Asp
4220                4225                4230

Val Phe Ser Gly Asp Met Val Arg Thr Leu Leu Tyr Gly Gly Glu
4235                4240                4245

Leu Ile Leu Cys Pro Glu Gln Ala Arg Ala Asn Pro Ala Ala Ile
4250                4255                4260

Ser Glu Leu Ile Arg Lys His Gln Ile Gln Met Phe Glu Ser Thr
4265                4270                4275

Pro Ala Leu Val Ile Pro Phe Met Asp Tyr Val Tyr Asp Asn Asn
4280                4285                4290

Leu Asp Ile Ser Ser Leu Lys Met Leu Ile Val Gly Ser Asp His
4295                4300                4305

Cys Pro Thr Ala Glu Phe Asp Lys Leu Thr Glu Arg Cys Gly Ser
4310                4315                4320

His Met Arg Ile Leu Asn Ser Tyr Gly Val Thr Glu Ala Cys Val
4325                4330                4335

Asp Ala Cys Tyr Tyr Glu Arg Thr Thr Pro Asp Ala Leu Arg Thr
4340                4345                4350

Leu Pro Ile Gly Lys Pro Leu Pro Ala Val Thr Met Tyr Ile Leu
4355                4360                4365

Asp Asp Asn Arg Ser Leu Gln Pro Ile Gly His Thr Gly Glu Leu
4370                4375                4380

Tyr Ile Gly Gly Ala Gly Val Gly Arg Gly Tyr Leu Asn Arg Pro
4385                4390                4395

Asp Leu Thr Val Glu Lys Phe Val Asp Asn Pro Phe Met Pro Gly
4400                4405                4410

Ala Arg Met Tyr Arg Thr Gly Asp Leu Ala Arg Trp Leu Pro Asp
4415                4420                4425

Gly Asn Ile Glu Tyr Ala Gly Arg Ile Asp His Gln Val Lys Ile
4430                4435                4440

Arg Gly Tyr Arg Ile Glu Ile Gly Glu Val Glu Ser Gln Leu Leu
4445                4450                4455

Ala Ala Ala Gly Val Arg Glu Ala Ala Val Val Ala Arg Glu Asp
4460                4465                4470

Gly Ser Gly Gln Lys Val Leu Cys Ala Tyr Phe Val Ala Asp Ser
4475                4480                4485

Ala Leu Thr Val Gly Glu Leu Arg Ala Ser Met Ala Gln Gln Leu
4490                4495                4500

Pro Gly Tyr Met Ile Pro Ala His Phe Val Gln Leu Glu Arg Met
4505                4510                4515

Pro Leu Thr Pro Asn Gly Lys Val Asp Arg Lys Gly Leu Pro Ala
4520                4525                4530

Pro Glu Gly Asn Ala Tyr Thr Gly Ala Glu His Val Ala Pro Arg
```

-continued

```
              4535                4540                4545

Thr Glu Ala Glu Lys Thr Leu Ala Ala Val Trp Gln Val Val Leu
    4550                4555                4560

Gly Ala Glu Gln Val Gly Leu Met Asp His Phe Phe Glu Leu Gly
    4565                4570                4575

Gly Asp Ser Ile Lys Ser Ile Gln Val Ser Ser Arg Leu His Gln
    4580                4585                4590

Ala Gly Tyr Lys Leu Glu Ile Arg Asp Leu Phe Lys Tyr Pro Thr
    4595                4600                4605

Ile Ala Glu Leu Ser Pro His Ile Gln Pro Ile Gly Arg Lys Ala
    4610                4615                4620

Asp Gln Gly Ala Val Thr Gly Glu Ala Ala Leu Thr Pro Ile Gln
    4625                4630                4635

His Trp Phe Phe Gly Gln Arg Phe Ala Asp Pro His His Tyr Asn
    4640                4645                4650

Gln Ser Ile Met Leu Tyr Arg Lys Glu Gly Phe Asp Glu Ala Ala
    4655                4660                4665

Ile Arg Lys Thr Leu Glu Lys Ile Ala Glu His His Asp Ala Leu
    4670                4675                4680

Arg Met Val Phe Arg Lys Thr Glu His Gly Tyr Ala Ala Trp Asn
    4685                4690                4695

Arg Gly Ile Gly Glu Gly Glu Leu Tyr Ser Leu Asn Val Ala Asp
    4700                4705                4710

Phe Thr Asp Asp Pro Ala Cys Tyr Arg Ala Ile Glu Ala Lys Ala
    4715                4720                4725

Asn Glu Ile Gln Ser Gly Ile Asn Leu Gln Ala Gly Pro Leu Leu
    4730                4735                4740

Arg Ala Gly Leu Phe Thr Cys Ala His Gly His His Leu Leu Ile
    4745                4750                4755

Val Ile His His Ala Val Thr Asp Gly Val Ser Trp Arg Ile Leu
    4760                4765                4770

Leu Glu Asp Ile Ala Ala Gly Tyr Glu Gln Ala Leu Lys Gly Glu
    4775                4780                4785

Ala Ile Arg Leu Pro Ala Lys Thr Asp Ser Tyr Leu Thr Trp Ser
    4790                4795                4800

Lys Gln Leu Ser Gly Tyr Ala Gln Ser Pro Ala Ile Glu Gln Glu
    4805                4810                4815

Arg Ser Tyr Trp Gln Arg Ile Ala Gln Ser Asn Thr Lys Pro Leu
    4820                4825                4830

Pro Lys Asp Arg Thr Val Asn Val Ser Leu Gln Arg Asp Ser Glu
    4835                4840                4845

Ser Val Ser Val Gln Trp Ser Arg Glu Asp Thr Glu Gln Leu Leu
    4850                4855                4860

Lys His Val His Arg Ala Tyr Asn Thr Asp Met Asn Asp Ile Leu
    4865                4870                4875

Leu Thr Ala Leu Gly Met Ala Ile Gln Gln Trp Ser Gly Arg Asp
    4880                4885                4890

Arg Met Leu Val Asn Leu Glu Gly His Gly Arg Glu Ser Ile Met
    4895                4900                4905

Ala Asp Val Asp Ile Ser Arg Thr Val Gly Trp Phe Thr Ser Glu
    4910                4915                4920

Tyr Pro Val Leu Leu Glu Met Glu Pro Asp Lys Ser Leu Ser His
    4925                4930                4935
```

```
Cys Ile Lys Lys Val Lys Glu Asp Leu Arg Gln Ile Pro His Lys
    4940            4945                4950
Gly Ile Gly Tyr Gly Ile Cys Arg Tyr Leu Ser Gly Thr Met Glu
    4955            4960                4965
Asp Ala Ala Trp Gly Thr Ala Pro Glu Ile Ser Phe Asn Tyr Leu
    4970            4975                4980
Gly Gln Phe Asp Gln Asp Leu Asn Ser Asn Gly Met Glu Met Ser
    4985            4990                4995
Pro Tyr Ser Ser Gly Thr Asp Ala Ser Gly Lys Gln Val Arg Gln
    5000            5005                5010
Tyr Ala Leu Asp Ile Asn Gly Gly Ile Thr Asp Gly Ser Leu Ser
    5015            5020                5025
Phe Asp Leu Ser Tyr Ser Arg Lys Glu Tyr Arg Arg Glu Thr Met
    5030            5035                5040
Glu Asp Leu Ala Gly Arg Leu Arg Glu Ser Leu Gln Glu Ile Ile
    5045            5050                5055
Ala His Cys Ala Ala Lys Glu Arg Thr Glu Leu Thr Pro Ser Asp
    5060            5065                5070
Val Leu Leu Gln Gly Leu Ser Val Glu Glu Leu Glu Leu Ile Val
    5075            5080                5085
Glu Gln Thr Arg His Val Gly Glu Ile Glu Asn Ile Tyr Ala Leu
    5090            5095                5100
Thr Pro Met Gln Lys Gly Met Trp Phe His Asn Ala Ile Asp Gln
    5105            5110                5115
Gln Ala Gly Ala Tyr Phe Glu Gln Thr Arg Phe Thr Ile Gln Gly
    5120            5125                5130
Val Leu Asp Val Asp Val Phe Ala Met Ser Leu Asn Val Leu Ala
    5135            5140                5145
Lys Arg His Ala Val Leu Arg Thr Asn Phe Tyr Ser Gly Trp Asn
    5150            5155                5160
Gly Glu Pro Leu Gln Ile Val Tyr Arg Asp Lys Arg Ile Ala Phe
    5165            5170                5175
Val Tyr Glu Asp Leu Arg His Leu Pro Ala Ala Glu Gln Thr Ala
    5180            5185                5190
His Ile Glu His Ala Ala Arg Glu Asp Lys Leu Lys Gly Phe Asp
    5195            5200                5205
Leu Glu Gln Asp Ala Leu Val Arg Val Ala Leu Met Arg Thr Gly
    5210            5215                5220
Ala Ala Ser Cys Arg Val Leu Trp Ser Ser His His Ile Leu Met
    5225            5230                5235
Asp Gly Trp Cys Leu Pro Gln Leu Thr Gln Glu Leu Phe Asp Thr
    5240            5245                5250
Tyr Ser Ser Tyr Met Lys Gln His His Asp Glu Gln Ala Leu Pro
    5255            5260                5265
Ala Tyr Ser Gln Ser Ser Tyr Ser Gln Tyr Ile Glu Trp Leu Glu
    5270            5275                5280
Gln Gln Asp Glu Glu Ala Ala Ala Gly Tyr Trp Ser Glu Tyr Leu
    5285            5290                5295
Ala Gly Tyr Asp Gln Gln Thr Leu Leu Pro Gln Gly Lys Thr Gln
    5300            5305                5310
Gly Arg Asp Glu Ala Tyr Val Leu Glu His Val Val Cys Glu Leu
    5315            5320                5325
```

Gly Lys Thr Leu Thr Gly Arg Met Ser Gln Leu Ala Lys Gln His
5330                5335                5340

Ser Val Thr Leu Asn Thr Leu Leu Gln Ala Ala Trp Gly Ile Ile
5345                5350                5355

Leu Gln Lys Tyr Asn Gly Thr Asp Asp Val Val Phe Gly Gly Val
5360                5365                5370

Val Ser Gly Arg Pro Ala Ala Ile Pro Gly Ile Glu Thr Met Ile
5375                5380                5385

Gly Leu Phe Ile Asn Thr Ile Pro Val Arg Val Ala Cys Ala Ala
5390                5395                5400

Glu Thr Ser Phe Thr Gln Val Met Arg Arg Leu Gln Glu Gln Ala
5405                5410                5415

Leu Asp Ser Gly Arg Tyr Asp Tyr Pro Leu Tyr Glu Ile Gln
5420                5425                5430

Ala Gln Cys Ala Gln Lys Gln Glu Leu Ile Ser His Ile Met Val
5435                5440                5445

Phe Glu Asn Tyr Pro Val Asp Glu Gln Met Glu Gln Thr Gly Ser
5450                5455                5460

Lys Asp Ser Gly Thr Leu Ser Ile Thr Asp Val Glu Val Ala Glu
5465                5470                5475

Gln Thr Asn Tyr Asp Phe Asn Leu Met Val Val Pro Gly Glu Glu
5480                5485                5490

Leu Val Val Arg Phe Asp Phe Asn Gly Ser Val Phe Asp Arg Thr
5495                5500                5505

Ser Ile Glu Arg Leu Thr Gly His Leu Val His Val Leu Glu Gln
5510                5515                5520

Ile Thr Ala Asn Pro Gln Ile Ser Val Gly Asp Leu Glu Leu Ala
5525                5530                5535

Thr Ala Ala Glu Lys Val Glu Ile Val Asp Val Phe Asn Asp Thr
5540                5545                5550

Ala Ala Asp Tyr Pro Arg Glu Lys Thr Ile His Gln Met Phe Glu
5555                5560                5565

Glu Gln Val Glu Arg Thr Pro Asp Ala Val Ala Val Met Phe Glu
5570                5575                5580

Gln Glu Arg Leu Thr Tyr Arg Glu Leu Asn Glu Cys Val Asn Arg
5585                5590                5595

Leu Ala Arg Thr Leu Arg Thr Gln Gly Val Gln Pro Asp Gln Arg
5600                5605                5610

Val Gly Ile Met Val Glu Arg Ser Leu Glu Met Met Val Gly Ile
5615                5620                5625

Met Ala Ile Leu Lys Ala Gly Gly Ala Tyr Val Pro Ile Ala Pro
5630                5635                5640

Asp Tyr Pro Glu Glu Arg Ile His Tyr Met Leu Glu Asp Ser Gly
5645                5650                5655

Ala Gln Val Leu Leu Leu Gln Gly Arg Ser Gly Glu Ser Val Ser
5660                5665                5670

Phe Ala Gly Arg Ile Val Asn Leu Asp Asp Glu Ser Ser Tyr Ala
5675                5680                5685

Glu Asp Gly Ser Asn Leu Glu Trp Val Asn Gln Ala Ser Asp Ala
5690                5695                5700

Ala Tyr Val Ile Tyr Thr Ser Gly Thr Thr Gly Lys Pro Lys Gly
5705                5710                5715

Val Leu Val Glu His Gly Ser Val Ile Asn Arg Leu Leu Trp Met

```
                        5720                    5725                    5730
Gln Lys Gln Tyr Pro Ile Asn Ala Asn Asp Thr Ile Met Gln Lys
    5735                    5740                    5745
Thr Ala Ile Thr Phe Asp Val Ser Val Trp Glu Leu Phe Trp Trp
        5750                    5755                    5760
Ala Phe Val Gly Ser Lys Val Cys Leu Leu Pro Val Gly Gly Glu
    5765                    5770                    5775
Lys Asn Pro Ala Val Ile Leu Asp Thr Ile Ala Gln Gln His Ile
    5780                    5785                    5790
Ser Thr Met His Phe Val Pro Ser Met Leu His Ala Phe Leu Glu
    5795                    5800                    5805
Tyr Val Glu Glu Gln Pro Ile Ala Glu Arg Glu Arg Ser Leu Ala
    5810                    5815                    5820
Ala Leu Ser Arg Val Phe Ala Ser Gly Glu Ala Leu Thr Leu Ser
    5825                    5830                    5835
Gln Val Glu Arg Phe Glu Arg Cys Ile Ala Pro Ala Ser Gly Ala
    5840                    5845                    5850
Arg Leu Ile Asn Leu Tyr Gly Pro Thr Glu Ala Thr Val Asp Val
    5855                    5860                    5865
Thr Tyr Tyr Asp Cys Glu Ala Gly Gln Pro Tyr Thr Ser Val Pro
    5870                    5875                    5880
Ile Gly Lys Pro Ile Asp Asn Thr Gln Ile Tyr Ile Val Asn Arg
    5885                    5890                    5895
Gln Asp Gln Leu Gln Pro Ile Gly Val Ala Gly Glu Leu Cys Ile
    5900                    5905                    5910
Ala Gly Val Gly Leu Ala Arg Gly Tyr Leu Lys Arg Pro Glu Leu
    5915                    5920                    5925
Thr Ala Glu Lys Phe Val Thr Ile Pro Phe Met Pro Gly Ala Arg
    5930                    5935                    5940
Met Tyr Arg Thr Gly Asp Leu Ala Arg Trp Leu Pro Asp Gly Ser
    5945                    5950                    5955
Ile Glu Tyr Leu Gly Arg Ile Asp His Gln Val Lys Ile Arg Gly
    5960                    5965                    5970
Tyr Arg Ile Glu Leu Gly Glu Ile Glu Ala Gln Leu Leu Gln Val
    5975                    5980                    5985
Glu Phe Ile Arg Glu Ala Val Val Val Ala Arg Glu Asp Glu Ser
    5990                    5995                    6000
Gly Gln Lys Ala Leu Cys Ala Tyr Phe Ala Ala Asp Ser Glu Leu
    6005                    6010                    6015
Pro Val Ser Glu Leu Arg Ser Ala Leu Ala Val Glu Leu Pro Gly
    6020                    6025                    6030
Tyr Met Ile Pro Ser Tyr Phe Val Gln Leu Glu Arg Leu Pro Leu
    6035                    6040                    6045
Ser Ala Asn Gly Lys Leu Asp Arg Lys Ala Leu Pro Ala Pro Gly
    6050                    6055                    6060
Gly Ser Met Arg Ser Gly Lys Glu His Val Ala Pro Arg Ser Leu
    6065                    6070                    6075
Leu Glu Val Lys Leu Val Arg Ile Trp Gln Glu Val Leu Gly Leu
    6080                    6085                    6090
Ala His Val Ser Val Lys Asp Asp Phe Glu Leu Gly Gly His
    6095                    6100                    6105
Ser Leu Arg Ala Thr Thr Leu Val Ser Lys Leu His Lys Glu Leu
    6110                    6115                    6120
```

-continued

Asn Ile Asn Leu Pro Leu Arg Asp Val Phe Arg Tyr Ser Ile Leu
6125                6130                    6135

Glu Asp Met Ala Leu Ala Ile Gly Arg Thr Glu Gln Arg Glu Phe
6140                6145                    6150

Gln Thr Ile Pro Gln Val Glu Ala Ser Asp Tyr Tyr Pro Leu Ser
6155                6160                    6165

Ser Ala Gln Lys Arg Leu Tyr Ile Val Gln Gln Val Glu Gly Ala
6170                6175                    6180

Glu Gln Ser Tyr Asn Met Pro Gly Ala Met Ser Ile Arg Gly Gln
6185                6190                    6195

Leu Asp Arg Asn Gln Phe Glu Ala Ala Phe Arg Gly Leu Ile Ala
6200                6205                    6210

Arg His Glu Val Phe Arg Thr Ser Phe Glu Met Val Gly Gly Glu
6215                6220                    6225

Pro Met Gln Arg Val His Gln Asp Thr Ala Phe Ala Val Glu Tyr
6230                6235                    6240

Met Gln Ala Asn Glu Glu Glu Ala Glu Ala Ile Ala His Gln Phe
6245                6250                    6255

Val Arg Thr Phe Asp Leu Glu Gln Pro Ser Leu Leu Arg Val Gly
6260                6265                    6270

Leu Ile Glu Leu Asp Arg Glu His His Ile Met Leu Phe Asp Met
6275                6280                    6285

His His Ile Ile Ser Asp Gly Val Ser Met Gly Ile Leu Val Glu
6290                6295                    6300

Glu Phe Ala Arg Leu Tyr Ser Gly Glu Glu Leu Pro Pro Leu Arg
6305                6310                    6315

Ile Gln Tyr Lys Asp Tyr Ala Ala Trp Gln Gln Ser Glu Ala Gln
6320                6325                    6330

Ser Glu Arg Ile Lys Gln Gln Glu Ala Tyr Trp Leu Asp Ala Leu
6335                6340                    6345

Asp Gly Glu Leu Pro Gln Leu Glu Leu Pro Thr Asp Phe Ala Arg
6350                6355                    6360

Pro Ala His Gln Ser His Glu Gly Asp Thr Leu Asp Phe Val Ile
6365                6370                    6375

Asp Ser His Met Ser Gly Gly Leu Gln Arg Leu Ala Glu His Thr
6380                6385                    6390

Gly Thr Thr Leu Tyr Met Val Leu Leu Ala Ala Tyr Thr Ile Leu
6395                6400                    6405

Leu His Lys Tyr Ser Asp Gln Glu Asp Ile Ile Val Gly Thr Pro
6410                6415                    6420

Ile Ala Gly Arg Thr His Ala Asp Val Glu Pro Leu Ile Gly Met
6425                6430                    6435

Phe Val Asn Ser Leu Ala Leu Arg Ser Tyr Pro Cys Gly Glu Lys
6440                6445                    6450

Ser Phe Leu Ser Tyr Leu Glu Glu Val Lys Glu Met Thr Leu Ala
6455                6460                    6465

Ala Tyr Glu Asn Gln Asp Tyr Pro Phe Ala Glu Leu Val Glu His
6470                6475                    6480

Val Gln Ala Val Trp Ser Pro Ser Arg Asn Pro Leu Phe Asp Thr
6485                6490                    6495

Met Phe Val Leu Gln Asn Thr Glu Asp Arg Asn Val Arg Phe Gly
6500                6505                    6510

```
Glu Leu Thr Ile Glu Pro Tyr Thr Gln His His Asn Val Ala Lys
6515                6520                6525

Phe Asp Leu Thr Leu Glu Ile Ala Leu Glu Asp Gly Val Met Ser
6530                6535                6540

Gly His Phe Glu Tyr Cys Thr Arg Leu Phe Thr Thr Asn Met Val
6545                6550                6555

Asp Asn Phe Ala Glu Asp Leu Leu Ser Ile Leu Ala Gln Ile Cys
6560                6565                6570

Glu Gln Pro Ala Ile Arg Leu Gly Asp Ile His Leu His Gly Asn
6575                6580                6585

Ala Glu Glu Asp Glu Glu Ala Ser Leu Ala Glu Glu Ile Asp Phe
6590                6595                6600

Val Phe
6605

<210> SEQ ID NO 6
<211> LENGTH: 19251
<212> TYPE: DNA
<213> ORGANISM: Paenibacillus thiaminolyticus OSY-SE

<400> SEQUENCE: 6
atgaacttgg catttgaaaa ggaaaccgat ttttggaatg cgcaattcga tgctgaagat     60
agtcctgcga tcctgcctta ctccacagct tcaatcagcg ttacagctcg cgatcattcc   120
aattccatca gcttatctgc cgacgtatcg caacgaatta gtcatatgag cagaggttcc   180
catctggccg aatacatgat cttactagca ggcatccaat gcttgcttta caaatataca   240
ggtgaagaga gtgtcatcgt aggcatgcca atcgttagaa agtccaagga cacacggcgg   300
cctatcaaca atgtggtgat ctcaaaaaat aagctaggtg caaaccgtac ctttaaatcg   360
ttgttgaccg aattgaaaac tacgcttacc gcagcaatca atcatcagaa catccctttt   420
cggaagatga cggagcattt gcatttagaa gctgtaaatg gagttcctgt cgtaaatacg   480
atggtttcta tgaaagaaat acataccatt gaattcagtc agagtgtagt ctccgatatc   540
ctattccaat ttgaatggga caagatgtg atttcattac atgtgaccta taacgaaaat   600
cgatacgata aaccattcat tacgcaaata atgaaccatg ttaactcttt atttgccgac   660
gttttatata ccccggaaag agtgctgcaa gacgtgaacc tgctatcaga gcaggagacg   720
gctcagcttc tttatgaatt caacgataca gcagcagact acccgcggga taagacgata   780
caccaattgt tgaagagca ggaggaacaa actccggacg cggtggcggt gctattcgag   840
gacaaacagc tgacctatgc ggagctgaat gccgctgcca atcgcattgc ccatctcctg   900
cgggaacgag gagtagcacg gggcactttg gttggcattt gtgtagagag atccctagag   960
atggtgattg gactgctggg gatcctcaaa gcaggcgggg catacgttcc gatcgatcct   1020
gactatccgg aggaacggac taacgccatg ctggaagata cggcaatcag cgtcctgctc   1080
acgcaggcgc atttgcagac aagcatgccg aacagcatcg attccgtctt gctcgatgca   1140
gcggcagaga cggctctgga aggaagctgg ccgaacttga cggatgcggc agggaccgcg   1200
gacgatgtgg cctacatcat ctatacgtcc gggtcgacgg gaattccgaa aggagtctgc   1260
gtcacgcatc gaggggtggt ccggctcatt gccgctgcca attatgtgga catcagcagc   1320
aaggacgtat ttctgcaagg ctcgacgata tcgttcgatg cggcaacgtt cgagatttgg   1380
ggcagcttgc tgaatggagc tgcgctggcc atttgcctc cgggaaatgt ttcgttgacc   1440
gaatggacag aggccattca acagcatcaa gtgacgatcc tgtggttaac ggcgggactc   1500
```

```
ttccacgtga tggtcgagaa ccaactccaa gccttgcaag gagtccagca attattggtg    1560
ggaggagacg tcgtctcgaa gacccatgcc aaaaaagtgc tggagcggta tcaggacatt    1620
cgtctggtca atgggtacgg tccaacggaa aatacgacct tcacctgctg ccacgagatt    1680
tccgccgccg atacgagcg gctctccatt ccgatcggac gtccgatcgc caatacgcaa    1740
gtgtacgtgc tggatgaagc aggcaagctg cttccggtag gagtggtcgg cgaattgtac    1800
accggaggag atggactggc ccgaggttac tggaatcgtc cggagctgac ggctgagaag    1860
ttcgtagaca gccccttcgt gccgggaaca cggctatacc gcacaggcga tctggcgaga    1920
tggctgccgg atggaacgat cgaatacgtg ggacgaatcg atgatcaagt gaaaattagc    1980
ggttaccgga ttgagcttgg cgaggtggaa gcgcatctgt tgaaagtgga atcggtgctg    2040
gacgcaatcg taatcgcccg gcaagacgaa agcggccaga gacgttgtg cgcgtacttt     2100
accgcgaatg cagagctgat ggcaggcgat ctgagagcag tgctgtcgca agaactgccg    2160
gcgtatatga tcccgacaca ctttgtgcag gtcgatcgga tgccgctgac gccgaacgga    2220
aaggtcgatc gcagagcgct gccggagccg gaaggcctca tcatgacagg aaaagagcat    2280
gtcgcgccgc ggacgccgct agagtctaat ctggcgcatc tgtggcaaga ggtgctcgga    2340
cttgagaaag tcagcgtgaa ggacagtttc ttcgagattg gcggacactc tttgcgtgcg    2400
acgacgctcg caagcaagct gcacaaggag ctgcatgtca gtctgccgct gcgggacatc    2460
ttccgccatc ctaccattga agagctgcg tgcctcattg acgggatgga acggcaggaa     2520
tacagacaga ttccgctgct ggatgaaagg gattggtacc cggtatcttc ggcgcaaaag    2580
aggctgtaca ttttgcatca gctggaaggg gcggagcaga gctacaacat gccggggtg     2640
atgctcctcg aagggcagct tgaccggaat cggttcgagg aggcgttccg cagcttgatc    2700
gggcgccacg aaacgctgcg caccggcttt gaaatggtga atggcgaacc ggtgcagcgt    2760
atatgccgcg aagtgaattt ctcggtggag atgatgcagg cgagcgaagg ggaagccgat    2820
gccgccatcc gttcctttat cgcccgttc gatctggaga agccgccgct cctccgagtg     2880
gggctgatcg agttaagcca ggatcggcat attctgatgt acgacatgca tcacatcata    2940
tccgacggcg tgtcgatgga aattgtggtg gaggagttcg tccgcttgta cggcggcgag    3000
aaactgccgc cgctgcgcat tcagtataag gattatgccg cgtggcagca gtccgagccg    3060
cagcaggagc tcatgaagca gcaggagagt tattggttgc aggcgtttgg cggagagctt    3120
ccggtgctgg aaatgccggc ggattatgcg cgtccttccg tccagagcta cgaaggggat    3180
accttcgaat tcgcgatcga tcctgggcta agcgaagcgc tgcgccggat tgcggcagag    3240
agcggaacga cattgtacat ggtgctgctt gctgcctata cgattctgct tcagaagtat    3300
acaggccagg aagacattat cgtgggaacg ccgaatgcgg gcagaacgca cggtgatttg    3360
cagccgctta tcggcatgtt cgtcaatacg ctggcgatcc gcaattatcc ggcaggctcg    3420
aagacgttcc tggaatattt ggagcaggtc aaagaaacga gcttgggcgc cttcgagaat    3480
caggattacc cgttcgaaga actggtggaa aagctgcagg tagcgcgaga tttgagccgc    3540
aatccgctgt tcgatacgat gttttctttg cacaatatgg acagcaagga tctggagctc    3600
gcagagcttc gcttgaagcc gtacccagct gaatacaagg tggcaaaatt cgacctgagc    3660
ctggacgtgg cggaaggcgc ggaagggatg gcatgcagtc tggaatacgc cacggcgcta    3720
tacagacggg aatcgattga agaatggcg aagcacttcg gccagctgct tgaggccatt     3780
acgcaagagc cggaggcgcg gctgtcctcg ctcggcatgc tcacagagga ggagaaggct    3840
cagattcagc atgtgttcaa cgatgcggag gcagggcgtt cgcagcagaa gacggtgcct    3900
```

-continued

```
gaattgttcg aggagcaggt ggagcgcacg ccggatcgga ttgcggtcgt gcatgaggac    3960
aagcagttga cgtaccggga gctgaacgaa cgggcgaacc ggctggcgcg cacgctgcgg    4020
gccgaggacg taaagcccga acagttggtc ggcatcatgg ccgatcgctc gctggacatg    4080
atcgtgggca ttatggccat cttgaaatcc ggcggcgcct atgtgccaat cgatccgaaa    4140
tatccggagg atcggattca ctatatgctg gacgattcga acgcgcaagt gctgctggcc    4200
cagcgtcatc tgcaagcgcg ggccgcattc tccggcagaa ggattacgct ggatgaggaa    4260
gcgttctacg acgaggacgg ctccaacctg gaacgggtga atcagccgga gcacctgagc    4320
tatgtcatct atacctcggg aacgacgggc aagccgaaag gggtcatgat cgagcacaga    4380
cagatggcag tcttgtcggc cgcgtgggaa agcgaatacg gcttgcggga agagagcatg    4440
cgctggatgc agtgggcgag cttttcattc gatgtcttct cgggagacct gatccgcgcg    4500
ctgctgcatg ggggtgaact catttttatgt ccggaagagt ccagggcgaa cccggccgaa    4560
atctacgagc tcattcgcaa gcatcggatt cagatgttcg atgtcactcc gtcgctcgcc    4620
attccgctga tggaatatgt atacgagaac aagctggaca tcagcagtat gaagctggca    4680
gtcgtagggg cggatcattg cccgaaggag gaattccaga agctgctgga acgattcggt    4740
tcgcaaatga ggatcgtgaa cagctacggg gtaacggaga cgaccatcga ttcctgctac    4800
ttcgagcagg cgagcacgga agggctgcga acgtgccaa tcggcaaacc tctgccgggt    4860
gtgacgatgt acattctgga tgatcaccat tctttgctgc cggtcgggat aacgggcgag    4920
ctctatattg gcggaccttg cgtgggccgg ggctattgga agcggccgga cctgacggcg    4980
gagaaattcg tcgacaatcc gttcgctccg ggcgagcgaa tgtaccggac aggcgacttg    5040
gcccggtggc tgccggacgg caacgtcgaa tatttgggc ggatcgatca tcaagtgaag    5100
atccggggct accggatcga gattggcgaa gtggagtccc aactgctgaa aacgccgttc    5160
atccgtgaag cggtcgtcgt cgcgcggaa gacgccggcg gacagaagtc attgtgcgca    5220
tacttcgtcg ccgaacgcga gctgacagtg agcgagctgc ggggagcatt ggccgcagaa    5280
ctgccgggtt acatgattcc atcgtacttc gtccagttga agcagctgcc gttgacgccg    5340
aacggaaaaa tcgaccgtaa agcgctgccg gctccggaag gaagcgcgca taccggaact    5400
gactatgtcg cgccgcgaac cgaggcggag aagactctgg cagccgtgtg gcaggctgta    5460
ttaggcgcag agcgtgttgg attgatggat catttcttcg agcttggagg cgactccatc    5520 aaaatcgattc aagtgtcttc ccggctgcat caagccggct acaagctgga atccgggat    5580 ttattcaaat atccgaccat cgcggagctc agtccgcata tccagccggt tggcagaatg    5640
gcagaccaag gcgaagtaag cggtacggta ccgctgactc cgattcaacg ctggtatttc    5700
gggcagcagt tcgccgatcc gcatcactat aaccaatcgg tcatgctgca ccggaaagag    5760
ggcttcgaca cagccgcgat ccgcaaggcg ctgcagaagc ttgtggagca tcatgatggg    5820
ctgcggatgt tgttccgcaa gacggaggaa ggatatacgg cgtggaatcg tggaatcgga    5880
gaaggcgagc tctatcgtct gtacgtggcg gactttacgg gggttgcggc gtgtgaacgg    5940
atgattgaag ccgcagcgaa cgagatacaa agcggcatcg atttgcaggc tggtccattg    6000
gtgagagccg ggttgttcca cggcgcggac ggggatcatt tgctcatcgt catccatcat    6060
gccgtcgttg acggcgtctc ttggcgcatc ttgctcgaag acttcgccgc aagctatgaa    6120
caagcgctga agggccaagc actgcgcttg ccttttcaaga ccgattccta tcgtacatgg    6180
tccgatcagc tcgttgaata cgcgcgcagt ccggtcatgc agcgcgaacg ggcgtattgg    6240
```

```
cagcgtatcg cgcagacggc agcgaagcct ctgcctaggg attatgaagc ggaatgctct    6300
ttgcagcagg atagtgaatc cgtcaccgtc cagtggagcc aagaggctac cgaacagcta    6360
ttgaagcatg tccatcgggc gtataacacg gaaatgaacg acattctgct gacggcgttg    6420
ggaatggccg tgcaaaaatg gtgtggccgc gacagagtgc tggttacgct ggaagggcac    6480
ggccgggaat ccatcatgac ggacatcgac atcacacgca ccgtcggttg gtttacgagc    6540
gagtatccgg tgttgctcga gatggagccg gacaaaagct tatcctcccg catcaagaag    6600
atgaaggagg acctgcgcca aattccgaac aaaggcatcg gctatggcat cggccgatat    6660
atgtccgagc tgcacgatga agccgtctgg ggaggagcag aaccggatat cagcttcaat    6720
tacttgggac agttcgatca ggatatgaag aacaatgaga tggaagtatc tccatattca    6780
agcggtatgg aagtgagccg tcaacaagcc cgcacccatg cgctggatat caacggaatg    6840
gtggcagacg ggtcactggc gctggaactg agttacagca ggaaggaata ccgcaaggag    6900
acaatcgagg cattgtccat atatctgcag gagagcctgc aggagattat actccattgc    6960
actgcgaaag aacggccgga ggtcacgccg agcgacatct tgctgcaagg attgagcgta    7020
gaggaactgg agcaaatagc gaagcagacg cagcgcatcg gagacatcga gaatatgtat    7080
accttgacgc cgatgcagaa ggggatgtgg ttccacagcg ccatggatca gcatgcgggc    7140
gcttattttg aacaaacgcg gtttaccctc cagggcgcgc tcgacgtaga ggtctttgcc    7200
aaaagcctga tgcattggc caagcaacat gccgtgctgc ggacgaactt ctataacggc    7260
tggaacggcg aactgctgca aattgtattt agagacaagc ggcttggatt cgcttatgaa    7320
gatttgtgcg ctttgccgga agccgagcga gagacgcatg tcgagacttt gacgcaagag    7380
gaccgtatgc ggggatttga tttggaacag gatgcgctca tgcgcgtatc ggtggtgcgc    7440
atggcggaag aaagctatca ggtgctgtgg agctcccatc atattctgat ggatggctgg    7500
tgcttgccgc agcttacaca ggaatggttc gacacatatt ccgcctatgt gcagcatcag    7560
catctcgagc ggacaacggc acctgcgtac agtcaatata tcgagtggtt ggaacaacag    7620
gatgaccaag cggcatcggc gtattgggcg aattatttgg ctggttatga ccaacaaacg    7680
gtactgccgc aagcgaaggg gcaaggtcgc agcgatgagt acgccgcgga gcgcatcttg    7740
tgcgaattgg gcaaggcctt gaccgggcgg atgagccatg tagccaagca gcaccaggtg    7800
acgctgaata cgttaatgca ggcggcatgg gccatccttt tgcagaaata caatggcaca    7860
gacgatgtgg tgttcggcgg ggtcgtatcg ggcagaccgg cggaaattcc agggattgaa    7920
gcgatgatcg gactgttcat caacacgatt ccggttcgcg tcacctgcga agcggagacg    7980
agctttgccg agttgatggg acggctgcag gagcaggcat tggaatccgg acgatacgat    8040
tattatccgc tgtatgagat tcaagcgcag tgcgagcaga agcaggatct aatttcccat    8100
ctcatggtat tcgagaacta cccgatggaa gaacagatgg agcaagccgg aagcgatgat    8160
cggggcaagc tgacgattac cgacgtcgag gtggcggaac aaacgaacta tgatttcaac    8220
ctggtcgtcg tgccaggtga cgaaattgtg attcgcctgg agtataacgc gaacgtgttc    8280
gatcgggaga gcatagagca gctgcagggt catctcgtgc atgtgcttga gcagattacg    8340
gccaacccgc atatggccgt gggcgagctg gaactggcga ccgccgggga gaaaacgcag    8400
ctgatgctcg cgttcaacga tacggcagcg gagtatccgc gggagaagac gatccatcag    8460
atgttcgaag aacaggccga acgaaccccg gatgcggcgg cggtcctgtt cgagcaggaa    8520
cagctgacgt accgggaact gaacgagcgc gcgaaccgct tggcccggac gctgcgagca    8580
ttaggagtac agccggatca gttggtcggc atcatggccg agcgttcgct ggagatgatg    8640
```

```
gttggcatca tggcgatttt gaaggctggc ggggcgtacg tgccgatcgc tgcggattct   8700
ccagaagagc gcatccgcta cctgctggag gattcgggag cgcaggtgct cttgctccag   8760
ggccgtgcgg gagaagaagt gtcctttgca ggccgcatcg ttaatctgga tgacgcaaat   8820
tcctatgccg cgacggttc gaatccggaa cgggtcaacc aggccagcga tgccgcttat   8880
gtcatctata cgtcggggac gacgggcaga ccgaaaggcg ttctggtgga gcacggttca   8940
gtcatcaacc gcttgctgtg gatgcagaaa cgatatccaa tcggtccgag cgatacgatt   9000
atgcagaaga cggcgattac gtttgacgtc tccgtctggg agctattctg gtgggctttc   9060
gtcggttcca aagtgtgcct gctgccggtc ggcggggaga agaacccggc cgtcattctg   9120
gatacgatcg agcggcagca tatcagcacg atgcattttg tgccgtccat gctgcatgcc   9180
ttccttgaat atgtcgagga gcagccggtc gcggaacggg agcgcagctt ggcttcattg   9240
cggcgggtgt tcgcgagtgg ggaggcacta actgcttcgc aggcagaaag attcgaacga   9300
tgcatcgcgc cggtgaatgg agcgcggctt atcaacctgt atgggccgac ggaagcgacc   9360
gtggatgtga cgtactttga ttgccaggca ggacagccat atacgagcgt gccgatcgga   9420
cgaccgattg acaatacgca aatctatatc gtgaaccggc agaatcaact gcagcctatc   9480
ggcgtagccg gggaattatg catcgcgggc gcaggcttgg ctcgaggcta ctgggagcgg   9540
ccggagctaa cggcggagaa attcgtggaa attccattca agcctagtga gcggatgtac   9600
cggacgggcg acttggcccg ctggctgccg gatggcaaca tcgaatattt aggccggctt   9660
gaccaccaag tgaaaattcg ggggtatcga atcgagcttg gcgaaatcga ggcccaactg   9720
ctgcaagccg cagccatccg ggaaacggtt gtcgtcgcgc gggaggatga gagcggacag   9780
aaagcattgt gtgcctactt cgccgcagac agcgagctga cggtaagcga gctgagatca   9840
gcgctggccg cacaattgcc ggactacatg attccgtcat acttcgtgca gcttgagcga   9900
ttgccgttgt cggcgaacgg gaaaatcgac cgcaaggcgc tgccgagccc agaaggaagc   9960
ttgtacaccg gaacagagta cgtcgccccg cggaccgagg cggaaaagac gatcgcagtc  10020
gtgtggcagg cggtgctggg catcgagcgg gtcggagtaa cggatcatt cttcgagctt  10080
ggcggcgatt ccatcaaatc cattcaagtg gcttcccggc tgcagcaggc cggctataag  10140
cttgaaatcc gggagctgtt caagtacccg accatcgcgc agttaagtct gcaggtccgg  10200
ccggttgcca aatggccga tcaaggagaa gtggcagggg agatgcctct gacaccaatc  10260
ttaagctggt tcatggaaca ggaattcgcg aatccgcatc actttaacca atcgattatg  10320
ctgcaccggc aggaagggtt cgacgaagtg gcgattcgaa aaacgctgca taatatcgtc  10380
gagcaccacg acgcgctgcg aatggtattc cgcaagacag aacatggcgg gtataaggcg  10440
tggaaccggc gaatcagcga aggcgatctc tacagtttgg acgtggcgga cttcaaagaa  10500
gatccggagt gcggccgttc gatcgaagcc aaggcgaatg agattcagag cggcatcgat  10560
ctgcagacgg gtccattggt gaaagcggga ttgttccact gtgcagacgg ggatcatcta  10620
ttgatcgtca tccatcatac cgtcatagac ggcatctctt ggcggatctt gcttgaagac  10680
attgcagatg ggtacgagca agcgttgaaa ggacaagaga ttcgtcttcc ggtcaaaacc  10740
gatagctacc gcatctggtc ggagcaactc gcaacgtacg cacatagttc tgacttggag  10800
aatgaacggg catactggca gcgcatcgcg cagacggaca cggagcctct gcccaaggac  10860
tgggaagcgg cctgctcctt gcagcgcgaa agcgagtccg tgaacgtcca atggagcagg  10920
gaggatacgg agcggctgtt gaagcatgtt caccgggcat acaatacgga gatgaacgat  10980
```

```
attttgctgg cggcattggg aatggccgtg cacaaatggt gcggtcgcga tcgagtgctg    11040
gtcacgctgg aaggccacgg ccgggaatcc atcttgacgg atatcgacat tacgcgtacc    11100
gtgggatggt ttacaagcga atatccagtt ttgattgaag cggagccgga caagacattg    11160
tcttatcgga tcaaacaggt gaaggagaat ttgcgccgca ttccgaacaa gggcatcggg    11220
tatggcatct gccgatattt atcgtctgcg caagaacctg catggacgga agcgttcacg    11280
cctgaacttc gcttcaacta tttgggacag ttcgatcagg atctgcaagg caacgagttg    11340
gaattatcat cttattcaag cggttcggat atgagtgacg aacaggtgcg caattacagt    11400
ttggatatta gcggaatgat cgtggatggc ttgctatcgc tggacgtgag ttacagcggc    11460
aaggaatacc gcaaggaaac catcgaagag ttggccggat gtttgctggt gagcctgcag    11520
gagatcattg accattgcgc agcaaaggaa cgtcctgaat taacgccgag cgatgttttg    11580
ctgcaaggat tgagcgtgga ggagcttgat cagatcgcgg aacaaacgcg gcgcaacgga    11640
gaaatcgaaa atatttatac gctgacgcca atgcagaaag gcatgtggtt ccacagcgcg    11700
atggaccggc agtcggggc gtatcatgaa cagacacgat ttacgataga aggagagctc    11760
gatacagatg tcttcgtcaa gagcctggac gcattggcga acaatcacgc cgtgctgcga    11820
acgaacttcc tgagcggctg gaatggcgaa ccgctgcaag tcgtgttccg cgataagcga    11880
attggattcg cttatgcaga tttgcgggag ctgcaagaag cggatcggaa cagatgcatc    11940
gaaaaatcgg cagctgagga tcatgctcgc ggattcgatc tggagcagga tgcgctgatg    12000
cgcgtaatgg tcatgcgtac gggagaatca agttatcagg tgatctggag ttcgcatcat    12060
attttgatgg acggctggtg cttgcctcag cttgccaaag agctgtttga cacgtactcc    12120
gtctacttgc agcagcacca ccccgagcag gcaacatcgg tgccggcgta cagtcaatat    12180
atcgaatggc tggagcagca agatgaagca gcggcctccg catattggag cgaatatctg    12240
gctggatatg atcagcaagc ggcattgccg caacagacgg cgcaaggccg gggcgaagaa    12300
tacgttgccg agaagctgac ctgcgaatta ggcaaaacct tgagcggacg catgagcagg    12360
gtggccagac agcatcaggt caccttgaat acgctgctgc aagcggcatg gggcatcatc    12420
ctgcagaaat acaacggaac ccgcgacaca gtgttcggca cgtcgtatc cggaaggccg    12480 gcggagattc cgggaatcga agcgatgatt gggttatta tcaacacgat accggtccgg    12540
gtcagctgcg aggcgaagac gagcttcgcg gaagtgatgg ggcggctgca agagcaggcg    12600
ttagaatctg gcaagtacga ctattatccg ttgtatgaaa ttcaggcccg ctgctcgcaa    12660
aagcaagatt taatatcgca gattatggtg ttcgagaact acccgatgga tgaacagatg    12720
gagcaagcag gcaacgacga tcagggaatg ctggcgataa cgaacgtcga agtggccgag    12780
caaacgaact atgatttcaa cttcatcgtc gtgccaggag aagagattgt catcaacttc    12840
gattacaatg cgcgcgtttt tgatcggacg agcatggagc ggttgcaagg tcatctggtg    12900
aatgttctgg aacaaatcgc ggccaacccg caagtgaccg taggggaact taagctggcg    12960 accgaggcg agcaagcgga gattacaagc atattcaata atgcgcgaac ggaatatccg    13020
cgggataaga cgattcaccg cttattcgag gagcaggcgg aacgaacccc tgatgcgatt    13080
gccgtcatgt atgagaacag tcagttgaca taccgagaat tgaacgaacg ggcgaaccgg    13140
ttggctagga cgctgagagc cgatggtgca ggggctgacc gtttggtggg tctgatggtt    13200
gaacgttccc tagacatgat ggtggggata atagcgattt tgaagtctgg aggggcatac    13260
gtgccaatcg acccggaata tccggaagag cgaatccgtt acatgctcga ggactccggg    13320
acgcaaatca tcgtaacgca gcgtcatctg caagagcgaa ttccgggggc aggcacacgc    13380
```

```
gtcatcttag atgatgagca ctcttatagc agcgacagca cgaatctgga tctgaacaac   13440
ggtcctgccg acttggcata tgtcatatac acgtcgggca cgacgggcaa accgaaaggg   13500
aatttgacga tgcaccgcaa tatcgtgcgg gtcgttcaag gcgctgacta tatcgacatt   13560
ggagagcagg acaatgtgct gcagctatcc agctatgcct tcgacggctc aacattcgat   13620
atgtacggag ctttgctgaa cggagccaga ctcgttctta ttccgcaaga gaccttgttg   13680
gatgtagaac ggctcgcaga gctaatcgaa cgcgagcgca tctccgtcat gttcattaca   13740
accgcgttct tcaatgtgct cgttgatgtg aaggctgact gcctgcgcca tattcgcgcc   13800
attttgttcg gcggagagcg cgtttccgtc agccatgtcc gcaaagcgct gcgtcatttg   13860
ggaccaggca aaatcaagca tgtttacggt ccgacggaga gtacggtttt tgccacttgt   13920
cacgacgtga atgaagtggc ggcggatgcc ctcaatgttc cgattggacg cccgatcagc   13980
aacacaacga tttacatcgt caacgaagag aacggcttgc agccgattgg ggtggccgga   14040
gaattgtgcg tagccggaga cgggctcgcg cggggctact tgaaccgtcc ggagttgacg   14100
gcggagaagt tcgtggacaa cccgttcgtt ccaggagagc ggatgtaccg gacaggtgac   14160
ttggcaagat ggctgccgga tggaagcatc gaatatgtag gcaggatcga ccatcaggtt   14220
aaaatacgcg gctatcgcat tgaattaggc gaagtggagg cgcatctgct gaaagtccag   14280
cctgttcagg aagggaccgt tgtcgcccgg gaaaccggaa gcggcgagaa gcagctgtgc   14340
gcatactttg tggcggaaag cacgctatcg gctagtgagc tgcgcggcgc tatggcgcaa   14400
caattgccgg gatacatgat cccgtcctat tttgtccagc tggagcggat gccgctgacg   14460
ccgaacggca aggttgacca gaaagcgctg cctgcgccgg aagagcatgt gcagacagga   14520
acggaatata ttgcgccccg cacgcctcag gaggagcagt tggcccgaat ctggcaagag   14580
gtgctcggac tggagaaggt cggcgtaaat gacaacttct tcgagctcgg cggacactcc   14640
ttgcgcgcca ctacgatggc aagcaagctg cataaggagc tgagcattga gctgccgctg   14700
cgggacgtat ttaagcaccc gaccctcgaa gcgatggctg agcgcattgc cggattggga   14760
cagcagatgt acacgtccat tccgctggtc gaagagcaag cgcattatcc gctatcctcg   14820
gcccagaaga ggctgtatat tttgcatcag ctggaaggag cggagcttag ctataacatg   14880
ccgaacatgc tgctgctgga gggggcgctc gatcggagc ggttcgaagc ggcgttccgc   14940
aagctgattg ctcggcacga atcgttccgc accggcttcg aaatgattaa cggcgaaccg   15000
atgcagcgga tatacgagaa tgtggacttt gcggtggagt atatgcaagc aagcgacaaa   15060
gaagccgaag caaggctgcg tcaattcgtg cgcgcgttca gcttgaggag gccgccgctc   15120
ctgcgggtag gattgatcga attggctcag gaacgccata ttctgatgtt cgatatgcat   15180
catatcgttt ccgacggcac gtcgatggga attctcatca acgaattcgt ccgcttgtac   15240
ggcggagaag aactgcagcc gctgcgcatt cagtacaagg attttgccgc atggcagcaa   15300
tccgacgcgc ggcaagagca gatgaagcaa caggaagctt attggctgca ggcgcttggc   15360
ggagagctgc cggtgctgga aatgccaacg gaccatgtac ggcctgctgt tcagagcttc   15420
cggggagata tactgcaatt cgttatcggc cgggaccaat gcgcagcatt gcggcatatc   15480
ggttcggaga acgcgcaac gttgtatatg gtgctattgg cagcctatac cgctctgctg   15540
cacaaatata cggacagga agacatcatc gtaggtacgc cgatcgcagg cagaaaccat   15600
ggagatgtgc agccgctcat cgggatgttc gtcaacacgc tggccatccg caattatccg   15660
atgggcgaga agacattcca ttcctacttg gaggaagtaa aagacacgac cttgggcgct   15720
```

```
tatgaaaacc agaactatcc gttcgaggat ctggtggaga acgtgcaggt cgcgcgggat    15780
atgagccgga atccgatttt tgacacgatg tttattttac aaaatgcgga gcagggcgag    15840
atgaatatca acgggctgca tatcgcgaac tatcagagcg agcataccgt gtcgaagttt    15900
gacttgacgt tccaggccga ggaagcggaa gaggagattg tgtgtagcat cgaatatgct    15960
accgagctat acgagctcga gacggtggaa cggatggcgg gccactttac gcagctcatc    16020
gatgccgtgg tcggaaatcc gcatgcaagg ctggcatcgc tgcagatggt gactgccgag    16080
gagcaggatc agatacaaaa tattttcaac gcgactgaca tgggctatcc gcgcgagaag    16140
actatccatc agatgttcga ggagcaggcg gagcgtacgc cggatgcgcc ggccgtctcc    16200 tttgggacg agatgctgac gtaccgggag ttgaaccgga aggcgaatca gctggcttgg    16260
gtgctgaggg acagaggggt cgcatcagag cggcccgtgg gaatcatggt cgagcgttcg    16320
atcgccatgg tcgtcggcgt attggctgtg ctcaaggcgg gcggaacgtt cgtcccgatc    16380
gatccggaat atccggagac gcggatccgt tacatgctgg aggatagcgg cgccaagctg    16440
gcgttgaccg agctggcctg gttcgaggtg attcctcccg aggtggagaa ggtagatatt    16500
cacgatgcat cgctctatca agggcatgac gagaacgtgc gaatgagag cgaaccgtcg    16560 aacttgctct atatcatcta cacgtccggc acgacgggca atccgaaggg cgtcatgctg    16620
gagcagcgca atttaatcaa tttgctgcat tatgagcagg tcggaacgag cattccgctt    16680
ccgtcccgca tattgcagta tgcgtcgaac agcttcgatg tgtgctacca ggagatgttc    16740
tccgcgctgt tgttcggggg ctgcctgttc ttgattccga acgaggcgcg taaagatccg    16800
gcgcaattgt tcacctggat tcaggacaac gggatcgagg tgctgtatct cccggtcgcg    16860
ttcctgaaat tcatctttgc cgagccggaa tgggcggaac gcttcccgga ctgtgtcacg    16920
catattatca ctgccgggga gcagctggtc gtcacgccgc agatccaagc gtgcctgcag    16980
cggcttcgca tcagcctgca caatcattac ggtccatcgg aaacgcatgt ggttaccgct    17040
tatacgatgg agccggacga tatcgcggtc ggcctgccgc cgattggcgc gccgattgcg    17100
aatacggcca tttacatctt gaacgacagg ctggagctgc agccgatcgg catcgcaggc    17160
gagctgtacg tgtccgggga ttgcgtaggt cgcggatatt ggggacgcca agagctgacg    17220
gacgagaaat tcatcgccaa cccgttcgcg ccgggcgacc tcatgtacaa gacgggagat    17280
gtggcgcggt ggctgccaga cggcaccatc gaatatgtag gccggagcga ccatcaggtg    17340
aaaattcgcg ggttccggat cgagctcggc gaggtggagt cgcagctctt gagcgtggaa    17400
ttcgtgcagg aagcgaccgt catggcccgg gaagatgacg gaggacagaa gcaattgtgc    17460
gcgtacttcg tggcggagcg gccgctgtcg gcagcggagc tgagagggg cttgtcccag    17520 gatttgccgg gatacatgat tccgtcgtac ttcgtacagc tggatcggct gccgttgacg    17580
ccgaacggaa agatcgaccg cagagcgctg ccggagccgg aaggcagcct gcataccgga    17640
gcggagttcg tagctccgcg cacgccgctg gaagcgcagc tggcccgaat ctggcaagat    17700
gtgctgggtc tgccggacgt gagcgtgaag gataatttct tcgatttggg tggacactcc    17760
ttgcgcgcga cgaccttggc aagcaaggtg ttcaaggaaa tgcacgtcaa tctgccgctg    17820
cgggatgtat tccggtgccc gacgattgag gagatggccg gatgatagc cgggatggag    17880 aagcaggaat atgccgcgat cccgttggct gaggaaagtg acgtctaccc gttgtcatcc    17940
gcccagaagc ggctgtacat cgtgagccag ttggaagggg cagatctgag ctacaacatg    18000
ccgggagtcg tgtcgctcga aggaacgctg gatcgcgagc gctttgaatt ggcattcttg    18060
aagctgattt cgcggcatga gacgctgcgc accggcttcg acatggttga cggggagccg    18120
```

```
atacagcgcg tgcaccgcag cgtgaagttt gtcgttgagc accgtaaggc ggctaccgtg   18180
caggatgctg agcagctcat tcgccgcttc atccgcacgt ttgatttgcg gaagccgcct   18240
ctgctccgtg ttgggctggt ggaattggaa cgagagcgtc atattttgat gttcgacatg   18300
catcacatta tttccgacgg tgcttccttg gggaatctgg tcagcgagtt cgcacagttg   18360
tatgcgggag aggagcgggc tccgctccgc attcaataca aggattacgc ggtgtggcag   18420 cagtccgag tgcacagcga gcacatgaaa cgtcaggaag cgtattggtt ggagaagctg   18480
gccggggaat tgccggttgt cgagctgccg accgattacg accggcctgc cgtccgcagc   18540
ttcgaaggag cgcagatcga gttcgaagtc gacgccgctc tcacccaacg tttgagccag   18600
cttgcgtcga atcgcgagag cacgctatac atggttctgt tgtccgcata ccgtgctg   18660 ctctccaaat acagcggaca ggaagacatc atcgtgggaa ctcctgtcgc gggaagagcg   18720
catgcggatt tggagccgct catcgggatg tttgtcaaca cattggccat cgcaatcat   18780 ccggcaggag acaagacctt cctgtcctta ctggaggaag tgaaggaaac ggccttgggc   18840
gccttcgagc atcaagatta tccgtttgag gaactggtag aacgcctgaa tgtgcaatgg   18900
gacgcaaacc ggaatccggt gttcgacacg atgtttgtca tgcaaaatac agaggaccat   18960
gaggtgcgat tggaagctct aaccttgtct ccttatgtgc ttgacaatcc gatcgatgcg   19020
aaattcgatc tcacgctgtt cgtttccgaa gacaatgatg taattaaggg aggcttccaa   19080
tacggcacca agttgttcaa ggctgccatg attcataaga tcatgagaga cttcctgctt   19140
gtgctggctc aaatcgtcga agaccccac attcggttac gcgatatcaa gtgcaatgag   19200
caatccgtta caatcagcg ctctattgaa acgatagagt tcgcattcta g            19251

<210> SEQ ID NO 7
<211> LENGTH: 6416
<212> TYPE: PRT
<213> ORGANISM: Paenibacillus thiaminolyticus OSY-SE

<400> SEQUENCE: 7

Met Asn Leu Ala Phe Glu Lys Glu Thr Asp Phe Trp Asn Ala Gln Phe
1               5                   10                  15

Asp Ala Glu Asp Ser Pro Ala Ile Leu Pro Tyr Ser Thr Ala Ser Ile
            20                  25                  30

Ser Val Thr Ala Arg Asp His Ser Asn Ser Ile Ser Leu Ser Ala Asp
        35                  40                  45

Val Ser Gln Arg Ile Ser His Met Ser Arg Gly Ser His Leu Ala Glu
    50                  55                  60

Tyr Met Ile Leu Leu Ala Gly Ile Gln Cys Leu Leu Tyr Lys Tyr Thr
65                  70                  75                  80

Gly Glu Glu Ser Val Ile Val Gly Met Pro Ile Val Arg Lys Ser Lys
                85                  90                  95

Asp Thr Arg Arg Pro Ile Asn Asn Val Val Ile Leu Lys Asn Lys Leu
            100                 105                 110

Gly Ala Asn Arg Thr Phe Lys Ser Leu Leu Thr Glu Leu Lys Thr Thr
        115                 120                 125

Leu Thr Ala Ala Ile Asn His Gln Asn Ile Pro Phe Arg Lys Met Thr
    130                 135                 140

Glu His Leu His Leu Glu Ala Val Asn Gly Val Pro Val Val Asn Thr
145                 150                 155                 160

Met Val Ser Met Lys Glu Ile His Thr Ile Glu Phe Ser Gln Ser Val
                165                 170                 175
```

```
Val Ser Asp Ile Leu Phe Gln Phe Glu Trp Glu Gln Asp Val Ile Ser
            180                 185                 190

Leu His Val Thr Tyr Asn Glu Asn Arg Tyr Asp Lys Pro Phe Ile Thr
            195                 200                 205

Gln Ile Met Asn His Val Asn Ser Leu Phe Ala Asp Val Leu Tyr Thr
        210                 215                 220

Pro Glu Arg Val Leu Gln Asp Val Asn Leu Leu Ser Glu Gln Glu Thr
225                 230                 235                 240

Ala Gln Leu Leu Tyr Glu Phe Asn Asp Thr Ala Ala Asp Tyr Pro Arg
                245                 250                 255

Asp Lys Thr Ile His Gln Leu Phe Glu Glu Glu Glu Gln Thr Pro
            260                 265                 270

Asp Ala Val Ala Val Leu Phe Glu Asp Lys Gln Leu Thr Tyr Ala Glu
            275                 280                 285

Leu Asn Ala Ala Ala Asn Arg Ile Ala His Leu Leu Arg Glu Arg Gly
        290                 295                 300

Val Ala Arg Gly Thr Leu Val Gly Ile Cys Val Glu Arg Ser Leu Glu
305                 310                 315                 320

Met Val Ile Gly Leu Leu Gly Ile Leu Lys Ala Gly Gly Ala Tyr Val
                325                 330                 335

Pro Ile Asp Pro Asp Tyr Pro Glu Glu Arg Thr Asn Ala Met Leu Glu
            340                 345                 350

Asp Thr Ala Ile Ser Val Leu Leu Thr Gln Ala His Leu Gln Thr Ser
        355                 360                 365

Met Pro Asn Ser Ile Asp Ser Val Leu Leu Asp Ala Ala Ala Glu Thr
        370                 375                 380

Ala Leu Glu Gly Ser Trp Pro Asn Leu Thr Asp Ala Ala Gly Thr Ala
385                 390                 395                 400

Asp Asp Val Ala Tyr Ile Ile Tyr Thr Ser Gly Ser Thr Gly Ile Pro
                405                 410                 415

Lys Gly Val Cys Val Thr His Arg Gly Val Val Arg Leu Ile Ala Ala
            420                 425                 430

Ala Asn Tyr Val Asp Ile Ser Ser Lys Asp Val Phe Leu Gln Gly Ser
        435                 440                 445

Thr Ile Ser Phe Asp Ala Ala Thr Phe Glu Ile Trp Gly Ser Leu Leu
        450                 455                 460

Asn Gly Ala Ala Leu Ala Ile Leu Pro Pro Gly Asn Val Ser Leu Thr
465                 470                 475                 480

Glu Trp Thr Glu Ala Ile Gln Gln His Gln Val Thr Ile Leu Trp Leu
                485                 490                 495

Thr Ala Gly Leu Phe His Val Met Val Glu Asn Gln Leu Gln Ala Leu
            500                 505                 510

Gln Gly Val Gln Gln Leu Leu Val Gly Gly Asp Val Val Ser Lys Thr
        515                 520                 525

His Ala Lys Lys Val Leu Glu Arg Tyr Gln Asp Ile Arg Leu Val Asn
        530                 535                 540

Gly Tyr Gly Pro Thr Glu Asn Thr Thr Phe Thr Cys Cys His Glu Ile
545                 550                 555                 560

Ser Ala Ala Asp Thr Glu Arg Leu Ser Ile Pro Ile Gly Arg Pro Ile
                565                 570                 575

Ala Asn Thr Gln Val Tyr Val Leu Asp Glu Ala Gly Lys Leu Leu Pro
            580                 585                 590
```

Val Gly Val Gly Glu Leu Tyr Thr Gly Gly Asp Gly Leu Ala Arg
        595                 600             605

Gly Tyr Trp Asn Arg Pro Glu Leu Thr Ala Glu Lys Phe Val Asp Ser
    610                 615                 620

Pro Phe Val Pro Gly Thr Arg Leu Tyr Arg Thr Gly Asp Leu Ala Arg
625                 630                 635                 640

Trp Leu Pro Asp Gly Thr Ile Glu Tyr Val Gly Arg Ile Asp Asp Gln
            645                 650                 655

Val Lys Ile Ser Gly Tyr Arg Ile Glu Leu Gly Glu Val Glu Ala His
            660                 665                 670

Leu Leu Lys Val Glu Ser Val Leu Asp Ala Ile Val Ile Ala Arg Gln
            675                 680                 685

Asp Glu Ser Gly Gln Lys Thr Leu Cys Ala Tyr Phe Thr Ala Asn Ala
    690                 695                 700

Glu Leu Met Ala Gly Asp Leu Arg Ala Val Leu Ser Gln Glu Leu Pro
705                 710                 715                 720

Ala Tyr Met Ile Pro Thr His Phe Val Gln Val Asp Arg Met Pro Leu
                725                 730                 735

Thr Pro Asn Gly Lys Val Asp Arg Arg Ala Leu Pro Glu Pro Glu Gly
            740                 745                 750

Leu Ile Met Thr Gly Lys Glu His Val Ala Pro Arg Thr Pro Leu Glu
            755                 760                 765

Ser Asn Leu Ala His Leu Trp Gln Glu Val Leu Gly Leu Glu Lys Val
    770                 775                 780

Ser Val Lys Asp Ser Phe Phe Glu Ile Gly Gly His Ser Leu Arg Ala
785                 790                 795                 800

Thr Thr Leu Ala Ser Lys Leu His Lys Glu Leu His Val Ser Leu Pro
                805                 810                 815

Leu Arg Asp Ile Phe Arg His Pro Thr Ile Glu Glu Leu Ala Cys Leu
            820                 825                 830

Ile Asp Gly Met Glu Arg Gln Glu Tyr Arg Gln Ile Pro Leu Leu Asp
            835                 840                 845

Glu Arg Asp Trp Tyr Pro Val Ser Ser Ala Gln Lys Arg Leu Tyr Ile
    850                 855                 860

Leu His Gln Leu Glu Gly Ala Glu Gln Ser Tyr Asn Met Pro Gly Val
865                 870                 875                 880

Met Leu Leu Glu Gly Gln Leu Asp Arg Asn Arg Phe Glu Glu Ala Phe
                885                 890                 895

Arg Ser Leu Ile Gly Arg His Glu Thr Leu Arg Thr Gly Phe Glu Met
            900                 905                 910

Val Asn Gly Glu Pro Val Gln Arg Ile Cys Arg Glu Val Asn Phe Ser
    915                 920                 925

Val Glu Met Met Gln Ala Ser Glu Gly Glu Ala Asp Ala Ala Ile Arg
930                 935                 940

Ser Phe Ile Arg Pro Phe Asp Leu Glu Lys Pro Leu Leu Arg Val
945                 950                 955                 960

Gly Leu Ile Glu Leu Ser Gln Asp Arg His Ile Leu Met Tyr Asp Met
            965                 970                 975

His His Ile Ile Ser Asp Gly Val Ser Met Glu Ile Val Glu Glu
            980                 985                 990

Phe Val Arg Leu Tyr Gly Gly Glu Lys Leu Pro Pro Leu Arg Ile Gln
    995                 1000                1005

Tyr Lys Asp Tyr Ala Ala Trp Gln Gln Ser Glu Pro Gln Gln Glu

-continued

```
            1010                1015                1020
Leu Met Lys Gln Gln Glu Ser Tyr Trp Leu Gln Ala Phe Gly Gly
        1025                1030                1035
Glu Leu Pro Val Leu Glu Met Pro Ala Asp Tyr Ala Arg Pro Ser
    1040                1045                1050
Val Gln Ser Tyr Glu Gly Asp Thr Phe Glu Phe Ala Ile Asp Pro
1055                1060                1065
Gly Leu Ser Glu Ala Leu Arg Arg Ile Ala Ala Glu Ser Gly Thr
    1070                1075                1080
Thr Leu Tyr Met Val Leu Leu Ala Ala Tyr Thr Ile Leu Leu Gln
        1085                1090                1095
Lys Tyr Thr Gly Gln Glu Asp Ile Ile Val Gly Thr Pro Asn Ala
        1100                1105                1110
Gly Arg Thr His Gly Asp Leu Gln Pro Leu Ile Gly Met Phe Val
        1115                1120                1125
Asn Thr Leu Ala Ile Arg Asn Tyr Pro Ala Gly Ser Lys Thr Phe
    1130                1135                1140
Leu Glu Tyr Leu Glu Gln Val Lys Glu Thr Ser Leu Gly Ala Phe
    1145                1150                1155
Glu Asn Gln Asp Tyr Pro Phe Glu Glu Leu Val Glu Lys Leu Gln
    1160                1165                1170
Val Ala Arg Asp Leu Ser Arg Asn Pro Leu Phe Asp Thr Met Phe
    1175                1180                1185
Ser Leu His Asn Met Asp Ser Lys Asp Leu Glu Leu Ala Glu Leu
    1190                1195                1200
Arg Leu Lys Pro Tyr Pro Ala Glu Tyr Lys Val Ala Lys Phe Asp
    1205                1210                1215
Leu Ser Leu Asp Val Ala Gly Ala Glu Gly Met Ala Cys Ser
    1220                1225                1230
Leu Glu Tyr Ala Thr Ala Leu Tyr Arg Arg Glu Ser Ile Glu Arg
    1235                1240                1245
Met Ala Lys His Phe Gly Gln Leu Leu Glu Ala Ile Thr Gln Glu
    1250                1255                1260
Pro Glu Ala Arg Leu Ser Ser Leu Gly Met Leu Thr Glu Glu Glu
    1265                1270                1275
Lys Ala Gln Ile Gln His Val Phe Asn Asp Ala Glu Ala Gly Arg
    1280                1285                1290
Ser Gln Gln Lys Thr Val Pro Glu Leu Phe Glu Glu Gln Val Glu
    1295                1300                1305
Arg Thr Pro Asp Arg Ile Ala Val Val His Glu Asp Lys Gln Leu
    1310                1315                1320
Thr Tyr Arg Glu Leu Asn Glu Arg Ala Asn Arg Leu Ala Arg Thr
    1325                1330                1335
Leu Arg Ala Glu Asp Val Lys Pro Glu Gln Leu Val Gly Ile Met
    1340                1345                1350
Ala Asp Arg Ser Leu Asp Met Ile Val Gly Ile Met Ala Ile Leu
    1355                1360                1365
Lys Ser Gly Gly Ala Tyr Val Pro Ile Asp Pro Lys Tyr Pro Glu
    1370                1375                1380
Asp Arg Ile His Tyr Met Leu Asp Asp Ser Asn Ala Gln Val Leu
    1385                1390                1395
Leu Ala Gln Arg His Leu Gln Ala Arg Ala Ala Phe Ser Gly Arg
    1400                1405                1410
```

```
Arg Ile Thr Leu Asp Glu Glu Ala Phe Tyr Asp Glu Asp Gly Ser
1415                1420                1425

Asn Leu Glu Arg Val Asn Gln Pro Glu His Leu Ser Tyr Val Ile
1430                1435                1440

Tyr Thr Ser Gly Thr Thr Gly Lys Pro Lys Gly Val Met Ile Glu
1445                1450                1455

His Arg Gln Met Ala Val Leu Ser Ala Ala Trp Glu Ser Glu Tyr
1460                1465                1470

Gly Leu Arg Glu Glu Ser Met Arg Trp Met Gln Trp Ala Ser Phe
1475                1480                1485

Ser Phe Asp Val Phe Ser Gly Asp Leu Ile Arg Ala Leu Leu His
1490                1495                1500

Gly Gly Glu Leu Ile Leu Cys Pro Glu Glu Ser Arg Ala Asn Pro
1505                1510                1515

Ala Glu Ile Tyr Glu Leu Ile Arg Lys His Arg Ile Gln Met Phe
1520                1525                1530

Asp Val Thr Pro Ser Leu Ala Ile Pro Leu Met Glu Tyr Val Tyr
1535                1540                1545

Glu Asn Lys Leu Asp Ile Ser Ser Met Lys Leu Ala Val Val Gly
1550                1555                1560

Ala Asp His Cys Pro Lys Glu Glu Phe Gln Lys Leu Leu Glu Arg
1565                1570                1575

Phe Gly Ser Gln Met Arg Ile Val Asn Ser Tyr Gly Val Thr Glu
1580                1585                1590

Thr Thr Ile Asp Ser Cys Tyr Phe Glu Gln Ala Ser Thr Glu Gly
1595                1600                1605

Leu Arg Thr Val Pro Ile Gly Lys Pro Leu Pro Gly Val Thr Met
1610                1615                1620

Tyr Ile Leu Asp Asp His His Ser Leu Leu Pro Val Gly Ile Thr
1625                1630                1635

Gly Glu Leu Tyr Ile Gly Gly Pro Cys Val Gly Arg Gly Tyr Trp
1640                1645                1650

Lys Arg Pro Asp Leu Thr Ala Glu Lys Phe Val Asp Asn Pro Phe
1655                1660                1665

Ala Pro Gly Glu Arg Met Tyr Arg Thr Gly Asp Leu Ala Arg Trp
1670                1675                1680

Leu Pro Asp Gly Asn Val Glu Tyr Leu Gly Arg Ile Asp His Gln
1685                1690                1695

Val Lys Ile Arg Gly Tyr Arg Ile Glu Ile Gly Glu Val Glu Ser
1700                1705                1710

Gln Leu Leu Lys Thr Pro Phe Ile Arg Glu Ala Val Val Val Ala
1715                1720                1725

Arg Glu Asp Ala Gly Gly Gln Lys Ser Leu Cys Ala Tyr Phe Val
1730                1735                1740

Ala Glu Arg Glu Leu Thr Val Ser Glu Leu Arg Gly Ala Leu Ala
1745                1750                1755

Ala Glu Leu Pro Gly Tyr Met Ile Pro Ser Tyr Phe Val Gln Leu
1760                1765                1770

Lys Gln Leu Pro Leu Thr Pro Asn Gly Lys Ile Asp Arg Lys Ala
1775                1780                1785

Leu Pro Ala Pro Glu Gly Ser Ala His Thr Gly Thr Asp Tyr Val
1790                1795                1800
```

Ala Pro Arg Thr Glu Ala Glu Lys Thr Leu Ala Ala Val Trp Gln
1805                1810                1815

Ala Val Leu Gly Ala Glu Arg Val Gly Leu Met Asp His Phe Phe
1820                1825                1830

Glu Leu Gly Gly Asp Ser Ile Lys Ser Ile Gln Val Ser Ser Arg
1835                1840                1845

Leu His Gln Ala Gly Tyr Lys Leu Glu Ile Arg Asp Leu Phe Lys
1850                1855                1860

Tyr Pro Thr Ile Ala Glu Leu Ser Pro His Ile Gln Pro Val Gly
1865                1870                1875

Arg Met Ala Asp Gln Gly Glu Val Ser Gly Thr Val Pro Leu Thr
1880                1885                1890

Pro Ile Gln Arg Trp Tyr Phe Gly Gln Gln Phe Ala Asp Pro His
1895                1900                1905

His Tyr Asn Gln Ser Val Met Leu His Arg Lys Glu Gly Phe Asp
1910                1915                1920

Thr Ala Ala Ile Arg Lys Ala Leu Gln Lys Leu Val Glu His His
1925                1930                1935

Asp Gly Leu Arg Met Val Phe Arg Lys Thr Glu Glu Gly Tyr Thr
1940                1945                1950

Ala Trp Asn Arg Gly Ile Gly Glu Gly Glu Leu Tyr Arg Leu Tyr
1955                1960                1965

Val Ala Asp Phe Thr Gly Val Ala Ala Cys Glu Arg Met Ile Glu
1970                1975                1980

Ala Ala Ala Asn Glu Ile Gln Ser Gly Ile Asp Leu Gln Ala Gly
1985                1990                1995

Pro Leu Val Arg Ala Gly Leu Phe His Gly Ala Asp Gly Asp His
2000                2005                2010

Leu Leu Ile Val Ile His His Ala Val Val Asp Gly Val Ser Trp
2015                2020                2025

Arg Ile Leu Leu Glu Asp Phe Ala Ala Ser Tyr Glu Gln Ala Leu
2030                2035                2040

Lys Gly Gln Ala Leu Arg Leu Pro Phe Lys Thr Asp Ser Tyr Arg
2045                2050                2055

Thr Trp Ser Asp Gln Leu Val Glu Tyr Ala Arg Ser Pro Val Met
2060                2065                2070

Gln Arg Glu Arg Ala Tyr Trp Gln Arg Ile Ala Gln Thr Ala Ala
2075                2080                2085

Lys Pro Leu Pro Arg Asp Tyr Glu Ala Glu Cys Ser Leu Gln Gln
2090                2095                2100

Asp Ser Glu Ser Val Thr Val Gln Trp Ser Gln Glu Ala Thr Glu
2105                2110                2115

Gln Leu Leu Lys His Val His Arg Ala Tyr Asn Thr Glu Met Asn
2120                2125                2130

Asp Ile Leu Leu Thr Ala Leu Gly Met Ala Val Gln Lys Trp Cys
2135                2140                2145

Gly Arg Asp Arg Val Leu Val Thr Leu Glu Gly His Gly Arg Glu
2150                2155                2160

Ser Ile Met Thr Asp Ile Asp Ile Thr Arg Thr Val Gly Trp Phe
2165                2170                2175

Thr Ser Glu Tyr Pro Val Leu Leu Glu Met Glu Pro Asp Lys Ser
2180                2185                2190

Leu Ser Ser Arg Ile Lys Lys Met Lys Glu Asp Leu Arg Gln Ile

```
                2195                2200                2205
Pro Asn Lys Gly Ile Gly Tyr Gly Ile Gly Arg Tyr Met Ser Glu
    2210                2215                2220

Leu His Asp Glu Ala Val Trp Gly Gly Ala Glu Pro Asp Ile Ser
    2225                2230                2235

Phe Asn Tyr Leu Gly Gln Phe Asp Gln Asp Met Lys Asn Asn Glu
    2240                2245                2250

Met Glu Val Ser Pro Tyr Ser Ser Gly Met Glu Val Ser Arg Gln
    2255                2260                2265

Gln Ala Arg Thr His Ala Leu Asp Ile Asn Gly Met Val Ala Asp
    2270                2275                2280

Gly Ser Leu Ala Leu Glu Leu Ser Tyr Ser Arg Lys Glu Tyr Arg
    2285                2290                2295

Lys Glu Thr Ile Glu Ala Leu Ser Ile Tyr Leu Gln Glu Ser Leu
    2300                2305                2310

Gln Glu Ile Ile Leu His Cys Thr Ala Lys Glu Arg Pro Glu Val
    2315                2320                2325

Thr Pro Ser Asp Ile Leu Leu Gln Gly Leu Ser Val Glu Glu Leu
    2330                2335                2340

Glu Gln Ile Ala Lys Gln Thr Gln Arg Ile Gly Asp Ile Glu Asn
    2345                2350                2355

Met Tyr Thr Leu Thr Pro Met Gln Lys Gly Met Trp Phe His Ser
    2360                2365                2370

Ala Met Asp Gln His Ala Gly Ala Tyr Phe Glu Gln Thr Arg Phe
    2375                2380                2385

Thr Leu Gln Gly Ala Leu Asp Val Glu Val Phe Ala Lys Ser Leu
    2390                2395                2400

Asp Ala Leu Ala Lys Gln His Ala Val Leu Arg Thr Asn Phe Tyr
    2405                2410                2415

Asn Gly Trp Asn Gly Glu Leu Leu Gln Ile Val Phe Arg Asp Lys
    2420                2425                2430

Arg Leu Gly Phe Ala Tyr Glu Asp Leu Cys Ala Leu Pro Glu Ala
    2435                2440                2445

Glu Arg Glu Thr His Val Glu Thr Leu Thr Gln Glu Asp Arg Met
    2450                2455                2460

Arg Gly Phe Asp Leu Glu Gln Asp Ala Leu Met Arg Val Ser Val
    2465                2470                2475

Val Arg Met Ala Glu Glu Ser Tyr Gln Val Leu Trp Ser Ser His
    2480                2485                2490

His Ile Leu Met Asp Gly Trp Cys Leu Pro Gln Leu Thr Gln Glu
    2495                2500                2505

Trp Phe Asp Thr Tyr Ser Ala Tyr Val Gln His Gln His Leu Glu
    2510                2515                2520

Arg Thr Thr Ala Pro Ala Tyr Ser Gln Tyr Ile Glu Trp Leu Glu
    2525                2530                2535

Gln Gln Asp Asp Gln Ala Ala Ser Ala Tyr Trp Ala Asn Tyr Leu
    2540                2545                2550

Ala Gly Tyr Asp Gln Gln Thr Val Leu Pro Gln Ala Lys Gly Gln
    2555                2560                2565

Gly Arg Ser Asp Glu Tyr Ala Ala Glu Arg Ile Leu Cys Glu Leu
    2570                2575                2580

Gly Lys Ala Leu Thr Gly Arg Met Ser His Val Ala Lys Gln His
    2585                2590                2595
```

-continued

```
Gln Val Thr Leu Asn Thr Leu Met Gln Ala Ala Trp Ala Ile Leu
                2600              2605              2610

Leu Gln Lys Tyr Asn Gly Thr Asp Asp Val Val Phe Gly Gly Val
                2615              2620              2625

Val Ser Gly Arg Pro Ala Glu Ile Pro Gly Ile Glu Ala Met Ile
                2630              2635              2640

Gly Leu Phe Ile Asn Thr Ile Pro Val Arg Val Thr Cys Glu Ala
                2645              2650              2655

Glu Thr Ser Phe Ala Glu Leu Met Gly Arg Leu Gln Glu Gln Ala
                2660              2665              2670

Leu Glu Ser Gly Arg Tyr Asp Tyr Tyr Pro Leu Tyr Glu Ile Gln
                2675              2680              2685

Ala Gln Cys Glu Gln Lys Gln Asp Leu Ile Ser His Leu Met Val
                2690              2695              2700

Phe Glu Asn Tyr Pro Met Glu Glu Gln Met Gln Ala Gly Ser
                2705              2710              2715

Asp Asp Arg Gly Lys Leu Thr Ile Thr Asp Val Glu Val Ala Glu
                2720              2725              2730

Gln Thr Asn Tyr Asp Phe Asn Leu Val Val Val Pro Gly Asp Glu
                2735              2740              2745

Ile Val Ile Arg Leu Glu Tyr Asn Ala Asn Val Phe Asp Arg Glu
                2750              2755              2760

Ser Ile Glu Gln Leu Gln Gly His Leu Val His Val Leu Glu Gln
                2765              2770              2775

Ile Thr Ala Asn Pro His Met Ala Val Gly Glu Leu Glu Leu Ala
                2780              2785              2790

Thr Ala Gly Glu Lys Thr Gln Leu Met Leu Ala Phe Asn Asp Thr
                2795              2800              2805

Ala Ala Glu Tyr Pro Arg Glu Lys Thr Ile His Gln Met Phe Glu
                2810              2815              2820

Glu Gln Ala Glu Arg Thr Pro Asp Ala Ala Val Leu Phe Glu
                2825              2830              2835

Gln Glu Gln Leu Thr Tyr Arg Glu Leu Asn Glu Arg Ala Asn Arg
                2840              2845              2850

Leu Ala Arg Thr Leu Arg Ala Leu Gly Val Gln Pro Asp Gln Leu
                2855              2860              2865

Val Gly Ile Met Ala Glu Arg Ser Leu Glu Met Met Val Gly Ile
                2870              2875              2880

Met Ala Ile Leu Lys Ala Gly Gly Ala Tyr Val Pro Ile Ala Ala
                2885              2890              2895

Asp Ser Pro Glu Glu Arg Ile Arg Tyr Leu Leu Glu Asp Ser Gly
                2900              2905              2910

Ala Gln Val Leu Leu Leu Gln Gly Arg Ala Gly Glu Glu Val Ser
                2915              2920              2925

Phe Ala Gly Arg Ile Val Asn Leu Asp Asp Ala Asn Ser Tyr Ala
                2930              2935              2940

Gly Asp Gly Ser Asn Pro Glu Arg Val Asn Gln Ala Ser Asp Ala
                2945              2950              2955

Ala Tyr Val Ile Tyr Thr Ser Gly Thr Thr Gly Arg Pro Lys Gly
                2960              2965              2970

Val Leu Val Glu His Gly Ser Val Ile Asn Arg Leu Leu Trp Met
                2975              2980              2985
```

```
Gln Lys Arg Tyr Pro Ile Gly Pro Ser Asp Thr Ile Met Gln Lys
    2990              2995                3000

Thr Ala Ile Thr Phe Asp Val Ser Val Trp Glu Leu Phe Trp Trp
3005              3010                3015

Ala Phe Val Gly Ser Lys Val Cys Leu Leu Pro Val Gly Gly Glu
3020              3025                3030

Lys Asn Pro Ala Val Ile Leu Asp Thr Ile Glu Arg Gln His Ile
3035              3040                3045

Ser Thr Met His Phe Val Pro Ser Met Leu His Ala Phe Leu Glu
3050              3055                3060

Tyr Val Glu Glu Gln Pro Val Ala Glu Arg Glu Arg Ser Leu Ala
3065              3070                3075

Ser Leu Arg Arg Val Phe Ala Ser Gly Glu Ala Leu Thr Ala Ser
3080              3085                3090

Gln Ala Glu Arg Phe Glu Arg Cys Ile Ala Pro Val Asn Gly Ala
3095              3100                3105

Arg Leu Ile Asn Leu Tyr Gly Pro Thr Glu Ala Thr Val Asp Val
3110              3115                3120

Thr Tyr Phe Asp Cys Gln Ala Gly Gln Pro Tyr Thr Ser Val Pro
3125              3130                3135

Ile Gly Arg Pro Ile Asp Asn Thr Gln Ile Tyr Ile Val Asn Arg
3140              3145                3150

Gln Asn Gln Leu Gln Pro Ile Gly Val Ala Gly Glu Leu Cys Ile
3155              3160                3165

Ala Gly Ala Gly Leu Ala Arg Gly Tyr Trp Glu Arg Pro Glu Leu
3170              3175                3180

Thr Ala Glu Lys Phe Val Glu Ile Pro Phe Lys Pro Ser Glu Arg
3185              3190                3195

Met Tyr Arg Thr Gly Asp Leu Ala Arg Trp Leu Pro Asp Gly Asn
3200              3205                3210

Ile Glu Tyr Leu Gly Arg Leu Asp His Gln Val Lys Ile Arg Gly
3215              3220                3225

Tyr Arg Ile Glu Leu Gly Glu Ile Glu Ala Gln Leu Leu Gln Ala
3230              3235                3240

Ala Ala Ile Arg Glu Thr Val Val Val Ala Arg Glu Asp Glu Ser
3245              3250                3255

Gly Gln Lys Ala Leu Cys Ala Tyr Phe Ala Ala Asp Ser Glu Leu
3260              3265                3270

Thr Val Ser Glu Leu Arg Ser Ala Leu Ala Ala Gln Leu Pro Asp
3275              3280                3285

Tyr Met Ile Pro Ser Tyr Phe Val Gln Leu Glu Arg Leu Pro Leu
3290              3295                3300

Ser Ala Asn Gly Lys Ile Asp Arg Lys Ala Leu Pro Ser Pro Glu
3305              3310                3315

Gly Ser Leu Tyr Thr Gly Thr Glu Tyr Val Ala Pro Arg Thr Glu
3320              3325                3330

Ala Glu Lys Thr Ile Ala Val Val Trp Gln Ala Val Leu Gly Ile
3335              3340                3345

Glu Arg Val Gly Val Thr Asp His Phe Phe Glu Leu Gly Gly Asp
3350              3355                3360

Ser Ile Lys Ser Ile Gln Val Ala Ser Arg Leu Gln Gln Ala Gly
3365              3370                3375

Tyr Lys Leu Glu Ile Arg Glu Leu Phe Lys Tyr Pro Thr Ile Ala
```

-continued

```
              3380                3385                   3390

Gln Leu Ser Leu Gln Val Arg Pro Val Ala Arg Met Ala Asp Gln
              3395                3400                   3405

Gly Glu Val Ala Gly Glu Met Pro Leu Thr Pro Ile Leu Ser Trp
              3410                3415                   3420

Phe Met Glu Gln Glu Phe Ala Asn Pro His His Phe Asn Gln Ser
              3425                3430                   3435

Ile Met Leu His Arg Gln Glu Gly Phe Asp Glu Val Ala Ile Arg
              3440                3445                   3450

Lys Thr Leu His Asn Ile Val Glu His His Asp Ala Leu Arg Met
              3455                3460                   3465

Val Phe Arg Lys Thr Glu His Gly Gly Tyr Lys Ala Trp Asn Arg
              3470                3475                   3480

Gly Ile Ser Glu Gly Asp Leu Tyr Ser Leu Asp Val Ala Asp Phe
              3485                3490                   3495

Lys Glu Asp Pro Glu Cys Gly Arg Ser Ile Glu Ala Lys Ala Asn
              3500                3505                   3510

Glu Ile Gln Ser Gly Ile Asp Leu Gln Thr Gly Pro Leu Val Lys
              3515                3520                   3525

Ala Gly Leu Phe His Cys Ala Asp Gly Asp His Leu Leu Ile Val
              3530                3535                   3540

Ile His His Thr Val Ile Asp Gly Ile Ser Trp Arg Ile Leu Leu
              3545                3550                   3555

Glu Asp Ile Ala Asp Gly Tyr Glu Gln Ala Leu Lys Gly Gln Glu
              3560                3565                   3570

Ile Arg Leu Pro Val Lys Thr Asp Ser Tyr Arg Ile Trp Ser Glu
              3575                3580                   3585

Gln Leu Ala Thr Tyr Ala His Ser Ser Asp Leu Glu Asn Glu Arg
              3590                3595                   3600

Ala Tyr Trp Gln Arg Ile Ala Gln Thr Asp Thr Glu Pro Leu Pro
              3605                3610                   3615

Lys Asp Trp Glu Ala Ala Cys Ser Leu Gln Arg Glu Ser Glu Ser
              3620                3625                   3630

Val Asn Val Gln Trp Ser Arg Glu Asp Thr Glu Arg Leu Leu Lys
              3635                3640                   3645

His Val His Arg Ala Tyr Asn Thr Glu Met Asn Asp Ile Leu Leu
              3650                3655                   3660

Ala Ala Leu Gly Met Ala Val His Lys Trp Cys Gly Arg Asp Arg
              3665                3670                   3675

Val Leu Val Thr Leu Glu Gly His Gly Arg Glu Ser Ile Leu Thr
              3680                3685                   3690

Asp Ile Asp Ile Thr Arg Thr Val Gly Trp Phe Thr Ser Glu Tyr
              3695                3700                   3705

Pro Val Leu Ile Glu Ala Glu Pro Asp Lys Thr Leu Ser Tyr Arg
              3710                3715                   3720

Ile Lys Gln Val Lys Glu Asn Leu Arg Arg Ile Pro Asn Lys Gly
              3725                3730                   3735

Ile Gly Tyr Gly Ile Cys Arg Tyr Leu Ser Ser Ala Gln Glu Pro
              3740                3745                   3750

Ala Trp Thr Glu Ala Phe Thr Pro Glu Leu Arg Phe Asn Tyr Leu
              3755                3760                   3765

Gly Gln Phe Asp Gln Asp Leu Gln Gly Asn Glu Leu Glu Leu Ser
              3770                3775                   3780
```

```
Ser Tyr Ser Ser Gly Ser Asp Met Ser Asp Glu Gln Val Arg Asn
3785             3790                3795

Tyr Ser Leu Asp Ile Ser Gly Met Ile Val Asp Gly Leu Leu Ser
3800             3805                3810

Leu Asp Val Ser Tyr Ser Gly Lys Glu Tyr Arg Lys Glu Thr Ile
3815             3820                3825

Glu Glu Leu Ala Gly Cys Leu Leu Val Ser Leu Gln Glu Ile Ile
3830             3835                3840

Asp His Cys Ala Ala Lys Glu Arg Pro Glu Leu Thr Pro Ser Asp
3845             3850                3855

Val Leu Leu Gln Gly Leu Ser Val Glu Glu Leu Asp Gln Ile Ala
3860             3865                3870

Glu Gln Thr Arg Arg Asn Gly Glu Ile Glu Asn Ile Tyr Thr Leu
3875             3880                3885

Thr Pro Met Gln Lys Gly Met Trp Phe His Ser Ala Met Asp Arg
3890             3895                3900

Gln Ser Gly Ala Tyr His Glu Gln Thr Arg Phe Thr Ile Glu Gly
3905             3910                3915

Glu Leu Asp Thr Asp Val Phe Val Lys Ser Leu Asp Ala Leu Ala
3920             3925                3930

Asn Asn His Ala Val Leu Arg Thr Asn Phe Leu Ser Gly Trp Asn
3935             3940                3945

Gly Glu Pro Leu Gln Val Val Phe Arg Asp Lys Arg Ile Gly Phe
3950             3955                3960

Ala Tyr Ala Asp Leu Arg Glu Leu Gln Glu Ala Asp Arg Asn Arg
3965             3970                3975

Cys Ile Glu Lys Ser Ala Ala Glu Asp His Ala Arg Gly Phe Asp
3980             3985                3990

Leu Glu Gln Asp Ala Leu Met Arg Val Met Val Met Arg Thr Gly
3995             4000                4005

Glu Ser Ser Tyr Gln Val Ile Trp Ser Ser His His Ile Leu Met
4010             4015                4020

Asp Gly Trp Cys Leu Pro Gln Leu Ala Lys Glu Leu Phe Asp Thr
4025             4030                4035

Tyr Ser Val Tyr Leu Gln Gln His His Pro Glu Gln Ala Thr Ser
4040             4045                4050

Val Pro Ala Tyr Ser Gln Tyr Ile Glu Trp Leu Glu Gln Gln Asp
4055             4060                4065

Glu Ala Ala Ala Ser Ala Tyr Trp Ser Glu Tyr Leu Ala Gly Tyr
4070             4075                4080

Asp Gln Gln Ala Ala Leu Pro Gln Gln Thr Ala Gln Gly Arg Gly
4085             4090                4095

Glu Glu Tyr Val Ala Glu Lys Leu Thr Cys Glu Leu Gly Lys Thr
4100             4105                4110

Leu Ser Gly Arg Met Ser Arg Val Ala Arg Gln His Gln Val Thr
4115             4120                4125

Leu Asn Thr Leu Leu Gln Ala Ala Trp Gly Ile Ile Leu Gln Lys
4130             4135                4140

Tyr Asn Gly Thr Arg Asp Thr Val Phe Gly Ser Val Val Ser Gly
4145             4150                4155

Arg Pro Ala Glu Ile Pro Gly Ile Glu Ala Met Ile Gly Leu Phe
4160             4165                4170
```

```
Ile Asn Thr Ile Pro Val Arg Val Ser Cys Glu Ala Lys Thr Ser
4175                4180                4185

Phe Ala Glu Val Met Gly Arg Leu Gln Glu Gln Ala Leu Glu Ser
4190                4195                4200

Gly Lys Tyr Asp Tyr Tyr Pro Leu Tyr Glu Ile Gln Ala Arg Cys
4205                4210                4215

Ser Gln Lys Gln Asp Leu Ile Ser Gln Ile Met Val Phe Glu Asn
4220                4225                4230

Tyr Pro Met Asp Glu Gln Met Glu Gln Ala Gly Asn Asp Asp Gln
4235                4240                4245

Gly Met Leu Ala Ile Thr Asn Val Glu Val Ala Glu Gln Thr Asn
4250                4255                4260

Tyr Asp Phe Asn Phe Ile Val Val Pro Gly Glu Glu Ile Val Ile
4265                4270                4275

Asn Phe Asp Tyr Asn Ala Arg Val Phe Asp Arg Thr Ser Met Glu
4280                4285                4290

Arg Leu Gln Gly His Leu Val Asn Val Leu Glu Gln Ile Ala Ala
4295                4300                4305

Asn Pro Gln Val Thr Val Gly Glu Leu Lys Leu Ala Thr Glu Ala
4310                4315                4320

Glu Gln Ala Glu Ile Thr Ser Ile Phe Asn Asn Ala Arg Thr Glu
4325                4330                4335

Tyr Pro Arg Asp Lys Thr Ile His Arg Leu Phe Glu Gln Ala
4340                4345                4350

Glu Arg Thr Pro Asp Ala Ile Ala Val Met Tyr Glu Asn Ser Gln
4355                4360                4365

Leu Thr Tyr Arg Glu Leu Asn Glu Arg Ala Asn Arg Leu Ala Arg
4370                4375                4380

Thr Leu Arg Ala Asp Gly Ala Gly Ala Asp Arg Leu Val Gly Leu
4385                4390                4395

Met Val Glu Arg Ser Leu Asp Met Met Val Gly Ile Ile Ala Ile
4400                4405                4410

Leu Lys Ser Gly Gly Ala Tyr Val Pro Ile Asp Pro Glu Tyr Pro
4415                4420                4425

Glu Glu Arg Ile Arg Tyr Met Leu Glu Asp Ser Gly Thr Gln Ile
4430                4435                4440

Ile Val Thr Gln Arg His Leu Gln Glu Arg Ile Pro Gly Ala Gly
4445                4450                4455

Thr Arg Val Ile Leu Asp Asp Glu His Ser Tyr Ser Ser Asp Ser
4460                4465                4470

Thr Asn Leu Asp Leu Asn Asn Gly Pro Ala Asp Leu Ala Tyr Val
4475                4480                4485

Ile Tyr Thr Ser Gly Thr Thr Gly Lys Pro Lys Gly Asn Leu Thr
4490                4495                4500

Met His Arg Asn Ile Val Arg Val Val Gln Gly Ala Asp Tyr Ile
4505                4510                4515

Asp Ile Gly Glu Gln Asp Asn Val Leu Gln Leu Ser Ser Tyr Ala
4520                4525                4530

Phe Asp Gly Ser Thr Phe Asp Met Tyr Gly Ala Leu Leu Asn Gly
4535                4540                4545

Ala Arg Leu Val Leu Ile Pro Gln Glu Thr Leu Leu Asp Val Glu
4550                4555                4560

Arg Leu Ala Glu Leu Ile Glu Arg Glu Arg Ile Ser Val Met Phe
```

```
                4565                4570                4575

Ile Thr Thr Ala Phe Phe Asn Val Leu Val Asp Val Lys Ala Asp
    4580                4585                4590

Cys Leu Arg His Ile Arg Ala Ile Leu Phe Gly Gly Glu Arg Val
    4595                4600                4605

Ser Val Ser His Val Arg Lys Ala Leu Arg His Leu Gly Pro Gly
    4610                4615                4620

Lys Ile Lys His Val Tyr Gly Pro Thr Glu Ser Thr Val Phe Ala
    4625                4630                4635

Thr Cys His Asp Val Asn Glu Val Ala Ala Asp Ala Leu Asn Val
    4640                4645                4650

Pro Ile Gly Arg Pro Ile Ser Asn Thr Thr Ile Tyr Ile Val Asn
    4655                4660                4665

Glu Glu Asn Gly Leu Gln Pro Ile Gly Val Ala Gly Glu Leu Cys
    4670                4675                4680

Val Ala Gly Asp Gly Leu Ala Arg Gly Tyr Leu Asn Arg Pro Glu
    4685                4690                4695

Leu Thr Ala Glu Lys Phe Val Asp Asn Pro Phe Val Pro Gly Glu
    4700                4705                4710

Arg Met Tyr Arg Thr Gly Asp Leu Ala Arg Trp Leu Pro Asp Gly
    4715                4720                4725

Ser Ile Glu Tyr Val Gly Arg Ile Asp His Gln Val Lys Ile Arg
    4730                4735                4740

Gly Tyr Arg Ile Glu Leu Gly Glu Val Glu Ala His Leu Leu Lys
    4745                4750                4755

Val Gln Pro Val Gln Glu Gly Thr Val Val Ala Arg Glu Thr Gly
    4760                4765                4770

Ser Gly Glu Lys Gln Leu Cys Ala Tyr Phe Val Ala Glu Ser Thr
    4775                4780                4785

Leu Ser Ala Ser Glu Leu Arg Gly Ala Met Ala Gln Gln Leu Pro
    4790                4795                4800

Gly Tyr Met Ile Pro Ser Tyr Phe Val Gln Leu Glu Arg Met Pro
    4805                4810                4815

Leu Thr Pro Asn Gly Lys Val Asp Gln Lys Ala Leu Pro Ala Pro
    4820                4825                4830

Glu Glu His Val Gln Thr Gly Thr Glu Tyr Ile Ala Pro Arg Thr
    4835                4840                4845

Pro Gln Glu Glu Gln Leu Ala Arg Ile Trp Gln Glu Val Leu Gly
    4850                4855                4860

Leu Glu Lys Val Gly Val Asn Asp Asn Phe Phe Glu Leu Gly Gly
    4865                4870                4875

His Ser Leu Arg Ala Thr Thr Met Ala Ser Lys Leu His Lys Glu
    4880                4885                4890

Leu Ser Ile Glu Leu Pro Leu Arg Asp Val Phe Lys His Pro Thr
    4895                4900                4905

Leu Glu Ala Met Ala Glu Arg Ile Ala Gly Leu Gly Gln Gln Met
    4910                4915                4920

Tyr Thr Ser Ile Pro Leu Val Glu Glu Gln Ala His Tyr Pro Leu
    4925                4930                4935

Ser Ser Ala Gln Lys Arg Leu Tyr Ile Leu His Gln Leu Glu Gly
    4940                4945                4950

Ala Glu Leu Ser Tyr Asn Met Pro Asn Met Leu Leu Leu Glu Gly
    4955                4960                4965
```

-continued

```
Ala Leu Asp Arg Glu Arg Phe Glu Ala Ala Phe Arg Lys Leu Ile
    4970                4975                4980

Ala Arg His Glu Ser Phe Arg Thr Gly Phe Glu Met Ile Asn Gly
    4985                4990                4995

Glu Pro Met Gln Arg Ile Tyr Glu Asn Val Asp Phe Ala Val Glu
    5000                5005                5010

Tyr Met Gln Ala Ser Asp Lys Glu Ala Glu Ala Arg Leu Arg Gln
    5015                5020                5025

Phe Val Arg Ala Phe Lys Leu Glu Glu Pro Pro Leu Leu Arg Val
    5030                5035                5040

Gly Leu Ile Glu Leu Ala Gln Glu Arg His Ile Leu Met Phe Asp
    5045                5050                5055

Met His His Ile Val Ser Asp Gly Thr Ser Met Gly Ile Leu Ile
    5060                5065                5070

Asn Glu Phe Val Arg Leu Tyr Gly Gly Glu Glu Leu Gln Pro Leu
    5075                5080                5085

Arg Ile Gln Tyr Lys Asp Phe Ala Ala Trp Gln Gln Ser Asp Ala
    5090                5095                5100

Arg Gln Glu Gln Met Lys Gln Gln Glu Ala Tyr Trp Leu Gln Ala
    5105                5110                5115

Leu Gly Gly Glu Leu Pro Val Leu Glu Met Pro Thr Asp His Val
    5120                5125                5130

Arg Pro Ala Val Gln Ser Phe Arg Gly Asp Ile Leu Gln Phe Val
    5135                5140                5145

Ile Gly Arg Asp Gln Cys Ala Ala Leu Arg His Ile Gly Ser Glu
    5150                5155                5160

Asn Gly Ala Thr Leu Tyr Met Val Leu Leu Ala Ala Tyr Thr Ala
    5165                5170                5175

Leu Leu His Lys Tyr Thr Gly Gln Glu Asp Ile Ile Val Gly Thr
    5180                5185                5190

Pro Ile Ala Gly Arg Asn His Gly Asp Val Gln Pro Leu Ile Gly
    5195                5200                5205

Met Phe Val Asn Thr Leu Ala Ile Arg Asn Tyr Pro Met Gly Glu
    5210                5215                5220

Lys Thr Phe His Ser Tyr Leu Glu Glu Val Lys Asp Thr Thr Leu
    5225                5230                5235

Gly Ala Tyr Glu Asn Gln Asn Tyr Pro Phe Glu Asp Leu Val Glu
    5240                5245                5250

Asn Val Gln Val Ala Arg Asp Met Ser Arg Asn Pro Ile Phe Asp
    5255                5260                5265

Thr Met Phe Ile Leu Gln Asn Ala Glu Gln Gly Glu Met Asn Ile
    5270                5275                5280

Asn Gly Leu His Ile Ala Asn Tyr Gln Ser Glu His Thr Val Ser
    5285                5290                5295

Lys Phe Asp Leu Thr Phe Gln Ala Glu Glu Ala Glu Glu Glu Ile
    5300                5305                5310

Val Cys Ser Ile Glu Tyr Ala Thr Glu Leu Tyr Glu Leu Glu Thr
    5315                5320                5325

Val Glu Arg Met Ala Gly His Phe Thr Gln Leu Ile Asp Ala Val
    5330                5335                5340

Val Gly Asn Pro His Ala Arg Leu Ala Ser Leu Gln Met Val Thr
    5345                5350                5355
```

-continued

```
Ala Glu Glu Gln Asp Gln Ile Gln Asn Ile Phe Asn Ala Thr Asp
    5360                5365                5370
Met Gly Tyr Pro Arg Glu Lys Thr Ile His Gln Met Phe Glu Glu
    5375                5380                5385
Gln Ala Glu Arg Thr Pro Asp Ala Pro Ala Val Ser Phe Gly Asp
    5390                5395                5400
Glu Met Leu Thr Tyr Arg Glu Leu Asn Arg Lys Ala Asn Gln Leu
    5405                5410                5415
Ala Trp Val Leu Arg Asp Arg Gly Val Ala Ser Glu Arg Pro Val
    5420                5425                5430
Gly Ile Met Val Glu Arg Ser Ile Ala Met Val Val Gly Val Leu
    5435                5440                5445
Ala Val Leu Lys Ala Gly Gly Thr Phe Val Pro Ile Asp Pro Glu
    5450                5455                5460
Tyr Pro Glu Thr Arg Ile Arg Tyr Met Leu Glu Asp Ser Gly Ala
    5465                5470                5475
Lys Leu Ala Leu Thr Glu Leu Ala Trp Phe Glu Val Ile Pro Pro
    5480                5485                5490
Glu Val Glu Lys Val Asp Ile His Asp Ala Ser Leu Tyr Gln Gly
    5495                5500                5505
His Asp Glu Asn Val Pro Asn Glu Ser Glu Pro Ser Asn Leu Leu
    5510                5515                5520
Tyr Ile Ile Tyr Thr Ser Gly Thr Thr Gly Asn Pro Lys Gly Val
    5525                5530                5535
Met Leu Glu Gln Arg Asn Leu Ile Asn Leu Leu His Tyr Glu Gln
    5540                5545                5550
Val Gly Thr Ser Ile Pro Leu Pro Ser Arg Ile Leu Gln Tyr Ala
    5555                5560                5565
Ser Asn Ser Phe Asp Val Cys Tyr Gln Glu Met Phe Ser Ala Leu
    5570                5575                5580
Leu Phe Gly Gly Cys Leu Phe Leu Ile Pro Asn Glu Ala Arg Lys
    5585                5590                5595
Asp Pro Ala Gln Leu Phe Thr Trp Ile Gln Asp Asn Gly Ile Glu
    5600                5605                5610
Val Leu Tyr Leu Pro Val Ala Phe Leu Lys Phe Ile Phe Ala Glu
    5615                5620                5625
Pro Glu Trp Ala Glu Arg Phe Pro Asp Cys Val Thr His Ile Ile
    5630                5635                5640
Thr Ala Gly Glu Gln Leu Val Val Thr Pro Gln Ile Gln Ala Cys
    5645                5650                5655
Leu Gln Arg Leu Arg Ile Ser Leu His Asn His Tyr Gly Pro Ser
    5660                5665                5670
Glu Thr His Val Val Thr Ala Tyr Thr Met Glu Pro Asp Asp Ile
    5675                5680                5685
Ala Val Gly Leu Pro Pro Ile Gly Ala Pro Ile Ala Asn Thr Ala
    5690                5695                5700
Ile Tyr Ile Leu Asn Asp Arg Leu Glu Leu Gln Pro Ile Gly Ile
    5705                5710                5715
Ala Gly Glu Leu Tyr Val Ser Gly Asp Cys Val Gly Arg Gly Tyr
    5720                5725                5730
Trp Gly Arg Gln Glu Leu Thr Asp Glu Lys Phe Ile Ala Asn Pro
    5735                5740                5745
Phe Ala Pro Gly Asp Leu Met Tyr Lys Thr Gly Asp Val Ala Arg
```

```
                    5750                    5755                    5760
Trp Leu Pro Asp Gly Thr Ile Glu Tyr Val Gly Arg Ser Asp His
    5765                    5770                    5775
Gln Val Lys Ile Arg Gly Phe Arg Ile Glu Leu Gly Glu Val Glu
    5780                    5785                    5790
Ser Gln Leu Leu Ser Val Glu Phe Val Gln Glu Ala Thr Val Met
    5795                    5800                    5805
Ala Arg Glu Asp Asp Gly Gly Gln Lys Gln Leu Cys Ala Tyr Phe
    5810                    5815                    5820
Val Ala Glu Arg Pro Leu Ser Ala Ala Glu Leu Arg Gly Gly Leu
    5825                    5830                    5835
Ser Gln Asp Leu Pro Gly Tyr Met Ile Pro Ser Tyr Phe Val Gln
    5840                    5845                    5850
Leu Asp Arg Leu Pro Leu Thr Pro Asn Gly Lys Ile Asp Arg Arg
    5855                    5860                    5865
Ala Leu Pro Glu Pro Glu Gly Ser Leu His Thr Gly Ala Glu Phe
    5870                    5875                    5880
Val Ala Pro Arg Thr Pro Leu Glu Ala Gln Leu Ala Arg Ile Trp
    5885                    5890                    5895
Gln Asp Val Leu Gly Leu Pro Asp Val Ser Val Lys Asp Asn Phe
    5900                    5905                    5910
Phe Asp Leu Gly Gly His Ser Leu Arg Ala Thr Thr Leu Ala Ser
    5915                    5920                    5925
Lys Val Phe Lys Glu Met His Val Asn Leu Pro Leu Arg Asp Val
    5930                    5935                    5940
Phe Arg Cys Pro Thr Ile Glu Glu Met Ala Gly Met Ile Ala Gly
    5945                    5950                    5955
Met Glu Lys Gln Glu Tyr Ala Ala Ile Pro Leu Ala Glu Glu Ser
    5960                    5965                    5970
Asp Val Tyr Pro Leu Ser Ser Ala Gln Lys Arg Leu Tyr Ile Val
    5975                    5980                    5985
Ser Gln Leu Glu Gly Ala Asp Leu Ser Tyr Asn Met Pro Gly Val
    5990                    5995                    6000
Val Ser Leu Glu Gly Thr Leu Asp Arg Glu Arg Phe Glu Leu Ala
    6005                    6010                    6015
Phe Leu Lys Leu Ile Ser Arg His Glu Thr Leu Arg Thr Gly Phe
    6020                    6025                    6030
Asp Met Val Asp Gly Glu Pro Ile Gln Arg Val His Arg Ser Val
    6035                    6040                    6045
Lys Phe Val Val Glu His Arg Lys Ala Ala Thr Val Gln Asp Ala
    6050                    6055                    6060
Glu Gln Leu Ile Arg Arg Phe Ile Arg Thr Phe Asp Leu Arg Lys
    6065                    6070                    6075
Pro Pro Leu Leu Arg Val Gly Leu Val Glu Leu Glu Arg Glu Arg
    6080                    6085                    6090
His Ile Leu Met Phe Asp Met His His Ile Ile Ser Asp Gly Ala
    6095                    6100                    6105
Ser Leu Gly Asn Leu Val Ser Glu Phe Ala Gln Leu Tyr Ala Gly
    6110                    6115                    6120
Glu Glu Arg Ala Pro Leu Arg Ile Gln Tyr Lys Asp Tyr Ala Val
    6125                    6130                    6135
Trp Gln Gln Ser Gly Val His Ser Glu His Met Lys Arg Gln Glu
    6140                    6145                    6150
```

| Ala | Tyr | Trp | Leu | Glu | Lys | Leu | Ala | Gly | Glu | Leu | Pro | Val | Val | Glu |
| 6155 | | | | 6160 | | | | | 6165 | | | | | |

Ala Tyr Trp Leu Glu Lys Leu Ala Gly Glu Leu Pro Val Val Glu
6155                6160                6165

Leu Pro Thr Asp Tyr Asp Arg Pro Ala Val Arg Ser Phe Glu Gly
6170                6175                6180

Ala Gln Ile Glu Phe Glu Val Asp Ala Ala Leu Thr Gln Arg Leu
6185                6190                6195

Ser Gln Leu Ala Ser Asn Arg Glu Ser Thr Leu Tyr Met Val Leu
6200                6205                6210

Leu Ser Ala Tyr Thr Val Leu Leu Ser Lys Tyr Ser Gly Gln Glu
6215                6220                6225

Asp Ile Ile Val Gly Thr Pro Val Ala Gly Arg Ala His Ala Asp
6230                6235                6240

Leu Glu Pro Leu Ile Gly Met Phe Val Asn Thr Leu Ala Ile Arg
6245                6250                6255

Asn His Pro Ala Gly Asp Lys Thr Phe Leu Ser Leu Leu Glu Glu
6260                6265                6270

Val Lys Glu Thr Ala Leu Gly Ala Phe Glu His Gln Asp Tyr Pro
6275                6280                6285

Phe Glu Glu Leu Val Glu Arg Leu Asn Val Gln Trp Asp Ala Asn
6290                6295                6300

Arg Asn Pro Val Phe Asp Thr Met Phe Val Met Gln Asn Thr Glu
6305                6310                6315

Asp His Glu Val Arg Leu Glu Ala Leu Thr Leu Ser Pro Tyr Val
6320                6325                6330

Leu Asp Asn Pro Ile Asp Ala Lys Phe Asp Leu Thr Leu Phe Val
6335                6340                6345

Ser Glu Asp Asn Asp Val Ile Lys Gly Gly Phe Gln Tyr Gly Thr
6350                6355                6360

Lys Leu Phe Lys Ala Ala Met Ile His Lys Ile Met Arg Asp Phe
6365                6370                6375

Leu Leu Val Leu Ala Gln Ile Val Glu Asp Pro His Ile Arg Leu
6380                6385                6390

Arg Asp Ile Lys Cys Asn Glu Gln Ser Val Asn Asn Gln Arg Ser
6395                6400                6405

Ile Glu Thr Ile Glu Phe Ala Phe
6410                6415

<210> SEQ ID NO 8
<211> LENGTH: 9513
<212> TYPE: DNA
<213> ORGANISM: Paenibacillus thiaminolyticus OSY-SE

<400> SEQUENCE: 8

```
atgaagtcgg tgtttgataa ggaagaggct tattggaacg agaaatttga ttccgaagac    60
agtataagcg ttctgccata tagcaattcc tccaataaca atatgggcg  cgtaaacacc   120 atgggcgtca tcaatcgcac acttccgcct gagttgtcac agagaatcat caccctggcg   180
aacggatcgg atatggccgt gtacatgatc gtattggcag gagtgacaag cttgctctat   240
aaatatacca accgcgaaaa tgtgttggta ggtatgcctg catatacggc gttacatggg   300
gagcatccgc ctatccatga ttttctggtg attaaaaata atgtgaacag taaaagcacg   360
ttcaaatcgt tgtttagggca aatcaaagcg tcagtcagtg aggcgcttga gcatcagcac   420
cttcctttcc gtaaaatgtt tcggcaattg aatttgcaag tggatcccca aggattgcct   480
```

```
atcgtgaata cactcgtttc ctatacaaac atacatactg cttcattgga acaaagcgca    540
gccgcagaag ccgcatttca atttgaattc gtaaatgacc gcattcaatt acgcatgagc    600
tttgatgata atcgataccg ttcggactat gtcgaatcaa tgctcgctca tttcttccgc    660
ctgctgtcgg tcgtattgtt tcaaccggag ctagaaatcg gaaaagtgga gctgctgtcc    720
gagcatgagc agcatcatct gcttgccatt ctgaacgata cgcgaacgga atatccgcgt    780
cagaagacac tccaccagct gttcgaggag caggcggaac gaatgccaga tgcgctggcg    840
gcgctattcg aggacaaacg gttgacctat gcggagctga atgctgctgc caatcgcatt    900
gcccgtctcc tgcgggatcg aggtgtagta cgaggcacat tggttggcat ttgcgcagag    960
agatccctag agatggtgat tggactgctg gaatcctca aagctggcgg ggcatacgtt    1020
ccgatcgatc cttcctatcc gcaagaacgg attaacgcca tgctggaaga tacagcaatc    1080
agcgtgatgc tcacgcaggc gcatctgcag acaagcgtgc cgaacagcct tgattccgtc    1140
ttgctcgata cagcagcaga gatgactctg aaggaagct ggccgaactt gacagatacg    1200
gcggcgaccg cggacgatgt ggcctacatc atctatacat ctggatcgac gggaattccg    1260
aaaggagtgt gcgtcacgca tcgagggtg gtccggctcg ttgtcgctgc caattatgtg    1320
gacatcagca gcaaggacgt atttctgcaa ggctcgacga tatcgttcga cgcggcaacg    1380
ttcgagattt ggggcagctt gctgaatgga gctgctctgg ccattttgcc tccagggaat    1440
ctatcgttga ccgaatggac acaggccatt caacagcatc aagtgacgat cctgtggtta    1500
acggcgggac tcttccacgt gatggtcgag aaccaactcc aagccttgca aggagtccag    1560
caattgttgg tgggtggaga tgtcgtctct caaacgcatg ccaaaaaagt tctggagcgg    1620
tataaggaca ttcgtctggt caatgggtat ggtccgacgg aaaatacgac cttttacctgc   1680
tgccacgaga tttccgccgc cgatatggag cggctctcta ttccgatcgg acgtccaatc    1740
gccaatacgc aagtgtacgt gctggatgag gcaggcaagc tgcttccggt aggagtggtc    1800
ggcgagttgt acaccggagg agacggactg gcccaagggt actggaatcg tccggagctg    1860
acggctgaga agttcgtgga taaccccttc gtgccgggaa cccggctata ccgcacaggc    1920
gatctggcga gatggctgcc ggatggaacg ctcgaatacg tgggacgaat cgatgatcaa    1980
gtgaaaattc gcggttaccg gattgagctt ggcgaggtgg aagcgcatct gttgaaagtg    2040
gaatcggtgc tggacgcaat cgtaatcgca cggcaagacg aaagcggtca gaagacgttg    2100
tgcgcgtact ttacagcgca tgcagagctg atggcgggcg atctgagagc agcactgtcg    2160
caagaactgc cggtctatat gatcccgaca cacttggtgc aggtcgatca gatgccgctg    2220
acgccgaacg gaaaagtcga tcgcagagcg ctgccggagc cggaaggcct catcatgacc    2280
ggaatagagc atgtcgcgcc gcggtcaccg ctagagtcca agctggcgca tatctggcaa    2340
gaggtgctcg gactcgagaa ggtcagcgtg aaggacagtt tcttcgagat tggcggacac    2400
tctttgcgtg caacgacgct cgcaagcaag ctgcacaagg agctgcatgt cagcctgctg    2460
ctgcgggaca tcttccgcca tcctaccatt gaagagctgg cacgtctcat tgatgggatg    2520
gaacggcagg cgtacagaca gattccgctg ctggatgaaa gggattggta cccggtatct    2580
tcggcgcaaa agaggctgta cattttgcat caactcgaag gggcagagca gagctacaac    2640
atgccggggg tgatgctcct tgaaggacag cttgaccgga atcggttcga ggaggcgttc    2700
ggcagcttga tcgggcgcca cgaaacgctg cgcaccggct ttgagatggt gaatggcgag    2760
ccggtgcagc gtgtatgccg cgaagtgaat ttctcggtag atgatgatca ggcgagcgaa    2820
gaggaagccg aagccgtcgt tcgctcattc attcgcccgt tcgatctgga gaagccgccg    2880
```

```
ctcctgcgag taggactgat cgagctggat caggatcggc atattctgat gtacgacatg    2940
catcatatca tctccgacgg cgtgtcgatg ggaattgtgg tggaggagtt cgtccgcttg    3000
tacgggggcg aggaactgcc gccgccgcgc attcagtaca aggattatgc cgcatggcag    3060
cagtccgagc cgcagcagga gctcatgaag cagcaggaga gttattggtt gcagtcgctt    3120
ggcggagagc ttccggtgct ggaactgccg gcggattatg cgcgtccttc cgtccagagc    3180
tatgagggcg atacccttcga attcgcgatc gatcctcggc taagcgaagc gctgcacggg    3240
gttgcggccg agagcggaac gacattgtac atggtgctgc ttgctgccta tcgattctg    3300 cttcataagt atacaggcca ggaagacatt atcgtgggga cgccgaatgc gggcagaacg    3360
cacggcgatt tgcagccgct tatcggcatg ttcgtcaata cgctggcgat ccgcaattat    3420
ccggctggct cgaagacgtt cctggaatac ttggaggaag tgaaagaaac gagcttgggc    3480
gccttcgaga atcaggatta cccgttcgaa gaactggtgg aaaagctgca ggtagcgcga    3540
gatttgagcc gcaatccgct gttcgatacg atgtttgctt tgcagaatat ggacgacaag    3600
gatctggagc tcgcagggct tcgcttgaag ccgtacccgg ctgaatacaa ggtggcgaaa    3660
ttcgacctga gcctggacgt ggcggaaggc gtggaaggga tggcgtgcag tctggaatac    3720
gccaccgcgt tataccgacc ggaatcgata gaaagaatgg cgaagcattt cgggcggctg    3780
cttgaagccg ttgcgcacga gccagaggcg cggctggctt cgctcggcat gctcacggag    3840
gaggaagagg agcagattcg gcatgtgttc aacgatacgg aggcagggcg ttcgcagcag    3900
aacacggtgc cagaactgtt cgaggagcag gtggagcgca cgccggatcg gattgcggtc    3960
gtgcatgagg acaagcagct gacgtaccgg gagctgaacg aacgggcgaa ccggctggcg    4020
cgtacgctgc gggccgaggg cgtgaagccc aacagctgg tcggcatcat ggccgatcgc    4080
tcgctggaga tgatcgtggg cattatggcc atcttgaaat ccggcggcgc ctatgtgccg    4140
attgacccgc aatatccgga ggatcggatt cactatatgc tggacaattc gaacgcgcaa    4200
gtgctgctgg cccagcgtca tctgcaagcg cgggccgcat tctccggcag aaggatcatg    4260
ctggatgaag aagcgttcta cggcgcagac ggttccaatc tggaacgggt gaatcagccg    4320
gagcatctga gctatgtcat ctataccctcc ggaacgacgg gcaagccgaa aggggtcatg    4380
atcgagcaca gacagatggc agtcttgtcg gccgcgtggg agcgcgaata cggcttgcag    4440
gaagagagca tgcgctggat gcaatgggcg agcttttcat tcgacgtctt ctcgggagac    4500
ctgatccgcg cgctgctgca tggggagaa cttattctat gtccggagga tgcaagggcg    4560
aacccggctg aaatctatga gctcattcgc aagcatcgga ttcagatgtt cgatgtcact    4620
ccgtcgctcg tcattccgct gatggaatat gtatacgaga acaagctgga catcagcagc    4680
atgaagctga cagtcgtggg ggcggatcat tgcccgaagg aagaattcca gaagctgctg    4740
gaacgattcg gttcgcaaat gaggatcgtc aacagctatg gggtaacgga gacgaccatc    4800
gattcctgct acttcgagca ggcgagcacg gaagggctgc gaacggtgcc aatcggcaaa    4860
cctctgccgg gtgtgacgat gtacattctg gatgatcagc attctttact gccggtcggg    4920
ataacgggcg agctctatat cggcggacct tgcgtaggcc gggggtattg gaagcggccg    4980
gacttgacgg cggagaaatt cgtcgacaat ccattcgctc cgggcgagcg aatgtaccgg    5040
acaggcgact ggcccggtg gctgccggac ggcaacgtcg aatatttggg gcggatcgac    5100
catcaagtga aaatccgggg ctaccggatc gagatcggcg aggtgagac ccaactactc    5160 agaacgccgt tcatccgtga agcggttgtc gtcgcgcggg aagacgttag cggacagaag    5220
```

```
tcattgtgcg cgtacttcgt cgccgaacgc gagctgacgg tgagcgagct gcggagagca   5280
ttggccgcag aacttccggg gtatatgatc ccatcgtatt tcgtccaaat ggagcggctt   5340
ccgttgacgc cgaacggcaa aatcgaccgc aaagcgctgc cggctccaga aggaagcgca   5400
catactggag cagagttcgt agctccgcgc acgtcgctgg aagcgcagct ggcccgaatc   5460
tggcaagagg tgctgggtct gccggacgtt agcgtgaagg ataatttctt cgatttgggc   5520
gggcactcct tgcgcgcgac gaccttggca agcaaggtgt tcaaggaaat gcacatcaat   5580
ctgccgctgc gggatgtgtt caggtacccg acgattgagg agctggccga actgatagcc   5640
gggatgaaaa agcaggaata tgccgtgatc ccgttggctg aggaaagaga cgtctacccg   5700
ttgtcttcgg cccagaaacg cctgtatatc gtgagccaat ggaagggggc cgagctgagc   5760
tacaacatgc cgggagtcat caccctcgaa ggaccgctgg atcgcactag attcgacggg   5820
gctttccagc agctgattgc gcggcacgag gcgctgcgca ccggcttcga gatggtgaac   5880
ggagaaccgg tccagcggat acatcgggat gtgcgcttga cagtggagta cgtgcaggca   5940
gacgaagaag aagcagagaa gctcgtacag cgctttgtcc gcagcttcga tctgaagctg   6000
cggcctctat tgcgggtagg acttatcgca atagagcggg agcggcatat tctgatgttc   6060
gatatgcatc atatcatttc agatggcgtt acgatgggga tattggtgga tgagttcgct   6120
aggctctatg cgggcgagga tttgccgccg ctccgcattc agtataagga ttatgcggta   6180
tggcagcaat ccgaagatcg cagcgtggag ttgcggcgtc aggaagcgta ttggctggag   6240
cgattacaag gagaattgcc ggtactagag ctgccgactg attatgtgcg ccccgctgtt   6300
caaaaatttg atgagacgt cgcattattc acgatcgatc cgcatctgag cgaacaattg   6360
cgccgactgg cgtcagacac aggttccacc ttgtacatgg tgctgctggc agcctacact   6420
acgctgctgc ataagtatac gggacaggaa gacatcatcg tggggacacc gattgcgggc   6480
agaagccata gcgatctcga gccgctcatc gggatgttcg tcaacacatt ggcggttcgc   6540
aattatcccg caagcgagaa ggcatttctg tcgtacctgg cggaagtgaa agaaacaacc   6600
ttgggcgcct tcgagcacca ggactatcca ttcgaggatc tggtagaaaa ggtgcgcgta   6660
tcgcgggact taagccggaa tccactgttc gacacgatgt tcagtctcga aatgcagag   6720
cagggggca tcgaaatcga aggcctccaa ttaaaatcat atccgaatga acatatgacg   6780
gccaaattcg acctgacttt ccatgcgaa gaaggagaag aaggcatcct atgcggcttg   6840
gtgtatgcaa ccgctttgta caagcgcgat acggtggagc ggatgatgct gcatttcaag   6900
cagttgcttg cagcaattgc acatgacccc cgcgcgcaac tttcaacatt gaacatgatg   6960
accgctcaag aaagagaaga gattatcggg gtgttcaatg cacgggac gaaatatccg   7020
cgcgagaaga cgattcagca tctattcgag gagcaggttg aacggactcc tgacgcagcg   7080
gctattgtgt acggagacga gcgaatgacg taccgcgaat tgaacgggcg ggcgaaccga   7140
ttggcaagga cattacgaac caagggagtg caagcagatc gcttggtagg tcttatggct   7200
gaacgttctc tggaaatgat agttggaatt ctggcgattc taaaagccgg gggagcatac   7260
gtgccgatcg acccggaata tccggaagag cgcgtccgct acatgctgga ggactccggg   7320
acccaaatca tactgacgca acatgaactg cagtcgagaa tcccggtgca agcctcgttc   7380
gtcctgttgg atgacgaaca ctcttacagt gcggacgatt cgaatctgga acagaataac   7440
ggtcctgccg atttggccta cgtcatttat acgtcgggga cgacaggcaa gccaaaaggg   7500
aatttggcga cgcatcgcaa catcgtgcgg gtcgtgcaag gcacgagcta cattgatttt   7560
agcgaacggg acaacgtgct gcagttatcc aattatgctt tcgacggatc gacctttgat   7620
```

```
atgtacggtg ctttgttaaa tggagccaag ctggtcctca tcccgcagga gacgctgttg    7680
gaggtaggga agttggcagg cttgatcgaa cgcgagcgca tttcggtgat gttcatcaca    7740
acggcgtact tcaacatcct cattgacatg aaagcagact gcttgcgcca tatccgcacc    7800
atactgttcg gcggggagcg cgtgtccatc tctcacgtcc gcaaagcgct ctatcagcta    7860
ggaccgggca aaatcaagca tgtgtacggg ccaacggaga gcacggtatt tgccacatgc    7920
cacgatgtga atgaagtggc agaggatgcc gtgaccgttc cgatcggacg cccgatcagc    7980
aacacgacca tttatatcgt caatgctcag aacgatctgc agccgatcgg agtggctggg    8040
gagctgtgca tagcaggaga cggactggcc cgaggctact tgaaccgtcc cgaattgacg    8100
gcagcgaagt tcgtcgacaa tccattcgcg ccgagggagc ggatgtaccg gacgggcgac    8160
ctggcaagat ggctgccgga tgggaccatc gagtacgtgg ggcggattga cgatcaggtg    8220
aaaatacgcg gctaccggat tgagcttggc gaggtagaaa cacatctatt gagagtggag    8280
cccattcagg aggcgaccgt gatcgcccgg gaatccgaca cgcgtgagaa gcgcttatgc    8340
gcctactacg tggcggatcg accgctgccg gccaacgagc tgagaggcat cctagcgcaa    8400
gatcttccag ggtacatgat tccgctgcac ttcgttcaac tggatcggat gccgctgaca    8460
cctaacggta aggtagaccg caaggcgctg cctgcgcctg aggatcactt gatgacaggg    8520
acggaatatg tggccccgcg cacgacgcag gaagctcagt tggcgcagat ctggcaggag    8580
gtgctgggca tcgagaaaat cggcgtgcag gacaatttct ttgagctggg cggacactcg    8640
attagcttga tgcagctgat acaccgaatc tacatcgaat tgggcgcgga aatcgctctc    8700
catagcgtgt ttcagcgacc gacagtggaa gcgatggcct atgagatcgt aaaagtcgag    8760
tacgaggaga aaagcagcag ccagttcacg aaattaaatg aaaatggtct tgtaaacgta    8820
ttttgcttgc ctcccggctt cgggtatggg ttaagttact tggaactggc gaagcaaatg    8880
gaaaacagct gcatcctata cggaattgat ttcattgatg atgccgaatc ttacgaggac    8940
atgctggacc ggtatgtgga cgcggtcgtt gccattcagt ctcagtctcc ttatgtgctg    9000
ctcggatatt cgctgggagg caatctgacg ttcgaaattg ccaaagcaat ggaaaagaga    9060
gggtaccgcg tatcggatat tattatgctc gactccacgc ggaagctggc cgctcagacg    9120
gtggacgagt tcgaaagcga tatcgatcaa atgcttgaag cggtgggtga acaggagatg    9180
cagctgctga gcaatcctct gattcgcgaa cgggtcaagc ataagatgcg cgcgtactgg    9240
acgtatggat ctcagctcgt gaatacgggc gcggttgagg cgaatattta tgcattgatt    9300
gcggaggatt ccgatgcagt cagaccggat aatgttactt ctgcattatg ggatggggca    9360
acccggcaag cctattgcga gcatcgactc attggtgtcc atgaggatgt gctgcttcct    9420
ggattcatag agcataacgt gaaagtgatt cacgcggtcg tccatcaaat catcgagcaa    9480
acgcgcggcg tccacgaggt gttatcgcga tag                                9513
```

<210> SEQ ID NO 9
<211> LENGTH: 3170
<212> TYPE: PRT
<213> ORGANISM: Paenibacillus thiaminolyticus OSY-SE

<400> SEQUENCE: 9

Met Lys Ser Val Phe Asp Lys Glu Glu Ala Tyr Trp Asn Glu Lys Phe
1               5                   10                  15

Asp Ser Glu Asp Ser Ile Ser Val Leu Pro Tyr Ser Asn Ser Ser Asn
            20                  25                  30

```
Asn Asn Met Gly Arg Val Asn Thr Met Gly Val Ile Asn Arg Thr Leu
             35                  40                  45

Pro Pro Glu Leu Ser Gln Arg Ile Ile Thr Leu Ala Asn Gly Ser Asp
 50                  55                  60

Met Ala Val Tyr Met Ile Val Leu Ala Gly Val Thr Ser Leu Leu Tyr
 65                  70                  75                  80

Lys Tyr Thr Asn Arg Glu Asn Val Leu Val Gly Met Pro Ala Tyr Thr
                 85                  90                  95

Ala Leu His Gly Glu His Pro Pro Ile His Asp Phe Leu Val Ile Lys
            100                 105                 110

Asn Asn Val Asn Ser Lys Ser Thr Phe Lys Ser Leu Leu Gly Gln Ile
            115                 120                 125

Lys Ala Ser Val Ser Glu Ala Leu Glu His Gln His Leu Pro Phe Arg
130                 135                 140

Lys Met Phe Arg Gln Leu Asn Leu Gln Val Asp Pro Gln Gly Leu Pro
145                 150                 155                 160

Ile Val Asn Thr Leu Val Ser Tyr Thr Asn Ile His Thr Ala Ser Leu
                165                 170                 175

Glu Gln Ser Ala Ala Glu Ala Ala Phe Gln Phe Glu Phe Val Asn
            180                 185                 190

Asp Arg Ile Gln Leu Arg Met Ser Phe Asp Asp Asn Arg Tyr Arg Ser
            195                 200                 205

Asp Tyr Val Glu Ser Met Leu Ala His Phe Phe Arg Leu Leu Ser Val
            210                 215                 220

Val Leu Phe Gln Pro Glu Leu Glu Ile Gly Lys Val Glu Leu Leu Ser
225                 230                 235                 240

Glu His Glu Gln His His Leu Leu Ala Ile Leu Asn Asp Thr Arg Thr
                245                 250                 255

Glu Tyr Pro Arg Gln Lys Thr Leu His Gln Leu Phe Glu Glu Gln Ala
            260                 265                 270

Glu Arg Met Pro Asp Ala Leu Ala Ala Leu Phe Glu Asp Lys Arg Leu
            275                 280                 285

Thr Tyr Ala Glu Leu Asn Ala Ala Ala Asn Arg Ile Ala Arg Leu Leu
290                 295                 300

Arg Asp Arg Gly Val Val Arg Gly Thr Leu Val Gly Ile Cys Ala Glu
305                 310                 315                 320

Arg Ser Leu Glu Met Val Ile Gly Leu Leu Gly Ile Leu Lys Ala Gly
                325                 330                 335

Gly Ala Tyr Val Pro Ile Asp Pro Ser Tyr Pro Gln Glu Arg Ile Asn
            340                 345                 350

Ala Met Leu Glu Asp Thr Ala Ile Ser Val Met Leu Thr Gln Ala His
            355                 360                 365

Leu Gln Thr Ser Val Pro Asn Ser Leu Asp Ser Val Leu Leu Asp Thr
370                 375                 380

Ala Ala Glu Met Thr Leu Glu Gly Ser Trp Pro Asn Leu Thr Asp Thr
385                 390                 395                 400

Ala Ala Thr Ala Asp Asp Val Ala Tyr Ile Ile Tyr Thr Ser Gly Ser
                405                 410                 415

Thr Gly Ile Pro Lys Gly Val Cys Val Thr His Arg Gly Val Val Arg
            420                 425                 430

Leu Val Val Ala Ala Asn Tyr Val Asp Ile Ser Ser Lys Asp Val Phe
435                 440                 445

Leu Gln Gly Ser Thr Ile Ser Phe Asp Ala Ala Thr Phe Glu Ile Trp
```

```
                450                 455                 460
Gly Ser Leu Leu Asn Gly Ala Ala Leu Ala Ile Leu Pro Pro Gly Asn
465                 470                 475                 480

Leu Ser Leu Thr Glu Trp Thr Gln Ala Ile Gln Gln His Gln Val Thr
                485                 490                 495

Ile Leu Trp Leu Thr Ala Gly Leu Phe His Val Met Val Glu Asn Gln
                500                 505                 510

Leu Gln Ala Leu Gln Gly Val Gln Gln Leu Leu Val Gly Gly Asp Val
                515                 520                 525

Val Ser Gln Thr His Ala Lys Lys Val Leu Glu Arg Tyr Lys Asp Ile
530                 535                 540

Arg Leu Val Asn Gly Tyr Gly Pro Thr Glu Asn Thr Thr Phe Thr Cys
545                 550                 555                 560

Cys His Glu Ile Ser Ala Ala Asp Met Glu Arg Leu Ser Ile Pro Ile
                565                 570                 575

Gly Arg Pro Ile Ala Asn Thr Gln Val Tyr Val Leu Asp Glu Ala Gly
                580                 585                 590

Lys Leu Leu Pro Val Gly Val Gly Glu Leu Tyr Thr Gly Gly Asp
                595                 600                 605

Gly Leu Ala Gln Gly Tyr Trp Asn Arg Pro Glu Leu Thr Ala Glu Lys
                610                 615                 620

Phe Val Asp Asn Pro Phe Val Pro Gly Thr Arg Leu Tyr Arg Thr Gly
625                 630                 635                 640

Asp Leu Ala Arg Trp Leu Pro Asp Gly Thr Leu Glu Tyr Val Gly Arg
                645                 650                 655

Ile Asp Asp Gln Val Lys Ile Arg Gly Tyr Arg Ile Glu Leu Gly Glu
                660                 665                 670

Val Glu Ala His Leu Leu Lys Val Glu Ser Val Leu Asp Ala Ile Val
                675                 680                 685

Ile Ala Arg Gln Asp Glu Ser Gly Gln Lys Thr Leu Cys Ala Tyr Phe
                690                 695                 700

Thr Ala His Ala Glu Leu Met Ala Gly Asp Leu Arg Ala Ala Leu Ser
705                 710                 715                 720

Gln Glu Leu Pro Val Tyr Met Ile Pro Thr His Leu Val Gln Val Asp
                725                 730                 735

Gln Met Pro Leu Thr Pro Asn Gly Lys Val Asp Arg Arg Ala Leu Pro
                740                 745                 750

Glu Pro Glu Gly Leu Ile Met Thr Gly Ile Glu His Val Ala Pro Arg
                755                 760                 765

Ser Pro Leu Glu Ser Lys Leu Ala His Ile Trp Gln Glu Val Leu Gly
770                 775                 780

Leu Glu Lys Val Ser Val Lys Asp Ser Phe Phe Glu Ile Gly Gly His
785                 790                 795                 800

Ser Leu Arg Ala Thr Thr Leu Ala Ser Lys Leu His Lys Glu Leu His
                805                 810                 815

Val Ser Leu Leu Leu Arg Asp Ile Phe Arg His Pro Thr Ile Glu Glu
                820                 825                 830

Leu Ala Arg Leu Ile Asp Gly Met Glu Arg Gln Ala Tyr Arg Gln Ile
                835                 840                 845

Pro Leu Leu Asp Glu Arg Asp Trp Tyr Pro Val Ser Ser Ala Gln Lys
                850                 855                 860

Arg Leu Tyr Ile Leu His Gln Leu Glu Gly Ala Glu Gln Ser Tyr Asn
865                 870                 875                 880
```

-continued

Met Pro Gly Val Met Leu Leu Glu Gly Gln Leu Asp Arg Asn Arg Phe
            885                 890                 895

Glu Glu Ala Phe Gly Ser Leu Ile Gly Arg His Glu Thr Leu Arg Thr
            900                 905                 910

Gly Phe Glu Met Val Asn Gly Glu Pro Val Gln Arg Val Cys Arg Glu
            915                 920                 925

Val Asn Phe Ser Val Glu Met Met Gln Ala Ser Glu Glu Ala Glu
    930                 935                 940

Ala Val Val Arg Ser Phe Ile Arg Pro Phe Asp Leu Glu Lys Pro Pro
945                 950                 955                 960

Leu Leu Arg Val Gly Leu Ile Glu Leu Asp Gln Asp Arg His Ile Leu
                965                 970                 975

Met Tyr Asp Met His His Ile Ile Ser Asp Gly Val Ser Met Gly Ile
            980                 985                 990

Val Val Glu Glu Phe Val Arg Leu Tyr Gly Gly Glu Glu Leu Pro Pro
            995                 1000                1005

Pro Arg Ile Gln Tyr Lys Asp Tyr Ala Ala Trp Gln Gln Ser Glu
    1010                1015                1020

Pro Gln Gln Glu Leu Met Lys Gln Gln Glu Ser Tyr Trp Leu Gln
    1025                1030                1035

Ser Leu Gly Gly Glu Leu Pro Val Leu Glu Leu Pro Ala Asp Tyr
    1040                1045                1050

Ala Arg Pro Ser Val Gln Ser Tyr Glu Gly Asp Thr Phe Glu Phe
    1055                1060                1065

Ala Ile Asp Pro Arg Leu Ser Glu Ala Leu His Gly Val Ala Ala
    1070                1075                1080

Glu Ser Gly Thr Thr Leu Tyr Met Val Leu Leu Ala Ala Tyr Thr
    1085                1090                1095

Ile Leu Leu His Lys Tyr Thr Gly Gln Glu Asp Ile Ile Val Gly
    1100                1105                1110

Thr Pro Asn Ala Gly Arg Thr His Gly Asp Leu Gln Pro Leu Ile
    1115                1120                1125

Gly Met Phe Val Asn Thr Leu Ala Ile Arg Asn Tyr Pro Ala Gly
    1130                1135                1140

Ser Lys Thr Phe Leu Glu Tyr Leu Glu Glu Val Lys Glu Thr Ser
    1145                1150                1155

Leu Gly Ala Phe Glu Asn Gln Asp Tyr Pro Phe Glu Glu Leu Val
    1160                1165                1170

Glu Lys Leu Gln Val Ala Arg Asp Leu Ser Arg Asn Pro Leu Phe
    1175                1180                1185

Asp Thr Met Phe Ala Leu Gln Asn Met Asp Asp Lys Asp Leu Glu
    1190                1195                1200

Leu Ala Gly Leu Arg Leu Lys Pro Tyr Pro Ala Glu Tyr Lys Val
    1205                1210                1215

Ala Lys Phe Asp Leu Ser Leu Asp Val Ala Glu Gly Val Glu Gly
    1220                1225                1230

Met Ala Cys Ser Leu Glu Tyr Ala Thr Ala Leu Tyr Arg Pro Glu
    1235                1240                1245

Ser Ile Glu Arg Met Ala Lys His Phe Gly Arg Leu Leu Glu Ala
    1250                1255                1260

Val Ala His Glu Pro Glu Ala Arg Leu Ala Ser Leu Gly Met Leu
    1265                1270                1275

```
Thr Glu Glu Glu Glu Gln Ile Arg His Val Phe Asn Asp Thr
    1280            1285             1290

Glu Ala Gly Arg Ser Gln Gln Asn Thr Val Pro Glu Leu Phe Glu
    1295            1300             1305

Glu Gln Val Glu Arg Thr Pro Asp Arg Ile Ala Val Val His Glu
    1310            1315             1320

Asp Lys Gln Leu Thr Tyr Arg Glu Leu Asn Glu Arg Ala Asn Arg
    1325            1330             1335

Leu Ala Arg Thr Leu Arg Ala Glu Gly Val Lys Pro Glu Gln Leu
    1340            1345             1350

Val Gly Ile Met Ala Asp Arg Ser Leu Glu Met Ile Val Gly Ile
    1355            1360             1365

Met Ala Ile Leu Lys Ser Gly Gly Ala Tyr Val Pro Ile Asp Pro
    1370            1375             1380

Gln Tyr Pro Glu Asp Arg Ile His Tyr Met Leu Asp Asn Ser Asn
    1385            1390             1395

Ala Gln Val Leu Leu Ala Gln Arg His Leu Gln Ala Arg Ala Ala
    1400            1405             1410

Phe Ser Gly Arg Arg Ile Met Leu Asp Glu Glu Ala Phe Tyr Gly
    1415            1420             1425

Ala Asp Gly Ser Asn Leu Glu Arg Val Asn Gln Pro Glu His Leu
    1430            1435             1440

Ser Tyr Val Ile Tyr Thr Ser Gly Thr Thr Gly Lys Pro Lys Gly
    1445            1450             1455

Val Met Ile Glu His Arg Gln Met Ala Val Leu Ser Ala Ala Trp
    1460            1465             1470

Glu Arg Glu Tyr Gly Leu Gln Glu Glu Ser Met Arg Trp Met Gln
    1475            1480             1485

Trp Ala Ser Phe Ser Phe Asp Val Phe Ser Gly Asp Leu Ile Arg
    1490            1495             1500

Ala Leu Leu His Gly Gly Glu Leu Ile Leu Cys Pro Glu Asp Ala
    1505            1510             1515

Arg Ala Asn Pro Ala Glu Ile Tyr Glu Leu Ile Arg Lys His Arg
    1520            1525             1530

Ile Gln Met Phe Asp Val Thr Pro Ser Leu Val Ile Pro Leu Met
    1535            1540             1545

Glu Tyr Val Tyr Glu Asn Lys Leu Asp Ile Ser Ser Met Lys Leu
    1550            1555             1560

Ala Val Val Gly Ala Asp His Cys Pro Lys Glu Glu Phe Gln Lys
    1565            1570             1575

Leu Leu Glu Arg Phe Gly Ser Gln Met Arg Ile Val Asn Ser Tyr
    1580            1585             1590

Gly Val Thr Glu Thr Thr Ile Asp Ser Cys Tyr Phe Glu Gln Ala
    1595            1600             1605

Ser Thr Glu Gly Leu Arg Thr Val Pro Ile Gly Lys Pro Leu Pro
    1610            1615             1620

Gly Val Thr Met Tyr Ile Leu Asp Asp Gln His Ser Leu Leu Pro
    1625            1630             1635

Val Gly Ile Thr Gly Glu Leu Tyr Ile Gly Gly Pro Cys Val Gly
    1640            1645             1650

Arg Gly Tyr Trp Lys Arg Pro Asp Leu Thr Ala Glu Lys Phe Val
    1655            1660             1665

Asp Asn Pro Phe Ala Pro Gly Glu Arg Met Tyr Arg Thr Gly Asp
```

```
              1670                1675                1680

Leu Ala Arg Trp Leu Pro Asp Gly Asn Val Glu Tyr Leu Gly Arg
        1685                1690                1695

Ile Asp His Gln Val Lys Ile Arg Gly Tyr Arg Ile Glu Ile Gly
        1700                1705                1710

Glu Val Glu Thr Gln Leu Leu Arg Thr Pro Phe Ile Arg Glu Ala
        1715                1720                1725

Val Val Val Ala Arg Glu Asp Val Ser Gly Gln Lys Ser Leu Cys
        1730                1735                1740

Ala Tyr Phe Val Ala Glu Arg Glu Leu Thr Val Ser Glu Leu Arg
        1745                1750                1755

Arg Ala Leu Ala Ala Glu Leu Pro Gly Tyr Met Ile Pro Ser Tyr
        1760                1765                1770

Phe Val Gln Met Glu Arg Leu Pro Leu Thr Pro Asn Gly Lys Ile
        1775                1780                1785

Asp Arg Lys Ala Leu Pro Ala Pro Glu Gly Ser Ala His Thr Gly
        1790                1795                1800

Ala Glu Phe Val Ala Pro Arg Thr Ser Leu Glu Ala Gln Leu Ala
        1805                1810                1815

Arg Ile Trp Gln Glu Val Leu Gly Leu Pro Asp Val Ser Val Lys
        1820                1825                1830

Asp Asn Phe Phe Asp Leu Gly Gly His Ser Leu Arg Ala Thr Thr
        1835                1840                1845

Leu Ala Ser Lys Val Phe Lys Glu Met His Ile Asn Leu Pro Leu
        1850                1855                1860

Arg Asp Val Phe Arg Tyr Pro Thr Ile Glu Glu Leu Ala Glu Leu
        1865                1870                1875

Ile Ala Gly Met Lys Lys Gln Glu Tyr Ala Val Ile Pro Leu Ala
        1880                1885                1890

Glu Glu Arg Asp Val Tyr Pro Leu Ser Ser Ala Gln Lys Arg Leu
        1895                1900                1905

Tyr Ile Val Ser Gln Leu Glu Gly Ala Glu Leu Ser Tyr Asn Met
        1910                1915                1920

Pro Gly Val Ile Thr Leu Glu Gly Pro Leu Asp Arg Thr Arg Phe
        1925                1930                1935

Asp Gly Ala Phe Gln Gln Leu Ile Ala Arg His Glu Ala Leu Arg
        1940                1945                1950

Thr Gly Phe Glu Met Val Asn Gly Glu Pro Val Gln Arg Ile His
        1955                1960                1965

Arg Asp Val Arg Leu Thr Val Glu Tyr Val Gln Ala Asp Glu Glu
        1970                1975                1980

Glu Ala Glu Lys Leu Val Gln Arg Phe Val Arg Ser Phe Asp Leu
        1985                1990                1995

Lys Leu Arg Pro Leu Leu Arg Val Gly Leu Ile Ala Ile Glu Arg
        2000                2005                2010

Glu Arg His Ile Leu Met Phe Asp Met His His Ile Ile Ser Asp
        2015                2020                2025

Gly Val Thr Met Gly Ile Leu Val Asp Glu Phe Ala Arg Leu Tyr
        2030                2035                2040

Ala Gly Glu Asp Leu Pro Pro Leu Arg Ile Gln Tyr Lys Asp Tyr
        2045                2050                2055

Ala Val Trp Gln Gln Ser Glu Asp Arg Ser Val Glu Leu Arg Arg
        2060                2065                2070
```

```
Gln Glu Ala Tyr Trp Leu Glu Arg Leu Gln Gly Glu Leu Pro Val
    2075                2080                2085

Leu Glu Leu Pro Thr Asp Tyr Val Arg Pro Ala Val Gln Lys Phe
    2090                2095                2100

Asp Gly Asp Val Ala Leu Phe Thr Ile Asp Pro His Leu Ser Glu
    2105                2110                2115

Gln Leu Arg Arg Leu Ala Ser Asp Thr Gly Ser Thr Leu Tyr Met
    2120                2125                2130

Val Leu Leu Ala Ala Tyr Thr Thr Leu Leu His Lys Tyr Thr Gly
    2135                2140                2145

Gln Glu Asp Ile Ile Val Gly Thr Pro Ile Ala Gly Arg Ser His
    2150                2155                2160

Ser Asp Leu Glu Pro Leu Ile Gly Met Phe Val Asn Thr Leu Ala
    2165                2170                2175

Val Arg Asn Tyr Pro Ala Ser Glu Lys Ala Phe Leu Ser Tyr Leu
    2180                2185                2190

Ala Glu Val Lys Glu Thr Thr Leu Gly Ala Phe Glu His Gln Asp
    2195                2200                2205

Tyr Pro Phe Glu Asp Leu Val Glu Lys Val Arg Val Ser Arg Asp
    2210                2215                2220

Leu Ser Arg Asn Pro Leu Phe Asp Thr Met Phe Ser Leu Glu Asn
    2225                2230                2235

Ala Glu Gln Gly Gly Ile Glu Ile Glu Gly Leu Gln Leu Lys Ser
    2240                2245                2250

Tyr Pro Asn Glu His Met Thr Ala Lys Phe Asp Leu Thr Phe His
    2255                2260                2265

Ala Glu Glu Gly Glu Glu Gly Ile Leu Cys Gly Leu Val Tyr Ala
    2270                2275                2280

Thr Ala Leu Tyr Lys Arg Asp Thr Val Glu Arg Met Met Leu His
    2285                2290                2295

Phe Lys Gln Leu Leu Ala Ala Ile Ala His Asp Pro Arg Ala Gln
    2300                2305                2310

Leu Ser Thr Leu Asn Met Met Thr Ala Gln Glu Arg Glu Glu Ile
    2315                2320                2325

Ile Gly Val Phe Asn Asp Thr Gly Thr Lys Tyr Pro Arg Glu Lys
    2330                2335                2340

Thr Ile Gln His Leu Phe Glu Glu Gln Val Glu Arg Thr Pro Asp
    2345                2350                2355

Ala Ala Ala Ile Val Tyr Gly Asp Glu Arg Met Thr Tyr Arg Glu
    2360                2365                2370

Leu Asn Gly Arg Ala Asn Arg Leu Ala Arg Thr Leu Arg Thr Lys
    2375                2380                2385

Gly Val Gln Ala Asp Arg Leu Val Gly Leu Met Ala Glu Arg Ser
    2390                2395                2400

Leu Glu Met Ile Val Gly Ile Leu Ala Ile Leu Lys Ala Gly Gly
    2405                2410                2415

Ala Tyr Val Pro Ile Asp Pro Glu Tyr Pro Glu Glu Arg Val Arg
    2420                2425                2430

Tyr Met Leu Glu Asp Ser Gly Thr Gln Ile Ile Leu Thr Gln His
    2435                2440                2445

Glu Leu Gln Ser Arg Ile Pro Val Gln Ala Ser Phe Val Leu Leu
    2450                2455                2460
```

```
Asp Asp Glu His Ser Tyr Ser Ala Asp Ser Asn Leu Glu Gln
    2465                2470            2475
Asn Asn Gly Pro Ala Asp Leu Ala Tyr Val Ile Tyr Thr Ser Gly
    2480                2485            2490
Thr Thr Gly Lys Pro Lys Gly Asn Leu Ala Thr His Arg Asn Ile
    2495                2500            2505
Val Arg Val Val Gln Gly Thr Ser Tyr Ile Asp Phe Ser Glu Arg
    2510                2515            2520
Asp Asn Val Leu Gln Leu Ser Asn Tyr Ala Phe Asp Gly Ser Thr
    2525                2530            2535
Phe Asp Met Tyr Gly Ala Leu Leu Asn Gly Ala Lys Leu Val Leu
    2540                2545            2550
Ile Pro Gln Glu Thr Leu Leu Glu Val Gly Lys Leu Ala Gly Leu
    2555                2560            2565
Ile Glu Arg Glu Arg Ile Ser Val Met Phe Ile Thr Thr Ala Tyr
    2570                2575            2580
Phe Asn Ile Leu Ile Asp Met Lys Ala Asp Cys Leu Arg His Ile
    2585                2590            2595
Arg Thr Ile Leu Phe Gly Gly Glu Arg Val Ser Ile Ser His Val
    2600                2605            2610
Arg Lys Ala Leu Tyr Gln Leu Gly Pro Gly Lys Ile Lys His Val
    2615                2620            2625
Tyr Gly Pro Thr Glu Ser Thr Val Phe Ala Thr Cys His Asp Val
    2630                2635            2640
Asn Glu Val Ala Glu Asp Ala Val Thr Val Pro Ile Gly Arg Pro
    2645                2650            2655
Ile Ser Asn Thr Thr Ile Tyr Ile Val Asn Ala Gln Asn Asp Leu
    2660                2665            2670
Gln Pro Ile Gly Val Ala Gly Glu Leu Cys Ile Ala Gly Asp Gly
    2675                2680            2685
Leu Ala Arg Gly Tyr Leu Asn Arg Pro Glu Leu Thr Ala Ala Lys
    2690                2695            2700
Phe Val Asp Asn Pro Phe Ala Pro Arg Glu Arg Met Tyr Arg Thr
    2705                2710            2715
Gly Asp Leu Ala Arg Trp Leu Pro Asp Gly Thr Ile Glu Tyr Val
    2720                2725            2730
Gly Arg Ile Asp Asp Gln Val Lys Ile Arg Gly Tyr Arg Ile Glu
    2735                2740            2745
Leu Gly Glu Val Glu Thr His Leu Leu Arg Val Glu Pro Ile Gln
    2750                2755            2760
Glu Ala Thr Val Ile Ala Arg Glu Ser Asp Ser Gly Glu Lys Arg
    2765                2770            2775
Leu Cys Ala Tyr Tyr Val Ala Asp Arg Pro Leu Pro Ala Asn Glu
    2780                2785            2790
Leu Arg Gly Ile Leu Ala Gln Asp Leu Pro Gly Tyr Met Ile Pro
    2795                2800            2805
Leu His Phe Val Gln Leu Asp Arg Met Pro Leu Thr Pro Asn Gly
    2810                2815            2820
Lys Val Asp Arg Lys Ala Leu Pro Ala Pro Glu Asp His Leu Met
    2825                2830            2835
Thr Gly Thr Glu Tyr Val Ala Pro Arg Thr Thr Gln Glu Ala Gln
    2840                2845            2850
Leu Ala Gln Ile Trp Gln Glu Val Leu Gly Ile Glu Lys Ile Gly
```

| | | | | | | | | | |
|---|---|---|---|---|---|---|---|---|---|
| | | 2855 | | | 2860 | | | 2865 | |
| Val | Gln | Asp | Asn | Phe | Phe | Glu | Leu | Gly | Gly | His | Ser | Ile | Ser | Leu |

Val Gln Asp Asn Phe Phe Glu Leu Gly Gly His Ser Ile Ser Leu
        2870              2875              2880

Met Gln Leu Ile His Arg Ile Tyr Ile Glu Leu Gly Ala Glu Ile
        2885              2890              2895

Ala Leu His Ser Val Phe Gln Arg Pro Thr Val Glu Ala Met Ala
        2900              2905              2910

Tyr Glu Ile Val Lys Val Glu Tyr Glu Lys Ser Ser Ser Gln
        2915              2920              2925

Phe Thr Lys Leu Asn Glu Asn Gly Leu Val Asn Val Phe Cys Leu
        2930              2935              2940

Pro Pro Gly Phe Gly Tyr Gly Leu Ser Tyr Leu Glu Leu Ala Lys
        2945              2950              2955

Gln Met Glu Asn Ser Cys Ile Leu Tyr Gly Ile Asp Phe Ile Asp
        2960              2965              2970

Asp Ala Glu Ser Tyr Glu Asp Met Leu Asp Arg Tyr Val Asp Ala
        2975              2980              2985

Val Val Ala Ile Gln Ser Gln Ser Pro Tyr Val Leu Leu Gly Tyr
        2990              2995              3000

Ser Leu Gly Gly Asn Leu Thr Phe Glu Ile Ala Lys Ala Met Glu
        3005              3010              3015

Lys Arg Gly Tyr Arg Val Ser Asp Ile Ile Met Leu Asp Ser Thr
        3020              3025              3030

Arg Lys Leu Ala Ala Gln Thr Val Asp Glu Phe Glu Ser Asp Ile
        3035              3040              3045

Asp Gln Met Leu Glu Ala Val Gly Glu Gln Glu Met Gln Leu Leu
        3050              3055              3060

Ser Asn Pro Leu Ile Arg Glu Arg Val Lys His Lys Met Arg Ala
        3065              3070              3075

Tyr Trp Thr Tyr Gly Ser Gln Leu Val Asn Thr Gly Ala Val Glu
        3080              3085              3090

Ala Asn Ile Tyr Ala Leu Ile Ala Glu Asp Ser Asp Ala Val Arg
        3095              3100              3105

Pro Asp Asn Val Thr Ser Ala Leu Trp Asp Gly Ala Thr Arg Gln
        3110              3115              3120

Ala Tyr Cys Glu His Arg Leu Ile Gly Val His Glu Asp Val Leu
        3125              3130              3135

Leu Pro Gly Phe Ile Glu His Asn Val Lys Val Ile His Ala Val
        3140              3145              3150

Val His Gln Ile Ile Glu Gln Thr Arg Gly Val His Glu Val Leu
        3155              3160              3165

Ser Arg
        3170

<210> SEQ ID NO 10
<211> LENGTH: 1713
<212> TYPE: DNA
<213> ORGANISM: Paenibacillus thiaminolyticus OSY-SE

<400> SEQUENCE: 10
atgggctgga tgatcgtcgg aatcatctct gctgttgcgg ccgcgattat tgagatatgg     60
accggcagct taatcgaaca attaacgacc aatgccggca acggggacgg gcagttggtc    120
gcccgcattg tatataccgt atttatcgtc attgcaattg agttccccgc gaaatatttc    180

```
atggtgtacg gcatcgaaaa aagcagcgct caagccatga gggaccttcg caaccagatg    240
atgaagcaca tcggcaaatt gcctgttcat tatttggaaa agaaacactc gggcgatatg    300
gtgtcaaggg tgactaatga cctccagatc atcaatcaat ttatgattcg cgatgtggcg    360
gaatggtttt atcatcccct gcttttatt ggctgctttg gctacttgct gtggatccga    420
tgggagcttg tgctgctcag cttgttgctt gttcccgttt ccttgttcgt ctcgcaatgg    480
gtaggcaagc aactgcagcg cctcacggaa gaagcacagg aaaacatggg ccagatgaat    540 gtcatttac aggatacatt gagtggcatg ccgctggtca aaagctattt gctgcaggga    600
atcctgttcc gatcgtatca atccctgctt ctgctgacgc tgaaaaagag gttggccgta    660
aataaacgcg aggcgatagt cactcccgtg ctgttcacgc tcatgatcag tccgatcgtg    720
ttcgctattc tatacggaag ttatttgata tcgaaaggat tgttcagcac gggagagctg    780
attgcctttc tctacttgct gaatttgtgt ttggagccat tgcagaacat cccgacgctc    840
attacgaata cgtttgagat gaccggagct ttaaaacgag cggcccaaat catgaatcaa    900
cccatcgaga atgaagaggg acattgcatt gtgagaactg ctcagcctcc catcgcgttt    960
cacaacgtca atttcgcata cgagaatagc ggttcccctc tgctgcgcaa tttgagcttc    1020
acggtagcga aagggcagac tgtagcgttg gtgggagcca gcggcggggg gaagagcacc    1080
gtgataaagc tgctctgcgg attttatcca ctgcaggctg atggcgggaa gatcgatgta    1140
tttggccaat cgatccgcga ctgcaatccg aaggagctgc gttcccattt gtcggtcgtt    1200
acccaagatt cctatttgtt cagcgggacg attgcagata atattgctta cgggcgggag    1260
aatgcctcga tggatgaagt gatcgaatct gcaaaatcag ccaacgcgca ctcctttatt    1320
atggagctgc cggaaggata tcagactgac gtgggggaac ggggagcgct gctatccggc    1380
gggcagcgtc agcgtatcac cattgcgcgc gcactgctca aggatgcccc catcctgctg    1440
ttggacgagc ccacttccgc attggacgcg gagtctgaat cactggttca ggaagcgttg    1500
aacgttctta tgaaggagag aacgaccatc gtcattgcgc atcggctgtc taccattcag    1560
aatgcggatg agatctgggt catggaggac gggcggatcg aagaggcagg gaatcatgct    1620
aagctgctgg agaaaagggg ctcttatgcc cggctgtacc atcaggaatt cgaaacggat    1680
cgaatgggaa gcaaggaggt ggcctatacg tga                                 1713
```

<210> SEQ ID NO 11
<211> LENGTH: 570
<212> TYPE: PRT
<213> ORGANISM: Paenibacillus thiaminolyticus OSY-SE

<400> SEQUENCE: 11

```
Met Gly Trp Met Ile Val Gly Ile Ile Ser Ala Val Ala Ala Ile
1               5                   10                  15

Ile Glu Ile Trp Thr Gly Ser Leu Ile Glu Gln Leu Thr Thr Asn Ala
                20                  25                  30

Gly Asn Gly Asp Gly Gln Leu Val Ala Arg Ile Val Tyr Thr Val Phe
            35                  40                  45

Ile Val Ile Ala Ile Gly Val Pro Ala Lys Tyr Phe Met Val Tyr Gly
        50                  55                  60

Ile Glu Lys Ser Ser Ala Gln Ala Met Arg Asp Leu Arg Asn Gln Met
65                  70                  75                  80

Met Lys His Ile Gly Lys Leu Pro Val His Tyr Leu Glu Lys Lys His
                85                  90                  95

Ser Gly Asp Met Val Ser Arg Val Thr Asn Asp Leu Gln Ile Ile Asn
```

```
                100                 105                 110
        Gln Phe Met Ile Arg Asp Val Ala Glu Trp Phe Tyr His Pro Leu Leu
                    115                 120                 125

Phe Ile Gly Cys Phe Gly Tyr Leu Leu Trp Ile Arg Trp Glu Leu Val
            130                 135                 140

Leu Leu Ser Leu Leu Leu Val Pro Val Ser Leu Phe Val Ser Gln Trp
        145                 150                 155                 160

Val Gly Lys Gln Leu Gln Arg Leu Thr Glu Glu Ala Gln Glu Asn Met
                        165                 170                 175

Gly Gln Met Asn Val Ile Leu Gln Asp Thr Leu Ser Gly Met Pro Leu
                    180                 185                 190

Val Lys Ser Tyr Leu Leu Gln Gly Ile Leu Phe Arg Ser Tyr Gln Ser
                195                 200                 205

Leu Leu Leu Leu Thr Leu Lys Lys Arg Leu Ala Val Asn Lys Arg Glu
            210                 215                 220

Ala Ile Val Thr Pro Val Leu Phe Thr Leu Met Ile Ser Pro Ile Val
        225                 230                 235                 240

Phe Ala Ile Leu Tyr Gly Ser Tyr Leu Ile Ser Lys Gly Leu Phe Ser
                        245                 250                 255

Thr Gly Glu Leu Ile Ala Phe Leu Tyr Leu Leu Asn Leu Cys Leu Glu
                    260                 265                 270

Pro Leu Gln Asn Ile Pro Thr Leu Ile Thr Asn Thr Phe Glu Met Thr
                275                 280                 285

Gly Ala Leu Lys Arg Ala Ala Gln Ile Met Asn Gln Pro Ile Glu Asn
            290                 295                 300

Glu Glu Gly His Cys Ile Val Arg Thr Ala Gln Pro Ile Ala Phe
        305                 310                 315                 320

His Asn Val Asn Phe Ala Tyr Glu Asn Ser Gly Ser Pro Leu Leu Arg
                        325                 330                 335

Asn Leu Ser Phe Thr Val Ala Glu Gly Gln Thr Val Ala Leu Val Gly
                    340                 345                 350

Ala Ser Gly Gly Gly Lys Ser Thr Val Ile Lys Leu Leu Cys Gly Phe
                355                 360                 365

Tyr Pro Leu Gln Ala Asp Gly Gly Lys Ile Asp Val Phe Gly Gln Ser
            370                 375                 380

Ile Arg Asp Cys Asn Pro Lys Glu Leu Arg Ser His Leu Ser Val Val
        385                 390                 395                 400

Thr Gln Asp Ser Tyr Leu Phe Ser Gly Thr Ile Ala Asp Asn Ile Ala
                        405                 410                 415

Tyr Gly Arg Glu Asn Ala Ser Met Asp Glu Val Ile Glu Ser Ala Lys
                    420                 425                 430

Ser Ala Asn Ala His Ser Phe Ile Met Glu Leu Pro Glu Gly Tyr Gln
                435                 440                 445

Thr Asp Val Gly Glu Arg Gly Ala Leu Leu Ser Gly Gly Gln Arg Gln
            450                 455                 460

Arg Ile Thr Ile Ala Arg Ala Leu Leu Lys Asp Ala Pro Ile Leu Leu
        465                 470                 475                 480

Leu Asp Glu Pro Thr Ser Ala Leu Asp Ala Glu Ser Glu Ser Leu Val
                        485                 490                 495

Gln Glu Ala Leu Asn Val Leu Met Lys Glu Arg Thr Thr Ile Val Ile
                    500                 505                 510

Ala His Arg Leu Ser Thr Ile Gln Asn Ala Asp Glu Ile Trp Val Met
                515                 520                 525
```

```
Glu Asp Gly Arg Ile Glu Glu Ala Gly Asn His Ala Lys Leu Leu Glu
    530                 535                 540

Lys Arg Gly Ser Tyr Ala Arg Leu Tyr His Gln Glu Phe Glu Thr Asp
545                 550                 555                 560

Arg Met Gly Ser Lys Glu Val Ala Tyr Thr
                565                 570

<210> SEQ ID NO 12
<211> LENGTH: 1749
<212> TYPE: DNA
<213> ORGANISM: Paenibacillus thiaminolyticus OSY-SE

<400> SEQUENCE: 12
atgttagctt atgtgaagga aatcaagtat atgatggact ttatgagcac acgacgcaaa      60
gttgagtatt atgttggcat gattgcaggc gggctcgtta acaccttgtt tatcctgtca     120
ttcaccttgg ttgtccagag tttagtagat tttgcagggt caagagatac ttcccttatg     180
tttcaggcgc tatatatttt gggaggctct atcttgctgt tgaacctgac ttcacccgga     240
ttcacttatt tgtttcgtcg cagcgtggaa ctgacgatcg tcgacatcag ggaacgtctc     300
tatcataagc tgtgcaagct tcgggccgat catttggagc ggacgcataa tggagatttc     360
ctatcacgga taaataacga tgtatccacc ctggaagtga cgtattgcgg aatctttttt     420
gctctgctgc tggatatcat gattagcatt ggatccatca ttatgatgtt tatcattcat     480
tggcagtttg cttgcgcttc ccttttgatt ttgctcgttt cctttatat aagcacgcgt      540
tttgtgcgct ccgttcgcgc gatgtatgat caatctcttc attctatagc caagctgaca     600
gagaaatttt cagactttat cgcgggcatc cagcttgtga aattgttcca cattagtccg     660
gtatatgctc agtatggagc catgaacgag aagctgacgc agctttcccg ccgcatcgcc     720
cacaaaaaag gcgtactggc agccgtcaat catttttgtaa gctacattac attttgcgga     780
atcattgtca ttggcagctt gctgtatagc tatggcatca ttggcatggg ggccgttgca     840
gccctggccg tcttgcaaat tcatttgacg cattccttca tgaacattgg aacaaccatg     900
tctttgattc aaaattcgtt ggcgggagcg cagcggattc aagaaatgct ggaggagcag     960
gaggagccgc aacggatcgg ctctgtggca agcgaccgtg attcggaggc aatggtggaa    1020
tttgattgcg ttgagtttgc ctatcaatcc gacagcccgg tgctgtgcaa tttgtccctg    1080
caagtgctcc ccgggcaagt ggcggctgtt gtgggtgcaa gcggcagcgg caaaagcacc    1140
ttgattaaat tgttgctggg cttctatccc gttgacagcg cgagatctt aatccaaggc    1200
aagtcgttcg gacattatac cttggaagag attcgtcaac ggattgctta tgtgccgcaa    1260
gaagctttct tgttcagcgg aacgattgaa gacaacatcc gttatggcaa tccgcaagct    1320
tcacaggagg aagtgattgc cgcggctcag gctgcttatg cccacaattt tattcaggaa    1380
ttgcccgagc aataccagac gcaagtgggt gagcgcggag cgtctttgtc cggcggacag    1440
cgtcagcgga ttgcgattgc ccgggcattg ctcaaaaatg ctccgatatt gctgctcgat    1500
gaggcaacat cggccttgga tgccgaatca gagtactggg tacagcaagc cttgaatcaa    1560
ttgatgaaag ccgcacgac cattctgatt gcccaccgct tgagcaccgt tgagaatgcc    1620
gatgtgatat ttgtcatcca acaaggatca gttgtggaac aaggcaccca tcagagcttg    1680
cttgcatgca gatcctacta tgcaggtatg tatggacagt ctggcctggc tcttgccgaa    1740
caagcttga                                                           1749
```

<210> SEQ ID NO 13
<211> LENGTH: 582
<212> TYPE: PRT
<213> ORGANISM: Paenibacillus thiaminolyticus OSY-SE

<400> SEQUENCE: 13

```
Met Leu Ala Tyr Val Lys Glu Ile Lys Tyr Met Met Asp Phe Met Ser
1               5                   10                  15

Thr Arg Arg Lys Val Glu Tyr Tyr Val Gly Met Ile Ala Gly Gly Leu
            20                  25                  30

Val Asn Thr Leu Phe Ile Leu Ser Phe Thr Leu Val Val Gln Ser Leu
        35                  40                  45

Val Asp Phe Ala Gly Ser Arg Asp Thr Ser Leu Met Phe Gln Ala Leu
    50                  55                  60

Tyr Ile Leu Gly Gly Ser Ile Leu Leu Asn Leu Thr Ser Pro Gly
65                  70                  75                  80

Phe Thr Tyr Leu Phe Arg Arg Ser Val Glu Leu Thr Ile Val Asp Ile
                85                  90                  95

Arg Glu Arg Leu Tyr His Lys Leu Cys Lys Leu Arg Ala Asp His Leu
            100                 105                 110

Glu Arg Thr His Asn Gly Asp Phe Leu Ser Arg Ile Asn Asn Asp Val
        115                 120                 125

Ser Thr Leu Glu Val Thr Tyr Cys Gly Ile Phe Phe Ala Leu Leu Leu
    130                 135                 140

Asp Ile Met Ile Ser Ile Gly Ser Ile Ile Met Met Phe Ile Ile His
145                 150                 155                 160

Trp Gln Phe Ala Cys Ala Ser Leu Leu Ile Leu Leu Val Ser Phe Tyr
                165                 170                 175

Ile Ser Thr Arg Phe Val Arg Ser Val Arg Ala Met Tyr Asp Gln Ser
            180                 185                 190

Leu His Ser Ile Ala Lys Leu Thr Glu Lys Phe Ser Asp Phe Ile Ala
        195                 200                 205

Gly Ile Gln Leu Val Lys Leu Phe His Ile Ser Pro Val Tyr Ala Gln
    210                 215                 220

Tyr Gly Ala Met Asn Glu Lys Leu Thr Gln Leu Ser Arg Arg Ile Ala
225                 230                 235                 240

His Lys Lys Gly Val Leu Ala Ala Val Asn His Phe Val Ser Tyr Ile
                245                 250                 255

Thr Phe Cys Gly Ile Ile Val Ile Gly Ser Leu Leu Tyr Ser Tyr Gly
            260                 265                 270

Ile Ile Gly Met Gly Ala Val Ala Ala Leu Ala Val Leu Gln Ile His
        275                 280                 285

Leu Thr His Ser Phe Met Asn Ile Gly Thr Thr Met Ser Leu Ile Gln
    290                 295                 300

Asn Ser Leu Ala Gly Ala Gln Arg Ile Gln Glu Met Leu Glu Glu Gln
305                 310                 315                 320

Glu Glu Pro Gln Arg Ile Gly Ser Val Ala Ser Asp Arg Asp Ser Glu
                325                 330                 335

Ala Met Val Glu Phe Asp Cys Val Glu Phe Ala Tyr Gln Ser Asp Ser
            340                 345                 350

Pro Val Leu Cys Asn Leu Ser Leu Gln Val Leu Pro Gly Gln Val Ala
        355                 360                 365

Ala Val Val Gly Ala Ser Gly Ser Gly Lys Ser Thr Leu Ile Lys Leu
    370                 375                 380
```

```
Leu Leu Gly Phe Tyr Pro Val Asp Ser Gly Glu Ile Leu Ile Gln Gly
385                 390                 395                 400

Lys Ser Phe Gly His Tyr Thr Leu Glu Glu Ile Arg Gln Arg Ile Ala
                405                 410                 415

Tyr Val Pro Gln Glu Ala Phe Leu Phe Ser Gly Thr Ile Glu Asp Asn
            420                 425                 430

Ile Arg Tyr Gly Asn Pro Gln Ala Ser Gln Glu Glu Val Ile Ala Ala
        435                 440                 445

Ala Gln Ala Ala Tyr Ala His Asn Phe Ile Gln Glu Leu Pro Glu Gln
    450                 455                 460

Tyr Gln Thr Gln Val Gly Glu Arg Gly Ala Ser Leu Ser Gly Gly Gln
465                 470                 475                 480

Arg Gln Arg Ile Ala Ile Ala Arg Ala Leu Leu Lys Asn Ala Pro Ile
                485                 490                 495

Leu Leu Leu Asp Glu Ala Thr Ser Ala Leu Asp Ala Glu Ser Glu Tyr
            500                 505                 510

Trp Val Gln Gln Ala Leu Asn Gln Leu Met Lys Gly Arg Thr Thr Ile
        515                 520                 525

Leu Ile Ala His Arg Leu Ser Thr Val Glu Asn Ala Asp Val Ile Phe
530                 535                 540

Val Ile Gln Gln Gly Ser Val Val Glu Gln Gly Thr His Gln Ser Leu
545                 550                 555                 560

Leu Ala Cys Arg Ser Tyr Tyr Ala Gly Met Tyr Gly Gln Ser Gly Leu
                565                 570                 575

Ala Leu Ala Glu Gln Ala
            580

<210> SEQ ID NO 14
<211> LENGTH: 52556
<212> TYPE: DNA
<213> ORGANISM: Paenibacillus thiaminolyticus OSY-SE

<400> SEQUENCE: 14
atggaaatga tgcatccgaa taccaccgtc tctaccgttg caggaacttt agtcattcga    60
ggcgaggtag acgcggctgt gctgaaggag tctatctgcc aagtaattac gcagcacgat   120
gctttccgca tcagaatcat gactcaagac aatcaaccca ttcagcggct cgagcccgaa   180
tcggctatca ctccagaagt agactatatg aatgggatg accatttgga agctaaagac   240
tggttgaatc gtttcaatcg aattccaatc agtattttg atgataaatt atataatttc   300
acagtattta acgttaacaa tcaagagtat tggattcact aaaaattaa ccatattata   360 gctgatggcg taacttcgca tcttataggc aataaaatca tgcaaaccta tggagctt   420 acaagcggaa cgttctcggc taatgacaag aagaactctt atctcgatta cacttatgcg   480
gagcaggaat atgaaaagtc cgatcgctat cagaaagata aggcatactg gctggaaaag   540
ttccaaacca tgcccgagac gacaggaatt aaaccgtatc ctccatactc cataagcacc   600
gaggcgaaaa gagcgtacgt tgccctcacc ggcgagcgtt acgaacagct gaaggtcttc   660
agcgagcaaa acaacattag cctgttcaca ctattttgg caacggtata catgttttta   720
tataaaacaa ctggaaattt ggatattgct gtggggacag catacgcgaa ccggacgtca   780
aggaaagaaa agaaatgtt gggcatgttt gtaagcacag tcgcgactcg attgtcgctt   840
gatcccaacc aagatctgat ttccatccta cataatgtct ccaaagagca aaagacgaat   900
ttgcgtcatc agaaatatcc gtacaaccag cttattctgg atttgagaaa ggagcataag   960
```

```
cacagcgata tccaagatct ctatggcgtg tctgtggact atatgcctat taattggtcc    1020
agctatggac agctcagcat tcagcagcgg agcagttttt gcggtcacga agtggatgac    1080
ttggcggttc atgtcgaaga tatgctggac gatcaacagc ttgtcatcaa tgtggattat    1140
cggattcaat tgttcgaaga gcgtgaaatc actcgaatta tcgagcagat gcttaccata    1200
gtcgatggaa ttctgcataa tccgcagcag acgctgcacg agctgaccat gttgaacaac    1260
gaagaagcgc gtaaaatatt gacccaattc aacgacacgg ccgcagagtt ccctagggac    1320
aagaccgtgc accaattatt cgaggagcaa gcggcgcgca cgcccaatca tgttgcggcc    1380
gtgtatgagg atgagcagtt gacataccgg gaattgaacg aacgggccaa tcggctagcg    1440
cggacattgc gagccgaggg cgtgcagccg gagcaattag tgggcattat ggcagaccgc    1500
tcgctggaga tgattgtggg cattctggct atcttgaaag ctggcggggc ttatgtgcca    1560
atcgatccgg aatacccgga ggagcgcatc cgctatatgc tggatgattc gaacgcgcgg    1620
gtgctgttgg cccagcgtca tctgcaggca cgaattgcgt tcaccggcac atgggtgatt    1680
cttgatgaga atgcgttcta cgacgaagac ggcaccaacc ttgaatcgaa caatgacccg    1740
tctaatttga gctatgtcat ctacacatca gggacgacag gcaagccgaa ggggtcatg    1800 atcgagcata gacagctggt ggccatggca cacgcctgga atcccggta tcacttgcat    1860 gaggcgggca ttcgctggtt gcagtgggcg agcttctcgt tcgacgtatt ctcgggagac    1920
atggtccgca cgctcttgaa tggcggagag cttattctgt gtcccggtca cgcgcgggcg    1980
aacccggaag ctatctgcga attgattcgc aagcatcgca tccagatgtt cgagtcgacg    2040
ccggccctcg ttgtcccgct gatggaatat atatacgaca acaaaatgga cattcacagt    2100
ctgcaattgt taatcatcgg ctcggattac tgtccggctg aagaattcca gaagctgatg    2160
gaacgattcg gctcacaaat gcgaattctg aatagctatg gcgtaaccga agcgtgcgtc    2220
gatgccagtt atttcgaaca gacggattcc gatgcgcttc gaacgctgcc gataggcaaa    2280
ccattaccag ccgtatccat gatggttctg gacgataacc gctcgttgca gccgatcggg    2340
ataacgggcg aactatatat cggcggggct tgtgtgggaa gaggatattt gaatcggcca    2400
gatctgacgc ccgagaagtt cgtcgacaat ccatatgcgc caagcgagat gatgtaccgg    2460
acgggcgact ggcgcgttg gttgccggac ggcaatatcg aatatttggg gcggatcgat    2520
catcaggtga agattcgggg ataccgcatc gagataggcg aaattgaatc tcaattgctc    2580
aaagcggagt ccgttcgaga gtcagtcgtc gtcgcacggg aggacggaag cggacagaag    2640
gtgctgtgtg catactacgt ggcagaccgc gagctcacag tgaatgagct gaggggaaag    2700
atggcggaag aactgccggg atacatgatt ccatcgtatt tcatgcagct ggaacagatg    2760
ccattgacgc cgaacggcaa ggtcgaccgc aagggggctgc cggctccgga aggaagcgcg    2820
cataccggaa cggaatatgt ggagccgagt tctgcagcgg agaagatgct ggctgccgtg    2880
tggcaagctg tattgggtat agaacgggtc ggcgcgagcg agcatttctt cgagcttggc    2940
ggcgattcca tcaagtcgat tcaagtgtct tcccgattgc gtcaggccgg ctacaaaatg    3000
gagatccggg atttattcaa ataccccgacc attgcggagc tgagtctgca catccagcca    3060
gccggaagaa tggccgatca gagcgaagtg gttgggaaag cggagctgac accgatccag    3120
cgttggtttt tcgcacaacg gttcgccgat ccgcatcact ataaccaatc gatcatgctg    3180
taccgcaagg aaggcttcga cgaagcagcg attcgcaaga cgctggagaa gatcgccgag    3240
catcacgatg cgttgcggat ggtattccgc aagaccgaat ccggatacgc cgcttggaac    3300
cgaggaatcg gagaaggcga gctatacagg ctgaatgtgg cggacttccg taatgaatcg    3360
```

```
gcttgcgggc cgttgattgc agcgcaagcg aacgagattc aaggcgggat cgacatcgag   3420
acagggccat tggtgcgggc aggattgttc caatgcgcgg atggggatca tttactgctc   3480
gtcattcacc atactgtcat tgatggcgtc tcttggcgca ttttactgga agatatcgcg   3540
gttggttacg agcaagcgtt gaagggagaa gaggttcgtc ttccgagcaa aaccgatgct   3600
tatcgcactt ggtccgagcg actggcctct tatgctgaca gtcagactgt aattaatgaa   3660
cgtgcctatt ggcagcgtat cacacagacg gaaatgaatc ctttgcctaa ggattatgaa   3720
gcggattgct ccttgcagaa ggatagcgaa tccgtcatcg tccagtggag cccagaggac   3780
acagagcagc tattgaaaca cgtgcacaag gcatataaca cggaaatgaa cgacattttg   3840
ttgacagctc tagggacggc tgtgcagaga tggagcggcc gcgaccgggt gctggtgaat   3900
ctggaaggac acgccgcga ggccatcatc gcagacatcg acatctcacg cactgtaggt   3960
tggtttacaa gcgagtatcc ggtgctgctc gaaatggagc aggccaaggg cttgtcctac   4020
cggattaaaa aggtgaagga ggacttgcgc caaatcccga caagggtat tgggtatggc   4080 atatgccgtt atatgtccga cctcccgtat gaagcctctt ggggcgcgaa tccagaaatc   4140
agctttaact acctggggca gttcgatcag gatttgcaaa gcaacgggat gctcatgtct   4200
cccttgtcga gcggctcgaa cacaagcggc aaccaagcgc gccaatacgc gctggacatc   4260
aacggaatga ttatgatgg ctcgttagtc ttcgatctaa gctatggcag caaggaatat   4320
cgaagggaga cgattgagga tcttgccggg atgctgcaag agatcctgcg ggaaatcatt   4380
gcgcactgca ctgcgaagga gcggccggaa ttgaccccga gcgatgtctt gctgcaggga   4440
ctgagtgtgg aggaactgga gcagatcgtg gaacagacac agcacatcgg ggacattgaa   4500
aatatgtaca agttgacacc gatgcagaaa ggtatgtggt tccacagcgc catggatcgg   4560
caggcgggcg cgtattttga acaaacgcgg tttaccttgc aaggggatct cgacgtggat   4620
gccttcgcca agagctggac cgcattggca gcgcggcata ctgtgttgcg gacgaatttc   4680
cacaacggtt ggaagggcga accgctgcaa atcgtatacc gtgacaagcg gattgggttc   4740
gcttatgaag atgtgagcgc tctgaagccg gctaagcaaa gagcgcatat cgagaacgct   4800
gtgaatgaag acaagctgcg cgggtttgac ttagagcaag atgaacttat gcgggtgtta   4860
gtgatgcgta cggcacaaga gagctatcac gtgctctgga gctcgcatca tatcctgatg   4920
gacggctggt gcttgccgct ggttgccaaa gaagtgttcg atacgtactc tgcctatgtg   4980
cggcatcggc atctcgaaaa gacaacggta cctgcgtaca gtcaatatat tgaatggttg   5040
gaacagcaag atgaagaggc ggcatccgca tattggtccg agtatttggc tggatacgac   5100
cagcatacgg cgctgccgca agggaaagat caaggacgaa gcgaagcata cgctgcggag   5160
cacatcgatt gcgaactggg caaagacttg agcgtgcggc tcaacgaggc ggcgaaacgg   5220
aatttggtga ccctgagtac gttactgcaa acaacatggg gcatcatgtt gcagaagtat   5280 aacgaaccg gcgacgtggt attcggcggc gtcgtatcgg ggagaccggc ggacatgccg   5340
gggattgaag agatgatcgg cctgttcatc aacacgattc ctgttcgcgt taccgccgat   5400 gcggggggaga gcttcgccga catcatgtgc aggctgcagg aacaggcgct ggcatccgcc   5460
aagcacgatc actatccgct gtatgagatt caggcacaga gcgcgcagaa gcaagaactg   5520
atcaatcata tcatggtatt cgagaactac ccgatggaag agcaaatcga gcaattggaa   5580
agcctcgacg gcaaagggct gaaattgaag gatgtcatgg taacggaaca aacgaactat   5640
gacttcaacc tggtcatcat gcccggggac gaaattgtga ttcgtctgga ttataacgga   5700
```

```
atcgtgtttg acagaacgag tatggagcag ttgaagggtc atttagtgaa catgctggag    5760
caaatcgcgg ccaacccgca aataccggtg ggagaactgg aactggcgac agcagcggag    5820
aaagcgcaga ttgtggatgt gttcaacaac acagttgtcg agtacccgcg ggagaagacg    5880
attcatcaat tgtttgaaga acggaagaa cgaattccgg acgcggtggc ggtgatattt    5940
gaggacaaac ggttgaccta tgcggagctg aatgccgctg ccaatcgaat tgctcatctc    6000
ttgcgggatc gaggcgtagc acgaggcaca ctggtcggca tttgcgcgga gagatccttg    6060
gagatggtgg tcggactgct gggaatcctc aaagccggcg gggcatacgt tccgatcgat    6120
ccttcctatc ctcaagaacg gattaatgcc atgctggaag atacagcaat cagcgtgatg    6180
ctcacgcagg cgcatctgca gacaagcgtg ccgaacagca ttgattccgt cttgcttgat    6240
gcagcagcag agacgattct ggaaggaagc tggccgaact tgacagatac ggcggcgacc    6300
gcggacgatg tggcctacat catctatacg tccggatcga cgggaattcc gaaaggagtc    6360
tgcgtcacgc atcgaggggt ggtccggctc gttgccgatg ccaattatgt ggacatcagc    6420
agcaaagacg tattttttgca aggctcgacg atatcgttcg atgcggcaac gttcgagatc    6480
tggggcagct tgctgaatgg agctgcgttg gctgtgttgc ctccgggcaa tgtatcgttg    6540
accgaatgga cacgggccat tcaacagcat caagtgacga tcctatggtt aacggcagga    6600
ctgttccacg tcatggtcga caatcagctc caagccttgc agggagtcca acaattgttg    6660
gtgggcggcg atgtcgtctc caagacgcat gccacaaagg ttctggagcg gtataacgga    6720
attcggctaa tcaatggata tggtccgacg gaaaatacga ccttcacttg ctgccacgag    6780
atttccgcag ccgatatgga gcggccgtcc attccaatcg ggcgtccaat cggcaatact    6840
caagcatatg tgctggatgg agcgggcaag ctgcttccgg caggcgtgat cggcgagttg    6900
tatacaggcg gagacggact ggcccaaggt tacttgaacc gtccggagct gacggcagag    6960
aagttcgtag acagccctat cgtgccggca acacggctat accgcacagg cgacttggcg    7020
agatggctgc cggatggaac aatcgaatac gtgggacgaa tcgatgatca agtgaaaatt    7080
cgcggttacc ggattgagct tggcgaggtg gaagcgcatc tgctgaaagt ggagccggtt    7140
cagagtgctg ccgtgatcgc acggaaggac gaaagcggcc agaatatgtt gtgcgcgtat    7200
tatgcagcgg ataaagagct tacggcaagc gagctgagat cggctttgtc gcaagaactg    7260
ccgggataca tgatcccgac acactttgtg caggtggagc ggatgccgct gacgccgaac    7320
ggaaaggtcg atcgcaaagc gctgccggag ccggaaggcc gcatcatgac aggaatagag    7380
catgtcgcgc cgcggacacc gctggaatcc aagctggcgc atatctggca agaagtgctc    7440
ggacttgaga aggtcagcgt gaaggacagt tcttcgagc ttggcggaca ctctttacgt    7500
gcaacgacgc tggtaagcaa gcttcaacag gagctgcatg tgagcatgcc gctgcgtgag    7560
gtgttccgct ccccgactat tgaagagcag gcgcaagtga ttggcgggat ggagcaagag    7620
gaatacagag cgatccctca ggtcggcgaa agagaatgct atccagtgtc ttcggcccag    7680
aagcggctat atattttgca tcaattggag ggcgccgagc agacctataa catgccgggc    7740
gtgatgacac tcgcaggacc gcttgatcgg gagcggctcg aaacagcgtt ccgtaagctg    7800
atttcgcgtc atgagacgct gcgcaccggc ttcgagatgg tggatggcgt acctgtgcag    7860
cgggtatacg aagaagtgga ttttgcggtg gagtatgcgc aggcaagtga agaagcagcc    7920
ggtgaagccg ttcatgcttt catccgcgcg tttgatttgc agaagcctcc gctcttgcga    7980
atcggtctga tcgagcttgc gaaggagcgc catctcctga tgttcgacat gcaccacatc    8040
atatccgacg gggcctcgat cgggattctg atcgaagagt tcgtccggtt gtaccgtgga    8100
```

```
gaagagatct cgcctttacg tattcaatat aaggattatg ccgcctggct gcagtctgaa    8160
gcgcagcagg attggtcgaa acagcaggaa gcctattggc tggatgcgct gcgcggggaa    8220
ctgccggtct tggaattgcc gacggactat gcgcggcctc tgttccgaag ctatgaaggc    8280
agtacgttcg agttcacgat tcagcggcgc gaggcggagc gcctgcggca gctagctgct    8340
gagtccggag ctacattata tatggtgctg ttggcacttt atacgaccat gctgcataaa    8400
tacacggggc aagaagacat catcgtgggg atgccgatcg caggcagaac gcatggagat    8460
ctgcagccgc tcatcggaat gtttgtcaac acactggcca ttcgcagcta tcctgccggg    8520
gagaagacat tcttgtcctt tttgaggaa gtcaaagaca caacgatgcg ggcctatgag    8580
catcaggatt atccatttga agaactggtg aaaatgtgc gggtgccgcg ggacgcaagc    8640
cgcaatccgt tgttcgatac ggtcttcgtc ctgcagaata cggagcaggg aacgttcgat    8700
atcgatgggc tgcagctgtt gccgcatccg gcagaacatc ctgtcgcgaa gttcgacctg    8760
accttccaca tcgaagaaga agaggaaggg ctggcatgca gcatcgaata cgccaccgcc    8820
ttgttccagc gggaaacggt cgcacggatg gcacagcact ccgccagtt ggttgaagcc    8880 gtcactggcg agccggtgga ccggttagat cggttggaga tgttgacggc agaagagaag    8940
gttcagcttg tggatcggtt caatgatacg ggagcggact atccacggga gaagacgatt    9000
cacctgctgt tcgaagaaca agcggaacgt accccggctg cagtggccgt aattttcgag    9060
aatgctcagt taacttatcg ggagctgaac gaacgtgcca atcgcttggc gcatacgctc    9120
cgggcaaaag acgtgcagac ggatagcttg gtgggcatta tggccgagcg ttcaccagaa    9180
atgatagtcg gtattctggc gatttttaaaa gccggcggag cttatgtgcc aattgatccg    9240
gaatatccgg aagagcggat tcgctacatg ctggacgatt ctggagcgca ggtgctgctg    9300
cttccgcatg atctgcggga caaagttggc tttgatggga cagtcgtgat gcttgatgac    9360
gagcaatcct atgttgaaga cagctctaat ccagcaacgg ccagcaagcc gtccgatttg    9420
gcttatgtca tctataccc tggtacaacg ggcaagccga aagggacatt gattgaacat    9480
aaaaatgtcg tgcgcttatt gttcaacagc aaaaatctgt tcgacttcaa ttcggcggat    9540
acgtggacat tgttccactc cttctgcttt gatttctcgg tctgggagat gtatgggcg    9600 ctgttatacg gaggcagatt ggtggtcgtg ccgcaattga ccgccaaaaa tccggcacag    9660
ttcctggaac tgcttcacga gcagcaagtg accatattga accagacacc gacttatttt    9720
tatcagctgc tgcgggaagc gctggcagag cccggacaag aactgaaagt aagaaaagtc    9780
attttcggag gagaagcatt aaatccgcag ctgctgaaag attggaaaac gaaatatccg    9840
catacccagt taatcaatat gtatggaata acggaaacga cggtccatgt cacttataaa    9900
gaaattactc aagtggaaat cgagcaagcg aaaagcaata tcgggcgccc gatcccgacc    9960
ttgaaggtat atgtgctgga tgcgaatcgc caatgcgtgc ctgtgggtgt agctggagag   10020
atgtatgtag cgggcgatgg cttggcgcgc ggttatctgc accgtccaga actgacggct   10080
gacaagttcg tggatagtcc tttcgagtca ggcggacgta tgtacagaac gggcgatttg   10140
gcccgctggc tgccagatgg caatatcgaa tatttgggac ggatcgatca tcaggtaaag   10200 attgcggct accggatcga actcggcgaa gtggaagcgc aattgacgaa ggtggatcct   10260
gttcgggagg ccatcgtcat cgcacgggaa gacggacacg gggagaagca gttatgcgcg   10320
tacttcgtgg ccgcccgtga gcttacggtg gcgaattga ggcaagaact gtcgcatgcg   10380
ttgccagcct atatgattcc cgcatatttc gtgcaattgg agcggatgcc gctgacgcct   10440
```

```
aatgggaaaa tcgaccgcaa agcgctgccg gctccggaag acagcgtaaa taccggcacg    10500
gaatatatag cgccgcggac cctattggag tccgacttga cgcgtatctg caagatgtg     10560
cttggactgg aaagcatcgg cgtcaaagac aatttctttg agcttggcgg ccattccttg    10620
cgtgcgacca cgttggtgaa caaggtcac  caagagatga atgtcaatct tccgttgcgg    10680
gacgtcttcc gcttctcgac gatagaggag atggcttgcg cgattgcaga gatggaacaa    10740
cgcacatata tgtccatacc agcgattgaa acaagagact attacccggt atcctctgcg    10800
cagaagaggc tgtatattct ccaccagatt gaggggggccg agcaaggcta caatatgccg   10860
ggcgtactgc tccttgaagg tatgctcgat caggagaaat tcgaagaagc gttccacgga    10920
atcgtagcgc gtcatgaaac attgcgcacc ggctttgaaa tggttaatgg cgaaccggtg    10980
cagcgagtat atgagaaagt ggattttgca gtggaatatc ggcaggcgga cgaggaagaa    11040
gtcgaggcgg tcgtacgaga tttcgtccgc acgttcgatt tagagaagcc gccgttgctg    11100
cgaataggtt tactcgaatt ggcgaaggag cgtcatgtgc tcttgtatga tatgcaccac    11160
atcatttccg acggcgtttc gatggggatc gtggtggaag agttcgtccg tttgtacgcc    11220
ggagcagcgt tggagccgct gcgtatccag tacaaggatt atgccgcatg gcagctgtcc    11280
gaagcgcagc aggattggat gaagcggcag gaaggatatt ggcgggacgt gttccgcgga    11340
gaacttccgg tattggaaat gccgacggat tatgtgcgtc ctgccgtgca acagtatgct    11400
ggcagcacgc tttcattcga catcgatcca caaatgagcg aaggattgcg ccggattgcg    11460
gccgaaaccg ggacaacgct gtacatggtg ctgctcgcag cctataccat cctgcttcat    11520
aagtatacgg ccaagagga  tgtcatcgtg gcacgccaa  ttgcgggaag aacccatggg    11580
gatctgcagc cgctcatcgg gatgttcgtc aacacgcttg ctattcgcaa ttatccggca    11640
ggggagaaaa cattccgctc ctatctggcg gaagtcaagg aaacgacctt gggggcctat    11700
gaacaccaga actatccgtt tgaagaattg gtggacaagt tgcaggtcgc gagagattta    11760
agccgtaatc cgctgttcga cactatgttc gcttttaata tacggagcc  cgagactttc    11820
cctctcgaag gactgcggct gacgccgtat cctagcgaat acacgatatc caaatttgat    11880
ttgagtttgg atgtgtcgga aaaaaatgac aggctggaat gcagtctgga atatgcgact    11940
gccttgtata aaccagacac ggcagaacgt atggcgcagc acttccaaca attaatcgat    12000
tccattgtcg accagccgga ggcgaagctg gtttcgctcg gcatgcttac ggaggaagag    12060
aaggctcaga ttcaacatgt gtttaacaga gcggaggcag ggcactcgca ggagaaaacg    12120
gtgcctgaat tgttcgagga gcaggtggag cgcacgccgg atcggattgc ggtcgtacac    12180
gaggacaagc agctgacgta ccgggagctg aacgaacggg cgaatcgcct ggcgcgcacg    12240
ttgagggccg agggtgtgga gcctgagcaa ctggtcggca tcatggctga tcgctcgctg    12300
gacatgatcg tgggcattat ggccatcttg aaatccggcg gagcctatgt gccgattgac    12360
ccgaaatatc cggaggatcg cattcgctac atgctgacg  attcgcacgc gcaggtgctg    12420
ctggcccagc gtcatatgca agcaagcgta gcgtttgccg gacatgggt  gattctggac    12480
gaagaagcgt tctaccatga agacggcacc aacttggagc cgctcaatga gccgatgcat    12540
ttatcgtacg tcatctacac atcaggaacg acgggcaatc cgaaaggcgt catgatcgag    12600
cacagacaac tagtggccat agctgacgcc tggaaacgcg aatatcgcct ggaggaggaa    12660
ggtatccgct ggctgcagtg ggccagcttc tcgtttgacg tgttctcggg ggatatggtc    12720
cgcacgctgc tgtatggagg agagctcatt ctgtgtccgg agcaggcgcg ggcgaacccg    12780
gcggctatct ctgagttgat tcgcaagcat cagatacaga tgttcgaatc gacaccggcc    12840
```

```
ctcgtcatcc cgttcatgga ttatgtgtac gacaacaact tggacattag cagcctgaag    12900
atgttgatcg tgggttcgga ccactgcccg acggcagaat tcgataagct gaccgagcgc    12960
tgcggttcac acatgcgaat actgaatagc tatggcgtga ccgaagcttg cgtcgatgct    13020
tgctactatg aacggacaac gccggatgcg ttgcggacgt tgccgattgg caagccgttg    13080
ccggctgtaa cgatgtatat tctggatgat aaccgctcgc tgcagcctat cggtcacacg    13140
ggtgaattat atatcggcgg agccggcgtc ggccgcggct atctgaatcg accggacttg    13200
accgtcgaga aattcgtgga caatccgttc atgccgggcg cgcggatgta ccggacgggc    13260
gacttggccc gctggctgcc ggacggcaat atcgaatatg cgggccggat cgaccatcaa    13320
gtgaagattc gagggtatcg tatcgagatt ggcgaagtgg agtcccagct gctggcagcg    13380
gcaggcgtcc gcgaagcggc cgtcgtcgcg cgggaggatg gaagcggaca gaaggtgctg    13440
tgcgcgtact tcgttgcaga cagcgctcta acggtaggcg aactgagagc atcaatggcc    13500
caacaattgc caggctatat gattcctgcg cattttgtgc aattggagcg catgccgttg    13560
acaccgaacg gcaaagttga tcgcaaggga ctgccggctc cagaaggaaa cgcgtatacc    13620
ggagcagagc atgttgcgcc gcgaaccgag gcggagaaga cgctggcagc cgtgtggcag    13680
gttgtattgg gcgcagagca ggttggcttg atggatcact tcttcgaact gggcggcgat    13740
tccatcaaat cgattcaagt gtcttcccgg ctgcatcagg ccggttacaa gctgagata    13800
cgcgacttgt ttaaatatcc gactatcgcg gagctaagtc cgcatattca gccgattggc    13860
aggaaagccg accagggcgc agtgaccggc gaggcggcgc tgacgccgat tcaacactgg    13920
ttcttcgggc agcggttcgc cgacccgcat cactataacc aatcgatcat gctataccgg    13980
aaggaaggct tcgacgaagc ggcgattcgc aagacgctgg agaagatcgc cgagcatcac    14040
gatgcgctgc ggatggtatt ccgcaagacg gagcacgggt atgcggcctg aacagaggg    14100
atcggagaag gcgagctcta cagtctcaac gtggcggact tcacggatga tccggcgtgc    14160
taccgggcga tcgaagccaa ggcgaacgag atacagagcg gtattaattt gcaagccggg    14220
ccactgctca gagcggggtt attcacttgc gcacacgggc atcatttgtt aatcgtcatt    14280
caccatgctg ttaccgacgg agtctcatgg cggatcttgc tggaggatat cgcggcaggt    14340
tacgagcagg cgctgaaggg agaagcgatt cgtctgcctg cgaagacgga ctcctatcta    14400
acctggtcca agcagctgag cggatacgcg cagagtccgg ccatagagca ggaacgatcg    14460
tattggcagc gtatcgcgca gtcgaacacg aagcctctgc caaaagatcg gacagtgaat    14520
gtttctttgc aacgggatag cgaatctgtc agcgtccaat ggagccggga ggatacggag    14580
cagctgttga agcacgtcca ccgggcatac aacaccgaca tgaacgacat tctgttgacg    14640
gcgctgggaa tggccataca gcaatggagc ggccgcgatc gcatgctggt gaatctggaa    14700
ggacacggcc gcgagtccat catggcggac gtcgatatct cgcgcactgt gggctggttt    14760
acgagcgagt atccagtgct gcttgagatg gagccggaca agagcttgtc ccattgcatc    14820
aaaaaggtga aggaggactt gcgccaaatt ccgcacaagg ggatcgggta tggcatctgc    14880
cgatatctgt ccggaacgat ggaagacgcg gcgtggggca cagcacccga aatcagcttc    14940
aactacttgg ggcagtttga tcaagatctg aacagcaacg ggatggagat gtctccgtat    15000
tcgagcggca cggatgcaag tggcaagcaa gtgcgccaat acgcgttgga catcaacgga    15060
ggcattacgg acgatcgtt gtcctttgac ctgagctaca gccggaagga ataccgcagg    15120
gagacgatgg aggatctggc cgggcggctg cgtgagagct tgcaggagat tatcgcgcac    15180
```

```
tgtgcagcga aagagcgcac ggaactgacg ccgagcgacg tgctgttgca ggggttgagt    15240
gtggaggaac tggagctgat agtggagcaa acgcggcacg ttggcgagat cgaaaatata    15300
tatgcgttga cgccgatgca aaagggtatg tggttccaca acgctatcga tcaacaggcg    15360
ggcgcttatt tcgagcaaac ccgattcacc atacagggag tactcgatgt ggatgtcttc    15420
gcgatgagtt tgaacgtatt ggctaagcgc catgcggtac tgcggacgaa cttctatagc    15480
ggctggaacg gcgaaccact ccaaattgtg taccgggaca agcggattgc attcgtttat    15540
gaagatctac gccatctgcc agcagccgag cagactgcac atatcgagca cgccgcaagg    15600
gaagacaagc tgaagggatt tgatttggag caggatgcgt tggtgcgggt agcgctgatg    15660
cgcacgggag cagcaagctg ccgcgtgctc tggagctccc accacattct gatggatggc    15720
tggtgcttgc cgcagcttac gcaagagctg ttcgacacat atagctccta catgaagcag    15780
catcatgatg aacaggcact gccagcgtac agtcagtcat catacagcca gtatatcgag    15840
tggttggagc agcaggacga ggaagcagca gctgggtatt ggagcgaata cttggcaggg    15900
tacgaccaac agacgttgct gccgcaaggg aagacgcaag ggagagacga agcttacgtg    15960
ctggagcatg tcgtgtgcga actgggcaag accttgacag gacggatgag ccagctggcc    16020
aagcagcatt cagtgacgct gaatacattg ctgcaggcgg cctggggcat catcctgcag    16080
aaatacaacg gcacagacga tgtggtgttc ggcggggtcg tttcgggcag accggcagca    16140
attccgggca ttgaaacgat gatcgggctg ttcatcaaca cgattccggt gcgcgtcgct    16200
tgcgcagcgg agacgagctt tactcaggtg atgagacggc tgcaggagca ggcattggac    16260
tctggccgat acgattatta tccgttgtat gagatacaag cacagtgtgc gcaaaagcag    16320
gagttaatat cccatattat ggtgttcgag aactatccgg tggatgagca gatggagcaa    16380
accggaagca aggacagcgg aacgctgagc atcacggacg tcgaagtggc agaacaaacg    16440
aactatgatt tcaacctaat ggtcgtgccg ggcgaagaac tcgtcgttcg tttcgacttc    16500
aacgaaagcg tgttcgacag aacgagcatc gagcggttga cggggcatct ggtgcatgtg    16560
cttgagcaaa ttacggccaa cccgcaaata tcggtgggag acctggaact ggcgacagca    16620
gcggagaaag tggaaattgt agatgtgttc aacgatacgg cggcggatta ccgcgggag    16680
aagacgatcc atcaaatgtt cgaagaacaa gtcgaacgaa ctccagatgc ggtggcggtc    16740
atgttcgagc aggaacggct gacgtaccgg gaactgaacg agtgtgtgaa ccgcttggcc    16800
cggacgctgc gaacgcaagg cgtccaaccg gatcagcgtg tcggcatcat ggtcgagcgc    16860
tcgttggaga tgatggtcgg catcatggcg attttgaagg ctggcgggc atatgtgccg    16920
attgctccgg attatccaga ggagcgcatt cactacatgc tggaagattc gggagcgcag    16980
gtgctcttgc tgcaaggccg ttcgggagag agcgtgtcct ttgcaggccg catcgtcaat    17040
ctggacgatg agagctccta cgccgaagat ggatcgaatc tggaatgggt caaccaggca    17100
agcgatgctg cttatgtcat ctatacgtcg gggacgacgg gcaaaccgaa gggggttctg    17160
gtggagcacg gttctgtcat caaccgcttg ctgtggatgc agaagcaata tccaatcaac    17220
gccaacgata cgattatgca gaagacggcg atcacatttg acgtctccgt ctgggagttg    17280
ttctggtggg ccttcgtcgg ttctaaagtg tgcctgctcc cggtcggcgg ggagaagaac    17340
ccggccgtca ttctggatac gatcgcgcag cagcatatca gcacgatgca ttttgtgccg    17400
tccatgctgc atgccttcct cgaatatgtc gaggagcagc cgattgcaga acggagcgc    17460
agcttagcgg cactctcgcg ggtgttcgca agcggcgagg cgctgaccct ctcgcaagtc    17520
gagagattcg agcgttgcat tgcgccggcg agtggagcgc gcctgatcaa tctgtacggg    17580
```

```
ccgacggaag cgaccgtaga cgtgacgtac tatgattgtg aggccgggca gccatatacg   17640
agcgtgccga ttgggaagcc gattgacaat acgcaaattt atatcgttaa tcgtcaagat   17700
caactgcagc cgattggcgt agccggagaa ttatgcatcg cgggtgtggg cttggcgcga   17760
ggttacttga agcgtccgga gctgacggcc gagaaattcg tgacgattcc gttcatgccg   17820
ggcgcgcgga tgtaccggac aggcgactta gcccgctggc tgccggatgg cagcattgaa   17880
tatttgggcc ggatcgacca tcaggtgaag atccgggggt atcgtatcga gctcggcgag   17940
atcgaggccc agctgctgca agtggaattc attcgggaag cggtcgttgt cgcgagggaa   18000
gatgagagcg ggcagaaggc attatgcgcc tacttcgccg cagatagcga attgccggta   18060
agcgagctga gatcagcgtt ggctgtagaa ttgccgggct acatgattcc gtcgtacttc   18120
gtgcagctgg agcgactgcc gttgtcagcg aacgggaagc tcgaccgcaa ggcgcttccg   18180
gctccgggag gaagcatgcg cagcggcaag gaacatgttg caccgcgctc gctgctcgaa   18240
gtgaagctgt gcgaatctg gcaagaagtg ctcggactgg cgcacgtcag cgtgaaggac   18300
gacttcttcg aactcggggg acattccttg cgcgccacca ccttggttag caagctgcat   18360
aaggagctga acatcaatct gccgttgaga gacgtgttcc gctattcgat tcttgaagac   18420
atggcgctcg ctatcggcag aacggaacaa cgagagttcc agaccattcc gcaggtcgaa   18480
gcaagcgatt attatccgtt gtcttctgcg cagaagcggc tgtacatcgt gcagcaggtg   18540
gaaggggcag aacaaagcta caatatgccg ggagcgatgt cgatcagagg gcaactggac   18600
cggaatcaat tcgaggcagc gttccgcgga ttaatcgcac gtcatgaagt gttccgcact   18660
agcttcgaga tggtgggcgg cgagccgatg cagcgtgtac atcaggatac ggcatttgcg   18720
gtggagtata tgcaggcaaa tgaagaagag gctgaagcaa tcgcgcacca attcgtccgc   18780
acctttgatt tggagcagcc ttccttgctg cgtgtcggtc tgatcgaatt agaccgggaa   18840
catcatatta tgttgtttga catgcatcac atcatctctg atggagtctc catgggcata   18900
ttggtggagg aatttgcccg cttgtacagc ggggaggagc tgccgccact gcgcatccaa   18960
tacaaggact atgccgcatg gcagcaatca gaggcgcaga gtgaacggat aaaacaacag   19020
gaagcgtatt ggcttgacgc attggatggc gagctcccgc agctggaatt gccaaccgat   19080
tttgcaagac cggctcatca gagccatgaa ggagacaccc ttgattttgt aatcgattcg   19140
cacatgagcg ggggctgca gcggctcgcc gagcataccg gcacgacgct gtacatggtg   19200
ttgttagcgg cctatacgat tttactgcat aaatactcgg atcaagaaga tatcatcgtg   19260
ggcactccga tcgcgggaag aacgcatgcg gatgtggagc cgctcatcgg gatgttcgtc   19320
aactcgcttg cattgcgcag ctatccgtgc ggggagaagt cattcctctc ctacctggag   19380
gaggttaagg aaatgacctt ggctgcttat gaaaatcagg attatccgtt tgcagagctt   19440
gtggagcacg tacaggccgt ttggagccca agcagaaatc cgctgtttga caccatgttc   19500
gtcttgcaaa atacagaaga ccggaacgtt cgcttcggag agctgaccat agaaccgtat   19560
acgcaacatc acaacgtcgc caaattcgat ctgacactgg agattgcgct ggaagacggt   19620
gtaatgagcg ggcactttga atattgcacc cgattgttta caacaaacat ggttgacaac   19680
tttgccgagg atctgttgtc tatccttgct cagatctgtg agcagcctgc tatccgctta   19740
ggtgacattc acttacacgg caatgcagag gaagatgaag aggcgtcctt agcagaagaa   19800
atcgattttg tgttctaatc ttctgttcac cggttgcgag tgtgcgctat cgcttatgta   19860
gaagagatcg ttcttgcaac cttctcggtg ctgaaaagtg gtcttttgaa cacgcactta   19920
```

-continued

```
tagcaatagc acacactccg gtgaatagga gcggcaatag cttggttgta ccccattgag  19980
agaggagaag atgaacttgg catttgaaaa ggaaaccgat ttttggaatg cgcaattcga  20040
tgctgaagat agtcctgcga tcctgcctta ctccacagct tcaatcagcg ttacagctcg  20100
cgatcattcc aattccatca gcttatctgc cgacgtatcg caacgaatta gtcatatgag  20160
cagaggttcc catctggccg aatacatgat cttactagca ggcatccaat gcttgcttta  20220
caaatataca ggtgaagaga gtgtcatcgt aggcatgcca atcgttagaa agtccaagga  20280
cacacggcgg cctatcaaca atgtggtgat tctcaaaaat aagctaggtg caaaccgtac  20340
cttaaaatcg ttgttgaccg aattgaaaac tacgcttacc gcagcaatca atcatcagaa  20400
catccctttt cggaagatga cggagcattt gcatttagaa gctgtaaatg gagttcctgt  20460
cgtaaatacg atggtttcta tgaaagaaat acataccatt gaattcagtc agagtgtagt  20520
ctccgatatc ctattccaat ttgaatggga acaagatgtg atttcattac atgtgaccta  20580
taacgaaaat cgatacgata aaccattcat tacgcaaata atgaaccatg ttaactcttt  20640
atttgccgac gttttatata ccccggaaag agtgctgcaa gacgtgaacc tgctatcaga  20700
gcaggagacg gctcagcttc tttatgaatt caacgataca gcagcagact acccgcggga  20760
taagacgata caccaattgt tgaagagca ggaggaacaa actccggacg cggtggcggt  20820
gctattcgag gacaaacagc tgacctatgc ggagctgaat gccgctgcca atcgcattgc  20880
ccatctcctg cgggaacgag gagtagcacg gggcactttg gttggcattt gtgtagagag  20940
atccctagag atggtgattg gactgctggg gatcctcaaa gcaggcgggg catacgttcc  21000
gatcgatcct gactatccgg aggaacggac taacgccatg ctggaagata cggcaatcag  21060
cgtcctgctc acgcaggcgc atttgcagac aagcatgccg aacagcatcg attccgtctt  21120
gctcgatgca gcggcagaga cggctctgga aggaagctgg ccgaacttga cggatgcggc  21180
agggaccgcg gacgatgtgg cctacatcat ctatacgtcc gggtcgacgg gaattccgaa  21240
aggagtctgc gtcacgcatc gagggtggt ccggctcatt ccgctgcca attatgtgga  21300
catcagcagc aaggacgtat ttctgcaagg ctcgacgata tcgttcgatg cggcaacgtt  21360
cgagatttgg ggcagcttgc tgaatggagc tgcgctggcc attttgcctc cgggaaatgt  21420
ttcgttgacc gaatggacag aggccattca acagcatcaa gtgacgatcc tgtggttaac  21480
ggcgggactc ttccacgtga tggtcgagaa ccaactccaa gccttgcaag gagtccagca  21540
attattggtg ggaggagacg tcgtctcgaa gacccatgcc aaaaaagtgc tggagcggta  21600
tcaggacatt cgtctggtca atgggtacgg tccaacggaa aatacgacct tcacctgctg  21660
ccacgagatt tccgccgccg atacggagcg gctctccatt ccgatcggac gtccgatcgc  21720
caatacgcaa gtgtacgtgc tggatgaagc aggcaagctg cttccggtag gagtggtcgg  21780
cgaattgtac accggaggag atggactggc ccgaggttac tggaatcgtc cggagctgac  21840
ggctgagaag ttcgtagaca gccccttcgt gccgggaaca cggctatacc gcacaggcga  21900
tctggcgaga tggctgccgg atggaacgat cgaatacgtg gacgaatcg atgatcaagt  21960
gaaaattagc ggttaccgga ttgagcttgg cgaggtggaa gcgcatctgt gaaagtgga  22020
atcggtgctg gacgcaatcg taatcgcccg gcaagacgaa agcggccaga agacgttgtg  22080
cgcgtacttt accgcgaatg cagagctgat ggcaggcgat ctgagagcag tgctgtcgca  22140
agaactgccg gcgtatatga tcccgacaca cttgtgcag gtcgatcgga tgccgctgac  22200
gccgaacgga aaggtcgatc gcagagcgct gccgagccg gaaggcctca tcatgacagg  22260
aaaagagcat gtcgcgccgc ggacgccgct agagtctaat ctggcgcatc tgtggcaaga  22320
```

```
ggtgctcgga cttgagaaag tcagcgtgaa ggacagtttc ttcgagattg gcggacactc   22380
tttgcgtgcg acgacgctcg caagcaagct gcacaaggag ctgcatgtca gtctgccgct   22440
gcgggacatc ttccgccatc ctaccattga agagctggcg tgcctcattg acgggatgga   22500
acggcaggaa tacagacaga ttccgctgct ggatgaaagg gattggtacc cggtatcttc   22560
ggcgcaaaag aggctgtaca ttttgcatca gctggaaggg gcggagcaga gctacaacat   22620
gccgggggtg atgctcctcg aagggcagct tgaccggaat cggttcgagg aggcgttccg   22680
cagcttgatc gggcgccacg aaacgctgcg caccggcttt gaaatggtga atggcgaacc   22740
ggtgcagcgt atatgccgcg aagtgaattt ctcggtggag atgatgcagg cgagcgaagg   22800
ggaagccgat gccgccatcc gttcctttat tcgcccgttc gatctggaga agccgccgct   22860
cctccgagtg gggctgatcg agttaagcca ggatcggcat attctgatgt acgacatgca   22920
tcacatcata tccgacggcg tgtcgatgga aattgtggtg gaggagttcg tccgcttgta   22980
cggcggcgag aaactgccgc cgctgcgcat tcagtataag gattatgccg cgtggcagca   23040
gtccgagccg cagcaggagc tcatgaagca gcaggagagt tattggttgc aggcgtttgg   23100
cggagagctt ccggtgctgg aaatgccggc ggattatgcg cgtccttccg tccagagcta   23160
cgaaggggat accttcgaat cgcgatcga tcctgggcta agcgaagcgc tgcgccggat   23220
tgcggcagag agcggaacga cattgtacat ggtgctgctt gctgcctata cgattctgct   23280
tcagaagtat acaggccagg aagacattat cgtgggaacg ccgaatgcgg gcagaacgca   23340
cggtgatttg cagccgctta tcggcatgtt cgtcaatacg ctggcgatcc gcaattatcc   23400
ggcaggctcg aagacgttcc tggaatattt ggagcaggtc aaagaaacga gcttgggcgc   23460
cttcgagaat caggattacc cgttcgaaga actggtggaa aagctgcagg tagcgcgaga   23520
tttgagccgc aatccgctgt tcgatacgat gttttctttg cacaatatgg acagcaagga   23580
tctggagctc gcagagcttc gcttgaagcc gtacccagct gaatacaagg tggcaaaatt   23640
cgacctgagc ctggacgtgg cggaaggcgc ggaagggatg gcatgcagtc tggaatacgc   23700
cacggcgcta tacagacggg aatcgattga agaatggcg aagcacttcg gccagctgct   23760
tgaggccatt acgcaagagc cggaggcgcg gctgtcctcg ctcggcatgc tcacagagga   23820
ggagaaggct cagattcagc atgtgttcaa cgatgcggag gcagggcgtt cgcagcagaa   23880
gacggtgcct gaattgttcg aggagcaggt ggagcgcacg ccggatcgga ttgcggtcgt   23940
gcatgaggac aagcagttga cgtaccggga gctgaacgaa cgggcgaacc ggctggcgcg   24000
cacgctgcgg gccgaggacg taaagcccga acagttggtc ggcatcatgg ccgatcgctc   24060
gctggacatg atcgtgggca ttatggccat cttgaaatcc ggcggcgcct atgtgccaat   24120
cgatccgaaa tatccggagg atcggattca ctatatgctg gacgattcga acgcgcaagt   24180
gctgctggcc cagcgtcatc tgcaagcgcg ggccgcattc tccggcagaa ggattacgct   24240
ggatgaggaa gcgttctacg acgaggacgg ctccaacctg gaacgggtga atcagccgga   24300
gcacctgagc tatgtcatct atacctcggg aacgacgggc aagccgaaag gggtcatgat   24360
cgagcacaga cagatggcag tcttgtcggc cgcgtgggaa agcgaatacg gcttgcggga   24420
agagagcatg cgctggatgc agtgggcgag cttttcattc gatgtcttct cgggagacct   24480
gatccgcgcg ctgctgcatg ggggtgaact cattttatgt ccggaagagt ccagggcgaa   24540 cccgccgaa atctacgagc tcattcgcaa gcatcggatt cagatgttcg atgtcactcc   24600
gtcgctcgcc attccgctga tggaatatgt atacgagaac aagctggaca tcagcagtat   24660
```

```
gaagctggca gtcgtagggg cggatcattg cccgaaggag gaattccaga agctgctgga   24720
acgattcggt tcgcaaatga ggatcgtgaa cagctacggg gtaacggaga cgaccatcga   24780
ttcctgctac ttcgagcagg cgagcacgga agggctgcga acggtgccaa tcggcaaacc   24840
tctgccgggt gtgacgatgt acattctgga tgatcaccat tctttgctgc cggtcgggat   24900
aacgggcgag ctctatattg gcggaccttg cgtgggccgg ggctattgga agcggccgga   24960
cctgacggcg gagaaattcg tcgacaatcc gttcgctccg ggcgagcgaa tgtaccggac   25020
aggcgacttg gcccggtggc tgccggacgg caacgtcgaa tatttggggc ggatcgatca   25080
tcaagtgaag atccggggct accggatcga gattggcgaa gtggagtccc aactgctgaa   25140
aacgccgttc atccgtgaag cggtcgtcgt cgcgcgggaa gacgccggcg gacagaagtc   25200
attgtgcgca tacttcgtcg ccgaacgcga gctgacagtg agcgagctgc ggggagcatt   25260
ggccgcagaa ctgccgggtt acatgattcc atcgtacttc gtccagttga agcagctgcc   25320
gttgacgccg aacggaaaaa tcgaccgtaa agcgctgccg gctccggaag gaagcgcgca   25380
taccggaact gactatgtcg cgccgcgaac cgaggcggag aagactctgg cagccgtgtg   25440
gcaggctgta ttaggcgcag agcgtgttgg attgatggat catttcttcg agcttggagg   25500
cgactccatc aaatcgattc aagtgtcttc ccggctgcat caagccggct acaagctgga   25560
aatccgggat ttattcaaat atccgaccat cgcggagctc agtccgcata tccagccggt   25620
tggcagaatg gcagaccaag gcgaagtaag cggtacggta ccgctgactc cgattcaacg   25680
ctggtatttc gggcagcagt tcgccgatcc gcatcactat aaccaatcgg tcatgctgca   25740
ccggaaagag ggcttcgaca cagccgcgat ccgcaaggcg ctgcagaagc ttgtggagca   25800
tcatgatggg ctgcggatgg tgttccgcaa gacggaggaa ggatatacgg cgtggaatcg   25860
tggaatcgga gaaggcgagc tctatcgtct gtacgtggcg gactttacgg gggttgcggc   25920
gtgtgaacgg atgattgaag ccgcagcgaa cgagatacaa agcggcatcg atttgcaggc   25980
tggtccattg gtgagagccg ggttgttcca cggcgcggac ggggatcatt tgctcatcgt   26040
catccatcat gccgtcgttg acggcgtctc ttggcgcatc ttgctcgaag acttcgccgc   26100
aagctatgaa caagcgctga agggccaagc actgcgcttg cctttcaaga ccgattccta   26160
tcgtacatgg tccgatcagc tcgttgaata cgcgcgcagt ccggtcatgc agcgcgaacg   26220
ggcgtattgg cagcgtatcg cgcagacggc agcgaagcct ctgcctaggg attatgaagc   26280
ggaatgctct ttgcagcagg atagtgaatc cgtcaccgtc cagtggagcc aagaggctac   26340
cgaacagcta ttgaagcatg tccatcgggc gtataacacg gaaatgaacg acattctgct   26400
gacggcgttg ggaatggccg tgcaaaaatg gtgtggccgc gacagagtgc tggttacgct   26460
ggaagggcac ggccgggaat ccatcatgac ggacatcgac atcacacgca ccgtcggttg   26520
gtttacgagc gagtatccgg tgttgctcga gatggagccg gacaaaagct tatcctcccg   26580
catcaagaag atgaaggagg acctgcgcca aattccgaac aaaaggcatc gctatggcat   26640
cggccgatat atgtccgagc tgcacgatga agccgtctgg ggaggagcag aaccggatat   26700
cagcttcaat tacttgggac agttcgatca ggatatgaag aacaatgaga tggaagtatc   26760
tccatattca gcggtatgg aagtgagccg tcaacaagcc cgcacccatg cgctggatat   26820
caacggaatg gtggcagacg ggtcactggc gctggaactg agttacagca ggaaggaata   26880
ccgcaaggag acaatcgagg cattgtccat atatctgcag gagagcctgc aggagattat   26940
actccattgc actgcgaaag aacggccgga ggtcacgccg agcgacatct tgctgcaagg   27000
attgagcgta gaggaactgg agcaaatagc gaagcagacg cagcgcatcg gagacatcga   27060
```

```
gaatatgtat accttgacgc cgatgcagaa ggggatgtgg ttccacagcg ccatggatca    27120
gcatgcgggc gcttattttg aacaaacgcg gtttaccctc cagggcgcgc tcgacgtaga    27180
ggtctttgcc aaaagcctgg atgcattggc caagcaacat gccgtgctgc ggacgaactt    27240
ctataacggc tggaacggcg aactgctgca aattgtattt agagacaagc ggcttggatt    27300
cgcttatgaa gatttgtgcg cttttgccgga agccgagcga gagacgcatg tcgagacttt    27360
gacgcaagag gaccgtatgc ggggatttga tttggaacag gatgcgctca tgcgcgtatc    27420
ggtggtgcgc atggcggaag aaagctatca ggtgctgtgg agctcccatc atattctgat    27480
ggatggctgg tgcttgccgc agcttacaca ggaatggttc gacacatatt ccgcctatgt    27540
gcagcatcag catctcgagc ggacaacggc acctgcgtac agtcaatata tcgagtggtt    27600
ggaacaacag gatgaccaag cggcatcggc gtattgggcg aattatttgg ctggttatga    27660
ccaacaaacg gtactgccgc aagcgaaggg gcaaggtcgc agcgatgagt acgccgcgga    27720
gcgcatcttg tgcgaattgg gcaaggcctt gaccgggcgg atgagccatg tagccaagca    27780
gcaccaggtg acgctgaata cgttaatgca ggcggcatgg gccatccttt tgcagaaata    27840
caatggcaca gacgatgtgg tgttcggcgg ggtcgtatcg ggcagaccgg cggaaattcc    27900
agggattgaa gcgatgatcg gactgttcat caacacgatt ccggttcgcg tcacctgcga    27960
agcggagacg agctttgccg agttgatggg acggctgcag gagcaggcat ggaatccgg    28020 acgatacgat tattatccgc tgtatgagat tcaagcgcag tgcgagcaga agcaggatct    28080
aatttcccat ctcatggtat tcgagaacta cccgatggaa gaacagatgg agcaagccgg    28140
aagcgatgat cggggcaagc tgacgattac cgacgtcgag gtggcggaac aaacgaacta    28200
tgatttcaac ctggtcgtcg tgccaggtga cgaaattgtg attcgcctgg agtataacgc    28260
gaacgtgttc gatcgggaga gcatagagca gctgcagggt catctcgtgc atgtgcttga    28320
gcagattacg gccaacccgc atatggccgt gggcgagctg gaactggcga ccgccgggga    28380
gaaaacgcag ctgatgctcg cgttcaacga tacggcagcg gagtatccgc gggagaagac    28440
gatccatcag atgttcgaag aacaggccga acgaaccccg gatgcggcgg cggtcctgtt    28500
cgagcaggaa cagctgacgt accgggaact gaacgagcgc gcgaaccgct tggcccggac    28560
gctgcgagca ttaggagtac agccggatca gttggtcggc atcatggccg agcgttcgct    28620
ggagatgatg gttggcatca tggcgatttt gaaggctggc ggggcgtacg tgccgatcgc    28680
tgcggattct ccagaagagc gcatccgcta cctgctggag gattcgggag cgcaggtgct    28740
cttgctccag ggccgtgcgg gagaagaagt gtcctttgca ggccgcatcg ttaatctgga    28800
tgacgcaaat tcctatgccg gcgacggttc gaatccggaa cgggtcaacc aggccagcga    28860
tgccgcttat gtcatctata cgtcggggac gacgggcaga ccgaaaggcg ttctggtgga    28920
gcacggttca gtcatcaacc gcttgctgtg gatgcagaaa cgatatccaa tcggtccgag    28980
cgatacgatt atgcagaaga cggcgattac gtttgacgtc tccgtctggg agctattctg    29040
gtgggctttc gtcggttcca aagtgtgcct gctgccggtc ggcggggaga agaacccggc    29100
cgtcattctg gatacgatcg agcggcagca tatcagcacg atgcattttg tgccgtccat    29160
gctgcatgcc ttccttgaat atgtcgagga gcagccggtc gcggaacggg agcgcagctt    29220
ggcttcattg cggcgggtgt tcgcgagtgg ggaggcacta actgcttcgc aggcagaaag    29280
attcgaacga tgcatcgcgc cggtgaatgg agcgcggctt atcaacctgt atgggccgac    29340
ggaagcgacc gtggatgtga cgtactttga ttgccaggca ggacagccat atacgagcgt    29400
```

```
gccgatcgga cgaccgattg acaatacgca aatctatatc gtgaaccggc agaatcaact    29460
gcagcctatc ggcgtagccg gggaattatg catcgcgggc gcaggcttgg ctcgaggcta    29520
ctgggagcgg ccggagctaa cggcggagaa attcgtggaa attccattca agcctagtga    29580
gcggatgtac cggacgggcg acttggcccg ctggctgccg gatggcaaca tcgaatattt    29640
aggccggctt gaccaccaag tgaaaattcg ggggtatcga atcgagcttg cgaaatcga    29700 ggcccaactg ctgcaagccg cagccatccg gaaacggtt gtcgtcgcgc gggaggatga    29760
gagcggacag aaagcattgt gtgcctactt cgccgcagac agcgagctga cggtaagcga    29820
gctgagatca gcgctggccg cacaattgcc ggactacatg attccgtcat acttcgtgca    29880
gcttgagcga ttgccgttgt cggcgaacgg gaaaatcgac cgcaaggcgc tgccgagccc    29940
agaaggaagc ttgtacaccg gaacagagta cgtcgccccg cggaccgagg cggaaaagac    30000
gatcgcagtc gtgtggcagg cggtgctggg catcgagcgg gtcggagtaa cggatcattt    30060
cttcgagctt ggcggcgatt ccatcaaatc cattcaagtg gcttcccggc tgcagcaggc    30120
cggctataag cttgaaatcc gggagctgtt caagtacccg accatcgcgc agttaagtct    30180
gcaggtccgg ccggttgcca gaatggccga tcaaggagaa gtggcagggg agatgcctct    30240
gacaccaatc ttaagctggt tcatggaaca ggaattcgcg aatccgcatc actttaacca    30300
atcgattatg ctgcaccggc aggaaggggt cgacgaagtg gcgattcgaa aaacgctgca    30360
taatatcgtc gagcaccacg acgcgctgcg aatggtattc cgcaagacag aacatggcgg    30420
gtataaggcg tggaaccggg gaatcagcga aggcgatctc tacagtttgg acgtggcgga    30480
cttcaaagaa gatccggagt gcggccgttc gatcgaagcc aaggcgaatg agattcagag    30540
cggcatcgat ctgcagacgg gtccattggt gaaagcggga ttgttccact gtgcagacgg    30600
ggatcatcta ttgatcgtca tccatcatac cgtcatagac ggcatctctt ggcggatctt    30660
gcttgaagac attgcagatg ggtacgagca agcgttgaaa ggacaagaga ttcgtcttcc    30720
ggtcaaaacc gatagctacc gcatctggtc ggagcaactc gcaacgtacg cacatagttc    30780
tgacttggag aatgaacggg catactggca gcgcatcgcg cagacggaca cggagcctct    30840
gcccaaggac tgggaagcgg cctgctcctt gcagcgcgaa agcgagtccg tgaacgtcca    30900
atggagcagg gaggatacgg agcggctgtt gaagcatgtt caccgggcat acaatacgga    30960
gatgaacgat attttgctgg cggcattggg aatggccgtg cacaaatggt gcggtcgcga    31020
tcgagtgctg gtcacgctgg aaggccacgg ccgggaatcc atcttgacgg atatcgacat    31080
tacgcgtacc gtgggatggt ttacaagcga atatccagtt ttgattgaag cggagccgga    31140
caagacattg tcttatcgga tcaaacaggt gaaggagaat ttgcgccgca ttccgaacaa    31200
gggcatcgga tatggcatct gccgatattt atcgtctgcg caagaacctg catgaccgga    31260
agcgttcacg cctgaacttc gcttcaacta tttgggacag ttcgatcagg atctgcaagg    31320
caacgagttg gaattatcat cttattcaag cggttcggat atgagtgacg aacaggtgcg    31380
caattacagt ttggatatta gcggaatgat cgtggatggc ttgctatcgc tggacgtgag    31440
ttacagcggc aaggaatacc gcaaggaaac catcgaagag ttggccggat gtttgctggt    31500
gagcctgcag gagatcattg accattgcgc agcaaaggaa cgtcctgaat taacgccgag    31560
cgatgttttg ctgcaaggat tgagcgtgga ggagcttgat cagatcgcgg aacaaacgcg    31620
gcgcaacgga gaaatcgaaa atatttatac gctgacgcca atgcagaaag gcatgtggtt    31680
ccacagcgcg atggaccggc agtcgggggc gtatcatgaa cagacacgat ttacgataga    31740
aggagagctc gatacagatg tcttcgtcaa gagcctggac gcattggcga caatcacgc    31800
```

```
cgtgctgcga acgaacttcc tgagcggctg gaatggcgaa ccgctgcaag tcgtgttccg   31860
cgataagcga attggattcg cttatgcaga tttgcgggag ctgcaagaag cggatcggaa   31920
cagatgcatc gaaaaatcgg cagctgagga tcatgctcgc ggattcgatc tggagcagga   31980
tgcgctgatg cgcgtaatgg tcatgcgtac gggagaatca agttatcagg tgatctggag   32040
ttcgcatcat attttgatgg acggctggtg cttgcctcag cttgccaaag agctgtttga   32100
cacgtactcc gtctacttgc agcagcacca ccccgagcag gcaacatcgg tgccggcgta   32160
cagtcaatat atcgaatggc tggagcagca agatgaagca gcggcctccg catattggag   32220
cgaatatctg gctggatatg atcagcaagc ggcattgccg caacagacgg cgcaaggccg   32280
gggcgaagaa tacgttgccg agaagctgac ctgcgaatta ggcaaaacct tgagcggacg   32340
catgagcagg gtggccagac agcatcaggt caccttgaat acgctgctgc aagcggcatg   32400
gggcatcatc ctgcagaaat acaacggaac ccgcgacaca gtgttcggca gcgtcgtatc   32460
cggaaggccg gcggagattc cgggaatcga agcgatgatt gggttattta tcaacacgat   32520
accggtccgg gtcagctgcg aggcgaagac gagcttcgcg gaagtgatgg ggcggctgca   32580
agagcaggcg ttagaatctg gcaagtacga ctattatccg ttgtatgaaa ttcaggcccg   32640
ctgctcgcaa aagcaagatt taatatcgca gattatggtg ttcgagaact acccgatgga   32700
tgaacagatg gagcaagcag gcaacgacga tcagggaatg ctggcgataa cgaacgtcga   32760
agtggccgag caaacgaact atgatttcaa cttcatcgtc gtgccaggag aagagattgt   32820
catcaacttc gattacaatg cgcgcgtttt tgatcggacg agcatggagc ggttgcaagg   32880
tcatctggtg aatgttctgg aacaaatcgc ggccaacccg caagtgaccg taggggaact   32940
taagctggcg accgaggcgg agcaagcgga gattacaagc atattcaata atgcgcgaac   33000
ggaatatccg cgggataaga cgattcaccg cttattcgag gagcaggcgg aacgaacccc   33060
tgatgcgatt gccgtcatgt atgagaacag tcagttgaca taccgagaat tgaacgaacg   33120
ggcgaaccgg ttggctagga cgctgagagc cgatggtgca ggggctgacc gtttggtggg   33180
tctgatggtt gaacgttccc tagacatgat ggtggggata atagcgattt tgaagtctgg   33240
aggggcatac gtgccaatcg acccggaata tccggaagag cgaatccgtt acatgctcga   33300
ggactccggg acgcaaatca tcgtaacgca gcgtcatctg caagagcgaa ttccgggggc   33360
aggcacacgc gtcatcttag atgatgagca ctcttatagc agcgacagca cgaatctgga   33420
tctgaacaac ggtcctgccg acttggcata tgtcatatac acgtcgggca cgacgggcaa   33480
accgaaaggg aatttgacga tgcaccgcaa tatcgtgcgg gtcgttcaag cgctgactna   33540
tatcgacatt ggagagcagg acaatgtgct gcagctatcc agctatgcct cgacggctc   33600 aacattcgat atgtacggag ctttgctgaa cggagccaga ctcgttctta ttccgcaaga   33660
gaccttgttg gatgtagaac ggctcgcaga gctaatcgaa cgcgagcgca tctccgtcat   33720
gttcattaca accgcgttct tcaatgtgct cgttgatgtg aaggctgact gcctgcgcca   33780
tattcgcgcc attttgttcg gcggagagcg cgtttccgtc agccatgtcc gcaaagcgct   33840
gcgtcatttg ggaccaggca aaatcaagca tgtttacggt ccgacggaga gtacggtttt   33900
tgccacttgt cacgacgtga atgaagtggc ggcggatgcc ctcaatgttc cgattggacg   33960
cccgatcagc aacacaacga tttacatcgt caacgaagag aacggcttgc agccgattgg   34020
ggtgccggga gaattgtgcg tagccggaga cgggctcgcg cggggctact tgaaccgtcc   34080
ggagttgacg gcggagaagt tcgtggacaa cccgttcgtt ccaggagagc ggatgtaccg   34140
```

```
gacaggtgac ttggcaagat ggctgccgga tggaagcatc gaatatgtag gcaggatcga   34200
ccatcaggtt aaaatacgcg gctatcgcat tgaattaggc gaagtggagg cgcatctgct   34260
gaaagtccag cctgttcagg aagggaccgt tgtcgcccgg gaaaccggaa gcggcgagaa   34320
gcagctgtgc gcatactttg tggcggaaag cacgctatcg gctagtgagc tgcgcggcgc   34380
tatggcgcaa caattgccgg gatacatgat cccgtcctat tttgtccagc tggagcggat   34440
gccgctgacg ccgaacggca aggttgacca gaaagcgctg cctgcgccgg aagagcatgt   34500
gcagacagga acggaatata ttgcgccccg cacgcctcag gaggagcagt tggcccgaat   34560
ctggcaagag gtgctcggac tggagaaggt cggcgtaaat gacaacttct tcgagctcgg   34620
cggacactcc ttgcgcgcca ctacgatggc aagcaagctg cataaggagc tgagcattga   34680
gctgccgctg cgggacgtat ttaagcaccc gaccctcgaa gcgatggctg agcgcattgc   34740
cggattggga cagcagatgt acacgtccat tccgctggtc gaagagcaag cgcattatcc   34800
gctatcctcg gcccagaaga ggctgtatat tttgcatcag ctggaaggag cggagcttag   34860
ctataacatg ccgaacatgc tgctgctgga ggggcgctc gatcgggagc ggttcgaagc   34920
ggcgttccgc aagctgattg ctcggcacga atcgttccgc accggcttcg aaatgattaa   34980
cggcgaaccg atgcagcgga tatacgagaa tgtggacttt gcggtggagt atatgcaagc   35040
aagcgacaaa gaagccgaag caaggctgcg tcaattcgtg cgcgcgttca agcttgagga   35100
gccgccgctc ctgcgggtag gattgatcga attggctcag gaacgccata ttctgatgtt   35160
cgatatgcat catatcgttt ccgacggcac gtcgatggga attctcatca acgaattcgt   35220
ccgcttgtac ggcggagaag aactgcagcc gctgcgcatt cagtacaagg attttgccgc   35280
atggcagcaa tccgacgcgc ggcaagagca gatgaagcaa caggaagctt attggctgca   35340
ggcgcttggc ggagagctgc cggtgctgga aatgccaacg gaccatgtac ggcctgctgt   35400
tcagagcttc cggggagata tactgcaatt cgttatcggc cgggaccaat gcgcagcatt   35460
gcggcatatc ggttcggaga acggcgcaac gttgtatatg gtgctattgg cagcctatac   35520
cgctctgctg cacaaatata cgggacagga agacatcatc gtaggtacgc cgatcgcagg   35580
cagaaaccat ggagatgtgc agccgctcat cgggatgttc gtcaacacgc tggccatccg   35640
caattatccg atgggcgaga agacattcca ttcctacttg gaggaagtaa aagacacgac   35700
cttgggcgct tatgaaaacc agaactatcc gttcgaggat ctggtggaga acgtgcaggt   35760
cgcgcgggat atgagccgga atccgatttt tgacacgatg tttattttac aaaatgcgga   35820
gcagggcgag atgaatatca acgggctgca tatcgcgaac tatcagagcg agcataccgt   35880
gtcgaagttt gacttgacgt tccaggccga ggaagcggaa gaggagattg tgtgtagcat   35940
cgaatatgct accgagctat acgagctcga gacggtggaa cggatggcgg gccactttac   36000
gcagctcatc gatgccgtgg tcggaaatcc gcatgcaagg ctggcatcgc tgcagatggt   36060
gactgccgag gagcaggatc agatacaaaa tattttcaac gcgactgaca tgggctatcc   36120
gcgcgagaag actatccatc agatgttcga ggagcaggcg gagcgtacgc cggatgcgcc   36180
ggccgtctcc tttggggacg agatgctgac gtaccgggag ttgaaccgga aggcgaatca   36240
gctggcttgg gtgctgaggg acagaggggt cgcatcagag cggcccgtgg gaatcatggt   36300
cgagcgttcg atcgccatgg tcgtcggcgt attggctgtg ctcaaggcgg gcggaacgtt   36360
cgtcccgatc gatccggaat atccggagac gcggatccgt tacatgctgg aggatagcgg   36420
cgccaagctg gcgttgaccg agctggcctg gttcgaggtg attcctcccg aggtggagaa   36480
ggtagatatt cacgatgcat cgctctatca agggcatgac gagaacgtgc cgaatgagag   36540
```

```
cgaaccgtcg aacttgctct atatcatcta cacgtccggc acgacgggca atccgaaggg   36600
cgtcatgctg gagcagcgca atttaatcaa tttgctgcat tatgagcagg tcggaacgag   36660
cattccgctt ccgtcccgca tattgcagta tgcgtcgaac agcttcgatg tgtgctacca   36720
ggagatgttc tccgcgctgt tgttcggggg ctgcctgttc ttgattccga acgaggcgcg   36780
taaagatccg gcgcaattgt tcacctggat tcaggacaac gggatcgagg tgctgtatct   36840
cccggtcgcg ttcctgaaat tcatctttgc cgagccggaa tgggcggaac gcttcccgga   36900
ctgtgtcacg catattatca ctgccgggga gcagctggtc gtcacgccgc agatccaagc   36960
gtgcctgcag cggcttcgca tcagcctgca caatcattac ggtccatcgg aaacgcatgt   37020
ggttaccgct tatacgatgg agccggacga tatcgcggtc ggcctgccgc cgattggcgc   37080
gccgattgcg aatacggcca tttacatctt gaacgacagg ctggagctgc agccgatcgg   37140
catcgcaggc gagctgtacg tgtccgggga ttgcgtaggt cgcggatatt ggggacgcca   37200
agagctgacg gacgagaaat tcatcgccaa cccgttcgcg ccgggcgacc tcatgtacaa   37260
gacgggagat gtggcgcggt ggctgccaga cggcaccatc gaatatgtag gccggagcga   37320
ccatcaggtg aaaattcgcg ggttccggat cgagctcggc gaggtggagt cgcagctctt   37380
gagcgtggaa ttcgtgcagg aagcgaccgt catggcccgg aagatgacg gaggacagaa   37440 gcaattgtgc gcgtacttcg tggcggagcg ccgctgtcg gcagcggagc tgagaggggg   37500
cttgtcccag gatttgccgg gatacatgat tccgtcgtac ttcgtacagc tggatcggct   37560
gccgttgacg ccgaacggaa agatcgaccg cagagcgctg ccggagccgg aaggcagcct   37620
gcataccgga gcggagttcg tagctccgcg cacgccgctg gaagcgcagc tggcccgaat   37680
ctggcaagat gtgctgggtc tgccggacgt gagcgtgaag gataatttct tcgatttggg   37740
tggacactcc ttgcgcgcga cgaccttggc aagcaaggtg ttcaaggaaa tgcacgtcaa   37800
tctgccgctg cggatgtat tccggtgccc gacgattgag gagatggccg ggatgatagc   37860
cgggatggag aagcaggaat atgccgcgat cccgttggct gaggaaagtg acgtctaccc   37920
gttgtcatcc gcccagaagc ggctgtacat cgtgagccag ttggaagggg cagatctgag   37980
ctacaacatg ccgggagtcg tgtcgctcga aggaacgctg gatcgcgagc gctttgaatt   38040
ggcattcttg aagctgattt cgcggcatga gacgctgcgc accggcttcg acatggttga   38100
cggggagccg atacagcgcg tgcaccgcag cgtgaagttt gtcgttgagc accgtaaggc   38160
ggctaccgtg caggatgctg agcagctcat tcgccgcttc atccgcacgt ttgatttgcg   38220
gaagccgcct ctgctccgtg ttgggctggt ggaattggaa cgagagcgtc atattttgat   38280
gttcgacatg catcacatta tttccgacgg tgcttccttg gggaatctgg tcagcgagtt   38340
cgcacagttg tatgcgggag aggagcgggc tccgctccgc attcaataca aggattaccg   38400
ggtgtggcag cagtccggag tgcacagcga gcacatgaaa cgtcaggaag cgtattggtt   38460
ggagaagctg gccggggaat tgccggttgt cgagctgccg accgattacg accggcctgc   38520
cgtccgcagc ttcgaaggag cgcagatcga gttcgaagtc gacgccgctc tcacccaacg   38580
tttgagccag cttgcgtcga atcgcgagag cacgctatac atggttctgt tgtccgcata   38640
taccgtgctg ctctccaaat acagcggaca ggaagacatc atcgtgggaa ctcctgtcgc   38700
gggaagagcg catgcggatt tggagccgct catcgggatg tttgtcaaca cattggccat   38760
tcgcaatcat ccggcaggag acaagacctt cctgtcctta ctggaggaag tgaaggaaac   38820
ggccttgggc gccttcgagc atcaagatta tccgtttgag gaactggtag aacgcctgaa   38880
```

```
tgtgcaatgg gacgcaaacc ggaatccggt gttcgacacg atgtttgtca tgcaaaatac   38940
agaggaccat gaggtgcgat tggaagctct aaccttgtct ccttatgtgc ttgacaatcc   39000
gatcgatgcg aaattcgatc tcacgctgtt cgtttccgaa gacaatgatg taattaaggg   39060
aggcttccaa tacggcacca agttgttcaa ggctgccatg attcataaga tcatgagaga   39120
cttcctgctt gtgctggctc aaatcgtcga agacccccac attcggttac gcgatatcaa   39180
gtgcaatgag caatccgtta acaatcagcg ctctattgaa acgatagagt tcgcattcta   39240
gacgatttca gacggaccta acaagcacat ggaaccagga gtgtgtgttc gctctaaatc   39300
gagccgcaca ctcccggtct tttcaataaa acagtaggat aggggatgtt tacgaatgaa   39360
gtcggtgttt gataaggaag aggcttattg gaacgagaaa tttgattccg aagacagtat   39420
aagcgttctg ccatatagca attcctccaa taacaatatg gggcgcgtaa acaccatggg   39480
cgtcatcaat cgcacacttc cgcctgagtt gtcacagaga atcatcaccc tggcgaacgg   39540
atcggatatg gccgtgtaca tgatcgtatt ggcaggagtg acaagcttgc tctataaata   39600
taccaaccgc gaaaatgtgt tggtaggtat gcctgcatat acggcgttac atggggagca   39660
tccgcctatc catgattttc tggtgattaa aaataatgtg aacagtaaaa gcacgttcaa   39720
atcgttgtta gggcaaatca aagcgtcagt cagtgaggcg cttgagcatc agcaccttcc   39780
tttccgtaaa atgtttcggc aattgaattt gcaagtggat ccccaaggat tgcctatcgt   39840
gaatacactc gtttcctata caaacataca tactgcttca ttggaacaaa gcgcagccgc   39900
agaagccgca tttcaatttg aattcgtaaa tgaccgcatt caattacgca tgagctttga   39960
tgataatcga taccgttcgg actatgtcga atcaatgctc gctcatttct tccgcctgct   40020
gtcggtcgta ttgttttcaac cggagctaga aatcggaaaa gtggagctgc tgtccgagca   40080
tgagcagcat catctgcttg ccattctgaa cgatacgcga acggaatatc cgcgtcagaa   40140
gacactccac cagctgttcg aggagcaggc ggaacgaatg ccagatgcgc tggcggcgct   40200
attcgaggac aaacggttga cctatgcgga gctgaatgct gctgccaatc gcattgcccg   40260
tctcctgcgg gatcgaggtg tagtacgagg cacattggtt ggcatttgcg cagagagatc   40320
cctagagatg tgtgattgga ctgctgggaat cctcaaagct ggcggggcat acgttccgat   40380
cgatccttcc tatccgcaag aacggattaa cgccatgctg gaagatacag caatcagcgt   40440
gatgctcacg caggcgcatc tgcagacaag cgtgccgaac agccttgatt ccgtcttgct   40500
cgatacagca gcagagatga ctctggaagg aagctggccg aacttgacag atacggcggc   40560
gaccgcggac gatgtggcct acatcatcta tacatctgga tcgacgggaa ttccgaaagg   40620
agtgtgcgtc acgcatcgag gggtggtccg gctcgttgtc gctgccaatt atgtggacat   40680
cagcagcaag gacgtatttc tgcaaggctc gacgatatcg ttcgacgcgg caacgttcga   40740
gatttggggc agcttgctga atggagctgc tctggccatt ttgcctccag ggaatctatc   40800
gttgaccgaa tggacacagg ccattcaaca gcatcaagtg acgatcctgt ggttaacggc   40860
gggactcttc cacgtgatgg tcgagaacca actccaagcc ttgcaaggag tccagcaatt   40920
gttggtgggt ggagatgtcg tctctcaaac gcatgccaaa aaagttctgg agcggtataa   40980
ggacattcgt ctggtcaatg ggtatggtcc gacggaaaat acgaccttta cctgctgcca   41040
cgagatttcc gccgccgata tggagcggct ctctattccg atcggacgtc caatcgccaa   41100
tacgcaagtg tacgtgctgg atgaggcagg caagctgctt ccggtaggag tggtcggcga   41160
gttgtacacc ggaggagacg gactgcccaa agggtactgg aatcgtccgg agctgacggc   41220
tgagaagttc gtggataacc ccttcgtgcc gggaacccgg ctataccgca caggcgatct   41280
```

```
ggcgagatgg ctgccggatg gaacgctcga atacgtggga cgaatcgatg atcaagtgaa    41340
aattcgcggt taccggattg agcttggcga ggtggaagcg catctgttga aagtggaatc    41400
ggtgctggac gcaatcgtaa tcgcacggca agacgaaagc ggtcagaaga cgttgtgcgc    41460
gtactttaca gcgcatgcag agctgatggc gggcgatctg agagcagcac tgtcgcaaga    41520
actgccggtc tatatgatcc cgacacactt ggtgcaggtc gatcagatgc cgctgacgcc    41580
gaacggaaaa gtcgatcgca gagcgctgcc ggagccggaa ggcctcatca tgaccggaat    41640
agagcatgtc gcgccgcggt caccgctaga gtccaagctg gcgcatatct ggcaagaggt    41700
gctcggactc gagaaggtca gcgtgaagga cagtttcttc gagattggcg acactctt    41760
gcgtgcaacg acgctcgcaa gcaagctgca caaggagctg catgtcagcc tgctgctgcg    41820
ggacatcttc cgccatccta ccattgaaga gctggcacgt ctcattgatg ggatggaacg    41880
gcaggcgtac agacagattc cgctgctgga tgaaagggat tggtacccgg tatcttcggc    41940
gcaaaagagg ctgtacattt tgcatcaact cgaaggggca gagcagagct acaacatgcc    42000
gggggtgatg ctccttgaag acagcttga ccggaatcgg ttcgaggagg cgttcggcag    42060
cttgatcggg cgccacgaaa cgctgcgcac cggctttgag atggtgaatg gcgagccggt    42120
gcagcgtgta tgccgcgaag tgaatttctc ggtagagatg atgcaggcga gcgaagagga    42180
agccgaagcc gtcgttcgct cattcattcg cccgttcgat ctggagaagc cgccgctcct    42240
gcgagtagga ctgatcgagc tggatcagga tcggcatatt ctgatgtacg acatgcatca    42300
tatcatctcc gacggcgtgt cgatgggaat tgtggtggag gagttcgtcc gcttgtacgg    42360
gggcgaggaa ctgccgccgc cgcgcattca gtacaaggat tatgccgcat ggcagcagtc    42420
cgagccgcag caggagctca tgaagcagca ggagagttat tggttgcagt cgcttggcgg    42480
agagcttccg gtgctggaac tgccggcgga ttatgcgcgt ccttccgtcc agagctatga    42540
gggcgatacc ttcgaattcg cgatcgatcc tcggctaagc gaagcgctgc acggggttgc    42600
ggccgagagc ggaacgacat tgtacatggt gctgcttgct gcctatacga ttctgcttca    42660
taagtataca ggccaggaag acattatcgt ggggacgccg aatgcgggca gaacgcacgg    42720
cgatttgcag ccgcttatcg gcatgttcgt caatacgctg gcgatccgca attatccggc    42780
tggctcgaag acgttcctgg aatacttgga ggaagtgaaa gaaacgagct ggggcgcctt    42840
cgagaatcag gattacccgt tcgaagaact ggtggaaaag ctgcaggtag cgcgagattt    42900
gagccgcaat ccgctgttcg atacgatgtt tgctttgcag aatatggacg acaaggatct    42960
ggagctcgca gggcttcgct tgaagccgta cccggctgaa tacaaggtgg cgaaattcga    43020
cctgagcctg gacgtggcgg aaggcgtgga agggatggcg tgcagtctgg aatacgccac    43080
cgcgttatac cgaccggaat cgatagaaag aatggcgaag catttcgggc ggctgcttga    43140
agccgttgcg cacgagccag aggcgcggct ggcttcgctc ggcatgctca cggaggagga    43200
agaggagcag attcggcatg tgttcaacga tacggaggca gggcgttcgc agcagaacac    43260
ggtgccagaa ctgttcgagg agcaggtgga gcgcacgccg gatcggattg cggtcgtgca    43320
tgaggacaag cagctgacgt accgggagct gaacgaacgg cgaaccggc tggcgcgtac    43380
gctgcgggcc gagggcgtga agcccgaaca gctggtcggc atcatggccg atcgctcgct    43440
ggagatgatc gtgggcatta tggccatctt gaaatccggc ggcgcctatg tgccgattga    43500
cccgcaatat ccggaggatc ggattcacta tatgctggac aattcgaacg cgcaagtgct    43560
gctggcccag cgtcatctgc aagcgcgggc cgcattctcc ggcagaagga tcatgctgga    43620
```

-continued

```
tgaagaagcg ttctacggcg cagacggttc caatctggaa cgggtgaatc agccggagca    43680
tctgagctat gtcatctata cctccggaac gacgggcaag ccgaaagggg tcatgatcga    43740
gcacagacag atggcagtct tgtcggccgc gtgggagcgc gaatacggct tgcaggaaga    43800
gagcatgcgc tggatgcaat gggcgagctt ttcattcgac gtcttctcgg agacctgat    43860
ccgcgcgctg ctgcatgggg gagaacttat tctatgtccg gaggatgcaa gggcgaaccc    43920
ggctgaaatc tatgagctca ttcgcaagca tcggattcag atgttcgatg tcactccgtc    43980
gctcgtcatt ccgctgatgg aatatgtata cgagaacaag ctggacatca gcagcatgaa    44040
gctggcagtc gtgggggcgg atcattgccc gaaggaagaa ttccagaagc tgctggaacg    44100
attcggttcg caaatgagga tcgtcaacag ctatgggta acggagacga ccatcgattc    44160
ctgctacttc gagcaggcga gcacggaagg gctgcgaacg gtgccaatcg gcaaacctct    44220
gccgggtgtg acgatgtaca ttctggatga tcagcattct ttactgccgg tcgggataac    44280
gggcgagctc tatatcggcg gaccttgcgt aggccggggg tattggaagc ggccggactt    44340
gacggcggag aaattcgtcg acaatccatt cgctccgggc gagcgaatgt accggacagg    44400
cgacttggcc cggtggctgc cggacggcaa cgtcgaatat ttggggcgga tcgaccatca    44460
agtgaaaatc cggggctacc ggatcgagat cggcgaggtg gagacccaac tactcagaac    44520
gccgttcatc cgtgaagcgg ttgtcgtcgc gcgggaagac gttagcggac agaagtcatt    44580
gtgcgcgtac ttcgtcgccg aacgcgagct gacggtgagc gagctgcgga gagcattggc    44640
cgcagaactt ccggggtata tgatcccatc gtatttcgtc caaatggagc ggcttccgtt    44700
gacgccgaac ggcaaaatcg accgcaaagc gctgccggct ccagaaggaa gcgcacatac    44760
tggagcagag ttcgtagctc cgcgcacgtc gctggaagcg cagctggccc gaatctggca    44820
agaggtgctg gtctgccgg acgttagcgt gaaggataat ttcttcgatt tgggcggca    44880
ctccttgcgc gcgacgacct tggcaagcaa ggtgttcaag gaaatgcaca tcaatctgcc    44940
gctgcgggat gtgttcaggt acccgacgat tgaggagctg ccgaactga tagccggat    45000
gaaaaagcag gaatatgccg tgatcccgtt ggctgaggaa agagacgtct acccgttgtc    45060
ttcggcccag aaacgcctgt atatcgtgag ccaattggaa ggggccgagc tgagctacaa    45120
catgccggga gtcatcaccc tcgaaggacc gctggatcgc actagattcg acggggcttt    45180
ccagcagctg attgcgcggc acgaggcgct gcgcaccggc ttcgagatgg tgaacggaga    45240
accggtccag cggatacatc gggatgtgcg cttgacagtg gagtacgtgc aggcagacga    45300
agaagaagca gagaagctcg tacagcgctt tgtccgcagc ttcgatctga agctgcggcc    45360
tctattgcgg gtaggactta tcgcaataga gcgggagcgg catattctga tgttcgatat    45420
gcatcatatc atttcagatg gcgttacgat ggggatattg gtggatgagt tcgctaggct    45480
ctatgcgggc gaggatttgc cgccgctccg cattcagtat aaggattatg cggtatggca    45540
gcaatccgaa gatcgcagcg tggagttgcg gcgtcaggaa gcgtattggc tggagcgatt    45600
acaaggagaa ttgccggtac tagagctgcc gactgattat gtgcgccccg ctgttcaaaa    45660
atttgatgga gacgtcgcat tattcacgat cgatccgcat ctgagcgaac aattgcgccg    45720
actgcgtcga gacacaggtt ccaccttgta catggtgctg ctggcagcct acactacgct    45780
gctgcataag tatacgggac aggaagacat catcgtgggg acaccgattg cgggcagaag    45840
ccatagcgat ctcgagccgc tcatcgggat gttcgtcaac acattggcgg ttcgcaatta    45900
tccccgcaagc gagaaggcat ttctgtcgta cctggcggaa gtgaaagaaa caaccttggg    45960
cgccttcgag caccaggact atccattcga ggatctggta gaaaaggtgc gcgtatcgcg    46020
```

```
ggacttaagc cggaatccac tgttcgacac gatgttcagt ctcgagaatg cagagcaggg   46080
gggcatcgaa atcgaaggcc tccaattaaa atcatatccg aatgaacata tgacggccaa   46140
attcgacctg actttccatg cggaagaagg agaagaaggc atcctatgcg gcttggtgta   46200
tgcaaccgct ttgtacaagc gcgatacggt ggagcggatg atgctgcatt tcaagcagtt   46260
gcttgcagca attgcacatg accccgcgc gcaactttca acattgaaca tgatgaccgc   46320
tcaagaaaga gaagagatta tcggggtgtt caatgacacg gggacgaaat atccgcgcga   46380
gaagacgatt cagcatctat tcgaggagca ggttgaacgg actcctgacg cagcggctat   46440
tgtgtacgga gacgagcgaa tgacgtaccg cgaattgaac gggcgggcga accgattggc   46500
aaggacatta cgaaccaagg gagtgcaagc agatcgcttg gtaggtctta tggctgaacg   46560
ttctctggaa atgatagttg gaattctggc gattctaaaa gccggggag catacgtgcc    46620
gatcgacccg gaatatccgg aagagcgcgt ccgctacatg ctggaggact ccgggaccca   46680
aatcatactg acgcaacatg aactgcagtc gagaatcccg gtgcaagcct cgttcgtcct   46740
gttggatgac gaacactctt acagtgcgga cgattcgaat ctggaacaga taacggtcc    46800
tgccgatttg gcctacgtca tttatacgtc ggggacgaca ggcaagccaa aagggaattt   46860
ggcgacgcat cgcaacatcg tgcgggtcgt gcaaggcacg agctacattg attttagcga   46920
acgggacaac gtgctgcagt tatccaatta tgctttcgac ggatcgacct ttgatatgta   46980
cggtgctttg ttaaatggag ccaagctggt cctcatcccg caggagacgc tgttggaggt   47040
agggaagttg gcaggcttga tcgaacgcga gcgcatttcg gtgatgttca tcacaacggc   47100
gtacttcaac atcctcattg acatgaaagc agactgcttg cgccatatcc gcaccatact   47160
gttcggcggg gagcgcgtgt ccatctctca cgtccgcaaa gcgctctatc agctaggacc   47220
gggcaaaatc aagcatgtgt acgggccaac ggagagcacg gtatttgcca catgccacga   47280
tgtgaatgaa gtggcagagg atgccgtgac cgttccgatc ggacgcccga tcagcaacac   47340
gaccatttat atcgtcaatg ctcagaacga tctgcagccg atcggagtgg ctggggagct   47400
gtgcatagca ggagacggac tggcccgagg ctacttgaac cgtcccgaat tgacggcagc   47460
gaagttcgtc gacaatccat tcgcgccgag ggagcggatg taccggacgg gcgacctggc   47520
aagatggctg ccggatggga ccatcgagta cgtgggggcgg attgacgatc aggtgaaaat   47580
acgcggctac cggattgagc ttggcgaggt agaaacacat ctattgagag tggagcccat   47640
tcaggaggcg accgtgatcg cccgggaatc cgacagcggt gagaagcgct tatgcgccta   47700
ctacgtggcg gatcgaccgc tgccggccaa cgagctgaga ggcatcctag cgcaagatct   47760
tccagggtac atgattccgc tgcacttcgt tcaactggat cggatgccgc tgacacctaa   47820
cggtaaggta gaccgcaagg cgctgcctgc gcctgaggat cacttgatga cagggacgga   47880
atatgtggcc ccgcgcacga cgcaggaagc tcagttggcg cagatctggc aggaggtgct   47940
gggcatcgag aaaatcggcg tgcaggacaa tttctttgag ctgggcggac actcgattag   48000
cttgatgcag ctgatacacc gaatctacat cgaattgggc gcggaaatcg ctctccatag   48060
cgtgtttcag cgaccgacag tggaagcgat ggcctatgag atcgtaaaag tcgagtacga   48120
ggagaaaagc agcagccagt tcacgaaatt aaatgaaaat ggtcttgtaa acgtattttg   48180
cttgcctccc ggcttcgggt atgggttaag ttacttggaa ctggcgaagc aaatggaaaa   48240
cagctgcatc ctatacggaa ttgatttcat tgatgatgcc gaatcttacg aggacatgct   48300
ggaccggtat gtggacgcgg tcgttgccat tcagtctcag tctccttatg tgctgctcgg   48360
```

```
atattcgctg ggaggcaatc tgacgttcga aattgccaaa gcaatggaaa agagagggta    48420
ccgcgtatcg gatattatta tgctcgactc cacgcggaag ctggccgctc agacggtgga    48480
cgagttcgaa agcgatatcg atcaaatgct tgaagcggtg ggtgaacagg agatgcagct    48540
gctgagcaat cctctgattc gcgaacgggt caagcataag atgcgcgcgt actggacgta    48600
tggatctcag ctcgtgaata cgggcgcggt tgaggcgaat atttatgcat tgattgcgga    48660
ggattccgat gcagtcagac cggataatgt tacttctgca ttatgggatg gggcaacccg    48720
gcaagcctat tgcgagcatc gactcattgg tgtccatgag gatgtgctgc ttcctggatt    48780
catagagcat aacgtgaaag tgattcacgc ggtcgtccat caaatcatcg agcaaacgcg    48840
cggcgtccac gaggtgttat cgcgatagca gcgatgttgc ttgtacaacg taacctataa    48900
tacatgtcat cctcatatac cgcctgcaca catgcgcatg ttgatgatgc aggcggttcg    48960
taggggagtt ccgtcacgac tatggtttaa aggggagaca aatgagtggc actgcgaaaa    49020
cgaaaagatg tgttgaccct atggaaatca gcccgctggt tatcgtcatt cgtgaaaccc    49080
catatgggct ggatgatcgt cggaatcatc tctgctgttg cggccgcgat tattgagata    49140
tggaccggca gcttaatcga acaattaacg accaatgccg gcaacgggga cgggcagttg    49200
gtcgcccgca ttgtatatac cgtatttatc gtcattgcaa ttggagttcc cgcgaaatat    49260
ttcatggtgt acggcatcga aaaaagcagc gctcaagcca tgagggacct tcgcaaccag    49320
atgatgaagc acatcggcaa attgcctgtt cattatttgg aaaagaaaca ctcgggcgat    49380
atggtgtcaa gggtgactaa tgacctccag atcatcaatc aatttatgat tcgcgatgtg    49440
gcggaatggt tttatcatcc cctgcttttt attggctgct ttggctactt gctgtggatc    49500
cgatgggagc ttgtgctgct cagcttgttg cttgttcccg tttccttgtt cgtctcgcaa    49560
tgggtaggca agcaactgca gcgcctcacg gaagaagcac aggaaaacat gggccagatg    49620
aatgtcattt tacaggatac attgagtggc atgccgctgg tcaaaagcta tttgctgcag    49680
ggaatcctgt tccgatcgta tcaatccctg cttctgctga cgctgaaaaa gaggttggcc    49740
gtaaataaac gcgaggcgat agtcactccc gtgctgttca cgctcatgat cagtccgatc    49800
gtgttcgcta ttctatacgg aagttatttg atatcgaaag gattgttcag cacgggagag    49860
ctgattgcct ttctctactt gctgaatttg tgtttggagc cattgcagaa catcccgacg    49920
ctcattacga atacgtttga gatgaccgga gcttttaaaac gagcggccca aatcatgaat    49980
caacccatcg agaatgaaga gggacattgc attgtgagaa ctgctcagcc tcccatcgcg    50040
tttcacaacg tcaatttcgc atacgagaat agcggttccc ctctgctgcg caatttgagc    50100
ttcacggtag cggaagggca gactgtagcg ttggtgggag ccagcggcgg ggggaagagc    50160
accgtgataa agctgctctg cggatttat ccactgcagg ctgatggcgg gaagatcgat    50220
gtatttggcc aatcgatccg cgactgcaat ccgaaggagc tgcgttccca tttgtcggtc    50280
gttacccaag attcctattt gttcagcggg acgattgcag ataatattgc ttacgggcgg    50340
gagaatgcct cgatggatga agtgatcgaa tctgcaaaat cagccaacgc gcactccttt    50400
attatggagc tgccggaagg atatcagact gacgtggggg aacggggagc gctgctatcc    50460
ggcgggcagc gtcagcgtat caccattgcg cgcgcactgc tcaaggatgc ccccatcctg    50520
ctgttggacg agcccacttc cgcattggac gcggagtctg aatcactggt tcaggaagcg    50580
ttgaacgttc ttatgaagga gagaacgacc atcgtcattg cgcatcggct gtctaccatt    50640
cagaatgcga tgagatctg ggtcatggag acgggcgga tcgaagaggc agggaatcat    50700
gctaagctgc tggagaaaag gggctcttat gcccggctgt accatcagga attcgaaacg    50760
```

-continued

```
gatcgaatgg gaagcaagga ggtggcctat acgtgaaaac cgccgggatg ttagcttatg    50820
tgaaggaaat caagtatatg atggacttta tgagcacacg acgcaaagtt gagtattatg    50880
ttggcatgat tgcaggcggg ctcgttaaca ccttgtttat cctgtcattc accttggttg    50940
tccagagttt agtagatttt gcagggtcaa gagatacttc ccttatgttt caggcgctat    51000
atattttggg aggctctatc ttgctgttga acctgacttc acccggattc acttatttgt    51060
ttcgtcgcag cgtggaactg acgatcgtcg acatcaggga acgtctctat cataagctgt    51120
gcaagcttcg ggccgatcat ttggagcgga cgcataatgg agatttccta tcacggataa    51180
ataacgatgt atccaccctg gaagtgacgt attgcggaat cttttttgct ctgctgctgg    51240
atatcatgat tagcattgga tccatcatta tgatgtttat cattcattgg cagtttgctt    51300
gcgcttccct tttgattttg ctcgtttcct tttatataag cacgcgtttt gtgcgctccg    51360
ttcgcgcgat gtatgatcaa tctcttcatt ctatagccaa gctgacagag aaattttcag    51420
actttatcgc gggcatccag cttgtgaaat tgttccacat tagtccggta tatgctcagt    51480
atggagccat gaacgagaag ctgacgcagc tttcccgccg catcgcccac aaaaaaggcg    51540
tactggcagc cgtcaatcat tttgtaagct acattacatt ttgcggaatc attgtcattg    51600
gcagcttgct gtatagctat ggcatcattg gcatggggGc cgttgcagcc ctggccgtct    51660
tgcaaattca tttgacgcat tccttcatga acattggaac aaccatgtct ttgattcaaa    51720
attcgttggc gggagcgcag cggattcaag aaatgctgga ggagcaggag gagccgcaac    51780
ggatcggctc tgtggcaagc gaccgtgatt cggaggcaat ggtggaattt gattgcgttg    51840
agtttgccta tcaatccgac agcccggtgc tgtgcaattt gtccctgcaa gtgctccccg    51900
ggcaagtggc ggctgttgtg ggtgcaagcg gcagcggcaa aagcaccttg attaaattgt    51960
tgctgggctt ctatcccgtt gacagcggcg agatcttaat ccaaggcaag tcgttcggac    52020
attataccct tggaagagatt cgtcaacgga ttgcttatgt gccgcaagaa ctttcttgt    52080 tcagcggaac gattgaagac aacatccgtt atggcaatcc gcaagcttca caggaggaag    52140
tgattgccgc ggctcaggct gcttatgccc acaatttat tcaggaattg cccgagcaat    52200
accagacgca agtgggtgag cgcggagcgt ctttgtccgg cggacagcgt cagcggattg    52260
cgattgcccg ggcattgctc aaaaatgctc cgatattgct gctcgatgag gcaacatcgg    52320
ccttggatgc cgaatcagag tactgggtac agcaagcctt gaatcaattg atgaaaggcc    52380
gcacgaccat tctgattgcc caccgcttga gcaccgttga aatgccgat gtgatatttg    52440 tcatccaaca aggatcagtt gtggaacaag gcacccatca gagcttgctt gcatgcagat    52500
cctactatgc aggtatgtat ggacagtctg gcctggctct tgccgaacaa gcttga    52556
```

<210> SEQ ID NO 15
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (3)..(3)
<223> OTHER INFORMATION: Xaa is the modified amino acid ornithine.

<400> SEQUENCE: 15

Val Thr Xaa Ser Val Lys Ser Ile Pro Val Lys Ile
1               5                   10

```
<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 16

Ser Val Lys Ser Ile Pro Val Lys Ile
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 17

Ser Ile Pro Val Lys Ile
1               5

<210> SEQ ID NO 18
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 18
caaacggttg acctatgcgg agctgaat                                         28

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
cctgcacaaa gtgtgtcggg atcatgta                                         28

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
cctgactatc cggaggaacg gactaacg                                         28

<210> SEQ ID NO 21
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 21
ccagatcgaa cgggcgaata aaggaac                                          27

<210> SEQ ID NO 22
<211> LENGTH: 28
<212> TYPE: DNA
<213> ORGANISM: Artificial Sequence
<220> FEATURE:
```

<223> OTHER INFORMATION: Synthetic oligonucleotide

<400> SEQUENCE: 22
tcatctgctt gccattctga acgatacg                                    28

<210> SEQ ID NO 23
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 23
ttgaacacat gccgaatctg ctcctctt                                    28

<210> SEQ ID NO 24
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 24
gggaattcca tatgttgacg gcagaagaga ag                               32

<210> SEQ ID NO 25
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 25
gggtatccgc tcgagtatat attccgtgcc ggt                              33

<210> SEQ ID NO 26
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 26
gggaattcca tatggtgact gccgaggagc ag                               32

<210> SEQ ID NO 27
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 27
gggtatccgc tcgagtacga actccgctcc ggt                              33

<210> SEQ ID NO 28
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 28

Met Ala Trp Ala Phe Asp Val Phe Ser Gly Asp Arg Glu Ser Ile Ile
1               5                   10                  15

```
Gly Ser Asp Leu Asn Ser Tyr Gly Val Thr Glu Ala Cys Val Asp Ala
            20                  25                  30

Ser Tyr

<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 29

Asp Val Gly Glu Ile Gly Ser Val Asp Lys
1               5                   10

<210> SEQ ID NO 30
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 30

Leu Asp Ala Ser Phe Asp Ala Ala Thr Phe Glu Gly Trp Leu Leu Val
1               5                   10                  15

Gly Gly Asp Ile Asn Gly Tyr Gly Pro Thr Glu Asn Thr Thr Phe Thr
            20                  25                  30

Cys Cys

<210> SEQ ID NO 31
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 31

Asp Ala Phe Trp Leu Gly Gly Thr Phe Lys
1               5                   10

<210> SEQ ID NO 32
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 32

Leu Asn Ser His Phe Asp Phe Ser Val Trp Glu Gly Asn Gln Ile Phe
1               5                   10                  15

Gly Gly Glu Ile Asn Met Tyr Gly Ile Thr Glu Thr Thr Val His Val
            20                  25                  30

Thr Tyr

<210> SEQ ID NO 33
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 33

Asp Phe Trp Asn Ile Gly Met Val His Lys
1               5                   10
```

<210> SEQ ID NO 34
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 34

```
Ile Ala Trp Ala Phe Asp Val Phe Ser Gly Asp Arg Glu Ser Ile Val
1               5                   10                  15
Gly Ser Asp Leu Asn Ser Tyr Gly Val Thr Glu Ala Cys Val Asp Ala
            20                  25                  30
Cys Tyr
```

<210> SEQ ID NO 35
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 35

```
Arg Trp Met Thr Phe Asp Val Ser Val Trp Glu Trp His Phe Phe Ala
1               5                   10                  15
Ser Gly Glu Ile Asn Leu Tyr Gly Pro Thr Glu Ala Thr Val Asp Val
            20                  25                  30
Thr Tyr
```

<210> SEQ ID NO 36
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 36

```
Asp Val Trp His Phe Ser Leu Val Asp Lys
1               5                   10
```

<210> SEQ ID NO 37
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 37

```
Leu Ala Ala Ser Phe Asp Ala Ala Thr Phe Glu Gly Trp Leu Leu Val
1               5                   10                  15
Gly Gly Asp Val Asn Gly Tyr Gly Pro Thr Glu Asn Thr Thr Phe Thr
            20                  25                  30
Cys Cys
```

<210> SEQ ID NO 38
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 38

```
Leu Ala Trp Ala Phe Asp Val Phe Ser Gly Asp Arg Asp Val Val Val
```

```
                1               5                  10                  15
Gly Ala Asp Val Asn Ser Tyr Gly Val Thr Glu Thr Thr Ile Asp Ser
            20                  25                  30

Cys Tyr

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 39

Asp Val Gly Asp Val Gly Ser Ile Asp Lys
1               5                  10

<210> SEQ ID NO 40
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 40

Arg Trp Met Thr Phe Asp Val Ser Val Trp Glu Trp His Phe Phe Ala
1               5                  10                  15

Ser Gly Glu Ile Asn Leu Tyr Gly Pro Thr Glu Ala Thr Val Asp Val
            20                  25                  30

Thr Tyr

<210> SEQ ID NO 41
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 41

Val Gly Ala Ser Phe Asp Gly Ser Thr Phe Asp Gly Phe Ile Leu Phe
1               5                  10                  15

Gly Gly Glu Lys His Val Tyr Gly Pro Thr Glu Ser Thr Val Phe Ala
            20                  25                  30

Thr Cys

<210> SEQ ID NO 42
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 42

Asp Gly Phe Phe Leu Gly Val Val Phe Lys
1               5                  10

<210> SEQ ID NO 43
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 43
```

-continued

```
Leu Tyr Glu Ala Phe Asp Val Cys Tyr Gln Glu Ser Tyr Leu Ile Thr
1               5                   10                  15

Ala Gly Glu His Asn His Tyr Gly Pro Ser Glu Thr His Val Val Thr
                20                  25                  30

Ala Tyr

<210> SEQ ID NO 44
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 44

Asp Val Gln Tyr Ile Ala His Val Val Lys
1               5                   10

<210> SEQ ID NO 45
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 45

Leu Ala Ala Ser Phe Asp Ala Ala Thr Phe Glu Gly Trp Leu Leu Val
1               5                   10                  15

Gly Gly Asp Val Asn Gly Tyr Gly Pro Thr Glu Asn Thr Thr Phe Thr
                20                  25                  30

Cys Cys

<210> SEQ ID NO 46
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 46

Leu Ala Trp Ala Phe Asp Val Phe Ser Gly Asp Arg Asp Val Val Val
1               5                   10                  15

Gly Ala Asp Val Asn Ser Tyr Gly Val Thr Glu Thr Thr Ile Asp Ser
                20                  25                  30

Cys Tyr

<210> SEQ ID NO 47
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 47

Val Gly Thr Ser Phe Asp Gly Ser Thr Phe Asp Gly Phe Ile Leu Phe
1               5                   10                  15

Gly Gly Glu Lys His Val Tyr Gly Pro Thr Glu Ser Thr Val Phe Ala
                20                  25                  30

Thr Cys

<210> SEQ ID NO 48
<211> LENGTH: 10
<212> TYPE: PRT
```

<213> ORGANISM: Artificial Sequence
<220> FEATURE:
<223> OTHER INFORMATION: Synthetic polypeptide

<400> SEQUENCE: 48

Ile Asn His Ile Ile Ala Asp Gly Val Thr
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 49

Glu His Phe Phe Glu Leu Gly Gly Asp Ser Ile
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 50

Phe Asn Tyr Leu Gly Gln
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 51

Ser His His Ile Leu Met Asp Gly Trp Cys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 52

Asp Ser Phe Phe Glu Leu Gly Gly His Ser Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 53

Met His His Ile Ile Ser Asp Gly Ala Ser
1               5                   10

<210> SEQ ID NO 54
<211> LENGTH: 11
<212> TYPE: PRT
<213> ORGANISM: Artificial Sequence

```
<220> FEATURE:
<223> OTHER INFORMATION: Synthetic polypeptide

<400> SEQUENCE: 54

Asp Asn Phe Phe Glu Leu Gly Gly His Ser Leu
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 55

Met His His Ile Ile Ser Asp Gly Val Ser
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 56

Asp His Phe Phe Glu Leu Gly Gly Asp Ser Ile
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 57

Asp Asp Phe Phe Glu Leu Gly Gly His Ser Leu
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 58

Asp Ser Phe Phe Glu Ile Gly Gly His Ser Leu
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 59

Met His His Ile Val Ser Asp Gly Thr Ser
1               5                   10

<210> SEQ ID NO 60
<211> LENGTH: 11
<212> TYPE: PRT
<213> ORGANISM: Artificial Sequence
<220> FEATURE:
```

```
<223> OTHER INFORMATION: Synthetic polypeptide

<400> SEQUENCE: 60

Asp Asn Phe Phe Asp Leu Gly Gly His Ser Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 61

Met His His Ile Ile Ser Asp Gly Val Thr
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 62

Asp Asn Phe Phe Glu Leu Gly Gly His Ser Ile
1               5                   10

<210> SEQ ID NO 63
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 63

Gly Tyr Ser Leu Gly
1               5

<210> SEQ ID NO 64
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is the modified amino acid ornithine.
<220> FEATURE:
<221> NAME/KEY: Xaa
<222> LOCATION: (4)..(4)
<223> OTHER INFORMATION: Xaa is the modified amino acid ornithine.

<400> SEQUENCE: 64

Xaa Val Thr Xaa Ser Val Lys Ser Ile Pro Val Lys Ile
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is a charged amino acid.
<220> FEATURE:
```

```
<221> NAME/KEY: Xaa
<222> LOCATION: (2)..(2)
<223> OTHER INFORMATION: Xaa is a hydrophobic amino acid.
<220> FEATURE:
<221> NAME/KEY: Xaa
<222> LOCATION: (3)..(3)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (4)..(4)
<223> OTHER INFORMATION: Xaa is a charged amino acid.
<220> FEATURE:
<221> NAME/KEY: Xaa
<222> LOCATION: (5)..(5)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (6)..(6)
<223> OTHER INFORMATION: Xaa is a hydrophobic amino acid.
<220> FEATURE:
<221> NAME/KEY: Xaa
<222> LOCATION: (7)..(7)
<223> OTHER INFORMATION: Xaa is a charged amino acid.
<220> FEATURE:
<221> NAME/KEY: Xaa
<222> LOCATION: (8)..(8)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (9)..(11)
<223> OTHER INFORMATION: Xaa is a hydrophobic amino acid.
<220> FEATURE:
<221> NAME/KEY: Xaa
<222> LOCATION: (12)..(12)
<223> OTHER INFORMATION: Xaa is a charged amino acid.
<220> FEATURE:
<221> NAME/KEY: Xaa
<222> LOCATION: (13)..(13)
<223> OTHER INFORMATION: Xaa is a hydrophobic amino acid.

<400> SEQUENCE: 65

Xaa Xaa Xaa Xaa Xaa Xaa Xaa Xaa Xaa Xaa Xaa Xaa Xaa
1               5                   10

<210> SEQ ID NO 66
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is a charged amino acid.
<220> FEATURE:
<221> NAME/KEY: Xaa
<222> LOCATION: (2)..(2)
<223> OTHER INFORMATION: Xaa is a hydrophobic amino acid.
<220> FEATURE:
<221> NAME/KEY: Xaa
<222> LOCATION: (4)..(4)
<223> OTHER INFORMATION: Xaa is a charged amino acid.
<220> FEATURE:
<221> NAME/KEY: Xaa
<222> LOCATION: (5)..(5)
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (7)..(7)
<223> OTHER INFORMATION: Xaa is a charged amino acid.
<220> FEATURE:
<221> NAME/KEY: Xaa
<222> LOCATION: (8)..(8)
```

```
<223> OTHER INFORMATION: Xaa is an amino acid that can form a hydrogen
      bond, a disulfide bond, a thioether bond, or an ester bond.
<220> FEATURE:
<221> NAME/KEY: Xaa
<222> LOCATION: (10)..(10)
<223> OTHER INFORMATION: Xaa is a hydrophobic amino acid.
<220> FEATURE:
<221> NAME/KEY: Xaa
<222> LOCATION: (12)..(12)
<223> OTHER INFORMATION: Xaa is a charged amino acid.

<400> SEQUENCE: 66

Xaa Xaa Thr Xaa Xaa Val Xaa Xaa Ile Xaa Val Xaa Ile
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (3)..(5)
<223> OTHER INFORMATION: Xaa is any amino acid.

<400> SEQUENCE: 67

His His Xaa Xaa Xaa Asp Gly
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa is Leu or Ile.
<220> FEATURE:
<221> NAME/KEY: Xaa
<222> LOCATION: (4)..(4)
<223> OTHER INFORMATION: Xaa is His or Asp.
<220> FEATURE:
<221> NAME/KEY: Xaa
<222> LOCATION: (6)..(6)
<223> OTHER INFORMATION: Xaa is Leu or Ile.

<400> SEQUENCE: 68

Xaa Gly Gly Xaa Ser Xaa
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 69

Leu Gly Gly Asp Ser
1               5

<210> SEQ ID NO 70
<211> LENGTH: 5
<212> TYPE: PRT
<213> ORGANISM: Artificial Sequence
<220> FEATURE:
<223> OTHER INFORMATION: Synthetic polypeptide
```

```
<400> SEQUENCE: 70

Leu Gly Gly His Ser
1               5
```

ANTIMICROBIAL AGENT, BACTERIAL STRAIN, BIOSYNTHESIS, AND METHODS OF USE

CROSS-REFERENCE TO RELATED APPLICATIONS

This application claims priority to U.S. Provisional Patent Nos. 61/566,831, filed on Dec. 5, 2011, and 61/643,617 filed on May 7, 2012, the contents of each of which are herein incorporated by reference.

FIELD

The disclosure relates to an isolated, biologically pure culture of a bacterial strain identified as *Paenibacillus thiaminolyticus* (designated as OSY-SE), isolated antimicrobial compounds produced by the strain, as well as compositions and methods of use thereof. The disclosure also relates to isolated nucleic acid molecules, isolated amino acid sequences, vectors, recombinant cells, and methods for the biosynthesis of antimicrobial compounds.

BACKGROUND

The emerging resistance of pathogenic bacteria to antibiotics that find use in medicinal application poses a serious health challenge. The identification of antibiotic resistant microbes such as methicillin resistant *Staphylococcus aureus* (MRSA), fluoroquinolone resistant *Pseudomonas aeruginosa* and *Clostridium difficile*, and multi-drug resistant *Salmonella* spp. represent a few notable examples of this emerging problem. The rate of discovery and approval of new antimicrobial agents does not match the rate at which antibiotics in use tend to lose efficacy. This discrepancy makes it urgent to search for new potent and safe antimicrobial agents. Environment remains an important reservoir for microbial strains capable of producing potent antimicrobials. Advances in sensitivity testing, material separation, and chemical structure elucidation facilitate the discovery of novel antimicrobials from natural sources.

There has been an increase in the amount of research relating to *Paenibacillus* as a potential source of new antimicrobials. These spore-forming species are widely distributed in the environment. Strains of *Paenibacillus* produce diverse antimicrobial agents including lantibiotics, lipopeptides, and macrolides. Lipopeptides are non-ribosomally synthesized compounds which are active against a wide range of bacteria, fungi, and oomycetes. In addition, lipopeptides can act as antiviral and antitumor agents, immunomodulators or specific toxins and enzyme inhibitors.

Accordingly, there is a need in the art to identify and develop antimicrobial agents that are effective against a broad spectrum of microbial pathogens such as Gram-positive and Gram-negative bacteria, as well as methods, vectors, and cells for synthesizing such antimicrobial agents.

SUMMARY

In an aspect, the disclosure relates to a biologically pure culture of a strain of *Paenibacillus thiaminolyticus*, identified as OSY-SE.

In an aspect, the disclosure relates to an isolated amino acid sequence comprising:
$R_1$-$X_1$-$X_2$-$X_3$-$X_4$-$X_5$-$X_6$-$X_7$-$X_8$-$X_9$-$X_{10}$-$X_{11}$-$X_{12}$-$X_{13}$ (SEQ ID NO:2)

wherein $R_1$ comprises an fatty acid group as described herein; $X_1$, $X_4$, $X_7$, and $X_{12}$ are each independently selected from an amino acid having a charged side chain moiety; $X_2$, $X_6$, $X_9$, $X_{10}$, $X_{11}$, and $X_{13}$ are each independently selected from an amino acid having a hydrophobic side chain moiety; and $X_3$, $X_5$, and $X_8$ are each independently selected from amino acids comprising a side chain moiety that can form a hydrogen bond, a disulfide bond, a thioether bond, or an ester bond.

In another aspect the disclosure relates to an isolated amino acid sequence comprising: $R_1$-Orn-Val-Thr-Orn-Ser-Val-Lys-Ser-Ile-Pro-Val-Lys-Ile (SEQ ID NO:1), wherein $R_1$ comprises an $C_1$-$C_{20}$ fatty acid group.

Some embodiments of the aspects relating to isolated amino acid sequences further comprise a linkage between any two amino acid residues thereby forming a cyclic peptide structure.

In another aspect the disclosure relates to an antimicrobial polypeptide prepared by a process comprising the steps of: (a) culturing *Paenibacillus thiaminolyticus* OSY-SE, *Paenibacillus thiaminolyticus* OSY-SE cells, or another organism, or host cell under conditions effective to produce the antimicrobial polypeptide having an amino acid sequence of SEQ ID NO:1, SEQ ID NO:2, SEQ ID NO:64, or SEQ ID NO:65; and (b) obtaining from the cells the antimicrobial polypeptide so produced.

In an aspect, the disclosure relates to a compound, or salt thereof, of Formula I:

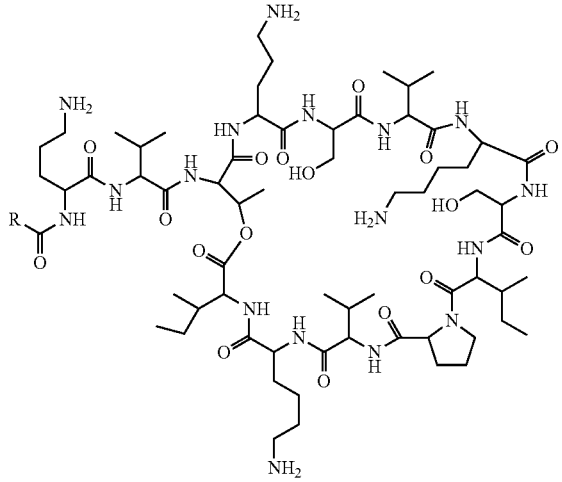

wherein R comprises H, —OH, $C_1$-$C_{20}$ alkyl, $C_2$-$C_{20}$ alkenyl, $C_2$-$C_{20}$ alkynyl group, or a hydrophobic group with aliphatic or hydrophobic ring structures.

In an aspect, the disclosure relates to a composition comprising at least one of the isolated amino acid sequences described herein, in combination with a substrate or a carrier. In some embodiments of this aspect the composition comprises a biologically pure culture of a strain of *Paenibacillus thiaminolyticus*, identified as OSY-SE. In embodiments of this aspect the carrier can be a pharmaceutically acceptable or an agriculturally acceptable carrier.

Aspects and embodiments of the disclosure also provide for an article of manufacture comprising the biologically pure culture, the amino acid sequence, and/or the compositions as detailed herein. In some embodiments the article of manufacture comprises a human food product, an animal food product, a beverage product, a packaging product, food processing equipment, medical equipment, and/or a personal care product.

In an aspect, the disclosure relates to a method of affecting microbial activity, wherein the method comprises contacting at least one of (i) a microbe and (ii) a substrate capable of supporting microbial activity with at least one of: (a) the biologically pure culture; (b) the amino acid sequence; (c) the composition; and (d) the compound as described herein, wherein the at least one of the microbe and the substrate is contacted with at least one of (a)-(d) in an amount effective to affect microbial activity.

In an aspect, the disclosure relates to a method of inhibiting growth or proliferation of a microbe in a subject comprising administering to the subject the at least one of: (a) the biologically pure culture; (b) the amino acid sequence; (c) the composition; and (d) the compound as described herein, wherein at least one of (a)-(d) is administered in an amount effective to inhibit growth or proliferation of the microbe.

In an aspect, the disclosure relates to a method of treating a condition or disease associated with the presence of a microbe comprising administering to a subject in need thereof the at least one of: (a) the biologically pure culture; (b) the amino acid sequence; (c) the composition; and (d) the compound as described herein, wherein at least one of (a)-(d) is administered in an amount effective to treat the condition or disease.

In an aspect, the disclosure relates to a method of treating a microbial infection comprising administering to a subject in need thereof the at least one of: (a) the biologically pure culture; (b) the amino acid sequence; (c) the composition; and (d) the compound as described herein, wherein at least one of (a)-(d) is administered in an amount effective to treat the microbial infection.

In an aspect, the disclosure relates to an isolated polynucleotide comprising a sequence encoding a polypeptide having at least 80% amino acid identity to at least one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments the isolated polynucleotide comprises a sequence encoding a polypeptide having at least 90% amino acid identity to at least one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments, the isolated polynucleotide comprises a sequence encoding at least one polypeptide of PbtA (SEQ ID NO: 5), PbtB (SEQ ID NO: 7), PbtC (SEQ ID NO: 9), PbtD (SEQ ID NO: 11), or PbtE (SEQ ID NO: 13).

In another aspect, the disclosure relates to an isolated polynucleotide comprising a sequence having at least 80% identity to at least one of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the isolated polynucleotide comprises a sequence having at least 90% identity to at least one of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the isolated polynucleotide comprises at least one sequence of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the vector comprises the pbt gene cluster (SEQ ID NO:14) encoding the non-ribosomal peptide synthetase (NRPS) subunits.

In embodiments of the above aspects, the polynucleotide can comprise a cDNA sequence. In some embodiments, the polynucleotide can encode a polypeptide that exhibits the same activity as at least one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments the polynucleotide comprises a sequence encoding for at least one of an NRPS subunit, such as a condensation subunit, an adenylation subunit, a thiolation subunit, an epimerization subunit, a transmembrane transporter, or a thioesterase subunit.

In some embodiments the polynucleotide can be operably connected to a promoter sequence. In some embodiments the polynucleotide can further comprise an enhancer sequence.

In another aspect, the disclosure provides a vector comprising an isolated polynucleotide comprising a sequence encoding a polypeptide having at least 80% amino acid identity to at least one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments the vector comprises an isolated polynucleotide comprising a sequence encoding a polypeptide having at least 90% amino acid identity to at least one PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments, the vector comprises an isolated polynucleotide comprising a sequence encoding at least one polypeptide of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments the vector comprises an isolated polynucleotide comprising a sequence having at least 80% identity to at least one of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the vector comprises an isolated polynucleotide comprising a sequence having at least 90% identity to at least one of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the vector comprises an isolated polynucleotide comprising at least one sequence of pbtA (SEQ ID NO: 4), pbtB (SEQ ID NO: 6), pbtC (SEQ ID NO: 8), pbtD (SEQ ID NO: 10), or pbtE (SEQ ID NO: 12). In some embodiments the vector comprises the pbt gene cluster (SEQ ID NO: 14).

In another aspect, the disclosure relates to an isolated polypeptide comprising a sequence having at least 80% amino acid identity to any one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments, the polypeptide has at least 90% amino acid identity to any one of PbtA (SEQ ID NO: 5), PbtB (SEQ ID NO: 7), PbtC (SEQ ID NO: 9), PbtD (SEQ ID NO: 11), or PbtE (SEQ ID NO: 13). In some embodiments the polypeptide comprises a sequence selected from the group of PbtA (SEQ ID NO: 5), PbtB (SEQ ID NO: 7), PbtC (SEQ ID NO: 9), PbtD (SEQ ID NO: 11), or PbtE (SEQ ID NO: 13).

In another aspect, the disclosure relates to a recombinant cell comprising a polynucleotide, a vector, or a polypeptide of any of the various aspects and embodiments disclosed herein. In some embodiments the recombinant cell comprises a prokaryotic cell. In some embodiments, the recombinant cell comprises a gram negative bacterial cell. In some embodiments, the recombinant cell comprises a gram positive bacterial cell. In some embodiments, the recombinant cell comprises a bacterial cell of the genus *Paenibacillus*.

In a further aspect, the disclosure relates to a method of modifying production of paenibacterin in *Paenibacillus thiaminolyticus* OSY-SE, or another organism, or host cell comprising introducing into *Paenibacillus thiaminolyticus* OSY-SE, or the another organism, or the host cell a polynucleotide or a vector of any of the aspects and embodiments disclosed herein.

In another aspect, the disclosure relates to a method for the biosynthetic production of an antimicrobial agent as disclosed herein or an analog thereof, comprising growing a recombinant cell under conditions that allow synthesis of the antimicrobial agent or an analog thereof, wherein the recombinant cell comprises polynucleotides encoding proteins, PbtA (SEQ ID NO: 5), PbtB (SEQ ID NO: 7), PbtC (SEQ ID NO: 9), PbtD (SEQ ID NO: 11), or PbtE (SEQ ID NO: 13), or homologs thereof, wherein the polynucleotides are operably connected to a promoter. In some embodiments the antimicrobial agent comprises paenibacterin or an analog thereof.

The disclosure provides for and encompasses additional aspects and embodiments, which will be apparent to those of skill in the art in light of the following description.

DETAILED DESCRIPTION

Figure 1:
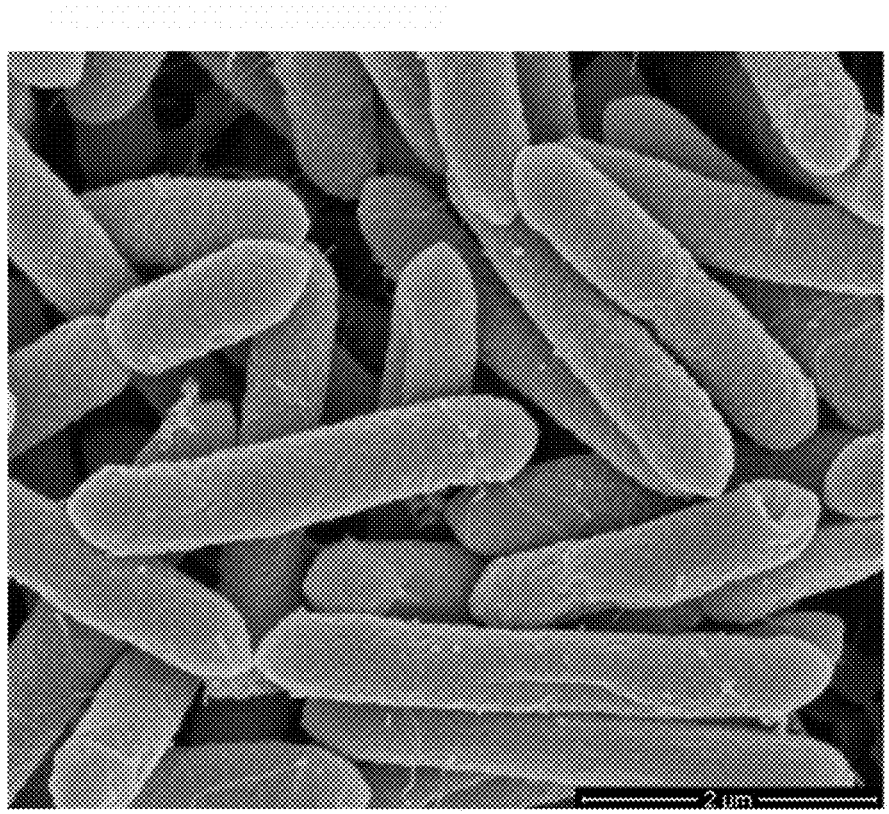
FIG. 1 depicts scanning electron microscope (SEM) image of *Paenibacillus thiaminolyticus* OSY-SE cells (scale bar at 2 μm).

In a general sense, the disclosure provides isolated and/or purified amino acid sequences as well as a biologically pure bacterial culture that exhibit antimicrobial activity. The disclosure also provides isolated amino acid sequences and isolated nucleotide sequences as well as vectors and recombinant cells that can be used in methods (e.g., biosynthesis) for making the antimicrobial agents disclosed herein. Further the disclosure relates to methods of use, compositions, and articles of manufacture comprising the sequences and bacterial culture as disclosed herein. The disclosure provides illustrative embodiments of the agents that exhibit antimicrobial activity based on a compound termed "paenibacterin," which is derived from the newly isolated *Paenibacillus thiaminolyticus* (OSY-SE), and which has been structurally characterized, as described herein. Unlike daptomycin, paenibacterin demonstrates antibacterial activity against both Gram-negative and Gram-positive bacteria.

As used herein, "antimicrobial agent," an agent that "exhibits antimicrobial activity," or an agent that "affects microbial activity" means a compound that slows or stops growth and/or proliferation, slows or stops the rate of growth and/or proliferation, or stuns, inactivates, or kills a microbe. Antimicrobial agents can encompass the terms antibiotics, antibacterials (e.g., bactericidal or bacteriostatic agents), antivirals (e.g., virucidal agents), antifungals (e.g., fungicidal or fungistatic agents), mold-inhibiting agents, anthelminthics (e.g., vermifuge or vermicidal agents), antiparasitics, and the like. For purposes of the disclosure, antimicrobial activity may be determined according to any procedure that is described herein or that is otherwise known in the art.

Antimicrobial Agents

As described above, aspects of the disclosure generally relate to antimicrobial agents and compositions comprising such agents. In embodiments, the antimicrobial agent can be synthesized and isolated from biologically pure culture of the OSY-SE bacterium disclosed herein. Embodiments of this aspect provide for an antimicrobial agent comprising the amino acid sequence:

```
                                         (SEQ ID NO: 64)
Orn-Val-Thr-Orn-Ser-Val-Lys-Ser-Ile-Pro-Val-Lys-

Ile
```

Some embodiments provide for a fatty acid derivative of SEQ ID NO:64.

```
                                          (SEQ ID NO: 1)
R₁-Orn-Val-Thr-Orn-Ser-Val-Lys-Ser-Ile-Pro-Val-

Lys-Ile
``` wherein $R_1$ comprises an fatty acid group.

Fatty acids are known in the art, and can include unsaturated (e.g., comprising at least one double bonds) or saturated (no double bonds) fatty acids. In some embodiments, the fatty acid group R1 can be a saturated or unsaturated fatty acid of any length such as, for example, short chain (containing aliphatic groups of less than six carbons), medium chain (containing aliphatic groups of six to twelve carbons), long chain (containing aliphatic groups of twelve to about twenty two carbons), or very long chain fatty acids (containing aliphatic groups of twenty two or more carbons). In embodiments comprising an unsaturated fatty acid, the fatty acid can adopt either a trans or cis configuration. Non-limiting examples of some medium, long, and very long chain unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid. In some embodiments the fatty acid can be any fatty acid that is commonly found in or associated with lipopeptides such as, for example, hydroxyl fatty acids (e.g., β-hydroxy fatty acids). In other embodiments, the fatty acid can be any hydrophobic group with aliphatic or hydrophobic ring structures.

In some embodiments wherein $R_1$ comprises a saturated fatty acid, the fatty acid can comprise between eight and twenty four carbon atoms. Non-limiting examples of some saturated fatty acids include lauric acid, myristic acid, palmitic acid, stearic acid, arachidic acid, behenic acid, lignoceric acid, cerotic acid. In some embodiments $R_1$ comprises a saturated fatty acid of about 10-17 carbon atoms. In some embodiments $R_1$ comprises a saturated fatty acid of 15 carbon atoms. In further embodiments the saturated fatty acid of 15 carbon atoms is selected from wherein "- - -" indicates the covalent bond to the amino group of the N-terminal amino acid of an antimicrobial agent as disclosed herein.

Without being limited by any mechanism of action, the antimicrobial activity of the agents described herein may arise in part through interaction of the agent and cell membranes of target microbes (microorganisms). In some embodiments, for example, the interaction can arise through non-specific binding to the membrane, e.g., in a membrane-parallel orientation, interacting only with one face of the bi-layer. In some embodiments the $R_1$ fatty acid group can be selected to increase the interaction between the antimicrobial agent and the cell membrane (e.g., by hydrophobic interaction or integration of the fatty acid moiety in the membrane lipid bilayer). While the structural nature of the $R_1$ fatty acid group can have an effect on the antimicrobial activity of peptide (e.g., confers or helps to confer an amount of antimicrobial activity to the peptide), the activity can be retained even in the absence of the $R_1$, similar to other peptide antibiotic/antimicrobials (e.g., polymyxins).

In some embodiments SEQ ID NO:1 comprises a cyclic structure through formation of an ester linkage between the C-terminal isoleucine and the hydroxyl moiety of the threonine residue (see also FIG. 11):

(SEQ ID NO: 1)

R₁-Orn-Val-Thr-Orn-Ser-Val-Lys-Ser-Ile-Pro-Val-Lys-Ile

Homologues & Structural Variation

In some embodiments, the antimicrobial agent comprises an amino acid sequence:

X1-X2-X3-X4-X5-X6-X7-X8-X9-X10-X11-X12-X13     (SEQ ID NO:65)

wherein
    X1, X4, X7, and X12 are each independently selected from an amino acid having a charged side chain moiety;
    X2, X6, X9, X10, X11, and X13 are each independently selected from an amino acid having a hydrophobic side chain moiety; and
    X3, X5, and X8 are each independently selected from amino acids comprising a side chain moiety that can form a hydrogen bond, a disulfide bond, a thioether bond, or an ester bond.

In some embodiments X1, X4, X7, and X12 are each independently selected from positively charged amino acids. In further embodiments X1, X4, X7, and X12 are each independently selected from ornithine (Orn), diaminobutyric acid (Dab), His, Lys, and Arg. In some embodiments X1, X4, X7, and X12 are each independently selected from negatively charged amino acids. In further embodiments X1, X4, X7, and X12 are each independently selected from Asp or Glu.

In some embodiments X2, X6, X9, X10, X11, and X13 are each independently selected from Leu, Ile, Pro, Val, Ala, Met, Phe, and Trp.

In some embodiments X3, X5, and X8 are each independently selected from Cys, Tyr, Thr and Ser. In further embodiments wherein X13 is Ile, X3, X5, and X8 are selected from Tyr, Thr, and Ser.

In embodiments relating to SEQ ID NO:65, the agent can include a fatty acid group, $R_1$, as described above with reference to SEQ ID NO:1. In embodiments relating to SEQ ID NO:65, the agent can optionally comprise a cyclic structure, such as described above with reference to SEQ ID NO:1, including an ester bond between two of the amino acids X1 through X13. In embodiments relating to SEQ ID NO:65, the agent can optionally include both a fatty acid group, $R_1$, and a cyclic structure. Accordingly, embodiments provide for the following variations to SEQ ID NO:2:

(SEQ ID NO: 2)
R1-X1-X2-X3-X4-X5-X6-X7-X8-X9-X10-X11-X12-X13;

(SEQ ID NO: 65)
X1-X2-X3-X4-X5-X6-X7-X8-X9-X10-X11-X12-X13;

(SEQ ID NO: 2)
R1-X1-X2-X3-X4-X5-X6-X7-X8-X9-X10-X11-X12-X13;

wherein the dashed line indicates an optional bond between two amino acid residues of X1-X13, producing a cyclic peptide structure, and wherein X1-X13 and R1 are as defined above. In embodiments, the cyclic linkage is formed between any of amino acids X1-X13 and fatty acid R1, wherein R1 comprises a carboxyl, amino, hydroxy, thiol, or thioether moiety. In some embodiments a cyclic peptide structure is formed between amino acid X13 and any of X1, X5, or X8, wherein X1, X5, or X8 comprise an amino acid having a hydroxyl moiety.

As detailed in the Examples, nuclear magnetic resonance (NMR) data acquired on the non-limiting antimicrobial peptide of SEQ ID NO:1 that comprises an $R_1$ fatty acid group and a cyclic structure allows for the generation of a structured peptide model that adopts a beta-strand conformation. This structural model of SEQ ID NO:1 indicates that four residues (V6, I9, V11, and I13) are located on one side of the beta-strand and could contribute to membrane binding activity, micelle formation, or other functions relating to antimicrobial activity or enhancement of antimicrobial activity. Therefore, some embodiments provide for an antimicrobial agent comprising SEQ ID NO:3:

(SEQ ID NO: 3)
R1-X1-X2-Thr-X4-X5-Val-Xy-X8-Ile-X10-Val-X12-Ile;

(SEQ ID NO: 66)
X1-X2-Thr-X4-X5-Val-X7-X8-Ile-X10-Val-X12-Ile;

(SEQ ID NO: 3)
R1-X1-X2-Thr-X4-X5-Val-X7-X8-Ile-X10-Val-X12-Ile;

wherein $R_1$, X1, X2, X4, X5, X7, X8, X10, X12, and "- - -" are all as defined above.

In some further embodiments, the disclosure provides a compound of Formula I:

wherein R comprises an [C8-C24] alkyl, alkenyl, or alkynyl group, optionally substituted (e.g., with one or more hydroxyl groups).

The structure, function, and chemistry of individual amino acids are well known to those of skill in the art. Amino acids as described herein can include alpha-amino acids of the general formula $H_2NCHRCOOH$, where R is an amino acid side chain comprising an organic substituent, as well as uniquely structured amino acids such as, for example, proline. Amino acids include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, aminobutryic acid (alpha, beta, and gamma) diaminobutyric acid, and the like. Accordingly, the term "amino acid side chain" refers to the various organic substituent groups (e.g., "R" in $H_2NCHRCOOH$) that differentiate one amino acid from another. A "derivative" of an amino acid side chain refers to an amino acid side chain that has been modified structurally (e.g., through chemical reaction to form new species, covalent linkage to another molecule, etc.).

In some embodiments, the amino acids of SEQ ID NOs:2, 3, 65, and 66 can be selected to interact with primary or secondary bindings site within or on a microbe.

Embodiments also provide for dehydration products of the molecules of SEQ ID NOs:1-3 and SEQ ID NOS:64-66. Embodiments also provide for derivatives of the amino acid side chains of the agents disclosed as SEQ ID NOs:1-3 and SEQ ID NOS:64-66. Embodiments also provide for agents of SEQ ID NOs:1-3 and SEQ ID NOS:64-66 as optically pure isomers. The antimicrobial agents described herein can be provided, isolated, and/or purified as salts such as, for example, basic or acidic addition salts. The selection and formation of salt forms are within the ability of one skilled in the art. See, e.g., Remington: The Science and Practice of Pharmacy, 21$^{st}$ ed., Lippincott Williams & Wilkins, A Wolters Kluwer Company, Philadelphia, Pa. (2006).

In some embodiments, the disclosure provides for an isolated and/or purified antimicrobial agent of SEQ ID NO:1, SEQ ID NO:2, SEQ ID NO:3, SEQ ID NO:64, SEQ ID NO:65, or SEQ ID NO:66 or any combination of two or more thereof. In such embodiments, the isolated and/or purified molecule provides for an effective antimicrobial agent, as well as for its use as an effective antimicrobial agent in a variety of compositions.

In embodiments, the antimicrobial agents described herein are active in amounts ranging from about 0.1 nM to about 1.0 mM or 500 µM, from about 0.1 nM to about 100 µM, from about 1 nM to about 50 µM, or from about 1 nM to about 10 µM. For example, the antimicrobial agent paenibacterin detailed in the illustrative examples below, and under those exemplary conditions, exhibits an activity against Escherichia coli K-12 of about 3200 AU/ml (arbitrary units) is based on spot-on-lawn test. However, it will be appreciated that the effective concentrations are likely different for various strains, and for the different active agents disclosed herein.

Polynucleotides And Polypeptide Sequences

In some embodiments of the disclosure, the function of the various Pbt NRPS modules, subunits, or polypeptides disclosed herein can be supplemented or provided by alternative proteins (e.g., homologous proteins from other bacterial strains or other NRPS modules and subunits) or synthetic chemical techniques that provide the same function/activity. Accordingly, some embodiments of the disclosure can provide a method comprising the partial biosynthesis of paenibacterin and further steps that include isolating the partially synthesized paenibacterin from the cell, and performing one or more additional synthetic steps (e.g., cleaving a leader polypeptide or a fusion polypeptide, forming a fusion polypeptide, and/or attaching a fatty acid ester to the paenibacterin.

In one aspect, the disclosure provides an isolated polynucleotide encoding a polypeptide having at least 80%, 85%, 90%, 95%, or greater (e.g., 96%, 97%, 98%, or 99%) amino acid identity to at least one protein selected from PbtA (SEQ ID NO:5), PbtB (SEQ ID NO:7), PbtC (SEQ ID NO:9), PbtD (SEQ ID NO:11), or PbtE (SEQ ID NO:13). In some embodiments, the polynucleotide encodes at least one of PbtA (SEQ ID NO:5), PbtB (SEQ ID NO:7), PbtC (SEQ ID NO:9), PbtD (SEQ ID NO:11), or PbtE (SEQ ID NO:13).

In some embodiments, the polynucleotide comprises a sequence that has at least 80%, 85%, 90%, 95%, or greater (e.g., 96%, 97%, 98%, or 99%) identity to at least one polynucleotide selected from pbtA (SEQ ID NO:4), pbtB (SEQ ID NO:6), pbtC (SEQ ID NO:8), pbtD (SEQ ID NO:10), or pbtE (SEQ ID NO:12). In some embodiments, the polynucleotide comprises at least one of pbtA (SEQ ID NO:4), pbtB (SEQ ID NO:6), pbtC (SEQ ID NO:8), pbtD (SEQ ID NO:10), or pbtE (SEQ ID NO:12).

In some embodiments the polynucleotide comprises a sequence having at least 80%, 85%, 90%, 95%, or greater (e.g., 96%, 97%, 98%, or 99%) identity to pbtA (SEQ ID NO:4), pbtB (SEQ ID NO:6), and pbtC (SEQ ID NO:8). In further embodiments such polynucleotides may further optionally comprise a sequence having at least 80%, 85%, 90%, 95%, or greater (e.g., 96%, 97%, 98%, or 99%) identity to one or both of pbtD (SEQ ID NO:10) and pbtE (SEQ ID NO:12). In some embodiments, the polynucleotide comprises the entire pbt gene cluster (SEQ ID NO:14).

In another embodiment, polynucleotide sequences encoding one or more specific polypeptides in the paenibacterin biosynthetic pathway can be replaced with polynucleotide sequences encoding analogous polypeptides, or modules or domains from other distinct but related polypeptides, such as those herein described or otherwise known in the art (e.g., NRPS machinery involved in biosynthesis of lipopeptide antibiotics such as polymyxin [Choi, S. K., et al., J. Bacteriol. (2009) 191: 3350-3358], fusaricidin [Choi, S. K., et al., Biochem. Biophys. Res. Commun. (2008) 365: 89-95], friulimcin [Müller, C., et al., Antimicrob. Agents Chemother (2007) 51: 1028-1037], and daptomycin [Baltz, R. H., et al., Nat. Prod. Rep. (2005) 22: 717-741]. See Fischbach and Walsh, 2006 for a general overview of NRPS. In some embodiments such proteins can be a native protein to a recombinant host cell. Accordingly, in some embodiments, genetically engineered bacteria expressing such sequences can be used to develop bacterial strains capable of synthesizing paenibacterin or analogs thereof.

In another aspect, the disclosure relates to an isolated polypeptide having at least 80%, 85%, 90%, 95%, or greater (e.g., 96%, 97%, 98%, or 99%) identity to PbtA (SEQ ID NO:5), PbtB (SEQ ID NO:7), PbtC (SEQ ID NO:9), PbtD (SEQ ID NO:11), or PbtE (SEQ ID NO:13), and having the corresponding catalytic activity of PbtA (SEQ ID NO:5), PbtB (SEQ ID NO:7), PbtC (SEQ ID NO:9), PbtD (SEQ ID NO:11), or PbtE (SEQ ID NO:13), respectively. In some embodiments, the polypeptide comprises at least one of PbtA (SEQ ID NO:5), PbtB (SEQ ID NO:7), PbtC (SEQ ID NO:9), PbtD (SEQ ID NO:11), or PbtE (SEQ ID NO:13).

As discussed herein, the disclosure also provides for one or more of the sequences PbtA (SEQ ID NO:5), PbtB (SEQ ID NO:7), PbtC (SEQ ID NO:9), PbtD (SEQ ID NO:11), or PbtE (SEQ ID NO:13) to be modified (e.g., post-translational modification) or genetically manipulated to alter the specificity or activity of the encoded protein. For example, the coding sequences could be modified by site-directed mutagenesis or random mutagenesis to make specific substitutions of one or more amino acids. Such modifications can also be used to optimize or otherwise modify the biosynthetic production of paenibacterin in a particular recombinant host cell (e.g., wherein one or more of the Pbt polypeptides has diminished, or no, activity in a particular host cell). The structure, function, and chemistry of individual amino acids are well known to those of skill in the art and art discussed herein.

In some embodiments, analogs (e.g., homologs) of the proteins encoded by the pbt gene cluster include, but are not limited to, proteins that share at least about 40%, 50%, 60%, 70% or more amino acid similarity and/or 25%, 35%, 45%, 55% or more amino acid identity and catalyzing analogous reactions. Analogs may share specific domains within the proteins, as discussed herein.

Vectors And Nucleic Acid Constructs

In an aspect, the disclosure provides for nucleic acid constructs comprising a polynucleotide sequence as described herein operably linked to one or more control sequences that direct the expression of the polynucleotide in a suitable host cell under conditions compatible with the control sequences.

In another aspect, the disclosure provides recombinant constructs and vectors comprising a polynucleotide disclosed herein operably linked to a promoter. Promoters may be any promoter active in the cell and capable of driving gene expression. Promoters include constitutive and inducible promoters. In some embodiments, a single promoter can drive the expression of one or more of the pbt sequences (e.g., when a single nucleotide is transcribed as a polycistronic mRNA, or when multiple nucleotides are under the control of the same promoter). A variety of suitable promoters are known to those of skill in the art. Suitably the promoter is not the promoter natively associated with the polynucleotide. A vector comprising one or more of the polynucleotides or the polynucleotides operably connected to a promoter are also provided. Suitable vectors include, but are not limited to, a plasmid, a cosmid, a transposon, a virus, a phage, a BAC, a YAC or any other vectors known to those of skill in the art or which may be subsequently developed.

A polynucleotide sequence as disclosed herein may be manipulated in a variety of ways to provide for expression of the polypeptide for which it encodes. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. Typically a promoter sequence contains transcriptional control sequences which ultimately mediate the expression of the polypeptide encoded by the polynucleotide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Non-limiting examples of suitable promoters for directing the transcription of the polynucleotide constructs described herein in a recombinant bacterial host cell include the promoters obtained from the *Escherichia coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformnis* penicillinase gene (penP), *Bacillus subtilis* xylA and xylB genes, prokaryotic beta-lactamase gene, as well as the tac promoter. Further promoters are known in the art (Sambrook et al., 1989). Similarly, a number of suitable promoters for directing the transcription of the nucleic acid constructs disclosed herein in other expression systems (e.g., fungal host cells, yeast host cells, etc.) are known in the art.

In some embodiments, the control sequence can comprise a suitable transcription terminator sequence that is recognized by a recombinant host cell to terminate transcription. Suitably, the terminator sequence is operably linked to the 3' terminus of the polynucleotide sequence encoding a polypeptide. Any terminator which is functional in the host cell of choice may be used.

A control sequence may also comprise a signal peptide coding region that codes for an amino acid sequence linked to the amino terminus of a polypeptide and directs the encoded polypeptide into a particular region of a cell such as, for example, the secretory pathway. In some embodiments the 5' end of the polynucleotide coding sequence may contain a signal peptide coding region which is foreign to the coding sequence. The foreign signal peptide coding region may be advantageous or even required where the polynucleotide coding sequence does not naturally contain a signal peptide coding region. Some embodiments provide for any signal peptide coding region that directs an antimicrobial agent (e.g., paenibacterin) into the secretory pathway of a host cell of choice. Such signal peptide coding regions for bacterial host cells, yeast host cells, other host cells are known in the art (see, for example Simonen and Palva, (1993) *Microbiological Reviews* (57)109-137; Romanos et al., (1992), *Yeast* (8)423-488.).

In some embodiments, the control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Such regulatory sequences can allow for advantageous timing for the ultimate production of an antimicrobial agent (e.g., paenibacterin) in a recombinant system. For example, if the recombinant host cell exhibits sensitivity to the antimicrobial action such as that action characteristic of, for example, paenibacterin, expression of one or more of the Pbt polypeptides can be inhibited in order to delay a synthetic step in the paenibacterin biosynthetic pathway. Non-limiting examples of regulatory systems in prokaryotic systems include the lac, tac, and trp operator systems. In yeast, the ADH2 system or GAL1 system may be used. Similar control sequences are known in a number of other expression systems.

Expression Vectors

The disclosure also relates to recombinant expression vectors comprising a polynucleotide or nucleic acid construct as disclosed herein. The various polynucleotide and control sequences described herein may be joined together to produce a recombinant expression vector which may include one or more convenient restriction sites to allow for insertion or substitution of the polynucleotide sequence encoding one or more polypeptides at such sites. Alternatively, the polynucleotide sequence may be expressed by inserting the polynucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced, and is well within the knowledge of one of ordinary skill in the art. The vectors may be linear or closed circular plasmids.

The vector may be an autonomously replicating vector (i.e., a vector which exists as an extrachromosomal entity, the replication of which is independent of chromosomal replication, e.g., a plasmid, an extrachromosomal element, a minichromosome, or an artificial chromosome). Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

In some embodiments, the vectors may contain one or more selectable markers which permit easy selection of successfully transformed cells that harbor the vector. Selectable markers are known in the art and can include a gene that provides for biocide or viral resistance, resistance to heavy metals, prototrophy to auxotrophs, and the like. A number of non-limiting examples of bacterial selectable markers are known in the art.

In some embodiments the vectors may contain one or more elements that permit stable integration of the vector into the recombinant host cell genome or autonomous replication of the vector in the cell independent of the genome. A number of strategies and sequences are known in the art for the integration of a vector into a host cell genome (e.g., by homologous or non-homologous recombination). More than one copy of a nucleotide sequence disclosed herein may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent. The procedures that can be used to ligate the elements described above to construct the recombinant expression vectors of the disclosure are well known in the art (see, e.g., Sambrook et al., 1989, supra).

Host Cells

In an aspect the disclosure relates to a recombinant host cell comprising the polynucleotide or nucleic acid construct (i.e., vector) which are advantageously used in the recombinant production of the polypeptides. As noted above, a vector comprising a polynucleotide can be introduced into a host cell so that the vector is maintained as a chromosomal integrant or as a self-replicating extra-chromosomal vector. The host cell may be a unicellular microorganism (a prokaryote or an eukaryote) or a non-unicellular microorganism (an eukaryote).

In some embodiments, the host cell comprises a bacterial cell such as gram-positive bacteria that does not ordinarily synthesize paenibacterin or analogs thereof. As disclosed herein, bacteria that do not natively possess the pbt biosynthetic gene cluster, for example, *Paenibacillus* strains other than *Paenibacillus thiaminolyticus* OSY-SE, (e.g., *Bacillus, Lactobacillus, Listeria, Clostridium, Streptococcus*, etc.), may be genetically modified to express polypeptides having at least 80%, 85%, 90%, 95% or greater amino acid identity to one or more of the various Pbt sequences disclosed herein. In some embodiments the polypeptide includes at least one PbtA (SEQ ID NO:5), PbtB (SEQ ID NO:7), PbtC (SEQ ID NO:9), PbtD (SEQ ID NO:11), or PbtE (SEQ ID NO:13). In some embodiments the bacterial cell comprises a gram-positive bacterial cell and can include a *Bacillus* sp., e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaternum, Bacillus stearothermophilus, Bacillus subtilis*, and *Bacillus thuringiensis*; or a *Streptomyces* sp., e.g., *Streptomyces lividans* or *Streptomyces murinus*. In some embodiments the bacterial cell comprises a gram-negative bacterium such as *Escherichia coli* and *Pseudomonas* sp. In some embodiments, the host cell may be a eukaryote, such as a mammalian, insect, plant, or fungal cell. In some embodiments, the fungal host cell is a yeast cell such as, for example, a *Candida, Hansenula, Kluyveromyces, Pichia, Saccharomyces, Schizosaccharomyces*, or *Yarrowia* cell.

Techniques for the introduction of a vector into a host cell are well known in the art and may include, for example, protoplast transformation, use of competent cells, electroporation, or conjugation.

Methods of Production

In an aspect, the disclosure provides a method for producing an antimicrobial agent (e.g., paenibacterin), wherein the method comprises (a) cultivating a host cell under conditions that allow for production of the polypeptide; and optionally (b) purifying/isolating the polypeptide.

Typically cells are cultivated in a nutrient medium suitable for production of the antimicrobial agent (e.g., paenibacterin) using common techniques known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. Any suitable nutrient medium (e.g., a medium comprising carbon and nitrogen sources, inorganic salts, etc.) can be used to cultivate the cells using procedures known in the art. In embodiments wherein the polypeptide is secreted from the cell into the nutrient medium, the polypeptide can be recovered directly from the medium. If the polypeptide is not secreted, it can be recovered from cell lysates or as inclusion bodies.

The resulting antimicrobial agent (e.g., paenibacterin) may be recovered by methods known in the art. For example, the polypeptide may be recovered from the nutrient medium by conventional procedures including, but not limited to, centrifugation, filtration, extraction, spray-drying, evaporation, or precipitation.

The antimicrobial agent disclosed herein may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Bacterial Culture

In an aspect the disclosure provides a biologically pure culture of a strain of *Paenibacillus thiaminolyticus*, identified as OSY-SE. As detailed in the Examples, the strain can be isolated from environmental sources (e.g., soil samples), identified and characterized using the techniques as detailed below (e.g., cell morphology, 16S ribosomal RNA sequence, biochemical assays), and purified and cultured to a purity that allows it to be useful as an antimicrobial agent such as, for example, in its isolated form or as part of a composition or an article of manufacture. Such a biologically pure culture can also be used to produce the antimicrobial amino acid sequences described herein. In some embodiments, the biologically pure culture of *Paenibacillus thiaminolyticus* comprises OSY-SE identified as ATCC deposit # PTA-12203 (deposited Nov. 1, 2011). In other embodiments, the biologically pure culture of *Paenibacillus thiaminolyticus* consists of OSY-SE identified as ATCC deposit # PTA-12203 (deposited Nov. 1, 2011). In some embodiments, the biologically pure culture can be used in a method that produces useful cell extract, cell suspension, cell homogenate, cell lysate, cell supernatant, cell filtrate, or cell pellet of *Paenibacillus thiaminolyticus* OSY-SE and wherein the product exhibits antimicrobial activity.

Any suitable methods and media useful for bacterial cell growth, maintenance, and/or protein production such as those described herein or otherwise known in the art, [Sambrook, J., et al., Molecular cloning: a laboratory manual, $2^{nd}$ ed., Cold Spring Harbor Laboratory Press, Cold Spring Harbor, N.Y. (1989); Drider, D., et al., Prokaryotic Antimicrobial Peptides: From Genes to Applications, Springer, N.Y. (2011), each incorporated by reference] can be used in combination with the *Paenibacillus thiaminolyticus* cells described herein.

Thus, some embodiments provide for an antimicrobial polypeptide prepared by a process comprising culturing *Paenibacillus thiaminolyticus* OSY-SE cells under conditions effective to produce the antimicrobial polypeptide having an amino acid sequence of SEQ ID NO:1, SEQ ID NO:2, SEQ ID NO:3, SEQ ID NO:64, SEQ ID NO:65, or SEQ ID NO:66; and isolating, purifying, or otherwise obtaining from the cells the antimicrobial polypeptide produced. In some embodiments, the *Paenibacillus thiaminolyticus* cells comprise ATCC # PTA-12203.

In some embodiments of this process, the antimicrobial agent (paenibacterin, for example) can be isolated and/or purified using any suitable technique known in the art, including liquid chromatography, phase separation, using organic solvents and/or aqueous solvent or buffer systems. In some embodiments the antimicrobial agent can be purified to about 75%, 80%, 85%, 90%, 91%, 92%, 93%, 94%, 95%, 96%, 97%, 98%, or 99% or more. Analysis of purity can be made using any suitable analytical method or technique such as, for example, mass spectrometry, gel electrophoresis, fluorescence, colorimetric assays, NMR, UV-Vis, total amino acid hydrolysis, chromatographic separation methods that utilize, for example, liquid chromatographic methods such as HPLC, FPLC, size exclusion, affinity binding, hydrophobic interaction, ionic charge, where purity can be assessed based on peak area.

Accordingly, the antimicrobial agents disclosed herein can be generated by a method that comprises culturing a *Paenibacillus thiaminolyticus* cell under conditions that allow for the production of any of the agents disclosed as SEQ ID NOs:1-3 and SEQ ID NOS:64-66, and isolating and/or purifying the agent(s) from the culture. The culturing and isolation and/or purification steps can be performed using standard techniques that are known in the art, and can be modified as necessary by those of skill in the art. Some embodiments provide for the manufacture of an antimicrobial agent having SEQ ID NOs:1-3 and SEQ ID NOS:64-66 by the particular methods described herein such as, for example, the procedures detailed in the Examples.

In other embodiments, the antimicrobial agents can be generated by standard chemical and/or protein and peptide synthetic techniques as are known in the art. Some embodiments relate to a synthetic strategy that incorporates a combination of chemical, peptide, and enzymatic (e.g., cyclase) synthetic steps.

Compositions and Formulations

Aspects of the disclosure relate to compositions and formulations, including pharmaceutical compositions and formulations, that comprise an effective amount of at least one antimicrobial agent as described herein. Such compositions and formulations comprise an effective amount of an agent in combination with a carrier, vehicle, excipient, or diluent, including pharmaceutically and/or agriculturally acceptable carriers, vehicles, excipients, and diluents. An "effective amount" relates to a quantity of an agent that high enough to provide a significant positive result (e.g., slow or stop microbial activity) or positive modification of the subject's condition to be treated, and is suitably low enough to avoid serious side effects (at a reasonable benefit/risk ratio). Carriers, vehicles, excipients, and diluents can be one or more compatible substances that are suitable for administration to a mammal such as, for example, solid or liquid fillers, diluents, hydrotopes, surface-active agents, and encapsulating substances. "Compatible" means that the components of the composition are capable of being commingled with the active agent, and with each other, in a manner such that there is no interaction which would substantially reduce the efficacy of the composition under ordinary use situations. Carriers, vehicles, excipients, and diluents are suitably of sufficiently high purity and sufficiently low toxicity to render them suitable for administration to the subject being treated. The carrier, vehicle, excipient, or diluent can be inert, or it can possess pharmaceutical benefits and/or aesthetic benefits, or both. Suitable carriers, vehicles, excipients, and diluents are known in the art and can be found in standard pharmaceutical texts, for example, *Remington's Pharmaceutical Sciences,* 18th edition, Mack Publishing Company, Easton, Pa., 1990, incorporated herein by reference.

In some embodiments, this aspect provides an antimicrobial composition comprising a fatty acid ester of an amino acid sequence and to its use as an active agent against microbes in various products and applications. Optionally, the composition disclosed may further comprise one or more additives that can exert an amount of antimicrobial action or preservative effect The disclosed antimicrobial compositions are applicable in a variety of products and applications, ranging from for example products of low and high pH-values, highly concentrated and diluted products, products usable in the technical field (e.g. in detergents for industrial or house-hold use), in the pharmaceutical field (e.g. for cleaning/disinfection of equipment or in the preparation of pharmaceutical compositions or their packaging), in personal care (e.g. in manufacture of cosmetics, shampoos, creams and lotions), in the feed industry (e.g. for cleaning of equipment, in the manufacture, storage, handling and preparation of animal feed and drink products) and in the food and drink industry. In embodiments relating to use of the compositions in a product, the antibacterial composition can be provided as an ingredient in the final product (e.g., cosmetic, detergent, pharmaceutical, food, or drink product). Accordingly, in some embodiments the compositions are effective against certain yeasts, fungi, and bacteria commonly associated with food-spoilage. Standard methods known in the art can be used in the manufacture of such products that comprise one or more of the antimicrobial agents and/or the bacterial culture.

In some embodiments, the antimicrobial composition may be present on the surface of said products or inside the products. In some embodiments, the disclosure relates to a method for reducing or preventing the presence, growth or activity of a microbe (e.g., gram-positive or gram-negative bacteria) in a product, such as a food or drink product wherein said method comprises contacting said food or drink product during one or more of the various stages in the food processing process including the stages of the manufacture, the handling, the storage and/or the preparation of said food or drink product with the antibacterial compositions that are disclosed herein. The antimicrobial composition may be applied or introduced by any suitable route or method such as, for example, as a spray, a rinse or a wash solution or as solution wherein the various food products are dipped. Further, the antimicrobial composition may be used to treat containers or packaging film prior to, simultaneously with or subsequently after packaging the products.

The compositions described herein may be provided in solid or liquid form. When in liquid form, the composition is typically an aqueous composition, which may be a solution, emulsion, or dispersion.

While the antimicrobial agent can be administered in the methods described herein alone, they may also be used in combination with one or more other active agents in pharmaceutical compositions (e.g., formulations). The antimicrobial agent and other active agent(s) may be formulated as separate pharmaceutical compositions, or together in a single composition. Suitably, the antimicrobial agent and the other active agent are formulated as separate pharmaceutical compositions. In each composition the antimicrobial agent and/or other active agent may be formulated with one or more pharmaceutically acceptable carriers, adjuvants, excipients, diluents, fillers, buffers, stabilizers, preservatives, lubricants, or other materials well known to those skilled in the art.

Accordingly, the methods described herein include administration of one or more pharmaceutical compositions, as discussed herein, in which an antimicrobial agent is admixed together with one or more pharmaceutically acceptable carriers, excipients, buffers, adjuvants, stabilizers, or other materials, as described herein. Standard and suitable carriers, excipients, adjuvants, and buffers, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods known in the art of pharmacy. Such methods include the step of bringing into association the active compound(s) with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichoro-tetrafluoroethane, carbon dioxide, or other suitable gases. Further formulations suitable for inhalation include those presented as a nebulizer.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Dosages

It will be appreciated that appropriate dosages of the active compounds, and compositions comprising the active compounds, can vary from subject to subject. Determining the optimal dosage will generally involve the balancing of the level of therapeutic benefit against any risk or deleterious side effects of the treatments described herein. The selected dosage level will depend on a variety of factors including, but not limited to, the species of the particular subject, the activity of the particular compound, the route of administration, the time of administration, the rate of excretion of the compound, the duration of the treatment, whether other drugs, compounds, and/or materials are used in combination, and the age, sex, weight, condition, general health, and prior medical history of the subject. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day.

Methods of Use

Aspects of the disclosure relate to various methods that employ the biologically pure bacterial culture, the antimicrobial agents, and the compositions comprising them. In an embodiment of this aspect the method can be used to affect microbial activity, wherein the method comprises contacting at least one active agent selected from (i) a microbe and (ii) a substrate capable of supporting microbial activity with at least one of (a) the biologically pure culture; (b) at least one of the antimicrobial agents (e.g., amino acid sequences and compounds); or a composition comprising at least one of the biologically pure culture and antimicrobial agent, wherein the contacting is performed an amount effective to affect microbial activity.

In another embodiment, the method relates to inhibiting growth or proliferation of a microbe in a subject wherein the method comprises administering to the subject at least one active agent selected from (a) the biologically pure culture; (b) at least one of the antimicrobial agents (e.g., amino acid sequences and compounds); or a composition comprising at least one of the biologically pure culture and antimicrobial agent, wherein the active agent is administered in an amount effective to inhibit growth or proliferation of the microbe.

In an embodiment, the method relates to treating a condition or disease associated with the presence of a microbe comprising administering to a subject in need thereof at least one active agent selected from (a) the biologically pure culture; (b) at least one of the antimicrobial agents (e.g., amino acid sequences and compounds); or a composition comprising at least one of the biologically pure culture and antimicrobial agent, wherein the active agent is administered in an amount effective to treat the condition or disease.

In an embodiment, the method relates to treating a microbial infection comprising administering to a subject in need thereof at least one active agent selected from (a) the biologically pure culture; (b) at least one of the antimicrobial agents (e.g., amino acid sequences and compounds); or a composition comprising at least one of the biologically pure culture and antimicrobial agent, wherein the active agent is administered in an amount effective to treat the condition or disease.

In some further embodiments of any of the above methods the method can further comprise administering an amount of an additional antimicrobial agent. The additional antimicrobial agent can be selected based on the particular method and indication, such that it can provide an additive or a synergistic antimicrobial effect when compared to administration of the antimicrobial agent alone.

As used herein, the terms "treatment," "treating," or "treat" refer to both therapeutic treatment and prophylactic or preventative measures. Those subjects in need of treatment include those already showing clinical signs of the particular disease, disorder, or condition as well as those prone to having or developing the disease, disorder, or condition, or those in which the disease, disorder, or condition is to be prevented. Many diseases, disorders, and conditions relate to the presence of microbes and are known to those of skill in the art, including secondary conditions resulting from opportunistic infections arising from other primary diseases and disorders (e.g., immune-suppressing conditions). Thus, a variety of patient classes can benefit from the methods of treatment described herein.

"Pharmaceutically acceptable," as used herein, pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

"Reducing proliferation of a cell," as used herein, refers to reducing, inhibiting, or preventing the survival, growth, or differentiation of a cell, including killing a cell. A cell can be derived from any organism or tissue type and includes, for example, a cancer cell (e.g., neoplastic cells, tumor cells, and the like). Thus, "affecting" microbial activity generally refers to reducing, ameliorating, or inhibiting the activity of a microbial cell and/or the clinical indications associated with the presence and activity of a microbial cell.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as fowl (e.g., ducks, chickens, etc.), amphibians, reptiles) and mammals, such as non-human primates, domesticated and/or agriculturally useful animals (such as horses, goats, sheep, dogs, cats, cows, pigs, etc.), and rodents (such as mice, rats, hamsters, guinea pigs, etc.).

In some embodiments the "effective amount" is an amount sufficient to stop or slow the progression of the disease, disorder, or condition. In some embodiments the effective amount is an amount sufficient to reverse disease, disorder, or condition, or repair the clinical signs of a disease, disorder, or condition. In embodiments the amount is sufficient to stop or slow the progression of an infection that is directly or indirectly related to a microbe. In some embodiments the effective amount is sufficient to stop or slow the proliferation and/or growth of a microbe. In further embodiments, the effective amount is sufficient to kill a microbe.

"Co-administered," as used herein, refers to simultaneous or sequential administration of multiple compounds or agents. A first compound or agent may be administered before, concurrently with, or after administration of a second compound or agent. The first compound or agent and the second compound or agent may be simultaneously or sequentially administered on the same day, or may be sequentially administered within 1 day, 2 days, 3 days, 4 days, 5 days, 6 days, 1 week, 2 weeks, 3 weeks or one month of each other. Suitably, compounds or agents are co-administered during the period in which each of the compounds or agents are exerting at least some physiological effect and/or has remaining efficacy. In some embodiments the methods described herein can comprise co-administering two or more active agents disclosed herein. In some embodiments, methods comprising co-administering two or more active agents includes at least one antimicrobial agent disclosed herein in combination with a known active agent against a particular indication. In some further embodiments, the known active agent also exhibits antimicrobial activity.

"Contacting," as used herein as in "contacting a cell," refers to contacting a cell directly or indirectly in vitro, ex vivo, or in vivo (i.e. within a subject, such as a mammal, including humans, mice, rats, rabbits, cats, and dogs). Contacting a cell, which also includes "reacting" a cell, can occur as a result of administration to a subject. Contacting encompasses administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as defined herein.

"Administration" or "administering," as used herein, refers to providing, contacting, and/or delivery of a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants.

It will be understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

Also, it is to be understood that the phraseology and terminology used herein is for the purpose of description and should not be regarded as limiting to the scope of the claims. Unless specific note is made otherwise, all the terms in this disclosure are used in accordance with the generally understood meaning of those terms. Some particular terms have been described herein, and to the extent the description differs from the commonly understood meaning, the description herein controls.

While the following examples provide further detailed description of some embodiments of the disclosure, they should be considered merely illustrative and not in any way limiting the claims.

EXAMPLES

Materials and Methods

Cultures and Media. Tryptose agar [Alpha Bioscience] was used for propagation of OSY-SE. For stock preparation, the culture was incubated overnight in tryptic soy broth [Alpha Bioscience] supplemented with 0.6% yeast extract (TSBYE). Incubated cultures were mixed with glycerol (final concentration 20%) and stored at −80° C.

Nuclear Magnetic Resonance (NMR). Unless stated otherwise, NMR experiments were performed at room temperature on a Bruker DMX-600 spectrometer (Bruker, Karlsruhe, Germany) equipped with a 5-mm ($^1$H, $^{13}$C, $^{15}$N) triple-resonance probe and three-axis gradients. These included 2D $^1$H-homonulcear COSY, TOCSY (60 ms DIPSI2 mixing time), and NOESY (200 ms mixing rime), 2D heteronuclear $^1$H-$^{13}$C HSQC, multiplicity-edited $^1$H-$^{13}$C HSQC, $^1$H-$^{13}$C HSQC-TOCSY (60 ms DIPSI2 mixing time), $^1$H-$^{13}$C HSQC-NOESY (200 ms mixing time), $^1$H-$^{13}$C HMBC, and $^1$H-$^{15}$N HSQC, all using standard Bruker pulse sequences. Water suppression was typically achieved using 3-9-19 WATERGATE technique [Sklenar, V., et al., J. Magn. Reson. (1993) 102:241-245] for the samples dissolved in $H_2O$, or presaturation to suppress residual HDO signal for the sample in $D_2O$ or $CD_3OD$. Data were processed with NMRPipe (Delaglio, F., et al., J. Biomol. NMR, (1995) 6:277-293) and visualized using NMRView (Johnson, B. A., and R. A. Blevins, J. Biomol. NMR, (1994) 4:603-614). Data were typically zero-filled prior to application of window functions followed by Fourier transform. Chemical shifts were referenced externally to sodium 2,2-dimethyl-2-silapentane-5-sulfonate (DSS) at 0.00 ppm.

Scanning Electron Microscopy (SEM). The scanning electron microscope observation was performed at The Ohio State University Campus Microscopy and Imaging Facility.

DNA Sequencing. Plasmid DNA was sequenced in Plant-Microbe Genomics Facility at The Ohio State University;

Mass Spectrometry (GC/MS, MS/MS). GC/MS was conducted in Mass Spectrometry and Proteomics Facility at The Ohio State University.

Example 1

Bacterial Strain Collection, Isolation, and Screening

Soil and food samples were collected and screened for microorganisms that produce antimicrobial agents. Soil samples were collected from different locations in Columbus, Ohio.

Soil samples were serially diluted and 100 μL aliquots were spread-plated on soil-extract agar [Hamaki, T., et al., (2005) 99:485-492] and dilute nutrient agar [Janssen, P. H., et al., Appl. Environ. Microbiol, (2002) 68:2391-2396]. Inoculated agar plates were incubated at 25° C. for two to eight weeks.

Several hundred isolates were screened for production of antimicrobial agents generally according to the protocol that follows. Colonies were transferred to tryptose agar plates in triplicate and incubated at 30° C. for several days. The incubated tryptose agar plates were overlaid with soft agar medium seeded with an indicator bacteria, either *Listeria innocua* ATCC 33090 or *Escherichia coli* K-12 (~$10^6$ CFU/mL in 10 mL soft agar). The plates were incubated at 37° C. overnight and checked for evidence of antimicrobial activity against the indicator bacteria. A soil sample yielded an isolate (OSY-SE) that was associated with potent antimicrobial action.

Example 2

Strain Identification

The morphological characteristics of OSY-SE isolate were examined after Gram staining, spore staining with malachite green and scanning electron microscopy.

For scanning electron microscopy examination, OSY-SE cells were incubated at 37° C. in TSBYE overnight, harvested by centrifugation, washed three times with phosphate buffer (0.05M, pH 7.0), resuspended in fixative (2.5% glutaraldehyde in 0.1M phosphate buffer with 0.1M sucrose, pH 7.4) and stored at 4° C. overnight. The cells were separated from the fixative by centrifugation and resuspended in phosphate buffer (0.05M, pH 7.0). The cell suspension was filtered through a 0.22 μm microbial filter (Millipore Corp., Bedford, Mass.) and bacteria on the filter were post-fixed for 1 hour in 1% osmium tetroxide. After dehydration using an ascending series of ethanol solutions (50%, 70% and 80% for 10 min. each, 95% with two changes within 10 min., 100% with three changes within 15 min.), the filter was treated with an ascending series of hexamethyldisilazane (HMDS) solutions in ethanol (25%, 50% and 75% for 15 min. each, 100% with three changes for 15 min. each) and was air dried. Subsequently, bacteria were coated with a thin layer of gold-palladium using a Cressington 108 Sputter Coater (Ted Pella Inc., Redding, Calif.) and examined under a scanning electron microscope (NOVA NanoSEM 400, FEI, Hillsboro, Oreg.). The accelerating voltage was 5 kV and images were collected digitally from the emitted secondary electron signal.

The isolate formed irregular and shiny colonies on tryptose agar and exhibited a facultative anaerobic behavior in broth culture. Morphologically, OSY-SE is rod-shaped (about 0.6 by 4.2 μm), Gram-positive, spore-forming bacterium (FIG. 1). The bacterium formed ellipsoidal spores in swollen sporangia. Motile cells can be observed directly under light microscope.

Example 3

16S Ribosomal DNA Sequence

The identity of the isolated bacteria was also characterized by sequence determination of its 16S ribosomal DNA [Drancourt, M., et al., J. Clin. Microbiol., (2000) 38:3623-3630]. Briefly, genomic DNA of the isolate was extracted using a commercial DNA extraction kit according to the manufacturer's instructions (DNeasy Blood & Tissue kit; QIAGEN, Valencia, Calif.). Universal primers specific for bacterial 16S rDNA [Weisburg, W. G., et al., J. Bacteriol. (1991) 173:697-703.) were used to amplify the corresponding gene. The targeted DNA sequence was amplified in a thermocycler as follows. After an initial 3-min incubation at 94° C., the reaction mixture was subjected to 30 cycles, each including 1 min at 94° C., 1 min at 52° C., and 2 min at 72° C. The final extension was performed at 72° C. for 10 min Amplified 16S rDNA was purified using a commercial DNA extraction kit according to the manufacturer's instructions (QIAquick gel extraction kit, QIAGEN, Valencia, Calif.). The resulting DNA was ligated (TA cloning) into a commercial vector (pGEM-T Easy, Promega Corporation, Madison, Wis.) and electro-transformed into *Escherichia coli* DH5α cells. Recombinant plasmid was extracted from an overnight culture of *Escherichia coli* DH5α using a kit (QIAprep Spin Miniprep, QIAGEN, Valencia, Calif.) and sequenced by an automated DNA analyzer (Applied Biosystems, Foster City, Calif.). The resultant DNA sequence was compared to known bacterial sequences in the National Center for Biotechnology Information database (NCBI GenBank) using the Basic Local Alignment Search Tool (BLAST) algorithm.

Biochemical tests were conducted to confirm isolate identity, including catalase, oxidase, nitrate reduction, production of acetylmethylcarbinol, dihydroxyacetone and indole, deamination of phenylalanine, and hydrolysis of starch and casein [Gordon, R. E., et al., Agriculture Handbook no. 427. U.S. Department of Agriculture, Washington, D.C. (1973)]. Two commercial biochemical test kits (API 50CH strips and API CHB medium, API 20E strips, BioMerieux, Inc., Durham, N.C.) were also used to characterize the new isolate. The results were recorded after incubating the inoculated kit wells at 30° C. for 24 and 48 h, and the identification was done by referring to the database provided by the kit manufacturer.

The isolate was positive for catalase, oxidase, hydrolysis of starch and casein but negative for nitrate reduction, production of acetylmethylcarbinol, dihydroxyacetone and indole, and deamination of phenylalanine.

The genetic analysis indicated this strain belongs to genus *Paenibacillus*. Its 16S rDNA sequence shares high similarity with that of *Paenibacillus apiarius* (99%), *P. alvei* (96%) and *Paenibacillus thiaminolyticus* (95%). Carbohydrates fermentation analysis (API 50 CH strips and API CHB medium) provided 96.2% similarity between this strain and *Paenibacillus thiaminolyticus*. Using another set of biochemical tests (API 20E), the isolate was positive for β-galactosidase, $H_2S$ production and urease, and negative for others reactions. The similarity of OSY-SE with *Paenibacillus thiaminolyticus* increased to 99.9% when the results of the two sets of biochemical tests were combined. Biochemically, however, the OSY-SE strain did not match closely any *Paenibacillus* species, including *Paenibacillus apiarius, Paenibacillus alvei*, in its characteristics. Nevertheless, in light of the entirety of the morphologic, genetic, and biochemical characterization, the new OSY-SE bacterial strain, was assigned as *Paenibacillus thiaminolyticus*.

Example 4

Isolation and Purification of Antimicrobial Agents

The isolate OSY-SE was streaked onto tryptose agar plates and incubated at 37° C. for 4 days. The colonies were scraped into a centrifuge tube, mixed with acetonitrile and agitated at 200 rpm for 30 minutes. The mixture was then centrifuged at 7710×g for 15 minutes. The supernatant, containing antimicrobial agents, was collected and evaporated in a chemical hood. The resulting powder was dissolved in 2 mL distilled water followed by filtration (0.22 µm, Millipore, Carrigtwohill, County Cork, Ireland). The solution was applied to high-performance liquid chromatography (HPLC) system (Hewlett Packard 1050, Agilent Technologies, Palo Alto, Calif.) for component identification, isolation, and purification. The purification was achieved using a reverse-phase column (Biobasic C18, 250×4.6 mm, 5 µm particle size, Thermo Electron Corp., Bellefonte, Pa.) using a linear gradient elution. The mobile phase consisted of (A) acetonitrile (ACN) with 0.1% trifluoroacetic acid (TFA), and (B) HPLC-grade water containing 0.1% TFA. Each run included loading a 40 µL aliquot of the extract to the column and separation by a linear gradient (0 to 70% ACN) over 20 min at a 1 mL/min flow rate. Elution was monitored using UV-detector set at 220 nm. Fractions of corresponding peaks from multiple runs were collected and pooled for antimicrobial activity assay. These fractions were stored at 4° C. until use.

Figure 2:
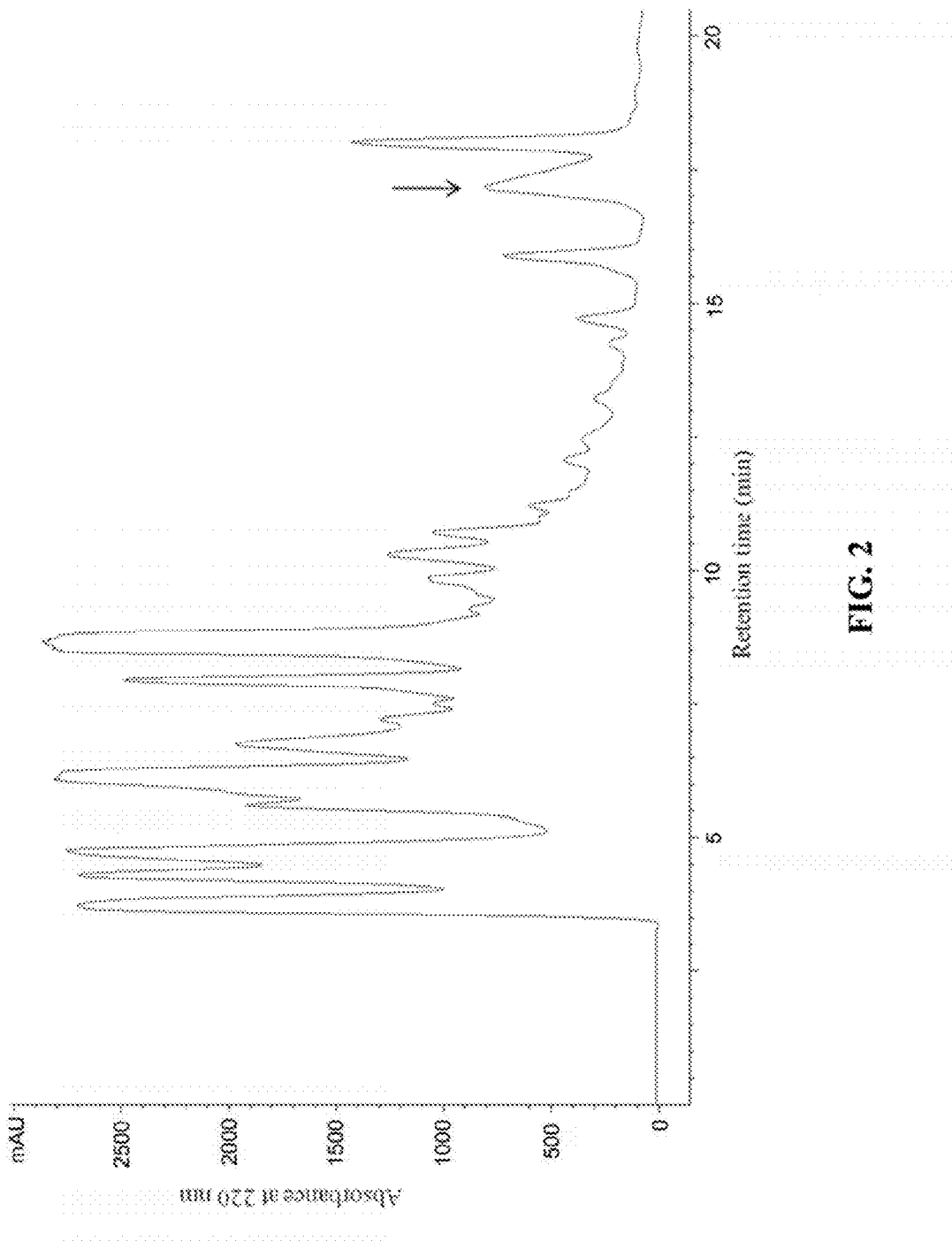
FIG. 2 depicts high performance liquid chromatography (HPLC) profile of the crude extract of *Paenibacillus thiaminolyticus* OSY-SE cells. Peak with retention time of 17.02 min (indicated by the arrow) showed antimicrobial activity against *Listeria innocua* and *Escherichia coli* as described herein.
Figure 3:
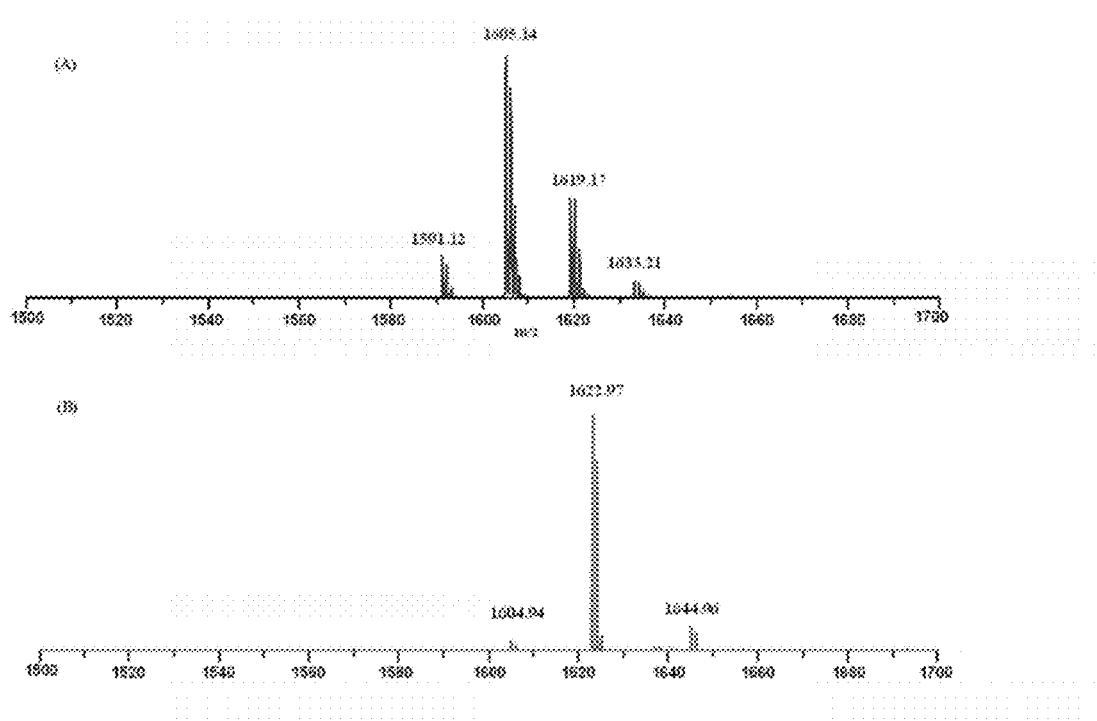
FIG. 3 depicts MALDI-TOF MS analysis of paenibacterin and its linear form produced by alkaline hydrolysis. (A) Spectrogram showing paenibacterin (m/z 1605.14) and its three homologues (m/z 1591.12, 1619.1 and 1633.21); (B) Linearized paenibacterin (m/z 1622.97); and the corresponding sodium adduct at m/z 1644.96.

An HPLC fraction corresponding to the peak with retention time of 17.02 min (FIG. 2) showed antagonistic activities against *L. innocua* ATCC 33090 and *Escherichia coli* K-12, and a single peak was displayed when re-injecting this fraction into HPLC. MALDI-TOF MS analysis indicated that the fraction contained a major compound with molecular weight of 1604, which was designated as paenibacterin, and three minor compounds with molecular weights of 1590, 1618 and 1632 (FIG. 3A). MS/MS were then performed to analyze these four compounds. Resultant fragmentation patterns were quite similar, which suggested that paenibacterin and the three minor components were homologues.

Example 5

Antimicrobial Activity Determination

Spot-on-lawn method [He, Z., et al., *Appl. Environ. Microbiol.*, (2007) 73:168-178] was used for the bioassay of antimicrobial activity. Bacterial indicators were incubated at 37° C. for 24 h, except *Pseudomonas putida, Clostridium difficile* and methycillin resistant *Staphylococcus aureus* which were incubated for 48 h (Table 1). The indicator overlay was prepared by pouring 10 ml soft agar (seeded with 10 µL indicator culture) onto tryptose agar as basal medium in a petri dish. Purified antimicrobials were two-fold serially diluted and aliquots (10 µL each) were spotted onto the soft agar. The plates were incubated overnight and inspected for the presence of growth inhibition zones. Antimicrobial activity was expressed in arbitrary units (AU)/mL; this value is the reciprocal of the highest dilution displaying a zone of inhibition corresponding to 1 mL of the non-diluted antimicrobial preparation.

Purified paenibacterin was used for the antimicrobial spectrum test. Microorganisms tested for sensitivity to this compound included pathogenic (e.g., *Salmonella Typhimurium, Escherichia coli* O157:H7, *Listeria monocytogenes*, and *Staphylococcus aureus*) and non-pathogenic (e.g., *Escherichia coli* K-12, *Pseudomonas putida*, and *Enterococcus faecalis*) bacteria (Table 1). Paenibacterin showed good activity against gram-negative pathogens such as *Escherichia coli* O157:H7 and gram-positive pathogens such as *L. monocytogenes*, but no activity was observed against *C. difficile* CL148 and *E. faecalis* ATCC 29212.

TABLE 1

Relative antimicrobial activity of paenibacterin against selected bacteria.

| Strain[a] | Broth medium[d] | Antimicrobial activity (AU/ml)[e] |
|---|---|---|
| Gram-negative bacteria | | |
| *Escherichia coli* K-12 | LB | 3200 |
| *E. coli* O157:H7 EDL 933 | LB | 1600 |
| *E. coli* O157:H7 ATCC 43889 | LB | 1600 |
| *Pseudomonas putida* ATCC 45491 | TSBYE | 400 |
| *Salmonella enterica* ser. Typhimurium | TSBYE | 400 |

TABLE 1-continued

Relative antimicrobial activity of paenibacterin against selected bacteria.

| Strain[a] | Broth medium[d] | Antimicrobial activity (AU/ml)[e] |
|---|---|---|
| S. enterica ser. Typhimurium DT 109 | TSBYE | 400 |
| S. enterica ser. Enteritidis | TSBYE | 800 |
| Yersinia enterocolitica | TSBYE | 1600 |
| Gram-positive bacteria | | |
| Bacillus cereus ATCC 14579 | TSBYE | 800 |
| B. cereus ATCC 11178 | TSBYE | 200 |
| Clostridium difficile A515[b] | BHIYE | 200 |
| C. difficile CL148[c] | BHIYE | 0 |
| Enterococcus faecalis ATCC 29212 | MRS | 0 |
| Listeria monocytogenes Scott A | TSBYE | 800 |
| L. monocytogenes OSY-8578 | TSBYE | 1600 |
| L. innocua ATCC 33090 | TSBYE | 1600 |
| Lactobacillus plantarum ATCC 8014 | MRS | 400 |
| L. lactis ATCC 11454 | MRS | 800 |
| Staphylococcus aureus ATCC 6538 | TSBYE | 100 |
| S. aureus (methycillin-resistant) | TSBYE | 100 |

[a]Strains obtained from the culture collection of the Ohio State University food safety laboratory.
[b]Strain obtained from Dr. J. T. Lejeune, College of Veterinary Medicine, The Ohio State University.
[c]Strain obtained from Dr. W. A. Gebreyes, Department of Veterinary Preventive Medicine, The Ohio State University.
[d]LB, Luria-Bertani medium; TSBYE, Tryptic soy broth supplemented with 0.6% yeast extract; MRS, Lactobacillus MRS broth; BHIYE, Brain heart infusion supplemented with 5% yeast extract (Rodriguez-Palaciosand Lejeune, Appl. Environ. Microbiol. (2011) 77: 3085-3091).
[e]Relative activity was measured in arbitrary units (AU)/mL

Example 6

Antimicrobial Activity in Response to Heat, pH and Enzymes

Crude extracts of *Paenibacillus thiaminolyticus* OSY-SE were tested for sensitivity to heat and pH change while purified antimicrobial compounds were used for enzyme sensitivity tests. For thermal stability test, crude extract solutions were exposed to 37° C., 55° C. (in incubators) or 80° C. (in a water bath) for 24 h or autoclaved at 121° C. for 5 minutes. For pH stability test, crude extract solutions were diluted with 25 mM phosphate buffer (pH 7.0) and adjusted to pH 3.0, 5.0 and 9.0, followed by incubation for 12 h. Samples were neutralized to pH 7.0 before the antimicrobial activity test. Enzyme sensitivity tests were performed in 25 mM phosphate buffer (pH 7.0) with trypsin (type I, 12705 U/mg), lipase (type I, 9 U/mg), pronase (6.31 U/mg), α-glucosidase (type I, 100U/1.93 mg), lysozyme (46400 U/mg) and in 25 mM phosphate buffer (pH 8.0) with polymyxin acylase (16 U/mg). All enzymes were purchased from Sigma (St. Louis, Mo.) except polymyxin acylase (Wako Chemicals USA, Inc., Richmond, Va.). Digesting solutions were prepared at concentration of 0.1 mg/mL for polymyxin acylase and 0.5 mg/mL for others. These mixtures of enzyme and antimicrobial compound (40 µL of final volume) were incubated at 37° C. for 10 h. Quantitative spot-on-lawn bioassay was used to measure antimicrobial activities after these treatments.

The crude extract of *Paenibacillus thiaminolyticus* OSY-SE was resistant to heat and pH changes. Most of its antimicrobial activity was retained after holding at 37° C., 55° C., and 80° C. for 24 h, autoclaving at 121° C. for 5 min and exposure to different pH at 3.0, 5.0 and 9.0. Paenibacterin was resistant to treatment of trypsin, lipase, α-glucosidase and lysozyme, but the activity was lost after digestion by pronase or polymyxin acylase. Polymyxin acylase is an enzyme which deacylates lipopeptide [Misumi, S., et al., *Biochem. Biophys. Res. Commun.* (1995) 217:632-639]. Inactivation by polymyxin acylase suggested that paenibacterin is a lipopeptide.

Example 7

Alkaline Hydrolysis

Mild alkaline hydrolysis was used to open any existing potential lactone linkage that might exist within this antimicrobial peptide [Yakimov, M. M., et al., *Appl. Environ. Microbiol.* (1995) 61:1706-1713]. The peptide was dissolved in 1 M NaOH and held at room temperature for 12 hours. After acidification, the solution was desalted using a peptide desalting trap (Michrom BioResources Inc., Auburn, Calif.) and the resulting (open ring) compound was analyzed by MALDI-TOF MS and MS/MS as described below.

MALDI-TOF MS Analysis. Matrix-assisted laser desorption ionization-time of flight mass spectrometry (MALDI-TOF MS) analysis was performed on a mass spectrometer (Bruker Reflex III time-of-flight, Bruker Daltonics Inc., Billerica, Mass.). Briefly, the sample of purified antimicrobial compound was mixed with the matrix, α-cyano-4-hydroxy cinnamic acid, prepared as a saturated solution in 50% acetonitrile with 0.1% TFA in water, at a ratio of 1:5 (sample: matrix). The mixture was then spotted (1 µL) on the target plate and allowed to air dry. The instrument was operated in reflection positive ion mode at an accelerating voltage of 28 kV. The $N_2$ laser was operated at the minimum threshold level required to generate signal and minimize dissociation.

Quadrupole-Time of Flight MS/MS. The MS/MS analysis was performed on a Micromass Q-T of II apparatus (Micromass, Wythenshawe, UK) equipped with an orthogonal electrospray source (Z-spray) and operated in positive ion mode. The instrument was calibrated with Angiotensin fragment prior to use. The sample was a diluted in a mixture of $H_2O$-ACN-HAc (50:50:2.5) and infused into the electrospray source at a flow rate of 2 µL/min. To achieve the optimal electrospray, capillary voltage was set at 3 kV, source temperature was 100° C., and cone voltage was 40 V. The first quadrupole, Q1, was set to pass ions between 200 and 2500 m/z. The target ion was isolated and fragmented within the second quadrupole. A voltage of 20 to 40 V was adjusted for the best quality of tandem MS spectra. The fragment ions were then analyzed in the time-of-flight tube (100-2000 m/z). Data were acquired in continuum mode until well-averaged data were obtained.

Initially, MS/MS analysis has failed to sequence the antimicrobial agent due to the lack of fragmentation information; leading to the speculation that the agent could be a cyclic compound. After the open-ring reaction, a peak with m/z at 1622.97 was observed (FIG. 3B). The mass difference was 18 Da, compared with intact peptide, suggesting the compound has a ring structure that can be opened by mild alkaline hydrolysis. Further MS/MS experiment was performed using the Q-tof. While more fragmentation information was obtained, no conclusive result could be achieved, including the amino acid composition. Therefore, we resorted to NMR to elucidate the structure of paenibacterin.

Example 8

Structural Analysis by NMR

The antimicrobial compound was subjected to 1D and 2D NMR analysis using a standard protocol [Wüthrich, K., *NMR* of *Proteins and Nucleic Acids.* (1986) Wiley Interscience, New York.] in order to determine the identity of constituent amino acid residues and the sequential arrangement. A first NMR sample was prepared by dissolving ~1 mg of the purified antimicrobial agent into 500 μL 90% H$_2$O/10% D$_2$O (referred to as H$_2$O hereafter). This sample was lyophilized and reconstituted into 500 μL 100% D$_2$O for a parallel NMR data set. A second NMR sample contained ~5 mg of the pure compound dissolved into 500 μL 99.8% CD$_3$OD (Cambridge Isotope Inc., Andover, Mass.).

Figure 4:
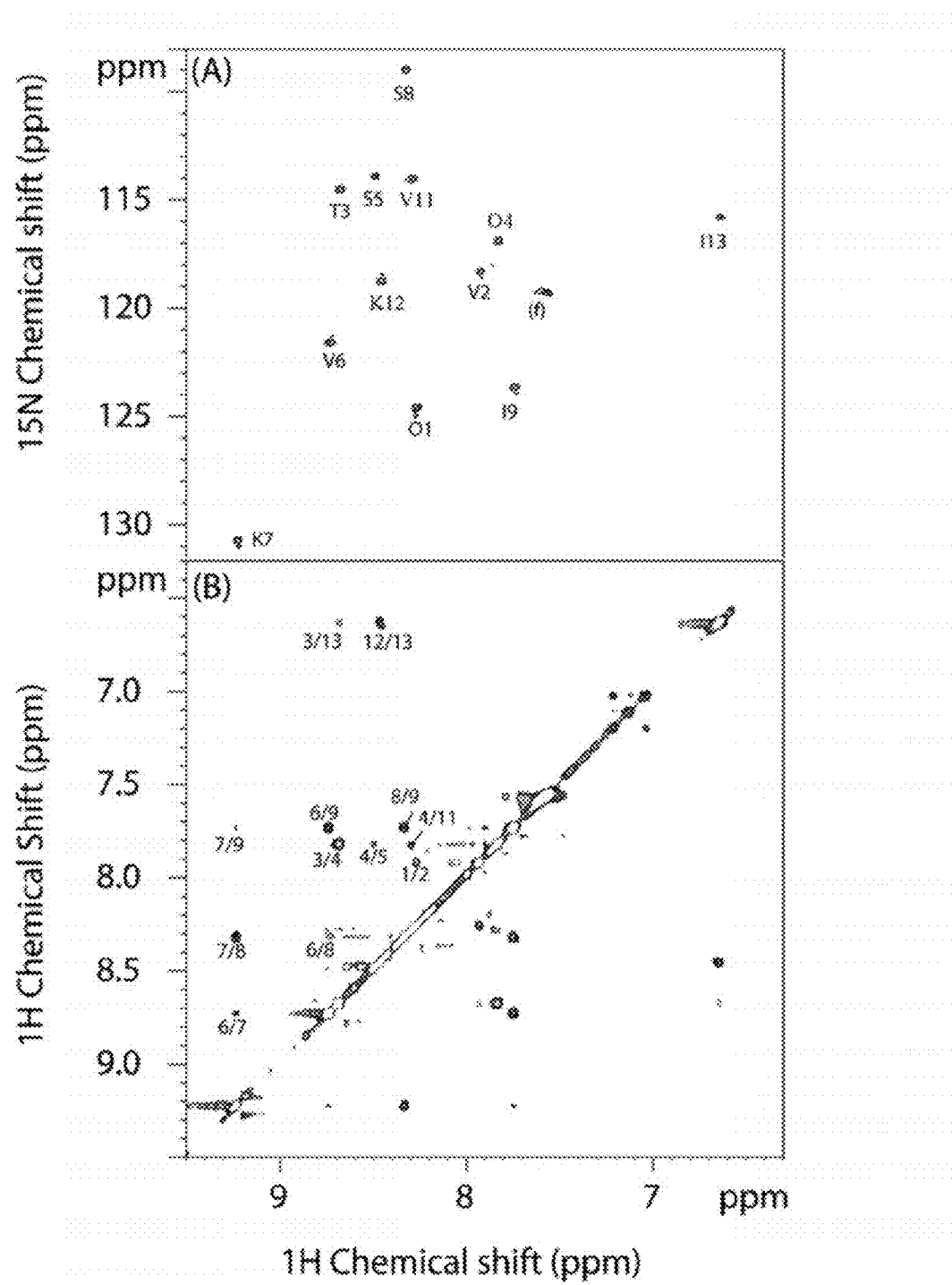
FIG. 4 depicts NMR analysis of the peptidyl fragment in the amide region. (A) 2D $^1$H-$^{15}$N HSQC recorded on the sample in $H_2O$ showing the 12 backbone NH amide cross-peaks and a cluster of folded peaks (labeled as "f") attributable to Arg, Lys or Orn sidechain $NH_3^+$ group; (B) 2D $^1$H NOESY recorded on the same sample showing the amide region cross-peaks with assignment.

Preliminary analysis of NH amide cross-peaks in 2D $^1$H-$^{15}$N HSQC (FIG. 4A) and C$^\alpha$ protons in 2D $^1$H-$^{13}$C HSQC (FIG. 5A) indicated the presence of 13 amino acids for the peptidyl fragment, including one proline residue evidenced by the observation of CH$_2^{\delta1/\delta2}$. The complete spin system of each amino acid was subsequently established from the COSY and TOCSY spectra. The results taken together with 2D $^1$H-$^{13}$C HSQC and HMBC analysis led to identification of 3 Val, 2 Ile, 2 Ser, 1 Thr, 1 Pro, 2 Lys, and 2 Orn—the unnatural amino acid that has been reported previously [Ball, L. J., et al., *Org. Biomol. Chem.* (2004) 2:1872-1878]. Their sequence was first deduced by analyzing sequential NOEs such as H$^N$(i)-H$^N$(i+1), H$^\alpha$(i)-H$^N$(i+1) and H$^\beta$(i)-H$^N$(i+1). In particular, the observation of strong NOEs between Pro10 H$^{\delta1,\delta2}$ and Val11 H$^\alpha$ led to their sequential assignment as well as the identification of the trans-conformation adopted by Pro10. However, the NOE-based sequential assignment could be equivocal particularly considering the cyclic nature of this peptide moiety as described later. For example, long-range NOEs such as the one between Thr3 H$^N$ and Ile13 H$^N$ could complicate the analysis without a prior knowledge (FIG. 4B). Therefore a 2D $^1$H-$^{13}$C HMBC of very high quality was necessitated for unambiguous sequence-specific assignments on the basis of $^1$H$^\alpha$(i)-$^{13}$C'(i+1) multiple-bond J-coupling correlations.

Figure 5:
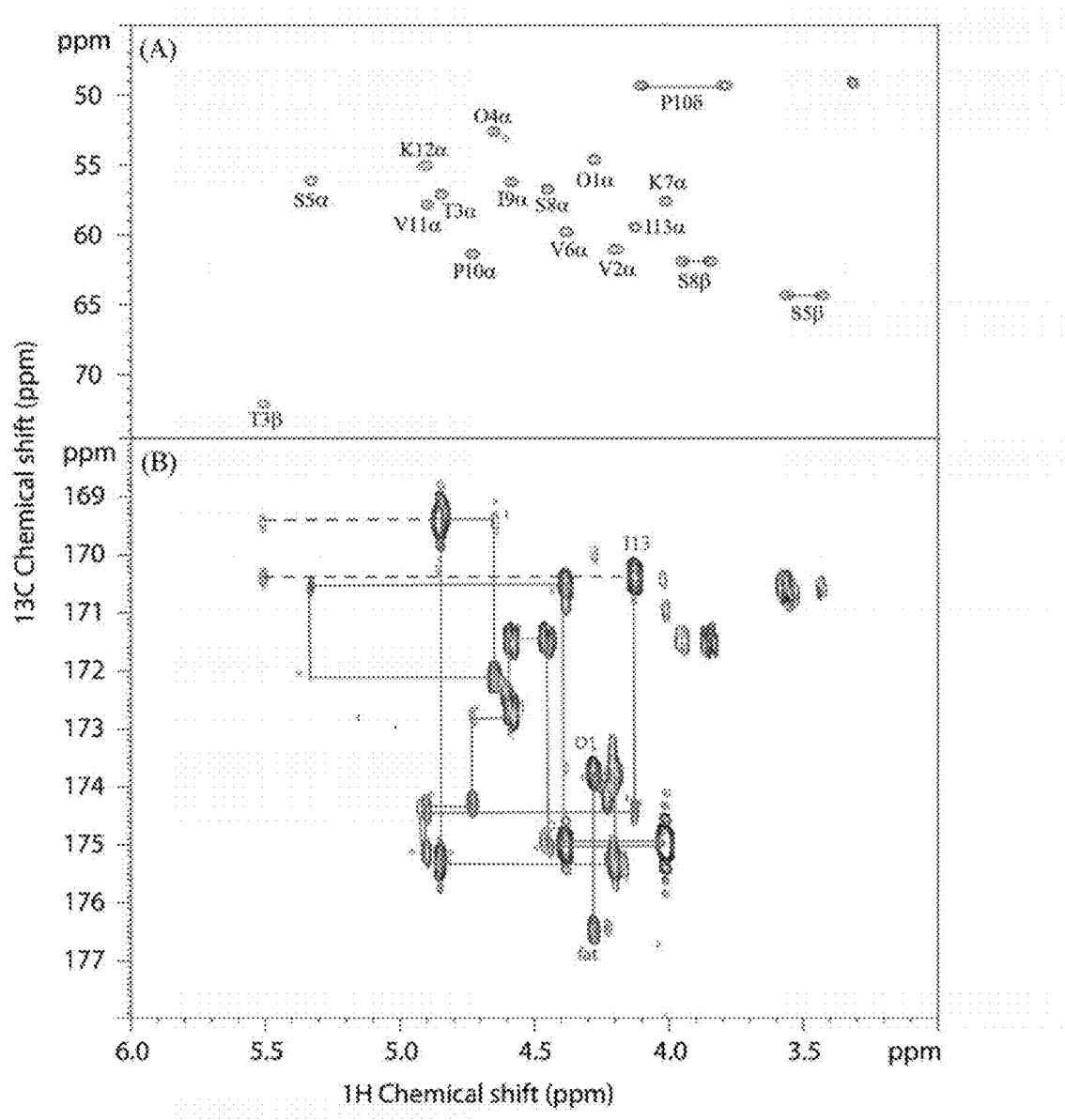
FIG. 5 depicts the elucidation of amino acid sequence and linkage of paenibacterin by HMBC. (A) 2D $^1$H-$^{13}$C HSQC recorded on the sample dissolved in $CD_3OD$ showing the $^{13}$C resonances in the region between 45 and 75 ppm. The CH$^\alpha$ assignments of the thirteen amino acids, together with Thr3 $CH_2^\beta$, Ser5 $CH_2^\beta$, Ser8 $CH_2^\beta$, and Pro10 $CH_2^\delta$ assignments are labeled to assist the analysis of cross-peaks in (B). The unlabeled cross-peak at 3.30/49.1 ppm ($^1$H/$^{13}$C) is attributed to the methyl group of the residual solvent methanol; (B) 2D $^1$H-$^{13}$C HMBC acquired on the same sample showing the connectives associated with H$^\alpha$ protons. Sequential assignment was made on the basis of intra-residue H$^\alpha$(i)-C'(i) and sequential C'(i−1)-H$^\alpha$(i) (marked by asterisk) multiple-bond J-coupling connectivities. The stretch starts from the fatty acid carbonyl carbon ("fat") to Orn1 H$^\alpha$, and ended with Lys12 C' to Ile13 H$^\alpha$. Also noted by the broken lines are the long range J-couplings of Thr3 H$^\beta$-Thr3 C' and Thr3 H$^\beta$-Ile13 C'. The latter is the strong evidence for a cyclic peptide with an ester bond formed between the Thr3 hydroxyl group and the Ile13 C-terminal carboxylic group. It is important to note that the tilted and spit heteronuclear multiple-bond correlation spectroscopy (HMBC) cross peaks are due to $^1$H-$^1$H coupling (J-modulation) [Furihata, K., and H. Seto, *Tetrahedron Lett.* (1998) 39:7337-7340].

A relatively large sample (~5 mg) of the purified antimicrobial agent was prepared for this insensitive 2D $^1$H-$^{13}$C HMBC analysis. However, severe line broadening was observed when the sample was dissolved in H$_2$O. CD$_3$OD was then used as the alternative NMR solvent, and the experiment was conducted on a Bruker DRX-800 spectrometer equipped with a cryoprobe. Some 2D experiments were also repeated to assist the NMR assignments. As shown in FIG. 5B, almost all of the intra-residue $^1$H$^\alpha$(i)-$^{13}$C'(i) as well as sequential $^{13}$C'(i-1)-$^1$H$^\alpha$(i) multiple-bond correlations have been observed, enabling the unequivocal determination of the peptide sequence as follows: Orn1-Val2-Thr3-Orn4-Ser5-Val6-Lys7-Ser8-Ile9-Pro10-Val11-Lys12-Ile13 (SEQ ID NO:64).

Figure 6:
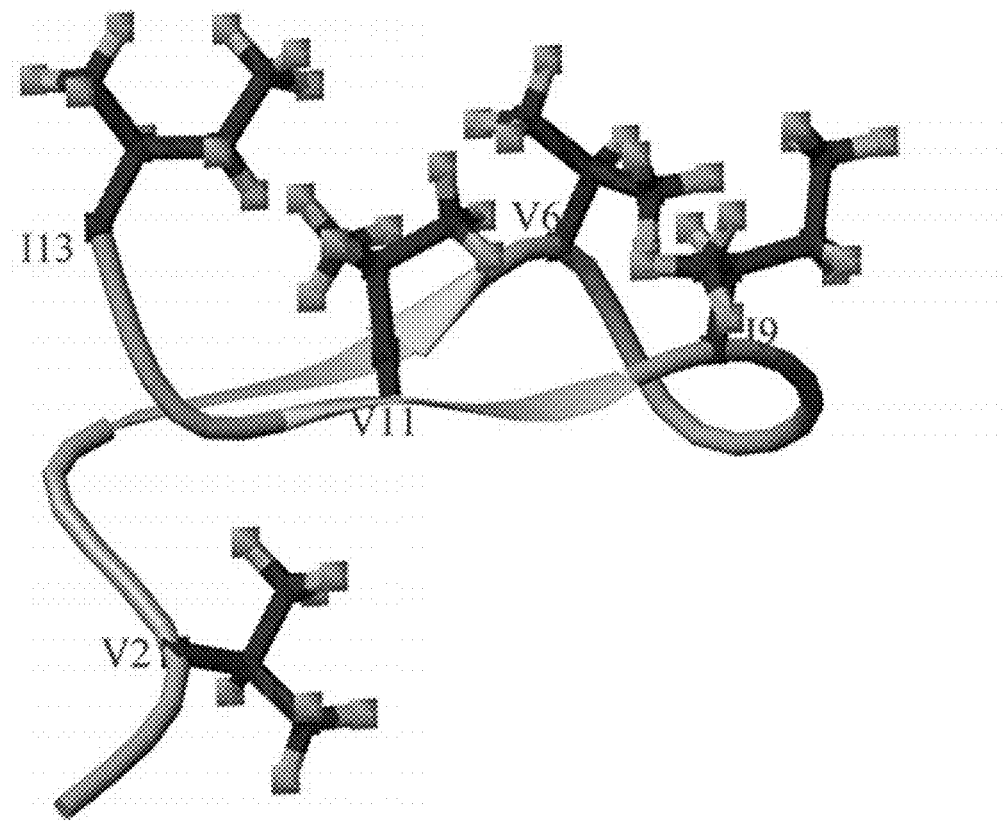
FIG. 6 depicts the tertiary structure of the peptide moiety of paenibacterin calculated from NMR constraints in aqueous solution. The five bulky aliphatic side chains (V2, V6, I9, V11 and I13) are highlighted.

Linkage elucidation. The above HMBC spectrum also revealed multiple-bond correlations of Thr3 H$^{\delta2}$ proton (5.49 ppm) with two carbonyl atoms: Thr3 C' at 170.8 ppm and Ile13 C' at 171.8 ppm (FIG. 5B). The latter suggests that Thr3 forms an ester linkage through its hydroxyl group to the C-terminal carboxylic group of Ile13. Consistently, both of Thr3 H$^\beta$ and C$^\beta$ chemical shifts experience unusual downfield shift similar to those "Threonine Shifts" reported in other lipopetides in which cyclization occurs involving a Thr side chain [Gerard, J., et al., *J. Nat. Prod.* (1997) 60:223-229; Kajimura, Y. & M. Kaneda, *J. Antibiot.* (1996) 49:129-135]. Furthermore, this cyclic nature was also supported by the long-range NOEs that have been observed, such as the one between Thr3 H$^\beta$ and Ile13 H$^{\delta1}$. Finally, it appears that the peptide moiety possesses some rigid conformation, most likely adopting a β-hairpin conformation. Assuming L-configuration for these residues, a tertiary structure of the peptidyl fragment was calculated using CNS software [Brunger, A. T., et al., *Acta. Crystallogr.* (1998) D 54:905-921] with a total of 162 NMR constraints, including 156 NOE-derived distance constraints (84 intra-residue, 40 sequential, and 32 non-sequential ones) and six χ1 constraints (V2, T3, V8, I9, V11 and K12) extracted from COSY and NOESY data sets, all from the NMR data recorded in aqueous solution. The residues of Orn4-Val6 and Ile-Lys12 form an anti-parallel β-sheet stabilized by hydrogen-bonds between Orn4 and Val11 as well as between Val6 and Ile9 (FIG. 6). It was also noticed that four of the five bulky aliphatic side chains (Val6, Ile9, Val11, and Ile13) group are on one side of the β-sheet and interact with each other. This structural feature may contribute to the amphiphatic nature of paenibacterin.

Figure 7:
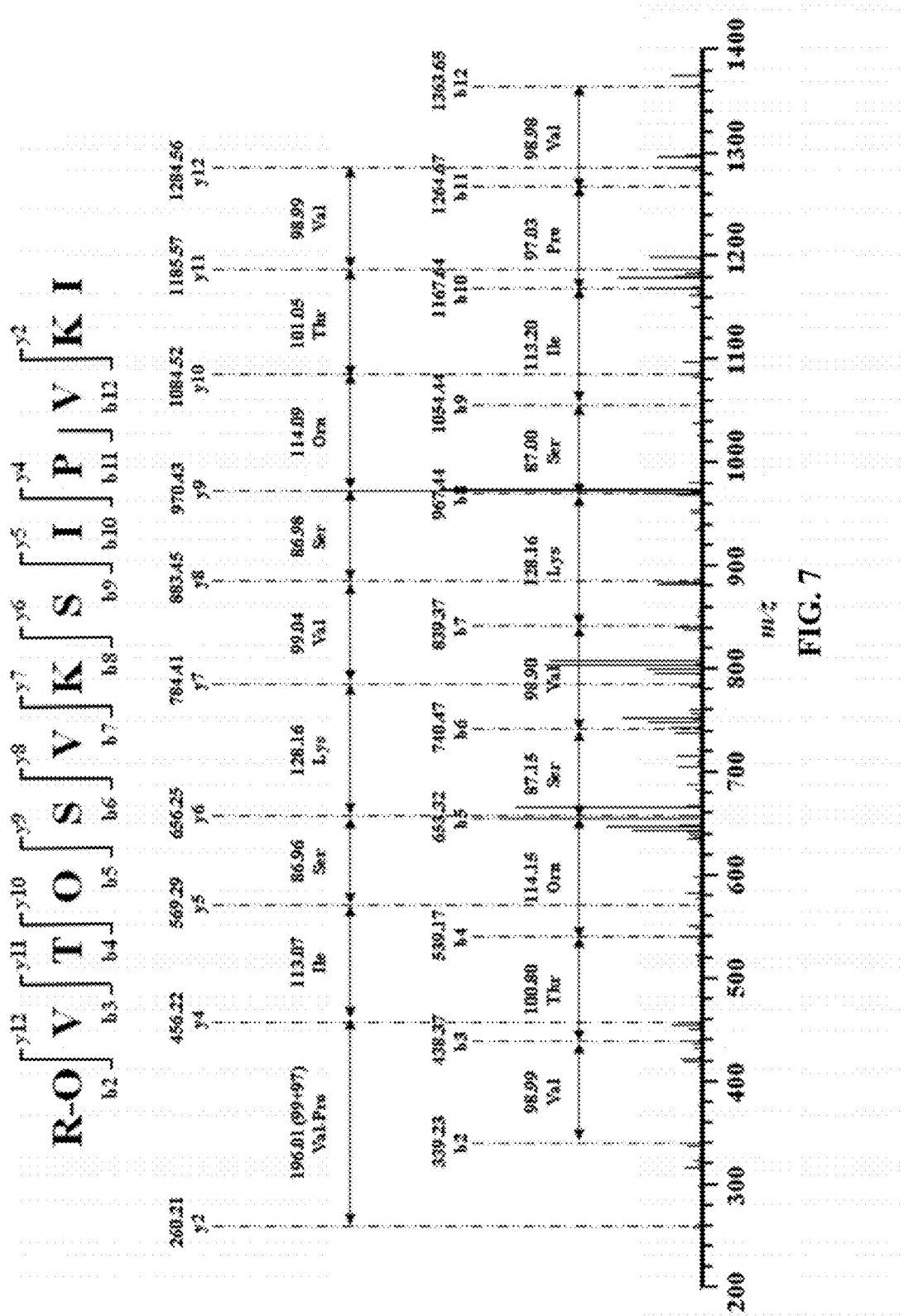
FIG. 7 depicts fragmentation of b and y ion series of linearized paenibacterin, examined by MS/MS.
Figure 8:
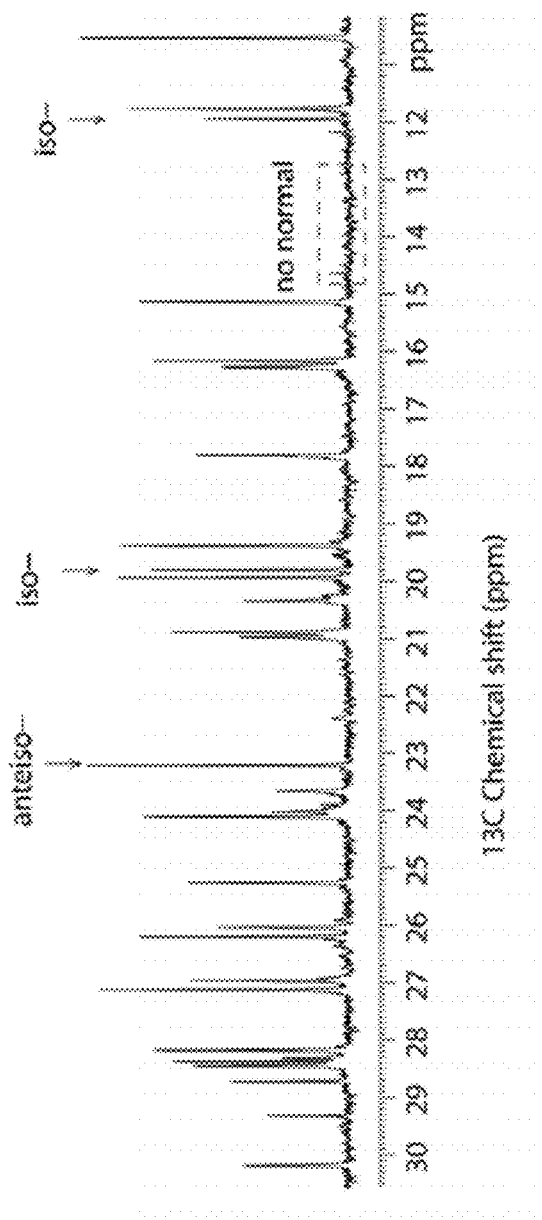
FIG. 8 depicts 1D $^{13}$C NMR spectrum revealing iso- and anteiso-fatty acyl chain.

Determination of the Acyl Moiety. Based on the peptide sequence derived from NMR, most of the fragmentation b and y ion series were observed in the MS/MS spectrum of linearized paenibacterin (FIG. 7). However, the discrepancy between the molecular weight of the thirteen amino acids and that of the whole compound indicated that paenibacterin contains other component, R (FIG. 7). MS was then performed on b2 ion at m/z 339, which confirmed that it comprises R and Orn. Therefore, the molecular weight of R was calculated as 225 either from the molecular weight difference between the thirteen amino acids taking into account of the ester linkage and intact paenibacterin or from b2 ion, and the formula of R was established as C$_{15}$H$_{29}$O. This suggested that paenibacterin is a lipopeptide containing a saturated C15 fatty acid and thirteen amino acids. The analysis of the 1D $^{13}$C NMR together with 2D $^1$H-$^{13}$C HSQC and HMBC suggested that the fatty acid is a mixture of anteiso- and iso-branched forms, as evidenced by the presence of $^{13}$C peaks at 11.9 and 23.2 ppm, respectively (FIG. 8) [Lin, S. C., et al., *Appl. Environ. Microbiol.* (1994) 60:31-38]. In 1D $^{13}$C NMR, the furthest downfield carbonyl carbon resonating at 180.1 ppm was assigned to the first atom of the fatty acid moiety. This C' atom shows HMBC correlations to the first CH$_2$ group at 2.30/38.2 ppm as well as the second CH$_2$ group at 1.59, 1.56/28.1 ppm. More importantly, it also has a HMBC correlation to Orn1 H$^\alpha$, indicating that the lipid chain is amidated to the N-terminal amine of Orn1. NOE was also observed between Orn1 H$^N$ and the first methylene protons (2.30 ppm) of the fatty acid side chain. A thorough analysis of the NMR data sets, particularly 2D $^1$H-$^{13}$C HSQC-TOCSY, HSQC-NOESY, HMBC, and multiplicity-edited HSQC, led to the complete assignments of fatty acid side chains.

GC/MS Analysis for Confirmation of Acyl Moiety. A mixture of the antimicrobial agent and polymyxin acylase in phosphate buffer (pH 8.0) was incubated at 37° C. for 24 h, followed by acidification to pH 3.0 and extraction with chloroform [Kline, T., et al., *J. Pept. Res.*, (2001) 57:175-187]. The chloroform phase, which contained any released fatty acids, was washed sequentially by saturated sodium chloride solution and distilled water, and the chloroform in the extract was evaporated by a stream of nitrogen gas. Resultant fatty acid was dissolved in a methylating reagent (Methylute, Thermo Scientific, Bellefonte, Pa.) and was applied to a capillary column (DB-23: 30 m×0.25 mm i.d.×0.25 μm film thickness; Agilent Technologies, Palo Alto, Calif.) on a gas chromatograph (TRACE2000 GC, Thermo-Finnigan, West Palm Beach, Fla.) coupled to a mass-spectrometer (TRACE MS, Thermo, West Palm Beach, Fla.). Pentadecanoic acid (Acros Organics, New Jersey) was dissolved in the methylating reagent and analyzed as a reference compound.

LC/MS/MS Analysis. The antimicrobial compound was digested by trypsin (Sequencing-grade, Promega, Madison, Wis.) in 100 mM NH$_4$HCO$_3$ buffer (pH 8.0) at 37° C. overnight before the reaction was quenched by adding 0.1% TFA.

The digests were analyzed by LC/MS/MS for amino acid sequence determination. Capillary-liquid chromatography-nanospray tandem mass spectrometry was performed on a mass spectrometer (LTQ orbitrap, Thermo-Finnigan) equipped with a nanospray source operated in positive ion mode (Michrom Bioresources Inc, Auburn, Calif.). Samples were separated on a capillary column (0.2×150 mm Magic $C_{18}AQ$, 3μ, 200 Å, Michrom Bioresources Inc, Auburn, Calif.) using an HPLC system (UltiMate™ 3000, LC-Packings, a Dionex Co., Sunnyvale, Calif.). Each sample was injected into the trapping column (LC-Packings), and desalted with 50 mM acetic acid for 10 minutes. The injector port was then switched to inject and the peptides were eluted off the trap onto the column Mobile phase A was 0.1% formic acid in water and mobile phase B was 0.1% formic acid in acetonitrile. Flow rate was set at 2 μL/min. Typically, mobile phase B was increased from 2% to 50% in 30 min before increased again from 50% to 90% in 5 min and then kept at 90% for another 5 min before being decreased quickly to 2% in 1 min. The column was equilibrated at 2% of mobile phase B (98% mobile phase A) for 30 min before the next sample injection. The MS/MS was acquired with a nanospray source operated with a spray voltage of 2 kV and a capillary temperature of 175° C. The scan sequence of the mass spectrometer was based on the data dependant TopTen™ method. Briefly, the analysis was programmed for a full scan recorded between 300 and 2000 Da and a MS/MS scan to generate product ion spectra to determine amino acid sequence in consecutive scans of the ten most abundant peaks in the spectrum. The resolution of full scan was set at $3 \times 10^4$ to achieve high mass accuracy MS determination. The collision induced dissociation (CID) fragmentation energy was set at 35%.

Figure 9:
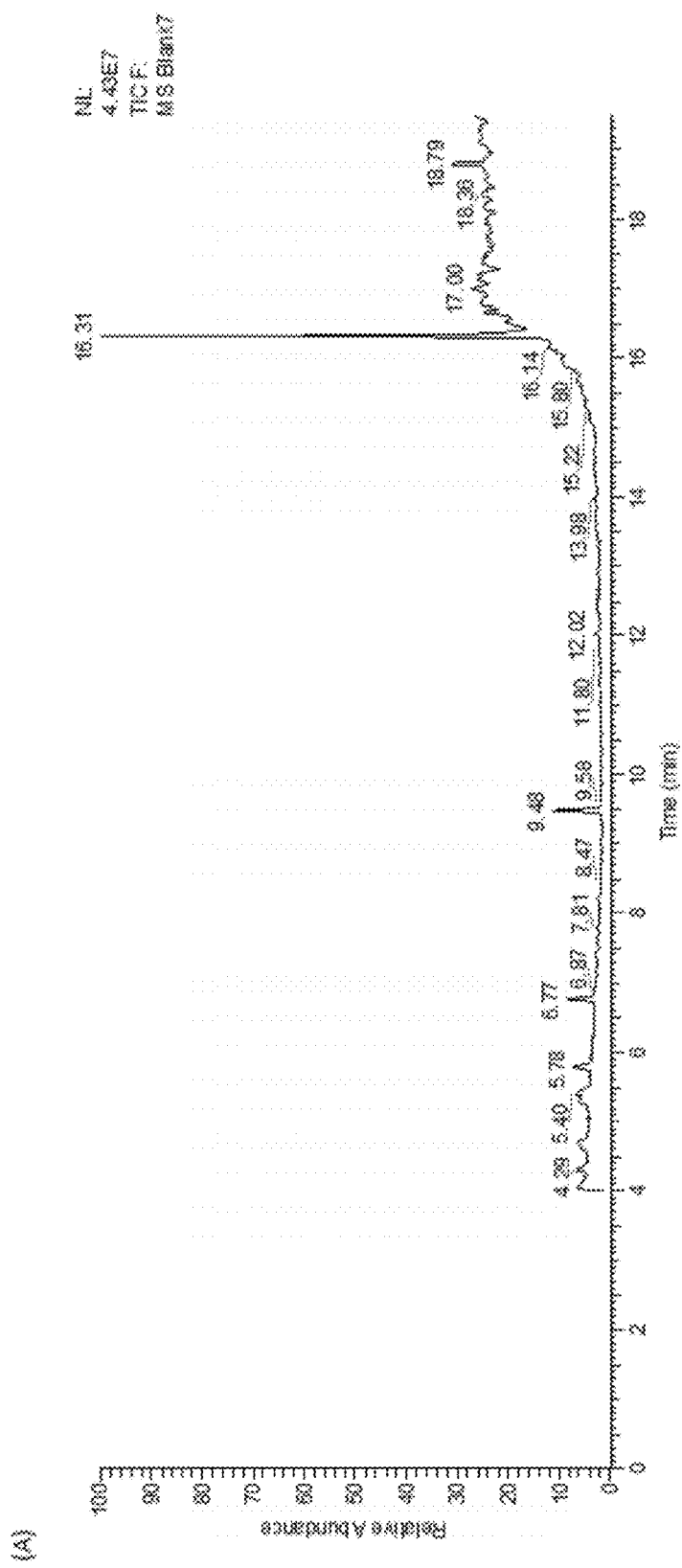
FIG. 9 depicts gas chromatography (GC) profile of fatty acid methyl esters. (A) GC profile of solvent used for derivatization, (B) GC profile of fatty acid methyl esters, (C) mass spectrometry (MS) spectrum.

GC/MS and LC/MS/MS were performed to verify the acyl moiety and the peptide sequence of paenibacterin, respectively. The fatty acids were successfully released from paenibacterin by polymyxin acylase digestion and analyzed by GC/MS as methyl esters. Three peaks at retention time of 4.87, 5.06 and 5.42 min were identified as methyl esters of iso-, anteiso- and normal chain C15 fatty acid, respectively, by comparing pentadecanoic acid chromatogram and referring their mass spectra to Wiley database (FIG. 9). Although the normal chain fatty acid was not evident in the NMR analysis, it was detected by GC/MS in low abundance. The dominated fatty acid in the sample was anteiso-chain form, but iso- and normal branched forms were also detected. Therefore, the C15 fatty acyl chain of paenibacterin could be normal, iso- or anteiso-forms.

Figure 10:
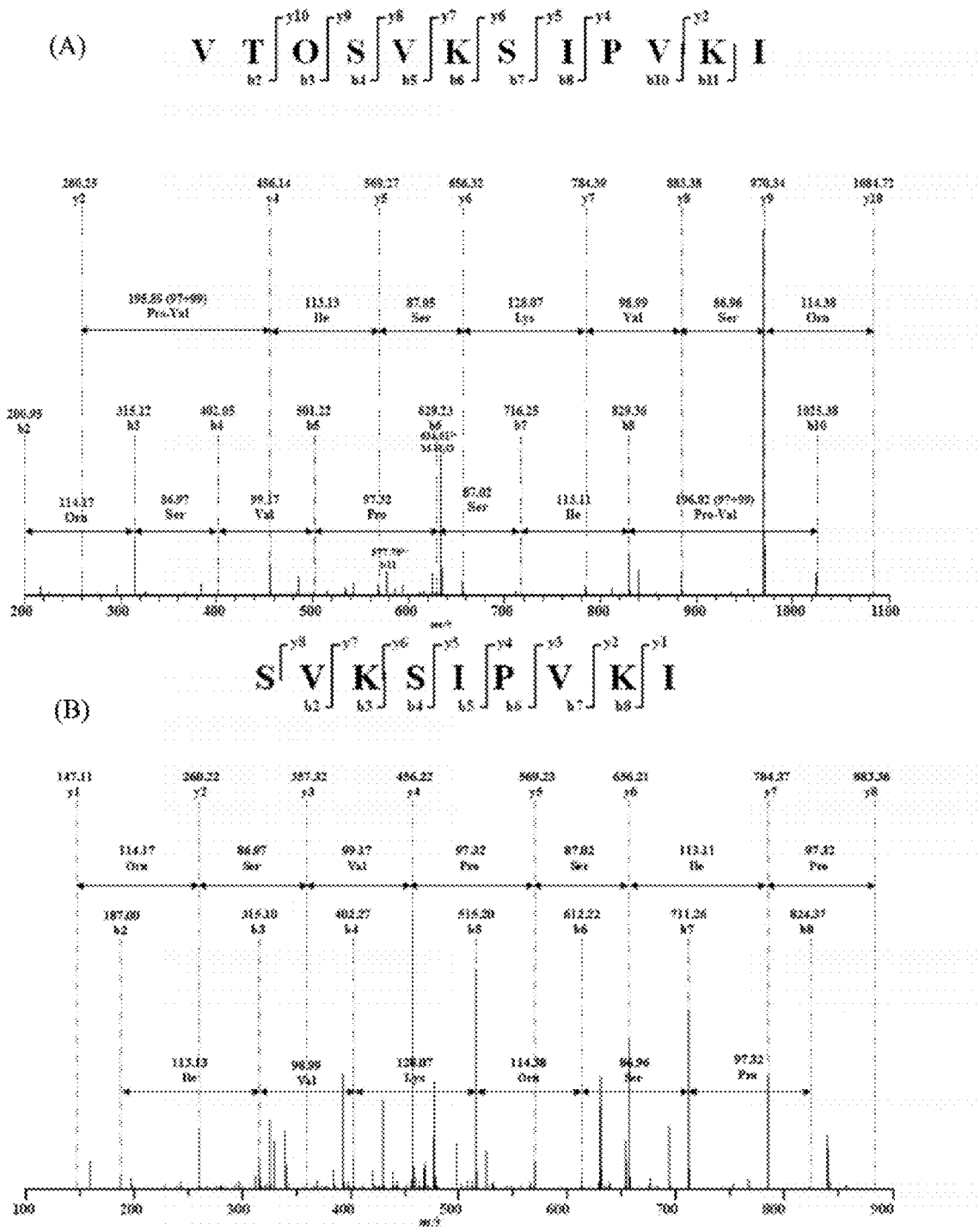
FIG. 10 depicts MS/MS spectra of tryptic-digested products of paenibacterin. (A) VTOSVKSIPVKI (SEQ ID NO:15), (B) SVKSIPVKI (SEQ ID NO:16) (C) and SIPVKI (SEQ ID NO:17).

The peptide sequence was confirmed by analyzing tryptic-digested paenibacterin using LC/MS/MS. Penibacterin was found to be resistant to trypsin based on antimicrobial activity test in phosphate buffer (pH 7.0). However, digested products were detected, including VTOSVKSIPVKI (SEQ ID NO:15), SVKSIPVKI (SEQ ID NO:16) and SIPVKI (SEQ ID NO:17) (FIG. 10). It was noticed that the linkage between Thr and C-terminal Ile was probably broken during incubation in the $NH_4HCO_3$ buffer (pH 8.0) using during enzyme digestion, evidenced by the presence of linearized paenibacterin in the same buffer without trypsin.

Figure 11:
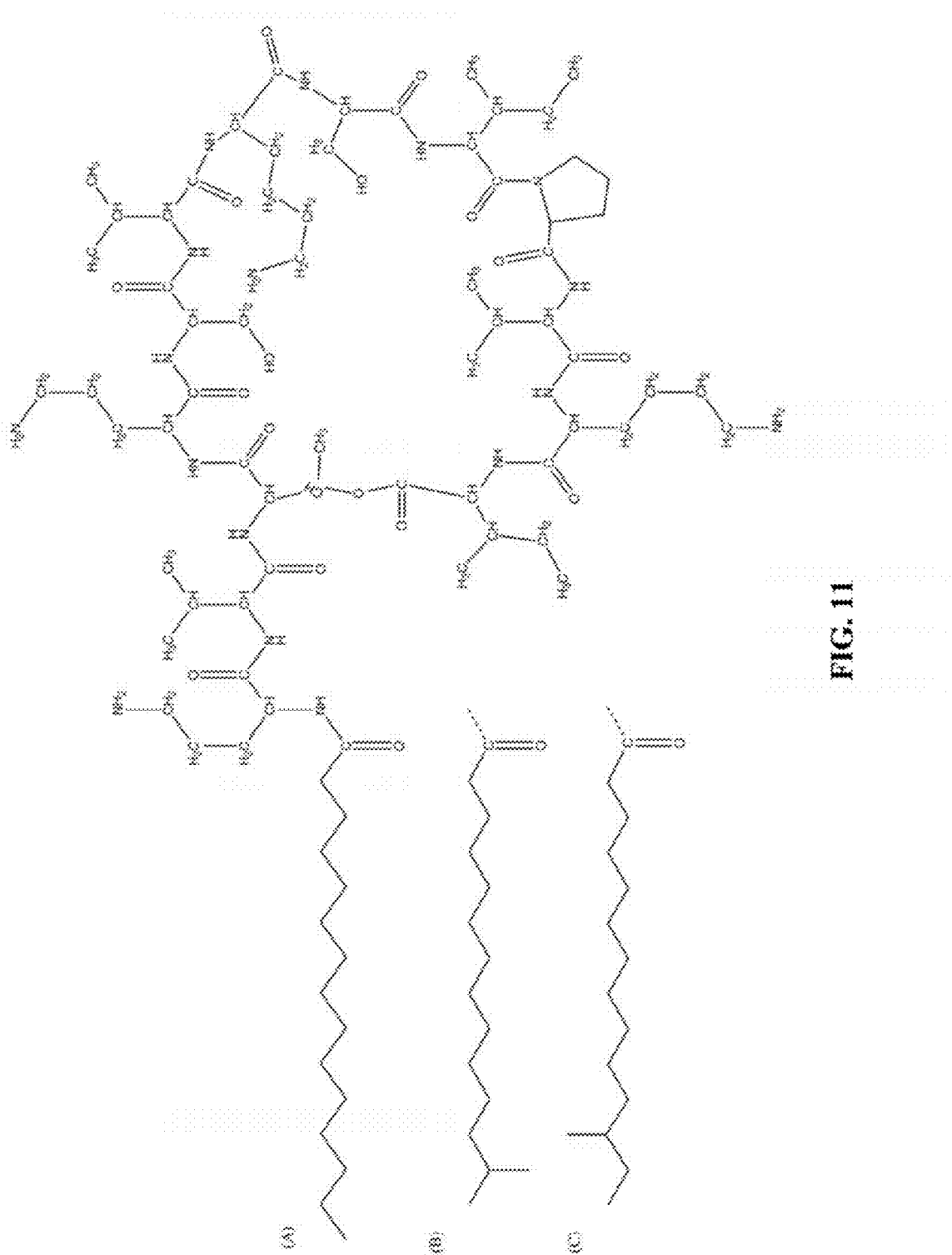
FIG. 11 depicts the molecular structure of paenibacterin; A, normal chain; B, iso-branched chain; C, anteiso-branched chain.

In conclusion, paenibacterin was identified as a lipopeptide consisting of a C15 fatty acyl chain (normal, iso or anteiso forms) and thirteen amino acids (FIG. 11). The chemical shift assignments of the peptidyl fragment and the fatty acyl chain in aqueous solution are summarized in Table 2 and Table 3, respectively, while the corresponding ones in methanol-$d_4$ are provided in Table 4 and Table 5, respectively.

TABLE 2

Chemical shift assignments of peptidyl fragment of paenibacterin (pH 4.5, 298.0K).

| Residue | $^1H^N/^{15}N$ | $^1H^\alpha/^{13}C^\alpha$ (ppm) | $^1H^\beta/^{13}C^\beta$ (ppm) | Others $^1H/^{13}C$ ($^{15}N$) and C' (ppm) |
|---|---|---|---|---|
| Orn1 | 8.26/124.6 | 4.24/56.5 | 1.80, 1.75/30.7 | $CH_2^\gamma$ 1.74, 1.67/26.1; $CH_2^\delta$ 3.00/41.6; C' 177.0 |
| Val2 | 7.92/118.3 | 4.09/62.8 | 2.07/32.8 | $CH_3^{\gamma1, \gamma2}$ 1.19/22.1, 0.95/21.7; C' 178.1 |
| Thr3 | 8.67/114.5 | 4.93/58.9 | 5.50/74.4 | $CH_3^{\gamma2}$ 1.14/17.6; C' 172.0 |
| Orn4 | 7.82/116.9 | 4.62/54.5 | 2.03, 1.76/32.7 | $CH_2^\gamma$ 1.58, 1.53/24.6; $CH_2^\delta$ 2.96/41.6; C' 173.9 |
| Ser5 | 8.49/113.9 | 5.31/57.4 | 3.57, 3.41/65.8 | C' 172.9 |
| Val6 | 8.73/121.6 | 4.27/61.9 | 1.88/34.9 | $CH_3^{\gamma1, \gamma2}$ 0.93/21.6, 0.90/20.7; C' 176.9 |
| Lys7 | 9.22/130.7 | 4.07/58.9 | 1.86/32.1 | $CH_2^\gamma$ 1.52, 1.49/25.0; $CH_2^\delta$ 1.70/29.0; $CH_2^\epsilon$ 2.99/41.7; C' 178.0 |
| Ser8 | 8.32/109.0 | 4.43/58.5 | 3.90, 3.86/63.1 | C' 173.7 |
| Ile9 | 7.74/123.6 | 4.68/57.5 | 2.10/39.5 | $CH_3^{\gamma2}$ 0.98/16.6; $CH_2^{\gamma1}$ 1.48, 1.23/28.9; $CH_3^{\delta1}$ 0.83/11.7; C' 173.8 |
| Pro10 |  | 4.70/63.0 | 2.36, 1.96/32.8 | $CH_2^\gamma$ 2.16, 1.97/27.5; $CH_2^\delta$ 3.95, 3.77/51.4 |
| Val11 | 8.28/114.0 | 4.86/59.6 | 2.33/36.0 | $CH_3^{\gamma1, \gamma2}$ 1.01/22.0, 0.73/19.2; C' 176.8 |
| Lys12 | 8.45/118.8 | 4.59/56.8 | 2.05, 1.76/31.7 | $CH_2^\gamma$ 1.45, 1.42/24.9; $CH_2^\delta$ 1.67/29.1; $CH_2^\epsilon$ 2.99/41.7; C' 177.3 |
| Ile13 | 6.65/115.8 | 4.14/61.3 | 1.81/38.0 | $CH_3^{\gamma2}$ 0.79/17.4; $CH_2^{\gamma1}$ 1.26, 1.09/27.5; $CH_3^{\delta1}$ 0.80/13.3; C' 174.0 |

TABLE 3

Chemical shift assignments of fatty acyl chain of paenibacterin (pH 4.5, 298.0K).

| Position | Iso- | $^1H/^{13}C$ (ppm) | Anteiso- | $^1H/^{13}C$ (ppm) |
|---|---|---|---|---|
| 1 | C' | 180.1 | C' | 180.1 |
| 2 | $CH_2$ | 2.30/38.2 | $CH_2$ | 2.30/38.2 |
| 3 | $CH_2$ | 1.59, 1.56/28.1 | $CH_2$ | 1.59, 1.56/28.1 |
| 4 | $CH_2$ | 1.26/31.5 | $CH_2$ | 1.26/31.5 |
| 5 | $CH_2$ | ~1.25/31.5 | $CH_2$ | ~1.25/31.5 |
| 6 | $CH_2$ | ~1.25/31.5 | $CH_2$ | ~1.25/31.5 |
| 7 | $CH_2$ | ~1.25/31.5 | $CH_2$ | ~1.25/31.5 |
| 8 | $CH_2$ | ~1.25/31.5 | $CH_2$ | ~1.25/31.5 |
| 9 | $CH_2$ | ~1.25/31.5 | $CH_2$ | ~1.25/31.5 |
| 10 | $CH_2$ | 1.26/29.2 | $CH_2$ | ~1.25/31.5 |
| 11 | $CH_2$ | 1.27, 1.08/38.6 | $CH_2$ | 1.26/29.2 |
| 12 | $CH_2$ | 1.29/36.5 | CH | 1.14/41.2 |
| 13 | CH | 1.30, 1.10/31.7 | $CH_2$ | 1.521/29.04 |
| 14 | $CH_3$ | 0.81/13.4 | $CH_3$ | 0.82/24.8 |
| 15 | $CH_3$ | 0.81/21.5 | $CH_3$ | 0.82/24.8 |

TABLE 4

Chemical shift assignments of peptideyl fragment of paenibacterin in methanol-$d_4$, 298.0 K.

| Residue | $^1H^\alpha/^{13}C^\alpha$ (ppm) | $^1H^\beta/^{13}C^\beta$ (ppm) | Others $^1H/^{13}C$ ($^{15}N$) and C' (ppm) |
|---|---|---|---|
| Orn1 | 4.267/54.61 | 1.768, 1.728/29.91 | $CH_2^\gamma$ 1.722/24.99; $CH_2^\delta$ 2.943/39.99; C' 173.77 |
| Val2 | 4.190/61.03 | 2.084/31.42 | $CH_3^{\gamma1,\gamma2}$ 1.198/20.65, 0.954/19.94; C' 175.25 |
| Thr3 | 4.836/57.12 | 5.492/72.10 | $CH_3^{\gamma2}$ 1.137/16.02; C' 169.43 |
| Orn4 | 4.636/52.62 | 2.050, 1.743/31.61 | $CH_2^\gamma$ 1.583, 1.554/23.37; $CH_2^\delta$ 2.915/40.12; C' 172.10 |
| Ser5 | 5.315/56.13 | 3.549, 3.419/64.32 | C' 170.52 |
| Val6 | 4.370/59.75 | 1.927/33.44 | $CH_3^{\gamma1,\gamma2}$ 0.969/19.64, 0.946/19.09; C' 174.99 |
| Lys7 | 4.001/57.59 | 1.842/30.90 | $CH_2^\gamma$ 1.582, 1.535/23.80; $CH_2^\delta$ 1.708/27.86; $CH_2^\epsilon$ 2.938/40.21; C' 174.95 |
| Ser8 | 4.440/56.75 | 3.938, 3.839/61.88 | C' 171.44 |
| Ile9 | 4.572/56.22 | 2.295/37.49 | $CH_3^{\gamma2}$ 1.001/14.87; $CH_2^{\gamma1}$ 1.627, 1.245/25.77; $CH_3^{\delta1}$ 0.877/10.24; C' 172.67 |
| Pro10 | 4.717/61.36 | 2.281, 1.948/31.43 | $CH_2^\gamma$ 2.197, 1.974/25.93; $CH_2^\delta$ 4.092, 3.784/49.33; C' 174.27 |
| Val11 | 4.887/57.85 | 2.232/34.81 | $CH_3^{\gamma1,\gamma2}$ 1.055/20.62, 0.725/17.55; C' 175.13 |
| Lys12 | 4.896/55.05 | 2.110, 1.703/30.58 | $CH_2^\gamma$ 1.514/23.70; $CH_2^\delta$ 1.723/28.02; $CH_2^\epsilon$ 2.975/40.40; C' 174.40 |
| Ile13 | 4.114/59.42 | 1.732/37.18 | $CH_3^{\gamma2}$ 0.835/15.88; $CH_2^{\gamma1}$ 1.396, 1.158/26.68; $CH_3^{\delta1}$ 0.869/11.40; C' 170.37 |

TABLE 5

Chemical shift assignments of fatty acyl chain of paenibacterin in methanol-$d_4$, 298.0K.

| Position | Iso- | $^1H/^{13}C$ (ppm) | Anteiso- | $^1H/^{13}C$ (ppm) |
|---|---|---|---|---|
| 1 | C' | 176.43 | C' | 176.43 |
| 2 | $CH_2$ | 2.256/36.73 | $CH_2$ | 2.256/36.73 |
| 3 | $CH_2$ | 1.598/26.84 | $CH_2$ | 1.598/26.84 |
| 4 | $CH_2$ | 1.321/30.39 | $CH_2$ | 1.321/30.39 |
| 5 | $CH_2$ | ~1.294/30.74 | $CH_2$ | ~1.294/30.74 |
| 6 | $CH_2$ | ~1.294/30.74 | $CH_2$ | ~1.294/30.74 |
| 7 | $CH_2$ | ~1.294/30.74 | $CH_2$ | ~1.294/30.74 |
| 8 | $CH_2$ | ~1.294/30.74 | $CH_2$ | ~1.294/30.74 |
| 9 | $CH_2$ | ~1.294/30.74 | $CH_2$ | ~1.294/30.74 |
| 10 | $CH_2$ | 1.266/28.07 | $CH_2$ | ~1.294/30.74 |
| 11 | $CH_2$ | 1.312, 1.101/37.70 | $CH_2$ | 1.287/28.34 |
| 12 | $CH_2$ | 1.305/35.57 | CH | 1.174/40.10 |
| 13 | CH | 1.343, 1.142/30.47 | $CH_2$ | 1.521/29.04 |
| 14 | $CH_3$ | 0.880/11.57 | $CH_3$ | 0.875/22.92 |
| 15 | $CH_3$ | 0.861/19.48 | $CH_3$ | 0.875/22.92 |

Example 9

Determination of the Configuration of Amino Acid in Paenibacterin

HPLC

The absolute configuration of constituent amino acids in paenibacterin was determined using the Marfey's reagents [Marfey, P., *Carlsberg Res Commun*, (1984) 49: 591-596] with some modifications. Briefly, HPLC-purified paenibacterin (1 mg) was dissolved in 0.5 ml HCl (6 M) in a sealed glass tube and incubated overnight at 110° C. to hydrolyze the paenibacterin peptide. The resulting free amino acids from acid hydrolysis was blow-dried with nitrogen gas, followed by addition of 200 µl of 1% Marfey's reagents, namely 1-Fluoro-2,4-dinitrophenyl-5-L-alanine amide (FDAA, Sigma, St. Louis, Mo.), and 40 µl of 1.0 M sodium bicarbonate. The contents were mixed and incubated at 40° C. in a water bath for 1 hour to form diastereomers of amino acids. After cooling to room temperature, 20 µl of 2 M HCl was added to the reaction mixture.

The L- and D-diastereomers from FDAA derivatization were separated by HPLC system equipped with a reverse phase column (Biobasic $C_{18}$, 250×4.6 mm, 5 µm particle size; Thermo Electron Corp., Bellefonte, Pa.). The mobile phases consisted of acetonitrile (A) and 50 mM triethylamine phosphate at pH 3.0 (B). Separation was achieved by a linear gradient of acetonitrile from 10% to 45% over 45 min at a flow rate of 1 ml/min. Elution was monitored using an UV monitor at a wavelength of 340 nm. Meanwhile, amino acids (Sigma or Acros Organics, New Jersey, USA) with known configurations were used as standards for derivatization and HPLC separation. The absolute configurations of amino acids from paenibacterin were determined by matching the retention time with the diastereomers from standard amino acids.

Amino Acid Configuration Analysis

Figure 12:
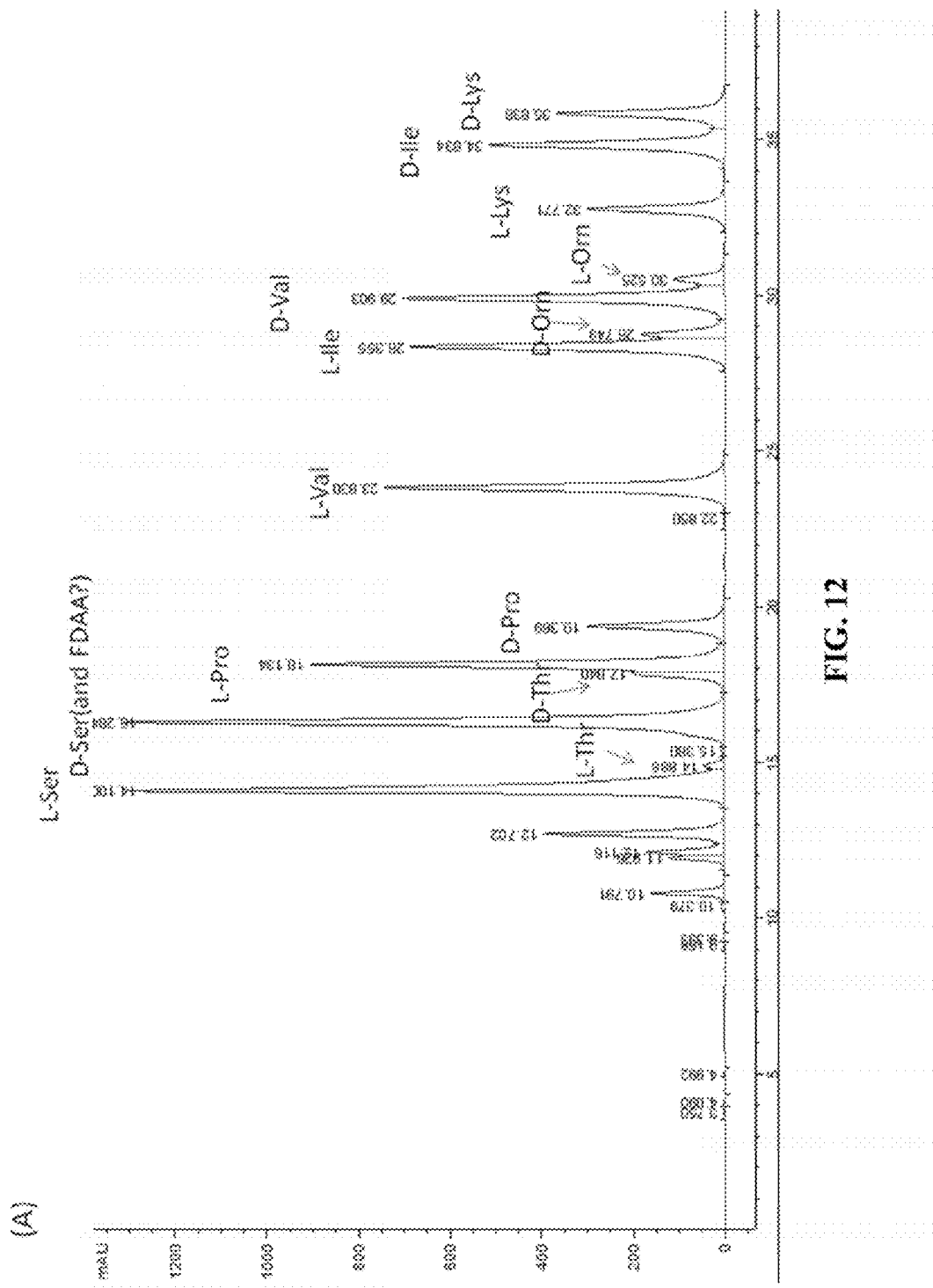
FIG. 12 depicts chiral analysis of constituent amino acids from paenibacterin. (A) High performance liquid chromatography (HPLC) profile of diastereomers of standard amino acids resulting from derivatization using Marfey's reagent; the D-Ser diastereomer peak overlapped with the Marfey's reagent, 1-Fluoro-2,4-dinitrophenyl -5-L-alanine amide (FDAA). (B) HPLC profile of diastereomers of paenibacterin amino acids from acid hydrolysis after derivatization using Marfey's reagent.
Figure 13:
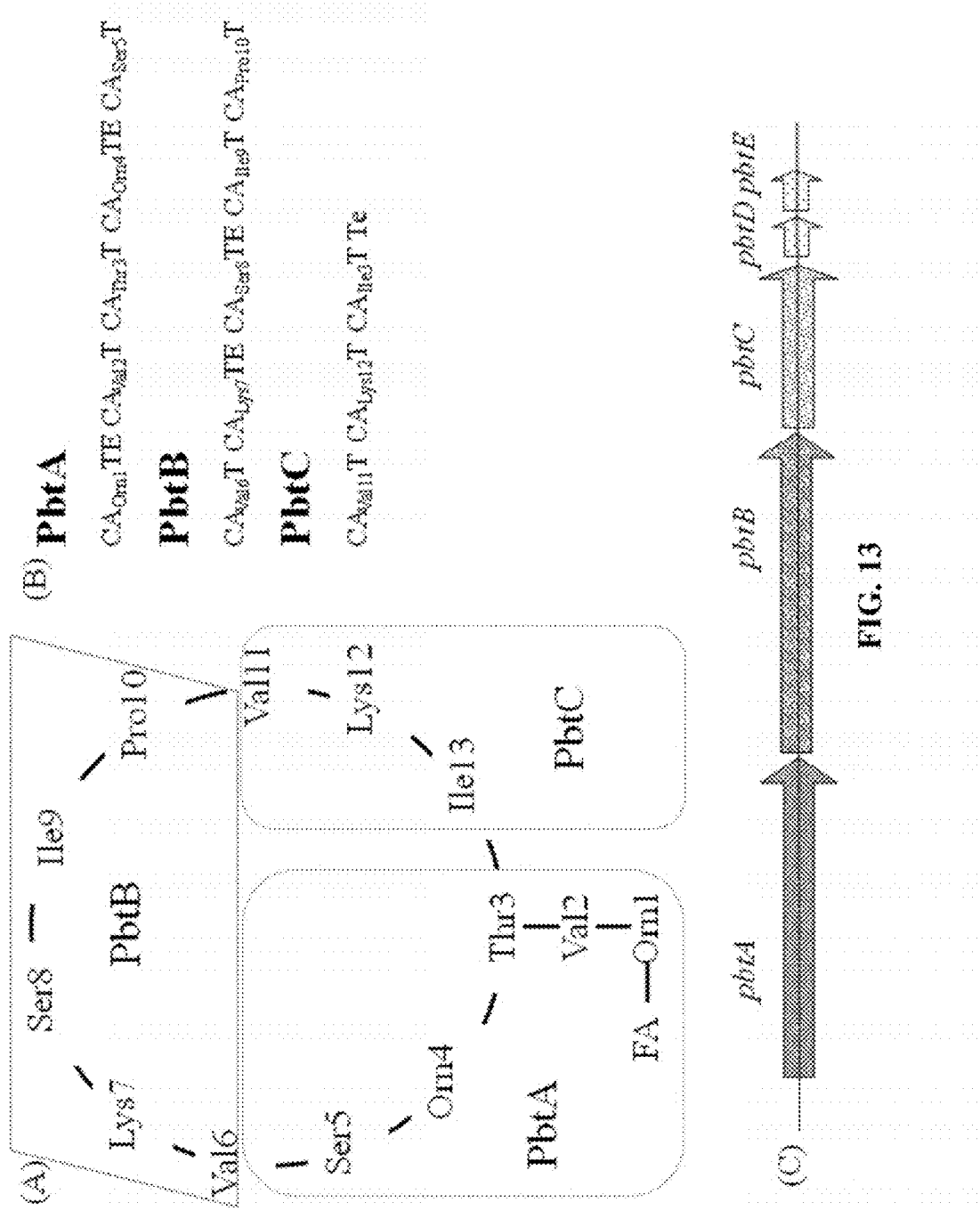
FIG. 13 depicts the organization of the paenibacterin gene cluster and NRPS subunits. (A) identifies the NRPS subunits, PbtA (SEQ ID NO:4), PbtB (SEQ ID NO:6), and PbtC (SEQ ID NO:8). The dotted lines enclose the amino acids catalyzed by each subunit. (B) Identifies modules and domains: C, A, T, E, and Te representing condensation domain, adenylation domain, thiolation domain, epimerization domain, and thioesterase domain, respectively. (C) Depicts the open reading frames (ORFs) in the paenibacterin gene cluster.

One of the prominent characteristics of nonribosomal peptide is the presence of D-amino acids [Stachelhaus, T., et al., *Biochemistry*, (2000) 39: 5775-5787]. Marfey's reagent reacts stoichiometrically with the α-amino group of L- and D-amino acids yielding diastereomers, which can be separated by HPLC with different retention time [Bhushan, R., et al., *Amino Acids* (2004) 27: 231-247]. Paenibacterin peptide was completely hydrolyzed with HCl as the catalyst; the released amino acids reacted with Marfey's reagent, followed by separation by HPLC. As shown in FIG. 12, chiral analysis indicated that $Val_2$, $Thr_3$, $Val_6$, $Pro_{10}$, $Ile_9$, $Val_{11}$, $Ile_{13}$ are L-amino acids, and that $Orn_1$ and $Orn_4$ are D-amino acids. These findings supported the predicted configurations of amino acids in paenibacterin. The prediction was based on the presence or absence of epimerization domain in each NRPS module (FIG. 13). According to sequence analysis, $Lys_7$ is likely D-amino acid while $Lys_{10}$ residue may have L-configuration. Chiral analysis also confirmed that two lysine residues in paenibacterin have different configurations. However, the chirality of individual lysine residue as a function of position cannot be finalized by this method due to the inherent limitation of the method. In addition, the peak of D-Ser in the HPLC profile overlapped with the FDAA reagents (FIG. 12); therefore, the configuration of two Ser residues has not been finalized by this method.

Example 10

Identification and Characterization of the pbt Gene Cluster

The following materials and methods were used to identify and characterize the pbt gene cluster that provides the NRPS biosynthetic machinery for paenibacterin in *Paenibacillus thiaminolyticus* strain OSY-SE.

Strains and Medium

The producer strain *Paenibacillus thiaminolyticus* was obtained from the culture collection of The Ohio State University food safety laboratory. The strain was grown in tryptic soy broth (Becton Dickinson, Sparks, Md.) supplemented with 0.6% yeast extract (TSBYE) at 30° C. with agitation at 200 rpm.

Genome Sequencing

RNase-treated genomic DNA in Tris-Cl (10 mM, pH 8.5) buffer was used for library construction and whole genome sequencing using the next-generation sequencing technology. Briefly, a paired-end library of OSY-SE DNA was prepared using a Truseq™ DNA sample preparation kit (Illumina, San Diego, Calif.) according to the manufacturer's instructions. The constructed library was sequenced (2×76 cycles) in a flow cell lane using the Illumina Genome Analyzer II at the Molecular and Cellular Imaging Center at the Ohio State University. De novo assembly of the *Paenibacills thiaminolyticus* OSY-SE genome was performed using CLC Genomics Workbench 4.7.2 (CLCBio, Cambridge, Mass.) on a desktop computer with 4 GB random access memory (RAM). The draft genome of the bacterium is available in the Genbank with the accession # ALKF00000000.

Paenibacterin Gene Cluster Identification and Analyses

The presence of non-proteinogenic amino acids (ornithine) in paenibacterin indicates that the compound is synthesized by a non-ribosomal mechanism. Examples of non-ribosomal lipopeptide antibiotics include polymyxin [Choi, S. K., et al., *J. Bacteriol.* (2009) 191: 3350-3358], fusaricidin [Choi, S. K., et al., *Biochem. Biophys. Res. Commun.* (2008) 365: 89-95; Li, J., et al., *Appl. Environ. Microbiol.* (2007) 73: 3480-3489], Friulimcin [Müller, C., et al., *Antimicrob. Agents Chemother* (2007) 51: 1028-1037] and daptomycin [Baltz, R. H., et al., *Nat. Prod. Rep.* (2005) 22: 717-741]. The nonribosomal peptide synthetase (NRPS) machinery is composed of modular multi-domain enzymes which act as an assembly line to incorporate each amino acid monomer by one module [Fischbach, M. A., et al., *Chem. Rev.* (2006) 106:3468-3496]. A typical module (C-A-T) in an NRPS contains a carrier thiolation (T) domain and two catalytic domains, an adenylation (A) domain for amino acid activation and selectivity, and a condensation (C) domain catalyzing peptide bond formation. In the termination module (C-A-T-Te), the Te-domain is responsible for releasing the assembled peptide. Additionally, optional epimerase (E) domain may also be present for L- to D-epimerization of amino acids [Fischbach, M. A., et al., *Chem. Rev.* (2006) 106:3468-3496]).

The identification of the NRPS genes involved in the biosynthesis of paenibacterin was performed using a local BLASTX analysis against the assembled *Paenibacillus thiaminolyticus* OSY-SE genome with fusaricidin synthetase (7908 amino acids, accession#: ABQ96384) from *P. polymyxa* as a driver sequence using CLC Genomics Workbench 4.7.2 (CLCBio, Cambridge, Mass.). The NRPS in *Paenibacills thiaminolyticus* OSY-SE genome was analyzed by NRPSpredictor2, a webserver for predicting NRPS adenylation domain [Rausch, C., et al., *Nucleic Acids Res.* (2005) 33: 5799-5808; Röttig, M, et al., *Nucleic Acids Res.* (2011) 39: W362-W367]. In addition, epimerization (E) domains and the Te domain were identified (PKS/NRPS analysis webserver at http://nrps.igs.umaryland.edu/nrps/; [Bachmann, B. O., et al., *Meth. Enzymol.* (2009) 458: 181-217]). The NRPS genes involved in paenibacterin biosynthesis were identified in four non-overlapping contigs; the gaps among contigs were filled by PCR with primers V2F and V2R, V6F and V6R, V11F and V11R (Table 6) under the following conditions initial denaturation at 94° C. for 3 min, followed by 30 cycles of denaturing at 94° C. for 1 min, annealing at 55° C. for 1 min, and extension at 72° C. for 3 min. The final extension was performed at 72° C. for 10 min. The resulting PCR products were sequenced via the Sanger DNA sequence technique using a DNA analyzer (3730 DNA analyzer; Applied Biosystems, Foster City, Calif.) at the Plant-Microbe Genomics Facility, The Ohio State University.

TABLE 6

Primers used in the identification and characterization of the pbt gene cluster.

| Primers | Nucleotide sequences | SEQ ID NO. |
|---|---|---|
| V2F | 5'-CAAACGGTTGACCTATGCGGAGCTGAAT-3' | 18 |
| V2R | 5'-CCTGCACAAAGTGTGTCGGGATCATGTA-3' | 19 |
| V6F | 5'-CCTGACTATCCGGAGGAACGGACTAACG-3' | 20 |
| V6R | 5'-CCAGATCGAACGGGCGAATAAAGGAAC-3' | 21 |
| V11F | 5'-TCATCTGCTTGCCATTCTGAACGATACG-3' | 22 |
| V11R | 5'-TTGAACACATGCCGAATCTGCTCCTCTT-3' | 23 |
| PbtThr3_NdeF | 5'-GGGAATTCCATATGTTGACGGCAGAAGAGAAG-3' | 24 |
| PbtThr3_XhoR | 5'-GGGTATCCGCTCGAGTATATATTCCGTGCCGGT-3' | 25 |
| PbtPro10_NdeF | 5'-GGGAATTCCATATGGTGACTGCCGAGGAGCAG-3' | 26 |
| PbtPro10_XhoR | 5'-GGGTATCCGCTCGAGTACGAACTCCGCTCCGGT-3' | 27 |

In addition, the epimerization (E) domains and thiolation (T) domains in NRPS were predicted by a webserver, PKS/NRPS analysis (http://nrps.igs.umaryland.edu/nrps/) [Bachmann, B. O., et al., *Meth. Enzymol.* (2009) 458: 181-217]. Two open reading frames (ORFs) immediately downstream of the peptide synthetase genes encode ATP binding cassette (ABC)-transporters as predicted by BLASTP search against the NCBI protein database. Predictions of transmembrane helices of ABC-transporters were carried out using the TMHMM server (version 2.0)[Emanuelsson, O., et al., *Nat. Protoc.* (2007) 2: 953-971].

The assembled draft genome of *Paenibacillus thiaminolyticus* OSY-SE consists of 6,931,767 bases with a GC content of 48.66%. The gene cluster responsible for paenibacterin biosynthesis was identified in a 52-kb DNA region, encoding 3 peptide synthetase units and 2 ABC-like transporters (Table 7). The peptide synthetase consists of 13 modules (FIG. 13) responsible for incorporating the 13 amino acids in paenibacterin. The adenylation (A) domain in each module possesses a conserved binding pocket for amino acid recognition and activation [Conti, E., et al., *EMBO J.* (1997) 16: 4174-4183; Stachelhaus, T., et al., *Chem. Biol.* (1999) 6: 493-505; Challis, G. L. et al., *Chem. Biol.* (2000) 7: 211-224]. The substrate specificity of A-domain for amino acid was identified using NRPSpredictor2, based on the fingerprint residues at the substrate-binding site[Rausch, C., et al., *Nucleic Acids Res.* (2005) 33: 5799-5808]. The predicted peptide sequence agreed with the chemical structure of paenibacterin determined by NMR (Tables 8 and 9). In addition, epimerization (E) domains were found in modules for $Orn_1$, $Orn_4$, $Lys_7$ and $Ser_8$, which indicated that those amino acids might be in D-form.

The first module in the peptide synthetase PbtA (SEQ ID NO:5) begins with a starter condensation ($C^{III}$) domain which may be involved in coupling the N-terminal fatty acyl moiety to $Orn_1$. Peptide bond formation is catalyzed by the condensation (C) domain. Various C domains are classified into three functional subtypes based on the types of reaction catalyzed and the chirality of substrates: (i) a $^LC_L$ domain catalyzes peptide bond formation between two L-amino acids; (ii) a $^DC_L$ domain adds an L-amino acid to a growing peptide chain ending with a D-amino acid; (iii) a starter C domain couples the fatty acyl moiety to the first amino acid in the peptide [Rausch, C., et al., *BMC Evol. Biol.* (2007) 7: 78]. Both $^LC_L$ and $^DC_L$ domains have a conserved His-motif in the active site; the consensus residues in this motif are HHxxxDG (SEQ ID NO:67; Table 9) where x denotes variant amino acids [Rausch, C., et al., *BMC Evol. Biol.* (2007) 7: 78]. This signature motif was proven to be critical for amide bond formation [Konz, D, et al., *Chem. Biol.* (1999) 6: R39-48]. Sequence alignment of thirteen C-domains from paenibacterin NRPS revealed the presence of three subtypes of C-domains (Table 9). Four $^DC_L$ domains immediately downstream of E domains are distinguishable from other C-domains by the residues at the active site (Table 9). Correlation of $^DC_L$ domains with preceding E-domains were demonstrated in tyrocidine synthetase [Clugston, S. L., et al., *Biochemistry* (2003) 42: 12095-12104]. A starter C-domain was found in the first module of PbtA (SEQ ID NO:5), which may involves coupling the $C_{15}$ fatty acyl moiety to the first ornithine residue.

Thiolation domain, the peptidyl carrier protein in NRPS, contains a consensus sequence (L/IGGH/DSL/I; SEQ ID NO:68), in which the conserved serine is involved in the covalent binding of substrate amino acids at the reaction center in NRPS [Schlumbohm, W, et al., *J. Biol. Chem.* (1991) 266: 23135-23141]. In the NRPS of paenibacterin, LGGDS (SEQ ID NO:69) motifs, rather than the more common LGGHS (SEQ ID NO:70), were found in the T-domains in modules that incorporate D-amino acids (Table 9); the specialized signature LGGDS (SEQ ID NO:69) motifs are important for the productive interaction with E-domains [Linne, U., et al., *Biochemistry* (2001) 40: 15824-15834].

The termination module in PbtC (SEQ ID NO:9) ends with a thioesterase (Te) domain that may be responsible for the intramolecular cyclization of peptide to form a macrolactone linkage between $Ile_{13}$ and $Thr_3$. In other words, the termination module in PbtC (SEQ ID NO:9) ends with a thioesterase (Te) domain that may be responsible for cycling the peptide between $Ile_{13}$ and $Thr_3$ via an ester bond. In common with Te domains in other NRPS, there is a putative catalytic triad in the paenibacterin Te domain, comprising $Asp_{94}$, $His_{197}$, and a $Ser_{67}$ residue in the signature GYSLG motif (Table 9) [Bruner, S. D., et al., *Structure* (2002) 10: 301-310; Kohli, R. M., et al., *Chem Commun* (Camb) (2003) 7: 297-307].

In addition to the three peptide synthetases, two putative ABC-like transporters, PbtD (SEQ ID NO:11); 570 amino acids) and pbtE (SEQ ID NO:13; 582 amino acids) are 38% identical. PbtD and PbtE share 70% and 66%, respectively, with the ABC transporters PmxC (accession number: ACA97578.1) and PmxD (accession number: ACA97579.1) encoded by the polymyxin biosynthetic gene cluster. Both PbtD (SEQ ID NO:11) and PbtE (SEQ ID NO:13) contain 5 membrane-spanning helices as predicted by TMHMM server 2.0, which indicated that PbtD (SEQ ID NO:11) and PbtE (SEQ ID NO:13) may be membrane proteins and may contribute to conferring resistance to paenibacterin via secretion by the producer cell.

TABLE 7

Paenibacterin NRPS gene cluster

| ORFs | Bases number | Amino acids number | Calc. mol. wt. (Da) | Function |
|---|---|---|---|---|
| pbtA (SEQ ID NO: 4) | 19818 | 6605 | 745827.1 | Peptide synthetase |
| pbtB (SEQ ID NO: 6) | 19251 | 6416 | 723020.7 | Peptide synthetase |
| pbtC (SEQ ID NO: 8) | 9513 | 3170 | 356884.2 | Peptide synthetase |
| pbtD (SEQ ID NO: 10) | 1713 | 570 | 63374.5 | ABC transporter |
| pbtE (SEQ ID NO: 12) | 1749 | 582 | 64584.7 | ABC transporter |

TABLE 8

Conserved amino acids in A-domains involved in substrate recognition

| Module | Active site residues with 8 Å of the amino acid substrate | Binding pocket | Predicted Substrate | Amino acid in Paenibacterin |
|---|---|---|---|---|
| PbtA1 | MAWAFDVFSGDRESIIGSDLNSYGVTEACVDASY (SEQ ID NO. 28) | DVGEIGSVDK (SEQ ID NO. 29) | D-Orn | Orn |
| PbtA2 | LDASFDAATFEGWLLVGGDINGYGPTENTTFTCC (SEQ ID NO. 30) | DAFWLGGTFK (SEQ ID NO. 31) | Val | Val |

TABLE 8-continued

Conserved amino acids in A-domains involved in substrate recognition

| Module | Active site residues with 8 Å of the amino acid substrate | Binding pocket | Predicted Substrate | Amino acid in Paenibacterin |
|---|---|---|---|---|
| PbtA3 | LNSHFDFSVWEGNQIFGGEINMYGITETTVHVTY (SEQ ID NO. 32) | DFWNIGMVHK (SEQ ID NO. 33) | Thr | Thr |
| PbtA4 | IAWAFDVFSGDRESIVGSDLNSYGVTEACVDACY (SEQ ID NO. 34) | DVGEIGSVDK (SEQ ID NO. 39) | D-Orn | Orn |
| PbtA5 | RWMTFDVSVWEWHFFASGEINLYGPTEATVDVTY (SEQ ID NO. 35) | DVWHFSLVDK (SEQ ID NO. 36) | Ser | Ser |
| PbtB1 | LAASFDAATFEGWLLVGGDVNGYGPTENTTFTCC (SEQ ID NO. 37) | DAFWLGGTFK (SEQ ID NO. 31) | Val | Val |
| PbtB2 | LAWAFDVFSGDRDVVVGADVNSYGVTETTIDSCY (SEQ ID NO. 38) | DVGDVGSIDK (SEQ ID NO. 39) | D-Orn[a] | Lys |
| PbtB3 | RWMTFDVSVWEWHFFASGEINLYGPTEATVDVTY (SEQ ID NO. 40) | DVWHFSLVDK (SEQ ID NO. 36) | D-Ser | Ser |
| PbtB4 | VGASFDGSTFDGFILFGGEKHVYGPTESTVFATC (SEQ ID NO. 41) | DGFFLGVVFK (SEQ ID NO. 42) | Ile | Ile |
| PbtB5 | LYEAFDVCYQESYLITAGEHNHYGPSETHVVTAY (SEQ ID NO. 43) | DVQYIAHVVK (SEQ ID NO. 44) | Pro | Pro |
| PbtC1 | LAASFDAATFEGWLLVGGDVNGYGPTENTTFTCC (SEQ ID NO. 45) | DAFWLGGTFK (SEQ ID NO. 31) | Val | Val |
| PbtC2 | LAWAFDVFSGDRDVVVGADVNSYGVTETTIDSCY (SEQ ID NO. 46) | DVGDVGSIDK (SEQ ID NO. 39) | Orn[a] | Lys |
| PbtC3 | VGTSFDGSTFDGFILFGGEKHVYGPTESTVFATC (SEQ ID NO. 47) | DGFFLGVVFK (SEQ ID NO. 42) | Ile | Ile |

[a] the predicted larger cluster includes Orn, Lys and Arg.

TABLE 9

Conserved motifs in adenylation (A), condensation (C), thiolation (T), and epimerization (E) domains of the NRPS involved in paenibacterin synthesis.

| Module | Binding pocket | Predicted Substrate | Residues in Paenibacterin | Conserved Motif in C-domain | Subtype of C-domain | Conserved Motif in T-domain | Conserved motif in E/Te-domain |
|---|---|---|---|---|---|---|---|
| PbtA1 | DVGEIGSVDK (SEQ ID NO. 29) | D-Orn | Orn | INHIIADGVT (SEQ ID NO. 48) | starter | EHFFE LGGDSI (SEQ ID NO. 49) | FNYLGQ[a] (SEQ ID NO. 50) |
| PbtA2 | DAFWLGGTFK (SEQ ID NO. 31) | Val | Val | SHHILMDGWC (SEQ ID NO. 51) | $^{D}C_L$ | DSFFE LGGHSL (SEQ ID NO. 52) | |
| PbtA3 | DFWNIGMVHK (SEQ ID NO. 33) | Thr | Thr | MHHIISDGAS (SEQ ID NO. 53) | $^{L}C_L$ | DNFFE LGGHSL (SEQ ID NO. 54) | |
| PbtA4 | DVGEIGSVDK (SEQ ID NO. 29) | D-Orn | Orn | MHHIISDGVS (SEQ ID NO. 55) | $^{L}C_L$ | DHFFE LGGDSI (SEQ ID NO. 56) | FNYLGQ[a] (SEQ ID NO. 50) |
| PbtA5 | DVWHFSLVDK (SEQ ID NO. 36) | Ser | Ser | SHHILMDGWC (SEQ ID NO. 51) | $^{D}C_L$ | DDFFE LGGHSL (SEQ ID NO. 57) | |
| PbtB1 | DAFWLGGTFK (SEQ ID NO. 31) | Val | Val | MHHIISDGVS (SEQ ID NO. 55) | $^{L}C_L$ | DSFFE IGGHSL (SEQ ID NO. 58) | |
| PbtB2 | DVGDVGSIDK (SEQ ID NO. 39) | D-Orn/ Lys/Arg | Lys | MHHIISDGVS (SEQ ID NO. 55) | $^{L}C_L$ | DHFFE LGGDSI (SEQ ID NO. 56) | FNYLGQ[a] (SEQ ID NO. 50) |

TABLE 9-continued

Conserved motifs in adenylation (A), condensation (C), thiolation (T), and epimerization (E) domains of the NRPS involved in paenibacterin synthesis.

| Module | Binding pocket | Predicted Substrate | Residues in Paenibacterin | Conserved Motif in C-domain | Subtype of C-domain | Conserved Motif in T-domain | Conserved motif in E/Te-domain |
|---|---|---|---|---|---|---|---|
| PbtB3 | DVWHFSLVDK (SEQ ID NO. 36) | D-Ser | Ser | SHHILMDGWC (SEQ ID NO. 51) | $^DC_L$ | DHFFE LGGDSI (SEQ ID NO. 56) | FNYLGQ[a] (SEQ ID NO. 50) |
| PbtB4 | DGFFLGVVFK (SEQ ID NO. 42) | Ile | Ile | SHHILMDGWC (SEQ ID NO. 51) | $^DC_L$ | DNFFE LGGHSL (SEQ ID NO. 54) | |
| PbtB5 | DVQYIAHVVK (SEQ ID NO. 44) | Pro | Pro | MHHIVSDGTS (SEQ ID NO. 59) | $^LC_L$ | DNFFD LGGHSL (SEQ ID NO. 60) | |
| PbtC1 | DAFWLGGTFK (SEQ ID NO. 31) | Val | Val | MHHIISDGAS (SEQ ID NO. 53) | $^LC_L$ | DSFFE IGGHSL (SEQ ID NO. 58) | |
| PbtC2 | DVGDVGSIDK (SEQ ID NO. 39) | Orn/Lys/Agr | Lys | MHHIISDGVS (SEQ ID NO. 55) | $^LC_L$ | DNFFD LGGHSL (SEQ ID NO. 60) | |
| PbtC3 | DGFFLGVVFK (SEQ ID NO. 42) | Ile | Ile | MHHIISDGVT (SEQ ID NO. 61) | $^LC_L$ | DNFFE LGGHSI (SEQ ID NO. 62) | GYSLG[b] (SEQ ID NO. 63) |

[a]conserved motif in E-domain.
[b]conserved motif in Te-domain.

The lipid side chains of lipopeptides can be incorporated in a number of ways. For example, in daptomycin biosynthesis the acyl-CoA ligase (DptE) preferentially activates and transfers branched mid-to long-chain fatty acids to an acyl carrier protein ACP (DptF), which are coupled to the $Trp_1$ by the starter condensation (C) domain [Wittmann, M., et al., *FEBS J.* (2008) 275: 5343-5354; Miao, V, et al., *Microbiology* (2005) 151:1507-1523]. As an example of a different route, surfactin biosynthesis does not rely on a dedicated Acyl-CoA ligase and an ACP for lipid incorporation but utilizes the fatty acyl CoAs generated from primary metabolism [Kraas, F. I., et al., *Chem. Biol.* (2010) 17: 872-880]. Likewise, genes encoding acyl-CoA ligase and ACP are absent in the paenibacterin gene cluster. The incorporation of lipid in paenibacterin biosynthesis may resemble the machinery of lipoinitiation in surfactin biosynthesis.

Daptomycin is an anionic cyclic peptide and the activity of daptomycin relies on the presence of $Ca^{2+}$[Robbel, L. et al., *J. Biol. Chem.* (2010) 285:27501-27508]. In contrast, paenibacterin is a cationic cyclic lipopeptide lacking the calcium binding amino acids. The chemical structure as well as its unique activity against Gram-negative strains suggests that the mode of action of paenibacterin may be different from that of daptomycin. The elucidation of the biosynthetic pathway allows for the genetic engineering of the NRPS to produce paenibacterin on a large scale and provides a platform for combinatorial biosynthesis of other antimicrobials derived from the paenibacterin structure, allowing for determination of structure-activity relationships.

Example 11

Determination of Adenylation Domain Substrate Specificity

The following materials and methods were used to clone, express, and purify A-domains from the NRPS biosynthetic machinery for paenibacterin in *Paenibacillus thiaminolyticus* strain OSY-SE. Functional analysis was performed on such A-domains.

Strains and Medium

*Escherichia coli* DH5α or *E. coli* BL21 (DE3) was cultivated in Luria-Bertani (Becton Dickinson) broth or on Luria-Bertani agar plate at 37° C. When appropriate, Luria-Bertani media were supplemented with 100 μg/ml ampicillin.

Amplification and Cloning of A-Domains

The gene encoding the third and tenth A-domain in the pbt gene cluster were amplified by PCR from genomic DNA of *Paenibacillus thiaminolyticus* OSY-SE, using the high-fidelity DNA polymerase (Phusion, NEB, Ipswich, Mass.). Primer sets (PbtThr3_NdeIF and PbtThr3_XhoR (SEQ ID NOS:24 and 25); PbtPro10_NdeIF and PbtPro10_XhoR (SEQ ID NOS:26 and 27); Table 6) with the Nde I or Xho I restriction site in forward and reverse primers were used for PCR amplification. PCR was carried out under the following conditions: initial denaturation at 98° C. for 30 seconds, followed by 35 cycles of denaturing at 98° C. for 10 seconds, annealing at 65° C. for 30 seconds, and extension at 72° C. for 90 seconds. The final extension was performed at 72° C. for 10 min. PCR products were purified using spin column method (QIAquick gel extraction kit, Qiagen, Valencia, Calif.), double-digested with Nde I and Xho I at 37° C. for 5 hours. After digestion, PCR products were gel-purified and ligated to vector pET15b (Novagen, Madison, Wis.) that has been cut with the same enzymes. Ligation was carried out with T4 ligase (NEB) at room temperature overnight. The ligation mixture was transformed into *Escherichia coli* competent cells (DH5α, NEB) by heat shock at 42° C. for 30 seconds. Subsequently, the confirmed recombinant plasmid (pET15b-Thr3 or pET15b-Pro10) carrying the A-domain sequence was introduced into the expression host *Escherichia coli* BL21 (DE3) (NEB) by heat shock.

Overexpression And Purification of A-Domains

For overexpression, a fresh recombinant *Escherichia coli* BL21 (DE3) culture (10 ml) was used to inoculate 500 ml Luria-Bertani broth supplemented with 100 μg/ml ampicillin. Cells were cultivated at 37° C. with agitation at 200 rpm. When the cell density ($OD_{600}$) reached ~0.5, isopropyl-b-D-thiogalactopyranoside (IPTG) at a final concentration of 400 μM was added to induce the expression of A-domains. Cells were grown at a 25° C. with agitation at 200 rpm overnight for protein expression. Bacterial cells were harvested by centrifugation at 3,074×g for 15 min at 4° C. Cell pellets were resuspended in 40 ml chilled equilibration buffer (50 mM sodium phosphate, 300 mM NaCl, pH 7.0).

To facilitate protein extraction, lysozyme (final concentration at 0.75 mg/ml, Sigma) and DNase I (40 μl, 2 unit $μl^{-1}$, NEB) were added to the cell suspension, followed by incubation on ice for 30 min. Subsequently, the cells in a beaker held on ice were treated with an ultrasonic processor (36860 series, Cole Parmer, Chicago, Ill.) for three times (30 seconds each pulse with a 2-min pause between each burst, 50% power). The disrupted cells were centrifuged at 11,952×g for 20 min to pellet the insoluble materials. The supernatant was carefully transferred to a clear tube without disturbing the pellet.

Recombinant A-domains in the supernatant were purified using an immobilized metal affinity chromatography (IMAC) resin charged with cobalt (1 ml, HisTALON gravity column, Clotech, Mountain View, Calif.). The column was equilibrated with 10 ml chilled equilibration buffer. After loading the supernatant, the column was washed with 8 ml equilibration buffer and 7 ml of wash buffer (i.e., equilibration buffer with 10 mM imidazole). The target proteins were eluted from the column with 5 ml elution buffer (i.e., equilibration buffer with 150 mM imidazole).

The purified A-domains were subjected to concentration and buffer exchange by ultrafiltration (10 kDa Ultracel-10 membrane, Millipore, Billerica, Mass.). Ultrafiltration was carried out by centrifugation at 5,050×g at 4° C. for 30 min for 3 times; water was added between each centrifugation step to replace the elution buffer. The concentrated A-domains in water (~500 µl) were mixed with glycerol (final concentration, 10%) and kept at −80° C. for long term storage. Protein concentration was determined using a spectrophotometer (NanoDrop 1000, Thermo Scientific, Franklin, Mass.).

Amino Acid Specificities of Purified A-Domains

The substrate specificity of purified A-domains was determined by malachite green colorimetric assay as described by McQuade et al. [McQuade, T. J., et al., Anal. Biochem. (2009) 386: 244-250] with some modifications. All 20 proteinogenic amino acids and ornithine were tested in a 96-well plate. The reaction mixture (100 µl) contained the following components: reaction buffer (50 mM NaCl, 10 mM MgCl$_2$, 50 mM Tris-Cl, pH 7.4), purified A-domain (6.5 µM), ATP (100 µM, cat. no. A7699, Sigma), amino acid (0.3 mM for tyrosine, 6 mM for all other amino acids), and inorganic pyrophosphatase (0.2 units, cat. no. 11643, Sigma). The reaction was initiated by adding ATP as the last component and incubated at 25° C. for 20 min. In the reactions, the activation of substrate by A-domain resulted in the release of pyrophosphate, which was converted to phosphate by pyrophosphatase. The phosphate concentration was quantified by adding 25 µl of the malachite green reagent (cat. no. POMG-25H, Bioassay Systems, Hayward, Calif.). After color development at 25° C. for 20 mM, absorbance at 600 nm was measured using a microtiter plate reader (Molecular Devices Corp., Menlo Park, Calif.). Each enzyme assay was performed with two replicates.

Functional Analysis of A-Domains

Figure 14:
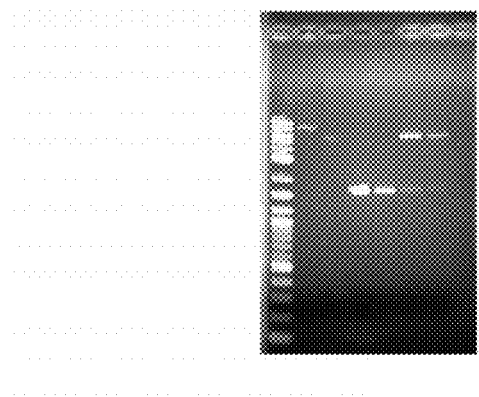
FIG. 14 depicts agarose gel electrophoresis showing DNA for A-domain cloning. Lane 1, 2-log DNA ladder (NEB); lane 2, pET15b plasmid; lane 3, pET15b plasmid digested with Nde I and Xho I; lane 4, PCR product of the third A-domain; lane 5, PCR product of the tenth A-domain; lane 6, recombinant plasmid pET15b-Thr3 digested with Nde I and Xho I; lane 7, recombinant plasmid pET15b-Pro 10 digested with Nde I and Xho I.
Figure 15:
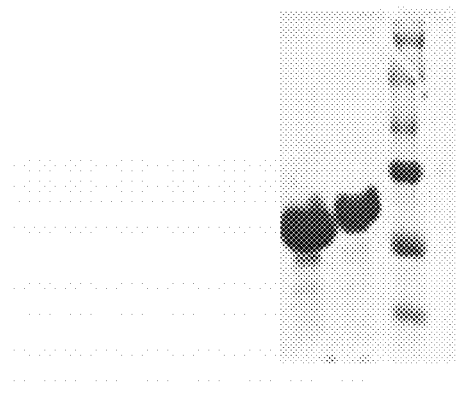
FIG. 15 depicts a commassie blue-stained 10% Tris-HCl SDS-PAGE gel showing the recombinant A-domains expressed in *Escherichia coli* BL21 (DE3). lane 1, the third A-domain purified by $Co^{2+}$-chelate affinity chromatography; lane 2, the tenth A-domain purified by $Co^{2+}$-chelate affinity chromatography; lane 3, prestained protein standard (Precision plus, Bio-Rad, Hercules, Calif.).
Figure 16:
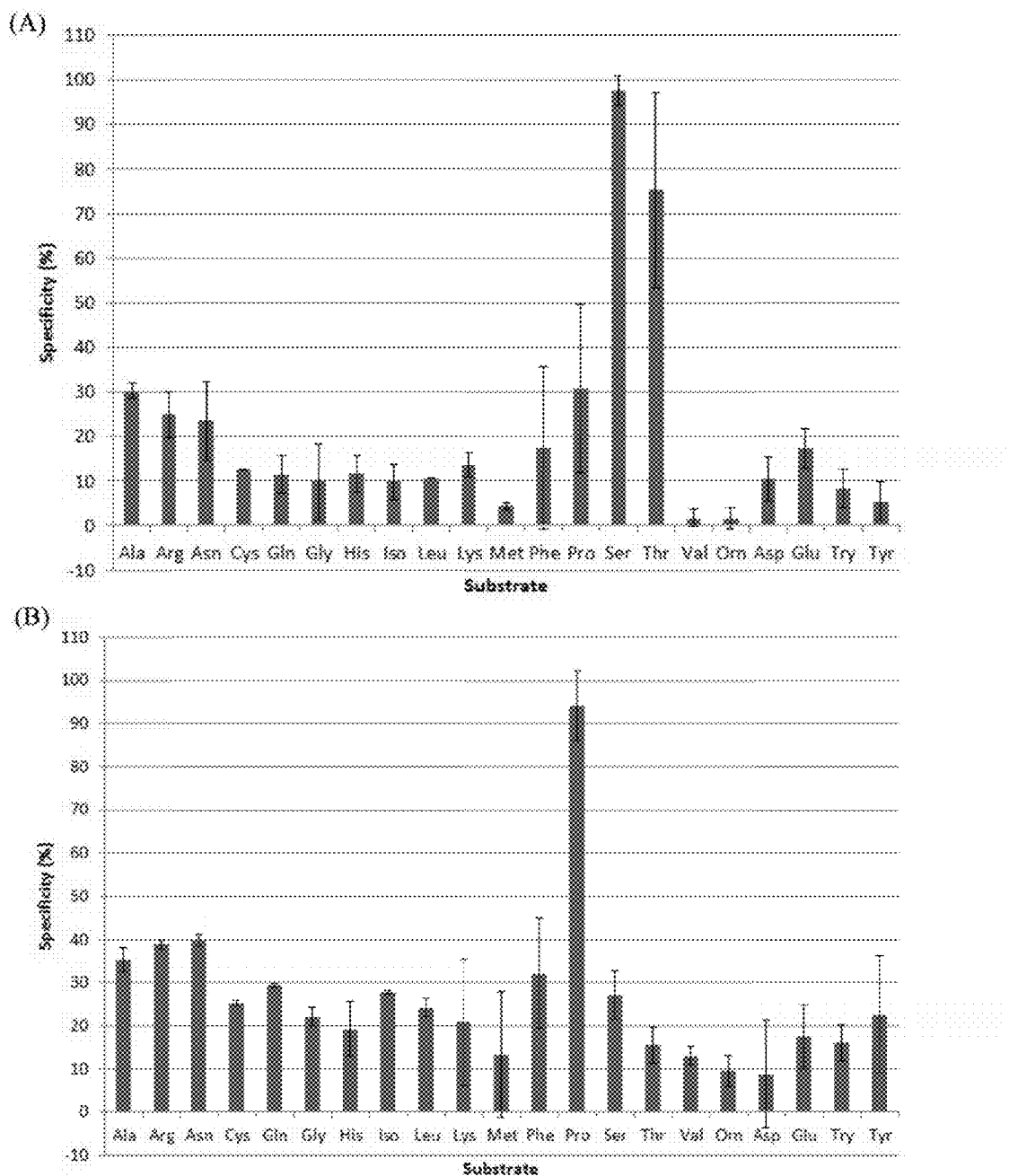
FIG. 16 depicts the determination of substrate specificity of purified A-domains by phosphate detection assay. (A) Relative activity of the third A-domain in paenibacterin gene cluster, showing highest activity on hydroxyl containing amino acids, serine and threonine. (B) Relative activity of the tenth A-domain in paenibacterin gene cluster, showing highest activity on proline.

Adenylation domains in NRPS determine the primary structure of the peptide. The substrate specificity of selected adenylation domains in the putative paenibacterin NRPS was examined by overexpression in Escherichia coli and protein function analyses in vitro. The third and tenth A-domains in paenibacterin NRPS are predicted to activate Thr and Pro residues, respectively (Table 9). To confirm the hypothesis, the A-domains were cloned and expressed in Escherichia coli BL21 (DE3) under the control of the T7 promoter. As shown in FIG. 14, the nucleotide sequences encoding A-domains were amplified by PCR and cloned into the prokaryotic expression vector pET15b. The recombinant A-domain proteins carried a His-tag at the N-terminus, which facilitates protein purification by immobilized metal affinity chromatography. FIG. 15 shows the SDS-PAGE gel of the purified A-domain proteins. Functional analyses revealed that the putative proline-activating A-domain has the highest activity on proline among 20 proteinogenic amino acids (FIG. 16). In addition, the recombinant third A-domain from Pbt NRPS, which is assumed to activate threonine, showed relatively relaxed specificity on hydroxyl-containing amino acids, serine and threonine. Overall, these findings agreed well with the chemical structure of paenibacterin and thus confirmed the function of paenibacterin biosynthetic gene cluster.

Example 12

Antimicrobial Activity of Paenibacterin and Other Anti-Microbial Agents

The activity of paenibacterin against several strains of Gram-positive and Gram-negative foodborne pathogens is summarized in Table 10. The data is reported as minimum inhibitory concentrations (MIC) as an average of three replicates for paenibacterin against the various listed bacterial strains. MIC refers to the lowest concentration of paenibacterin that resulted in no visible growth of bacterial cells. MICs were determined according to the CLSI broth microdilution method (see, Clinical and Laboratory Standards Institute (CLSI). 2009. Methods for dilution antimicrobial susceptibility tests for bacteria that grow aerobically; approved standard. M77-A8. CLSI, Wayne, Pa.). Briefly, HPLC-purified paenibacterin was dissolved in methanol and diluted to appropriate concentration with cation-adjusted Mueller-Hinton II broth (Difco). Aliquots (25 µl) of serially-diluted paenibacterin was dispensed into wells of a 96-well plate; an equal amount of 1/10 diluted overnight bacterial culture was added to wells. Plates were incubated at 35° C. for 24 h. Cell growth after incubation was examined and determined using a microtiter plate reader at 600 nm. Concentration of paenibacterin is determined based on a molecular weight of 1604 Da.

TABLE 10

Minimum inhibitory concentration (MIC) of paenibacterin.

| | µg/ml | | µM | |
|---|---|---|---|---|
| Strain | Average | Std. Dev. | Average | Std. Dev. |
| Escherichia coli O157:H7 EDL933 | 7.81 | 0.00 | 4.87 | 0.00 |
| Salmonella enterica serovar Typhimurium | 7.81 | 0.00 | 4.87 | 0.00 |
| Yersinia enterocolitica | 3.26 | 1.13 | 2.03 | 0.70 |
| Listeria monocytogenes Scott A | 1.95 | 0.00 | 1.22 | 0.00 |
| Bacillus cereus ATCC14579 | 15.6 | 0.00 | 9.74 | 0.00 |

The activity of paenibacterin was also tested against clinical isolates of the following Gram-negative bacterial strains: four strains of the species Pseudomonas aeruginosa (PAE), three strains of the species Acinetobacter baumannii (ABA), two strains of the species Escherichia coli (ECO), and four strains of the species Klebsiella pneumoniae (KPN). Particularly, the strains of Gram-negative bacteria included polymyxin B-resistant (PMB-R) and polymyxin B-sensitive (PMB-S) strains of each above listed species. The activity of paenibacterin against these strains of Gram-negative bacteria is summarized in Tables 11 and 12. The MICs were determined using the above described CLSI broth microdilution method, in which the method was performed with both non-binding surface coated (NBS) and polystyrene (PS) 96-well plates (Tables 11 and 12, respectively). The MICs were generally lower in the NBS 96-well plates as compared to the PS 96-well plates.

Paenibacterin activity was the same for polymyxin B-resistant and polymyxin B-sensitive strains of Acinetobacter baumannii (Table 11, MIC of 2 µg/ml). Paenibacterin yielded MICs of 8 µg/ml for polymixin B-sensitive strains of Pseudomonas aeruginosa, Escherichia coli, and Klebsiella pneumoniae, but yielded 4-8 fold higher MICs with some polymyxin B-resistant strains (e.g., 32-64 µg/ml for PAE.2281 and KPN.2317). However, higher MICs were not observed with other polymyxin B-resistant strains, for example, ABA.2315, ECO.2276, and KPN.2463.

TABLE 11

Minimum inhibitory concentration (MIC) of paenibacterin in non-binding surface coated 96-well plates.

|  | PAE.44[a] | PAE.999 | PAE.2325 | PAE.2281 | ABA.2232[b] | ABA.1570 | ABA.2315 |
|---|---|---|---|---|---|---|---|
| Paenibacterin | 8 | 8 | 16 | 32-64 | 2 | 2 | 2 |
| polymyxin B sulfate | 0.125 | 0.25 | 0.25 | 16 | 0.06 | 0.0625 | 8 |
| tobramycin | 0.5 | 32 | >32 | 1-2 | 0.5 | 32 | >32 |
| meropenem #413 | 1 | >8 | 2-4 | 1-2 | 0.125-0.25 | 8 | >8 |

|  | ATCC 25922 ECO.35[c] | ECO.2276 | KPN.674[d] | PMB-S[e], KPN.2461 | PMB-R[f], KPN.2463 | KPN.2317 |
|---|---|---|---|---|---|---|
| Paenibacterin | 8 | 8 | 8 | 4 | 8 | 64 |
| polymyxin B sulfate | 0.06 | 8 | 0.125 | 0.06-0.13 | 2-8 | >64 |
| tobramycin | 1 | 1-2 | 8 | 32 | 32 | >32 |
| meropenem #413 | 0.03 | 0.03-0.06 | 0.0625 | >8 | >8 | 0.0625 |

[a]PAE: *Pseudomonas aeruginosa*
[b]ABA: *Acinetobacter baumannii*
[c]ECO: *Escherichia coli*
[d]KPN: *Klebsiella pneumonia*
[e]PMB-S: polymyxin B-sensitive
[f]PMB-R: polymyxin B-resistant

TABLE 12

Comparison of minimum inhibitory concentration (MIC) of paenibacterin in non-binding surface coated (NBS) and polystyrene (PS) 96-well plates.

|  | Paenibacterin | | polymyxin B | | tobramycin | | Meropenem | |
|---|---|---|---|---|---|---|---|---|
|  | PS | NBS | PS | NBS | PS | NBS | PS | NBS |
| PAE.44 | 64 | 8 | 2 | 0.125 | 0.5 | 0.5 | ND | 1 |
| PAE.999 | 64 | 8 | 2 | 0.25 | >32 | 32 | >8 | >8 |
| PAE.2325 | 64 | 16 | 2 | 0.25 | >32 | >32 | 2 | 2-4 |
| PAE.2281 | 64 | 32-64 | 16 | 16 | 1 | 1-2 | 0.5 | 1-2 |
| ABA.2232 | 32 | 2 | 2 | 0.06 | 1 | 0.5 | 0.5 | 0.125-0.25 |
| ABA.1570 | 32 | 2 | 2 | 0.06 | 16 | 32 | >8 | 8 |
| ABA.2315 | 32 | 2 | 64 | 8 | >32 | >32 | >8 | >8 |
| ECO.35 | 16 | 8 | 2 | 0.06 | 1 | 1 | 0.016 | 0.03 |
| ECO.2276 | 16 | 8 | 8 | 8 | 2 | 1-2 | 0.03 | 0.03-0.06 |
| KPN.674 | 32 | 8 | 2 | 0.125 | 8 | 8 | 0.03 | 0.0625 |
| KPN.2461 | 32 | 4 | 2 | 0.06-0.13 | 32 | 32 | >8 | >8 |
| KPN.2463 | 32 | 8 | 32 | 2-8 | 32 | 32 | >8 | >8 |
| KPN.2317 | 64 | 64 | >64 | >64 | >32 | >32 | 0.03 | 0.06 |

The activity of paenibacterin was further tested against clinical isolates of the following Gram-positive bacteria: methicillin-sensitive *Staphylococcus aureus* (MSSA), methicillin-resistant *S. aureus* (MRSA), vancomycin-sensitive *Enterococcus faecalis*, vancomycin-resistant *E. faecalis* (VRE), *Streptococcus pneumoniae*, and laboratory derived daptomycin-resistant (DR) MSSA, MRSA, and VRE strains. The activity of paenibacterin against these strains of Gram-positive bacteria is summarized in Table 13. The MICs were determined using the above described CLSI broth microdilution method, in which the method was performed with non-binding surface coated (NBS) 96-well plates. MICs of 32-64 μg/ml were observed with paenibacterin for *Staphylococcus aureus, Enterococcus faecalis*, and *Streptococcus pneumoniae*. No increase in MICs for paenibacterin was observed in vancomycin- or daptomycin-resistant strains.

TABLE 13

Minimum inhibitory concentration (MIC) of paenibacterin.

|  | MSSA[a] ATCC 29213 SAU.42[h] | DR-MSSA[b] from SAU.42 SAU.278 | MRSA[c] ATCC 43300 SAU.399 | DR-MRSA[d] from MW2 SP SAU.1616 | WT[e] ATCC 29212 EFS.43[i] | DS-VRE[f] ATCC 700802 EFS.807 | DR-VRE[g] from EFS.807 EFS.2731 | WT ATCC 49619 SPN.31[j] |
|---|---|---|---|---|---|---|---|---|
| Paenibacterin | 32 | 64 | 32 | 32 | 32-64 | 64 | 8 | 64 |
| tobramycin | 0.5 | 0.5 | >32 | 0.5 | 8 | >32 | >32 | 0.25 |
| vancomycin | 1 | 2 | 2 | 2 | 2-4 | 16-32 | 32 | 16 |

TABLE 13-continued

Minimum inhibitory concentration (MIC) of paenibacterin.

| | MSSA[a] ATCC 29213 SAU.42[h] | DR-MSSA[b] from SAU.42 SAU.278 | MRSA[c] ATCC 43300 SAU.399 | DR-MRSA[d] from MW2 SP SAU.1616 | WT[e] ATCC 29212 EFS.43[i] | DS-VRE[f] ATCC 700802 EFS.807 | DR-VRE[g] from EFS.807 EFS.2731 | WT ATCC 49619 SPN.31[j] |
|---|---|---|---|---|---|---|---|---|
| daptomycin NBS[k] | 0.5 | 8 | 0.5 | 16 | 2 | 1 | >32 | 0.5 |
| meropenem | 0.125 | NT | NT | NT | 2 | 4 | NT | NT |

[a]MSSA: methicillin-sensitive *Staphylococcus aureus*
[b]DR-MSSA: daptomycin-resistant MSSA
[c]MRSA: methicillin-resistant *Staphylococcus aureus*
[d]DR-MRSA: daptomycin-resistant MRSA
[e]WT: wild-type
[f]DS-VRE: daptomycin-sensitivve vancomycin-resistant *Enterococus faecalis*
[g]DR-VRE: daptomycin-resistant vancomycin-resistant *Enterococus faecalis*
[h]SAU: *Staphylococcus aureus*
[i]EFS: *Enterococus faecalis*
[j]SPN: *Streptococcus pneumoniae*
[k]NBS: non-binding surface coated The data demonstrates that paenibacterin as well as other antimicrobial agents based on its structure provide for broad antimicrobial action against a number of pathogenic organisms.

We claim:

1. An isolated amino acid sequence consisting of Orn-Val-Thr-Orn-Ser-Val-Lys-Ser-Ile-Pro-Val-Lys-Ile (SEQ ID NO:64).

2. The isolated amino acid sequence of claim 1, wherein the sequence further consists of a linkage between any two amino acid residues thereby forming a cyclic peptide structure.

3. The isolated amino acid sequence of claim 2, wherein the linkage comprises a covalent bond between Thr and the C-terminal Ile.

4. An isolated amino acid sequence consisting of:

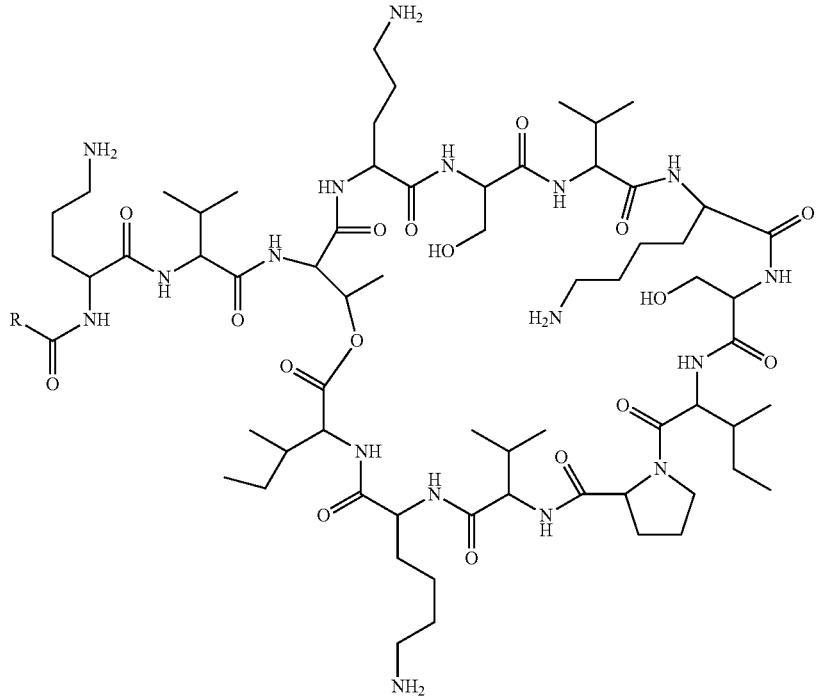

or a salt thereof,
wherein R is selected from the group: H and —OH.

* * * * *